United States Patent
Sole Feu et al.

(10) Patent No.: US 9,518,050 B2
(45) Date of Patent: Dec. 13, 2016

(54) CYCLOHEXYL AND QUINUCLIDINYL CARBAMATE DERIVATIVES HAVING β2 ADRENERGIC AGONIST AND M3 MUSCARINIC ANTAGONIST ACTIVITY

(71) Applicant: ALMIRALL, S.A., Barcelona (ES)

(72) Inventors: Laia Sole Feu, Barcelona (ES); Ines Carranco Moruno, Barcelona (ES); Jose Aiguade Bosch, Barcelona (ES); Carlos Puig Duran, Barcelona (ES); Silvia Fonquerna Pou, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 14/653,048

(22) PCT Filed: Dec. 17, 2013

(86) PCT No.: PCT/EP2013/076973
§ 371 (c)(1),
(2) Date: Jun. 17, 2015

(87) PCT Pub. No.: WO2014/095920
PCT Pub. Date: Jun. 26, 2014

(65) Prior Publication Data
US 2015/0329535 A1     Nov. 19, 2015

Related U.S. Application Data

(60) Provisional application No. 61/750,959, filed on Jan. 10, 2013.

(30) Foreign Application Priority Data

Dec. 18, 2012   (EP) .................................. 12382513

(51) Int. Cl.
| | | |
|---|---|---|
| *C07D 453/04* | (2006.01) |
| *A61K 31/4709* | (2006.01) |
| *A61K 31/475* | (2006.01) |
| *A61K 31/4704* | (2006.01) |
| *C07D 413/12* | (2006.01) |
| *A61K 45/06* | (2006.01) |
| *A61K 47/48* | (2006.01) |
| *A61K 31/13* | (2006.01) |
| *A61K 31/4184* | (2006.01) |
| *A61K 31/439* | (2006.01) |
| *C07C 271/38* | (2006.01) |
| *C07D 453/02* | (2006.01) |
| *C07D 213/75* | (2006.01) |
| *C07D 215/26* | (2006.01) |
| *C07D 401/12* | (2006.01) |
| *C07D 249/18* | (2006.01) |

(52) U.S. Cl.
CPC ............ *C07D 453/04* (2013.01); *A61K 31/13* (2013.01); *A61K 31/4184* (2013.01); *A61K 31/439* (2013.01); *A61K 31/4704* (2013.01); *A61K 31/475* (2013.01); *A61K 31/4709* (2013.01); *A61K 45/06* (2013.01); *A61K 47/481* (2013.01); *C07C 271/38* (2013.01); *C07D 213/75* (2013.01); *C07D 215/26* (2013.01); *C07D 249/18* (2013.01); *C07D 401/12* (2013.01); *C07D 413/12* (2013.01); *C07D 453/02* (2013.01); *C07C 2101/14* (2013.01)

(58) Field of Classification Search
CPC ... C07D 453/02; C07D 453/04; C07D 271/38; C07D 2101/14; C07D 413/12; C07D 249/18; C07D 401/12; A61K 31/439; A61K 31/4184; A61K 31/13; A61K 31/4704; A61K 31/475; A61K 31/4709; A61K 45/06
See application file for complete search history.

(56) References Cited

U.S. PATENT DOCUMENTS

| | | |
|---|---|---|
| 4,556,653 A | 12/1985 | Giani et al. |
| 5,397,800 A | 3/1995 | Alker et al. |
| 6,673,908 B1 | 1/2004 | Stanton, Jr. |
| 9,072,734 B2 * | 7/2015 | Mitsuyama ........ A61K 31/4709 |
| 9,233,108 B2 | 1/2016 | Aiguade Bosch et al. |
| 9,315,463 B2 | 4/2016 | Prat Quinones et al. |
| 2012/0046467 A1 * | 2/2012 | Mitsuyama ........ A61K 31/4709 546/91 |
| 2013/0053359 A1 | 2/2013 | Prat Quinones et al. |
| 2013/0281415 A9 | 10/2013 | Prat Quinones et al. |
| 2014/0303127 A1 | 10/2014 | Bosch et al. |
| 2014/0378421 A1 | 12/2014 | Bosch et al. |
| 2016/0009698 A1 | 1/2016 | Julia Jane et al. |

(Continued)

FOREIGN PATENT DOCUMENTS

| | | |
|---|---|---|
| CN | 101544572 A | 9/2009 |
| EP | 0147475 | 10/1985 |

(Continued)

OTHER PUBLICATIONS

Ray, Nicholas C. et al., "Muscarinic antagonist-β-adrenergic agonist dual pharmacology molecules as bronchodilators: a patent review," Informa Healthcare, vol. 19, No. 1, pp. 1-12 (2009).

(Continued)

*Primary Examiner* — D M Seaman
(74) *Attorney, Agent, or Firm* — Finnegan, Henderson, Farabow, Garrett & Dunner LLP

(57) ABSTRACT

The present invention relates to novel compounds having β2 adrenergic agonist and M3 muscarinic antagonist dual activity, to pharmaceutical compositions containing them, to the process for their preparation and to their use in respiratory therapies.

46 Claims, No Drawings

(56) References Cited

U.S. PATENT DOCUMENTS

| | | |
|---|---|---|
| 2016/0015704 A1 | 1/2016 | Aparici Virgili et al. |
| 2016/0143915 A1 | 5/2016 | Aiguade Bosch et al. |
| 2016/0166566 A1 | 6/2016 | Julia Jane et al. |
| 2016/0175295 A1 | 6/2016 | Aparici Virgili et al. |
| 2016/0200718 A1 | 7/2016 | Aiguade Bosch et al. |

FOREIGN PATENT DOCUMENTS

| | | |
|---|---|---|
| EP | 1 078 629 | 2/2001 |
| EP | 1 894 568 | 3/2008 |
| EP | 2 386 555 | 11/2011 |
| EP | 2 426 121 | 3/2012 |
| EP | 2 592 077 | 5/2013 |
| EP | 2 592 078 | 5/2013 |
| WO | WO 98/09632 | 3/1998 |
| WO | WO 99/30703 | 6/1999 |
| WO | WO 01/14339 | 3/2001 |
| WO | WO 2004/074246 | 9/2004 |
| WO | WO 2004/074276 | 9/2004 |
| WO | WO 2004/089892 | 10/2004 |
| WO | WO 2004/106333 | 12/2004 |
| WO | WO 2005/080375 | 9/2005 |
| WO | WO 2005/111004 | 11/2005 |
| WO | WO2005/123693 A1 | 12/2005 |
| WO | WO 2006/023454 | 3/2006 |
| WO | WO 2006/023457 | 3/2006 |
| WO | WO 2006/023460 | 3/2006 |
| WO | WO 2007/017670 | 2/2007 |
| WO | WO 2007/090859 | 8/2007 |
| WO | WO 2007/107828 | 9/2007 |
| WO | WO 2008/000483 | 1/2008 |
| WO | WO 2008/017824 | 2/2008 |
| WO | WO 2008/017827 | 2/2008 |
| WO | WO 2008/041095 | 4/2008 |
| WO | WO 2008/087437 | 7/2008 |
| WO | WO 2008/096127 | 8/2008 |
| WO | WO 2008/096129 | 8/2008 |
| WO | WO 2008/149110 | 12/2008 |
| WO | WO 2009/013244 | 1/2009 |
| WO | WO 2009/017813 | 2/2009 |
| WO | WO 2009/098448 | 8/2009 |
| WO | WO 2009/139709 | 11/2009 |
| WO | WO 2010/004517 | 1/2010 |
| WO | WO 2010/015792 | 2/2010 |
| WO | WO 2010/069504 A1 | 6/2010 |
| WO | WO 2010/123766 | 10/2010 |
| WO | WO 2011/012897 | 2/2011 |
| WO | WO 2011/141180 | 11/2011 |
| WO | WO 2012/044825 | 4/2012 |
| WO | WO 2012/085582 | 6/2012 |
| WO | WO 2012/085583 | 6/2012 |
| WO | WO 2012/168349 | 12/2012 |
| WO | WO 2012/168359 | 12/2012 |
| WO | WO 2013/068552 | 5/2013 |
| WO | WO 2013/068554 | 5/2013 |
| WO | WO2013/068875 | 5/2013 |
| WO | WO2013/071009 A1 | 5/2013 |
| WO | WO2013/071169 A1 | 5/2013 |
| WO | WO 2014/086924 | 6/2014 |
| WO | WO 2014/086927 | 6/2014 |
| WO | WO 2014/095920 | 6/2014 |
| WO | WO 2004/074812 | 9/2014 |
| WO | WO 2014/131652 | 9/2014 |
| WO | WO 2014/131851 | 9/2014 |
| WO | WO 2015/011244 | 1/2015 |
| WO | WO 2015/011245 | 1/2015 |
| WO | WO 2016/046390 | 3/2016 |

OTHER PUBLICATIONS

International Search Report for International Application No. PCT/EP2013/076973, Mar. 11, 2014.
U.S. Appl. No. 13/697,060, filed Nov. 9, 2012.
U.S. Appl. No. 14/357,344, filed May 9, 2014.
U.S. Appl. No. 14/357,400, filed May 9, 2014.
U.S. Appl. No. 14/770,200, filed Aug. 27, 2015.
U.S. Appl. No. 14/770,206, filed Aug. 27, 2015.
U.S. Appl. No. 14/956,767, filed Dec. 2, 2015.
U.S. Appl. No. 14/966,836, filed Dec. 2, 2015.
International Search Report, PCT/EP2012/072309, Dec. 18, 2012.
International Search Report PCT/EP2012/072311, Dec. 10, 2012.
International Search Report PCT/EP2011/002376, Aug. 1, 2011.
International Search Report PCT/EP2014/053674, Apr. 17, 2014.
International Search Report PCT/EP2014/053871, Mar. 27, 2014.
International Search Report PCT/EP2014/065966, Aug. 19, 2014.
International Search Report PCT/EP2014/065965, Sep. 18, 2014.
Barnes, Peter J., "Airway Pharmacology," Textbook of Respiratory Medicine, 3rd Edition, Chapter 11, 2000, pp. 267-272.
Glossop, Paul A. et al., "Progress in the Development of Inhaled, Long-Acting β2-Adrenoceptor Agonists," Annual Reports in Medicinal Chemstry, vol. 41, 2006, pp. 237-248.
Hoffman, Brian B. "Catecholamines, Sympathomimetic Drugs, and Adrenergic Receptor Antagonists," Goodman & Gilman's The Pharmacological Basis of Therapeutics $10^{th}$ Edition, Chapter 10, pp. 215-232, 2001.
Hughes, Adam et al., Dual-pharmacology Muscarinic Antagonist and β2 Agonist Molecules for the Treatment of Chronic Obstructive Pulmonary Disease, Future Med. Chem., (2011), 3(13), pp. 1585-1605.
Jacobsen, John R., "Third-generation Long-Acting β2 Adrenoceptor Agonists: Medicinal Chemistry Strategies Employed in the Identification of Once-Daily Inhaled β2-Adrenoceptor Agonists," Future Med Chem., 2011, 3(13), pp. 1607-1622.
Naito, Roy et al., "Synthesis and Antimuscarinic Properties of Quinuclidin-3-yl 1,2,3,4-Tetrahydroisoquinoline-2-carboxylate Derivatives as Novel Muscarinic Receptor Antagonists," J. Med Chem., 2005, 48, pp. 6597-6606.
Van Noord, J.A., "Comparison of tiotropium once Daily, Formoterol Twice Daily and Both Combined Once Daily in Patients with COPD," European Respiratory Journal, vol. 26, No. 2, pp. 214-222, 2005.
Bateman, E.D., "Pharmacodynamics of GSK961081, a bi-functional molecule, in patients with COPD," Pulmonary Pharmacology & Therapeutics, vol. 26, pp. 581-587 (2013).
Hughes, A.D. et al., "Multivalent Dual Pharmacology Muscarinic Antagonist and β2 Agonist (MABA) Molecules for the Treatment of COPD, Progress in Medicinal Chemistry," vol. 51, pp. 71-96 (2012).
Hughes, A.D. "Discovery of Muscarinic Acetylcholine Receptor Antagonist and Beta-2 Adrenoceptor Agonist (MABA) Dual Pharmacology Molecules,"Respiratory Drug Delivery Europe, pp. 47-58 (2013).
McNamara, A., et al., Preclinical Efficacy of THRX-200495, a Dual Pharmacology Mascarinic Receptor Antagonist and β2-Adrenoceptor Agonist (MABA), Pulmonary Pharmacology & Therapeutics, xxx pp. 1-7 (2012). Article in press.
Norman, P., "Evaluation of WO-2012085582 and WO-2012085583 two identified MABAs: backups to AZD-21157?" Expert Opin, Ther. Patents, 22(11), pp. 1377-1383 (2012).
Norman, P., "Novel dihydroquinoline-based MABAs, clues to the identity of LAS-190792: evaluation of WO20111411802," Expert Opin. Ther. Patents, 22:2, pp. 186-192 (2012).
Norris, V. et al., "Bronchodilation and Safety of Supratherapeutic Doses of Salbutamol or Ipratroplum Bromide Added to Single Dose GSK961081 in Patients with Moderate to Severe COPD," Pulmonary Pharmacology and Therapeutics, vol. 26, pp. 574-580 (2013).
Welders, Pascal L.M.L. et. al., "A New Class of Bronchodilator Improves Lung Function in COPD: a trial with GSK961081" Eur Respir J. 42: pp. 972-981 (2013).
Banerjee, R., et al., "Synthon Robustness in Saccharinate Salts of Some Substituted Pyridines," CrystEngComm, 8: pp. 680-685 (2006).
Bastin, R.J., et. al., "Salt Selection and Optimisation Procedures for Pharmaceutical New Chemical Entities,"Org. Process Res Dev, 4, pp. 427-435 (2000).
Chung, K.F., "p38 Mitogen-Activated Protein Kinase Pathways in Asthma and COPD," Chest, 139(6), pp. 1470-1479 (2011).

(56) References Cited

OTHER PUBLICATIONS

Miller-Larsson, A., "Advances in Asthma and COPD Treatment: Combination Therapy with Inhaled Corticosteroids and Long-Actino β2 Agonists," Curr Pharm Des, 12(25): pp, 3261-3279 (2006).
Rogers, D.F., "Tachykinin Receptor Antagonists for Asthma and COPD," Exert Opin Ther Patents, 11(7): pp. 1097-1121 (2001).
Shan, W. et al., "Dual β2-adrenoceptor Agonists-PDE4 inhibitors for the Treatment of Asthma and COPD," Bioorg Med Chem Lett, 22: pp. 1523-1526 (2012).
Thorsson, L., "Factors guiding the choice of delivery device for inhaled corticosteroids in the long-term management of stable of stable asthma and COPD: Focus on budesonide," Respir Med, 99: pp. 836-849 (2005).
Restriction Requirement dated Feb. 20, 2015, in U.S. Appl. No. 13/697,060.
Restriction Requirement dated Feb. 18, 2015, in U.S. Appl. No. 14/357,400.
Office Action dated Feb. 3, 2015, U.S. Appl. No. 14/357,344.
Office Action dated Jun. 2, 2016, U.S. Appl. No. 14/357,344.
Notice of Allowance dated Sep. 2, 2015, in U.S. Appl. No. 14/357,344.
U.S. Appl. No. 14/906,957, filed Jan. 22, 2016.
U.S. Appl. No. 14/906,991, filed Jan. 22, 2016.
U.S. Appl. No. 15/068,926, filed Mar. 14, 2016.
Requirement for Restriction/Election dated Feb. 11, 2016, for U.S. Appl. No. 14/770,200.
Requirement for Restriction/Election dated Mar. 21, 2016, for U.S. Appl. No. 14/956,767.
Notice of Allowance dated Dec. 15, 2015, in U.S. Appl. No. 13/697,060.
Non-Final Office Action dated Aug. 4, 2015, for U.S. Appl. No. 13/697,060.
Non-Final Office Action dated Mar. 8, 2016, for U.S. Appl. No. 14/956,636.
Non-Final Office Action dated May 5, 2016, for U.S. Appl. No. 14/770,206.
Non-Final Office Action dated Jun. 10, 2016, for U.S. Appl. No. 14/770,200.
Non-Final Office Action dated Jul. 8, 2016, for U.S. Appl. No. 14/956,767.
Non-Final Office Action dated Jul. 11, 2016, for U.S. Appl. No. 15/056,926.
Barge; S. et al., Pharmaceut. Sc., 1977, vol. 66(1), pp. 1-19.

* cited by examiner

CYCLOHEXYL AND QUINUCLIDINYL CARBAMATE DERIVATIVES HAVING β2 ADRENERGIC AGONIST AND M3 MUSCARINIC ANTAGONIST ACTIVITY

This application is a national stage filing under 35 U.S.C. §371 of International Application No. PCT/EP2013/076973, filed on Dec. 17, 2013, which claims priority of European Patent Application No. 12382513.5, filed on Dec. 18, 2012, and also claims priority of U.S. Provisional Patent Application No. 61/750,959 filed on Jan. 10, 2013. The contents of these applications are each incorporated herein by reference.

FIELD OF THE INVENTION

The present invention relates to novel compounds having β2 adrenergic agonist and M3 muscarinic antagonist dual activity. This invention also relates to pharmaceutical compositions containing them, process for their preparation and their use in respiratory therapies.

BACKGROUND OF THE INVENTION

Bronchodilator agents play an outstanding role in the treatment of respiratory disorders such as COPD and asthma. Beta-adrenergic agonists and cholinergic muscarinic antagonists are well established bronchodilator agents in widespread clinical use. Beta-adrenergic agonists currently used by the inhaled route include short-acting agents such as salbutamol (qid) or terbutaline (tid) and long-acting agents as salmeterol and formoterol (bid). These agents produce bronchodilation through stimulation of adrenergic receptors on airway smooth muscle, reversing the bronchoconstrictor responses to a variety of mediators, such as acetylcholine. Inhaled muscarinic antagonists currently used include the short-acting ipratropium bromide or oxitropium bromide (qid) and the long-acting tiotropium (qd). These agents produce bronchodilation by reducing vagal cholinergic tone of airway smooth muscle. In addition to improve lung function these agents also improve quality of life and reduce exacerbations. There are in the clinical literature a number of studies strongly demonstrating that the administration of a combination of a beta-2 agonist and a M3 antagonist is more efficacious for the treatment of COPD than either of the components alone (for example, van Noord, J. A., et al., Eur. Respir. J., 2005, 26, 214-222). Pharmaceutical compositions containing a combination of both types of bronchodilator agents are also known in the art for use in respiratory therapy. As an example, WO2009013244 discloses a medical composition containing salmeterol as beta-adrenergic agonist agent and tiotropium as antimuscarinic agent.

A single molecule possessing dual activity at muscarinic M3 and adrenergic β2 receptors (MABA) would be desirable both in terms of efficacy and side-effects in the treatment of COPD. It would show also a relevant advantage in terms of formulation compared with the two-component combination. It would be also easier to co-formulate with other therapeutic agents such as inhaled anti-inflammatories to create triple therapy combinations. Thus there is a need for new compounds having both beta2 receptor agonist and muscarinic activity and being suitable for the treatment of respiratory diseases, such as asthma and COPD.

SUMMARY OF THE INVENTION

The invention provides novel compounds that possess both β2 adrenergic receptor agonist and muscarinic receptor antagonist activities. Accordingly, there is provided a compound of formula (A), and pharmaceutically acceptable salts, and deuterated derivates thereof.

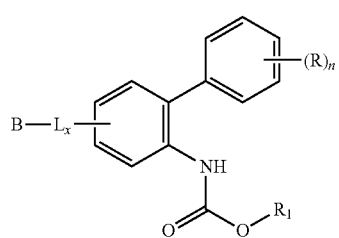

Formula (A)

wherein
R is selected from the group consisting of a hydrogen atom, a halogen atom, a hydroxyl group, a linear or branched $C_{1-4}$ alkyl group, a linear or branched $C_{1-4}$ hydroxyalkyl group and a linear or branched $C_{1-4}$ alkoxy group, n has a value of 1 or 2, $R_1$ represents a group of formula:

i)

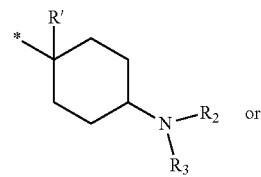

ii)

wherein:
$R_2$ and $R_3$ independently represent a hydrogen atom, a linear or branched $C_{1-6}$ alkyl group, preferably a linear or branched $C_{1-4}$ alkyl group, a ($C_{5-6}$ aryl)-($C_{1-4}$)alkyl group or a linear or branched $C_{1-4}$ alkoxy group, R' represents a hydrogen atom or a lineal or branched $C_{1-4}$ alkyl group,

* represents the point of attachment of $R_1$ to the remainder of the molecule of formula (A), $L_x$ is a suitable covalent linker, and B is a moiety having a beta2-adrenergic binding activity.

$L_x$ is a linker defined as a covalent bond between the beta2-agonist moiety B and the biphenyl moiety of formula (A).

In one embodiment of the present invention, the linker $L_x$ has the following formula:

Formula (La)

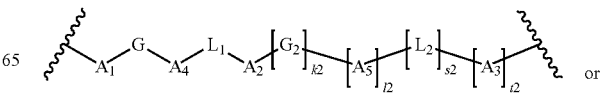

or

Formula (Lb)

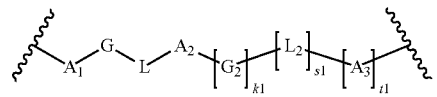

wherein k1, k2, s1, s2, l2, t1 and t2 independently have a value of 0 or 1;

A₁, A₂, A₃, A₄ and A₅ each independently are selected from the group consisting of a direct bond, a $C_{1-10}$ alkylene group, a $C_{2-10}$ alkenylene group and a $C_{2-10}$ alkynylene group, wherein said groups are optionally substituted with one or more substituents selected from a halogen atom, a hydroxy group, a linear or branched $C_{1-4}$ alkyl group, a linear or branched $C_{1-4}$ alkoxy group, a $C_{5-6}$ aryl group and a $C_{3-7}$ cycloalkyl group, L, L₁ and L₂ independently are selected from a direct bond, —O—, —NR$^c$—, —S—, —S(O)—, —SO₂—, —NR$^c$(CO)—, —(CO)NR$^c$—, —NR$^c$(CO)(CH₂)$_q$O—, —O(CH₂)$_q$(CO)NR$^c$—, —NR$^c$(CO)(CH₂)$_q$NR$^c$(CO)—, —O(CH₂)$_q$NR$^c$—, —NR$^c$(CH₂)$_q$O—, —NR$^c$(CO)NR$^d$—, —C(O)—, —C(O)O—, —OC(O)—, —S(O)₂NR$^c$—, —NR$^c$S(O)₂—, —NR$^c$S(O)₂NR$^d$—, —C(O)NR$^c$S(O)₂— and —S(O)₂NR$^c$C(O)—, wherein R$^c$ and R$^d$ are independently selected from a hydrogen atom and a linear or branched $C_{1-4}$ alkyl group and q has a value of 0, 1, 2, 3 or 4.

G and G₂ independently are selected from the group consisting of a direct bond, a $C_{3-10}$ mono- or bicyclic cycloalkyl group, a $C_5$-$C_{14}$ mono- or bicyclic aryl group, a 3 to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system comprising two monocyclic ring systems which are linked between each other by a covalent bond or by a —O— or —NH— group, wherein said monocyclic ring systems are independently selected from a $C_{3-8}$ cycloalkyl group, a $C_{5-6}$ aryl group, a 3- to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy group, a cyano group, a nitro group, a hydroxy group, an oxo group, a trifluoromethyl group and a trifluoromethoxy group.

In a preferred embodiment, all of k1, k2, s1, s2, l2, t1 and t2 have a value of 0

In a still preferred embodiment the linker L has the following formula (Lb1):

Formula (Lb1)

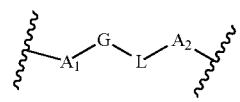

wherein A₁, A₂, L₁ and G are as defined above.

In a preferred embodiment, compounds of the present invention have the following formula (B):

Formula(B)

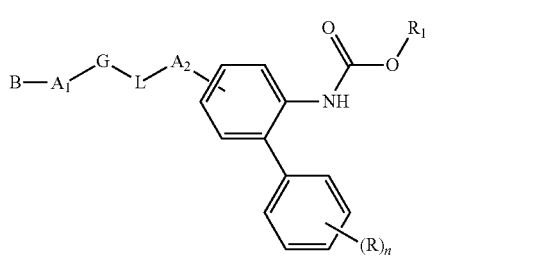

Wherein A₁, A₂, B, L, G, n, R and R₁ are as defined above.

The invention also provides synthetic processes and intermediates described herein, which are useful for preparing compounds of the invention.

The invention further provides a pharmaceutical composition comprising at least a compound of the invention and a pharmaceutically-acceptable carrier.

The invention also provides a compound of the invention as described herein for use in the treatment of human or animal body by therapy.

The invention is also directed to the compounds as described herein, for use in the treatment of a pathological condition or disease associated with dual β2 adrenergic receptor and muscarinic receptor activities in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention also provides the use of the compounds of the invention as described herein, for the manufacture of a medicament for the treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention is also directed to a method of treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease, comprising administering a therapeutically effective amount of the compounds of the invention or a pharmaceutical composition of the invention to a subject in need of such treatment.

The invention also provides a combination product comprising (i) at least a compound of the invention as described herein; and (ii) one or more active ingredients selected from the group consisting of a corticosteroid and/or a PDE4 inhibitor, for simultaneous, separate or sequential use in the treatment of the human or animal body.

DETAILED DESCRIPTION OF THE INVENTION

When describing the compounds, compositions and methods of the invention, the following terms have the following meanings, unless otherwise indicated.

As used herein the term $C_{1-6}$ alkyl embraces linear or branched radicals having 1 to 6, preferably 1 to 4 carbon atoms. Examples include methyl, ethyl, n-propyl, i-propyl, n-butyl, sec-butyl, t-butyl, n-pentyl and n-hexyl.

As used herein, the term $C_1$-$C_{10}$ alkylene embraces divalent alkyl moieties typically having from 1 to 10 carbon atoms, preferably from 1 to 6 carbon atoms, more preferably from 1 to 4 carbons atoms. Examples of $C_1$-$C_{10}$ alkylene radicals include methylene, ethylene, propylene, butylene, pentylene and hexylene radicals.

As used herein, the term $C_2$-$C_{10}$ alkenylene embraces divalent alkenyl moieties typically having from 2 to 10 carbon atoms, preferably from 2 to 6 carbon atoms, more preferably from 2 to 4 carbons atoms. Examples of $C_2$-$C_{10}$ alkenylene radicals include vinylene, propenylene, butenylene, pentenylene, hexenylene, heptenylene, octenylenyl radicals.

As used herein, the term $C_2$-$C_{10}$ alkynylene embraces divalent alkynyl moieties having 2 to 10 carbon atoms, preferably from 2 to 6 carbon atoms, more preferably from 2 to 4 carbons atoms. Examples include propynylene, butynylene, heptynylene, octynylene.

As used herein, the term $C_{1-4}$ alkoxy (or alkyloxy) embraces optionally substituted, linear or branched oxy-containing radicals each having alkyl portions of 1 to 4 carbon atoms. Preferred alkoxy radicals include methoxy, ethoxy, n-propoxy, i-propoxy, n-butoxy, sec-butoxy and t-butoxy.

As used herein, the term $C_{4-6}$ cycloalkyl group embraces saturated carbocyclic radicals monocyclic or polycyclic ring having from 4 to 6 carbon atoms, preferably from 3 to 5 carbon atoms. Examples include cyclopropyl, cyclobutyl, cyclopentyl and cyclohexyl. It is preferably cyclopropyl, cyclobutyl and cyclopentyl.

As used herein, the term $C_5$-$C_{14}$ aryl radical embraces typically a $C_5$-$C_{14}$, preferably a $C_6$-$C_{14}$, more preferably a $C_6$-$C_{10}$ monocyclic or polycyclic aryl radical. Examples of aryl radicals include phenyl, naphthyl, naphthalenyl, anthranyl and phenanthryl.

As used herein, the term 5- to 14-membered heteroaryl radical embraces typically a 5- to 14-membered ring system comprising at least one heteroaromatic ring and containing at least one heteroatom selected from O, S and N. A 5- to 14-membered heteroaryl radical may be a single ring or two or more fused rings wherein at least one ring contains a heteroatom.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl and the various pyrrolopyridyl radicals.

As used herein, the term 3- to 14-membered heterocyclyl radical embraces typically a non-aromatic, saturated or unsaturated $C_3$-$C_{14}$ carbocyclic ring system in which one or more, for example 1, 2, 3 or 4 of the carbon atoms preferably 1 or 2 of the carbon atoms are replaced by a heteroatom selected from N, O and S. A heterocyclic radical may be a single ring or two or more fused rings wherein at least one ring contains a heteroatom, and may have one or more double bonds Examples of 3 to 14-membered heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1(3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiephanyl, azepanyl, 1,4-dioxepanyl, 1,4-oxathiepanyl, 1,4-oxaazepanyl, 1,4-dithiepanyl, 1,4-thiezepanyl, 1,4-diazepanyl, tropanyl, (1S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

As used herein, the term halogen atom embraces chlorine, fluorine, bromine or iodine atoms typically a fluorine, chlorine or bromine atom. The term halo when used as a prefix has the same meaning.

Also included within the scope of the invention are the isomers, polymorphs, pharmaceutically acceptable salts, N-oxides, isotopes, solvates and prodrugs of the compounds of formula (I). Any reference to a compound of formula (I) throughout the present specification includes a reference to any isomer, polymorph, pharmaceutically acceptable salt, N-oxide, isotope, solvate or prodrug of such compound of formula (I).

Isomers

Compounds containing one or more chiral centre may be used in enantiomerically or diastereoisomerically pure form, in the form of racemic mixtures and in the form of mixtures enriched in one or more stereoisomer. The compounds of the present invention as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomehc mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

The compounds of Formula (I) may exhibit the phenomena of tautomerism and structural isomerism. Tautomers exist as mixtures of a tautomeric set in solution. In solid form, usually one tautomer predominates. Even though one tautomer may be described, the present invention includes all tautomers of the compounds of Formula (I).

Polymorphs

The compounds of the present invention may exist in different physical forms, i.e. amorphous and crystalline forms.

Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of the present invention, including all polymorphic forms ("polymorphs") thereof, are included within the scope of the invention.

Salts

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

N-Oxides

As used herein, an N-oxide is formed from the tertiary basic amines or imines present in the molecule, using a convenient oxidising agent.

Isotopes

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2H$) is present at a natural abundance of 0.015 molar %.

Solvates

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

Prodrugs

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in Design of Prodrugs by H. Bundgaard (Elsevier, 1985).

Typically B is a moiety having a beta2-adrenergic binding activity such that the $IC_{50}$ of the compound is 1 mM or less, preferably 100 μM or less, more preferably 10 μM or less, more preferably 1 μM or less, more preferably 500 nM or less, most preferably 250 nM or less, as measured in a beta2-adrenergic binding assay.

Typically said beta2-adrenergic binding assay comprises:
a) providing a membrane suspension comprising Sf9 cells in an assay buffer
b) incubating with 3H-CGP12177 in plates previously treated with assay buffer containing a coating agent
c) measuring binding of test compound in the presence of propanolol
d) maintaining incubation
e) terminating the binding reactions
f) determining the affinity of the test compound for the receptor by repeating steps a) to e) using multiple different test compound concentrations.
g) calculating an $IC_{50}$ using the four parameters-log equation.

Typically B represents a group of formula (IB):

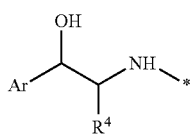

Formula (IB)

wherein:
$R^4$ is selected from the group consisting of a hydrogen atom, a linear or branched $C_{1-4}$ alkyl group and a linear or branched $C_{1-4}$ alkoxy group,
Ar is selected from the group consisting of a $C_{3-10}$ saturated or unsaturated, mono- or bicyclic cycloalkyl group, a $C_5$-$C_{14}$ mono- or bicyclic aryl group, a 3 to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and wherein the cyclic groups independently are optionally substituted with one or more substituents selected from a halogen atom, a cyano group, a nitro group, an oxo group, a carboxy group, a $C_{1-4}$ alkyl group, a $C_{1-4}$ alkoxy group, —$CF_3$, —$OCF_3$, —$NR^eR^f$, —$(CH_2)_p$—OH, —$NR^e(CO)R^f$, —$NR^e$—$SO_2$—$R^g$, —$SO_2NR^eR^f$, —$OC(O)R^h$ and —$NR^e(CH_2)_{(0-2)}$—$R^i$, wherein p has a value of 0, 1 or 2 and wherein:
$R^e$ and $R^f$ independently represent a hydrogen atom or a linear or branched $C_{1-4}$ alkyl group,
$R^g$ is selected from the group consisting of a linear or branched $C_{1-4}$ alkyl group, a $C_{5-6}$ aryl group, a saturated or unsaturated $C_{3-8}$ cycloalkyl, wherein the cyclic groups independently are optionally substituted with one or more substituents selected from a halogen atom, a $C_{1-4}$ alkyl group and a $C_{1-4}$ alkoxy group,
$R^h$ is selected from a hydrogen atom, —$NR^eR^f$ and a $C_{5-6}$ aryl group which is optionally substituted with one or more substituents selected from a $C_{1-4}$ alkyl group and a $C_{1-4}$ alkoxy group,
$R^i$ is selected from the group consisting of a $C_{5-6}$ aryl group, a $C_{3-8}$ cycloalkyl group and a 3 to 8 membered saturated or unsaturated heterocyclyl group, which groups independently are optionally substituted with one or more substituents selected from a halogen atom, a $C_{1-4}$ alkyl group and a $C_{1-4}$ alkoxy group.

Preferably, Ar represents a group of formula:

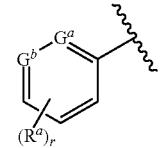

(a)

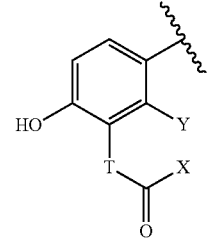

(b)

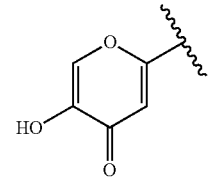

(c)

(d)

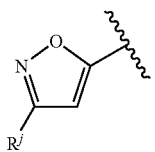

wherein
- $G^a$ and $G^b$ independently are selected from a nitrogen atom and a carbon atom,
- r has a value of 0, 1, 2 or 3 and
- $R^a$ is selected from the group consisting of a halogen atom, an amino group, a cyano group, a nitro group, an oxo group, a carboxy group, a $C_{1-4}$ alkyl group, a $C_{1-4}$ alkoxy group, —$CF_3$, —$OCF_3$, —$(CH_2)_p$—OH, —NH(CO)H, —NH—$SO_2$—$R^g$, —$SO_2NH_2$, —OC(O)H, —O(CO)-(4-methyl)phenyl, —O(CO)—N(CH$_3$)$_2$, —OC(O)NH$_2$ and —NH(CH$_2$)$_{(1-2)}$—$R^i$, group, wherein p is as defined above and $R^g$ and $R^i$ independently are selected from a phenyl group optionally substituted with a one substituent selected from a methyl group or a methoxy group,
- $R^j$ represents a halogen atom,
- T is selected from the group consisting of —CH$_2$— and —NH—,
- Both X and Y represent a hydrogen atom or X together with Y form the group —CH$_2$—CH$_2$—, —CH═CH—, —CH$_2$—O— or —S—, wherein in the case of —CH$_2$—O— the methylene group is bound to the carbonyl group holding X and the oxygen atom is bound to the carbon atom in the phenyl ring holding Y, Preferably, Ar represents a compound of formula (a) or (b) wherein:

(a)

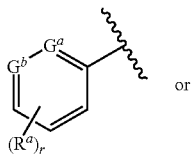

or (b)

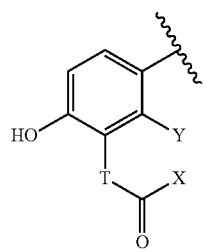

Both $G^a$ and $G^b$ represent a carbon atom,
$R^a$ is selected from the group consisting of halogen atom, amino group, cyano group, nitro group, —(CH$_2$)$_p$—OH, —NH(CO)H, —NH—SO$_2$—CH$_3$, —SO$_2$NH$_2$, —OC(O)H, —O(CO)-(4-methyl)phenyl, —O(CO)—N(CH$_3$)$_2$, —OC(O)NH$_2$ and —CF$_3$ group, wherein p has a value of 0, 1 or 2,
T represents —NH— group,
Both X and Y represent a hydrogen atom or X together with Y form the group —CH═CH—, —CH$_2$—CH$_2$—, —CH$_2$—O— or —S—, wherein in the case of —CH$_2$—O— the methylene group is bound to the carbon atom in the amido substituent holding X and the oxygen atom is bound to the carbon atom in the phenyl ring holding Y In a still preferred embodiment Ar is selected from the group consisting of 3-bromoisoxazol-5-yl, 3,4-dihydroxyphenyl, 4-hydroxy-3-(methylsulfonamido)phenyl, 3,4-bis(4-methylbenzoyloxy)phenyl, 3,5-bis(dimethylcarbamoyloxy)phenyl, (5-hydroxy-6-hydroxymethyl)pyrid-2-yl, (4-amino-3,5-dichloro)phenyl, 4-hydroxyphenyl, 4-hydroxy-3-(2-hydroxyethyl)phenyl, 4-hydroxy-3-(hydroxymethyl)phenyl, [4-amino-3-chloro-5-(trifluoromethyl)]phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, 5-hydroxy-3-oxo-3,4-dihydro-2H-benzo[b][1,4]oxazin-8-yl, 4-hydroxy-2-oxo-2,3-dihydrobenzo[d]thiazol-7-yl. Preferably Ar is selected from the group consisting of 4-hydroxy-3-(hydroxymethyl)phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl and 5-hydroxy-3-oxo-3,4-dihydro-2H-benzo[b][1,4]oxazin-8-yl.

In another embodiment Ar represents a compound of formula (b) wherein X and Y are as defined above and T represents a —NH— group.

Still in another embodiment of the present invention, compounds of the present invention have the following formula (I):

Formula (I)

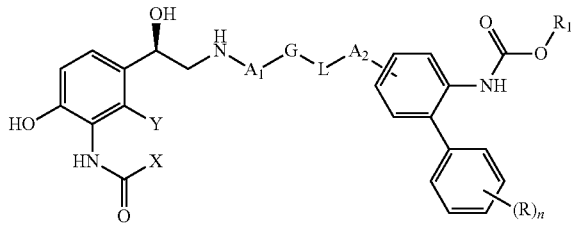

Wherein:
- R is selected from the group consisting of a hydrogen atom, a halogen atom, a hydroxyl group, a linear or branched $C_{1-4}$ alkyl group, a linear or branched $C_{1-4}$ hydroxyalkyl group and a linear or branched $C_{1-4}$ alkoxy group,
- n has a value of 1 or 2,
- X and Y are both hydrogen atoms or X together with Y form the group —CH═CH—, —CH$_2$—O— or —S—, wherein in the case of —CH$_2$—O— the methylene group is bound to the carbon atom in the amido substituent holding X and the oxygen atom is bound to the carbon atom in the phenyl ring holding Y,
- $A_1$ and $A_2$ independently are selected from the group consisting of a direct bond, a $C_{1-10}$ alkylene group, a $C_{2-10}$ alkenylene group and a $C_{2-10}$ alkynylene group, wherein said groups are optionally substituted with one or more substituents selected from a halogen atom, a hydroxy group, a linear or branched $C_{1-4}$ alkyl group, a linear or branched a $C_{1-4}$ alkoxy group, a $C_{5-6}$ aryl group and a $C_{3-7}$ cycloalkyl group,
- G is selected from the group consisting of a direct bond, a $C_{3-10}$ mono- or bicyclic cycloalkyl group, a $C_{5-14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system consisting of two monocyclic ring systems which are linked between each other by a covalent bond or by a —O— group, wherein said monocyclic ring systems are independently selected from a $C_{3-8}$ cycloalkyl group, a $C_{5-6}$ aryl group, a 3- to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy, group, a cyano group, a nitro group, a hydroxy group, an oxo group, a trifluoromethyl group and a trifluoromethoxy group.

L is selected from a direct bond, —O—, —$NR^c$—, —S—, —S(O)—, —$SO_2$—, —$NR^c$(CO)—, —(CO)$NR^c$—, —$NR^c$(CO)$(CH_2)_q$O—, —O$(CH_2)_q$(CO)$NR^c$—, —$NR^c$(CO)$(CH_2)_q$$NR^c$(CO)—, —O$(CH_2)_q$$NR^c$—, —$NR^c$$(CH_2)_q$O—, —$NR^c$(CO)$NR^d$—, —C(O)—, —C(O)O—, —OC(O)—, —$S(O)_2$$NR^c$—, —$NR^c$$S(O)_2$—, —$NR^c$$S(O)_2$$NR^d$—, —C(O)$NR^c$$S(O)_2$— and —$S(O)_2$$NR^c$C(O)—, wherein $R^c$ and $R^d$ are independently selected from a hydrogen atom and a linear or branched $C_{1-4}$ alkyl group and q has a value of 0, 1, 2, 3 or 4.

$R_1$ represents a group of formula:

i)

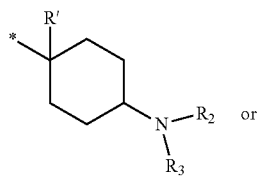

ii)

wherein $R_2$ and $R_3$ independently represent a hydrogen atom, a linear or branched $C_{1-4}$ alkyl group or a ($C_{5-6}$ aryl)-$(C_{1-4})$alkyl group, and R' represents a hydrogen atom or a linear or branched $C_{1-4}$ alkyl group.

Typically, $A_1$ and $A_2$ independently are selected from the group consisting of $C_{1-6}$ alkylene group, $C_{1-6}$ alkenylene group and $C_{1-6}$ alkynylene group, wherein said groups are optionally substituted with one or more substituents selected from a halogen atom, a hydroxy group, a $C_{1-2}$ alkyl group, a $C_{1-2}$ alkoxy group, a $C_{5-6}$ aryl group and a $C_{3-6}$ cycloalkyl group.

Preferably, $A_1$ and $A_2$ independently represent a $C_{1-6}$ alkylene group optionally substituted with one or more substituents selected from a $C_{1-2}$ alkyl group, a $C_{1-2}$ alkoxy group and a phenyl group, preferably $A_1$ and $A_2$ independently represent a $C_{1-4}$ alkylene group optionally substituted with one or two substituents selected from a methyl group and a methoxy group, more preferably substituted with one or two methyl groups.

Typically, X together with Y form the group —CH=CH— or —$CH_2$—O—. Preferably, X together with Y form the group —CH=CH—.

Typically, L is selected from the group consisting a direct bond, —O—, —$NR^c$—, —S—, —S(O)—, —$SO_2$—, —$NR^c$(CO)—, —(CO)$NR^c$—, —$NR^c$(CO)$(CH_2)_q$O—, —O$(CH_2)_q$(CO)$NR^c$—, —$NR^c$(CO)$(CH_2)_q$$NR^c$(CO)—, —O$(CH_2)_q$$NR^c$—, —$NR^c$(CO)$NR^d$—, —C(O)—, —C(O)O—, —OC(O)—, —$S(O)_2$$NR^c$—, —$NR^c$$S(O)_2$—, —$NR^c$$S(O)_2$$NR^d$—, —C(O)$NR^c$$S(O)_2$— and —$S(O)_2$$NR^c$C(O)—, wherein $R^c$ and $R^d$ are independently selected from a hydrogen atom and a linear or branched $C_{1-4}$ alkyl group and q has a value of 0, 1, 2, 3 or 4.

Preferably, L is selected from the group consisting of direct bond, —O—, —$NR^c$—, —$NR^c$(CO)—, —(CO)$NR^c$—, —$NR^c$(CO)$(CH_2)_q$O—, —O$(CH_2)_q$(CO)$NR^c$—, —$NR^c$(CO)$(CH_2)_q$$NR^c$(CO)—, —O$(CH_2)_q$$NR^c$—, —$NR^c$$(CH_2)_q$O—, —$NR^c$(CO)$NR^d$—, —C(O)—, —C(O)O—, —OC(O)— wherein $R^c$ and $R^d$ independently are selected from a hydrogen atom and a methyl group.

Preferably L is selected from a direct bond, —O—, —$NR^c$(CO)—, —(CO)$NR^c$—, —$NR^c$(CO)$(CH_2)_q$O—, —O$(CH_2)_q$(CO)$NR^c$— and —C(O)—, wherein $R^c$ and $R^d$ independently are selected from a hydrogen atom and a methyl group. More preferably L is selected from a direct bond, —$NR^c$(CO)—, —(CO)$NR^c$—, —O$(CH_2)_q$(CO)$NR^c$— and —C(O)—, being most preferably a direct bond, —$NR^c$(CO)— and —(CO)$NR^c$—, wherein $R^c$ represents a hydrogen atom or a methyl group.

Typically G is selected from the group consisting of a direct bond, a $C_{3-7}$ cycloalkyl group, a $C_{5-14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system comprising two monocyclic ring systems which are linked between each other by a covalent bond or by a —O— group, wherein said monocyclic ring system is independently selected from the group consisting of a $C_{3-8}$ cycloalkyl group and a $C_{5-6}$ aryl group, wherein the cyclic groups independently are optionally substituted with one or more substituents selected from a halogen atom, a $C_{1-4}$ alkyl group, a $C_{1-4}$ alkoxy group, a carboxy, group, a cyano group, a nitro group, a hydroxy group, an oxo group, a trifluoromethyl group and a trifluoromethoxy group.

Preferably G is selected from the group consisting of a direct bond, a $C_{3-7}$ cycloalkyl group, a $C_5$-$C_6$ aryl group, a 8- to 10-membered saturated or unsaturated bicyclic heterocyclyl group having one or more heteroatoms selected from N, S and O, a 8- to 10-membered bicyclic heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a cyano group, a nitro group, a hydroxy group and an oxo group.

More preferably G is selected from the group consisting of a $C_{3-7}$, cycloalkyl group, a $C_5$-$C_6$ aryl group, or a group of formula

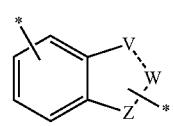

Formula (Iwa)

wherein

V, W and Z are independently selected from a —N—, —NH, —C—, —CH—, —S—, —O— and —C(O)—, wherein the cyclic groups independently are optionally substituted with one or more substituents selected from a halogen atom, a $C_{1-4}$ alkyl group and a $C_{1-4}$ alkoxy group.

The dashed lines in formula (Iwa) represents a single bond or double bond depending on the nature of V, W and Z.

Typically W represents a —N—, —NH— or —C(O)— group, preferably W represents a —C(O)— group.

Typically, V represents a —N—, —NH—, —S— or —O— group, preferably V is a —N—, —NH— or —O— group.

In a preferred embodiment V represents a —N—, —NH—, or —O— group while W represents a —C(O)— group and Z is a —N— or —NH— group.

In a still preferred embodiment, G represents a phenylene group or a cylohexyl group or a group of formula

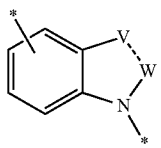

Formula (Iwb)

Wherein V represents a —N—, —NH— or —O— group and W represents a —C(O)— group, and wherein the cyclic groups are independently optionally substituted with one or two substituents selected from a chlorine atom, methyl group and methoxy group.

Typically, $R_1$ represents a group of formula:

i)

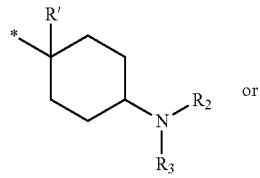

ii)

wherein R', $R_2$ and $R_3$ independently represent a hydrogen atom or a $C_{1-2}$ alkyl group.

Preferably $R_1$ represents a group of formula:

i)

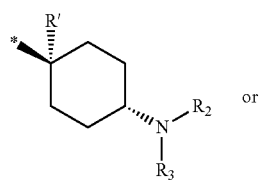

or ii)

wherein R', $R_2$ and $R_3$ independently represent a hydrogen atom or a $C_{1-2}$ alkyl group, preferably R', $R_2$ and $R_3$ independently represent a hydrogen atom or a methyl group, more preferably both $R_2$ and $R_3$ represent a hydrogen atom and R' represents a hydrogen atom or a methyl group.

More preferably, when $R_1$ represents the azabicyclo group of formula ii), the asymmetric carbon atom of said azabicyclo group to which the rest of the molecule is bounded, has the (R) configuration.

Typically R is selected from the group consisting of a hydrogen atom, a halogen atom or a hydroxy group, preferably R represents a hydrogen atom or a hydroxy group, more preferably R represents a hydrogen.

Typically n has a value of 1 or 2, preferably 1.

In one embodiment of the present invention $A_1$ and $A_2$ independently represent a direct bond, a $C_{1-6}$ alkylene group optionally substituted with a methyl group, X together with Y form the group —CH=CH—, L is selected from the group consisting of a direct bond, —O—, —NR$^c$(CO)—, —NR$^c$(CO)O—, —O(CO)NR$^c$—, —NR$^c$(CO)—(CH$_2$)$_4$NR$^c$(CO)—, —NR$^c$(CO)—, and —(CO)NR$^c$—, wherein R$^c$ represents a hydrogen atom or a methyl group, G represents a phenylene group or a cylohexyl group or a group of formula:

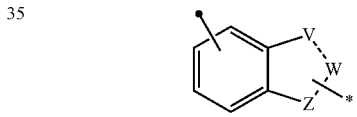

Formula (Iwa)

Wherein V and Z independently are selected from the group consisting of —N—, —NH—, —O— and —S—, and W represents a —N—, —NH—, —O—, or a —C(O)— group, and wherein the cyclic groups are independently optionally substituted with one or two substituents selected from a chlorine atom, methyl group and methoxy group, $R^1$ represents a group of formula:

i)

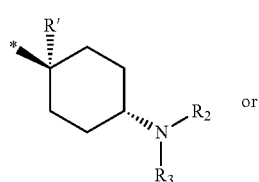

or ii)

wherein both $R_2$ and $R_3$ are independently selected from a hydrogen atom, a methyl group and a propyl group substituted with a phenyl group, R' represents a hydrogen atom or a methyl group, R represents a hydrogen atom and n has a value of 1.

In a still preferred embodiment, $A_1$ and $A_2$ independently represent a $C_{1-4}$ alkylene group optionally substituted with one or two methyl groups, X together with Y form the group —CH=CH—, L is selected from the group consisting of a direct bond, —$NR^c(CO)$— and —$(CO)NR^c$—, wherein $R^c$ represents a hydrogen atom or a methyl group, G represents a phenylene group or a cylohexyl group or a group of formula

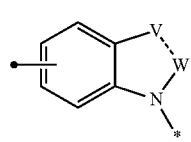

Formula (Iwb)

Wherein V represents a —N—, —NH— or —O— group and W represents a —C(O)— group, and wherein the cyclic groups are independently optionally substituted with one or two substituents selected from a chlorine atom, methyl group and methoxy group, $R^1$ represents a group of formula:

i)

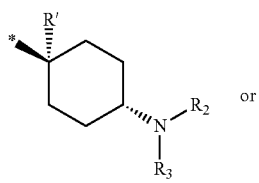

or ii)

wherein preferably both $R_2$ and $R_3$ represent a hydrogen atom, R' represents a hydrogen atom or a methyl group, R represents a hydrogen atom and n has a value of 1.

In a still preferred embodiment, the present invention provides compounds of formula (I), wherein R represents a hydrogen atom and n has a value of 1, $A_1$ and $A_2$ independently represent a $C_{1-5}$ alkylene group optionally substituted with one or two methyl groups, X together with Y form the group —CH=CH—, L is selected from the group consisting of a direct bond, —O—, —$NR^c(CO)O$—, —$NR^c(CO)$—, —$(CO)NR^c$—, —$O(CH_2)(CO)NR^c$—, wherein $R^c$ represents a hydrogen atom or a methyl group, G represents a phenylene group or a pyridyl group or a group of formula Formula (Iwc)

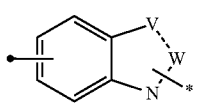

Wherein V represents a —CH—, —N—, —NH—, —S—, or —O— group and W represents a —CH—, —N=, —NH—, —C(O)— group, and wherein the cyclic groups are independently optionally substituted with one or two substituents selected from a chlorine atom, methyl group and methoxy group, $R^1$ represents a group of formula:

ii)

More preferably, in compounds of formula (I), R represents a hydrogen atom and n has a value of 1, $A_1$ and $A_2$ independently represent a $C_{1-4}$ alkylene group optionally substituted with one or two methyl groups, X together with Y form the group —CH=CH—, L is selected from the group consisting of a direct bond, —$NR^c(CO)$— and —$(CO)NR^c$—, wherein $R^c$ represents a hydrogen atom or a methyl group, G represents a phenylene group or a group of formula Formula (Iwb)

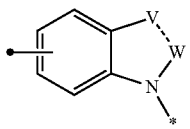

Wherein V represents a —N—, —NH—, or —O— group and W represents a —C(O)— group, and wherein the cyclic groups are independently optionally substituted with one or two substituents selected from a chlorine atom, methyl group and methoxy group, $R^1$ represents a group of formula:

ii)

wherein preferably the moiety attached to $R^1$ is in the 3- or the 4-position with respect to the quinuclidinyl radical.

In one embodiment, the present invention provides compounds of formula (I)

Formula (I)

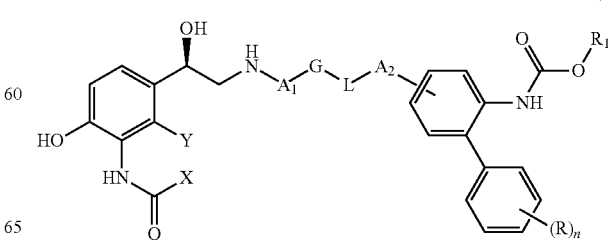

Wherein, R represents a hydrogen atom and n has a value of 1, $A_1$ and $A_2$ independently represent a direct bond or a $C_{1-6}$ alkylene group optionally substituted with a methyl group, X together with Y form the group —CH═CH— —CH$_2$—CH$_2$— or —CH$_2$—O—, L is selected from the group consisting of a direct bond, —O—, —NR$^c$(CO)O—, —O(CH$_2$)(CO)NR$^c$—, —NR$^c$(CO)—(CH$_2$)$_4$NR$^c$(CO)—, —(CH$_2$)$_{(0-1)}$NR$^c$(CO)—, —(CO)NR$^c$— and —NH(CO)NH—, wherein R$^c$ represents a hydrogen atom or a methyl group, G represents a direct bond, a phenylene group, a pyridyl group, a cyclobutyl group, a cylohexyl group or a group of formula:

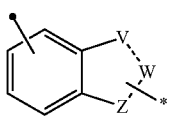

Formula (Iwa)

Wherein V and Z independently are selected from the group consisting of —N—, —NH—, —C—, —O— and —S—, and W represents a —N—, —NH—, —C—, or a —C(O)— group, and wherein the phenylene group, pyridyl group, cyclobutyl group, cylohexyl group and the group of formula (Iwa) are independently optionally substituted with one or two substituents selected from a chlorine atom, methyl group and methoxy group, $R^1$ represents a group of formula:

i)

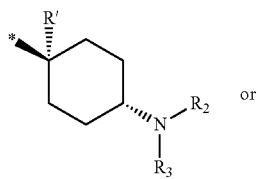 or ii)

wherein $R_2$ and $R_3$ are independently selected from a hydrogen atom, a methyl group, a hexyl group and a propyl group substituted with a phenyl group and R' represents a hydrogen atom or a methyl group.

Particular individual compounds of the invention include:
(3R)-1-azabicyclo[2.2.2]oct-3-yl(4-{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate,
(3R)-1-azabicyclo[2.2.2]oct-3-yl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate trans-4-(methylamino)cyclohexyl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate,
(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate,
(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}biphenyl-2-yl)carbamate,
(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-indol-1-yl]propyl}biphenyl-2-yl)carbamate,
(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate,
trans-4-aminocyclohexyl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate,
(3R)-1-azabicyclo[2.2.2]oct-3-yl(4-{4-[3-({[(2R)-2-hydroxy-2-(8-hydroxy-2-oxo-1,2-dihydroquinolin-5-yl)ethyl]amino}methyl)phenoxy]butyl}biphenyl-2-yl)carbamate,
(3R)-1-azabicyclo[2.2.2]oct-3-yl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate,
trans-4-aminocyclohexyl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate,
(3R)-1-azabicyclo[2.2.2]oct-3-yl(4-{4-[5-({[(2R)-2-hydroxy-2-(8-hydroxy-2-oxo-1,2,3,4-tetrahydroquinolin-5-yl)ethyl]amino}methyl)-1,3-benzoxazol-2-yl]butyl}biphenyl-2-yl)carbamate,
(3R)-1-azabicyclo[2.2.2]oct-3-yl(4-{3-[3-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate,
(3R)-1-azabicyclo[2.2.2]oct-3-yl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]-propyl}biphenyl-2-yl)carbamate,
(3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-1H-indol-1-yl]butyl}biphenyl-2-yl)carbamate,
(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzothiazol-3(2H)-yl]butyl}biphenyl-2-yl)carbamate,
(3R)-1-azabicyclo[2.2.2]oct-3-yl(4-{3-[4-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate,
(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-1,3-benzoxazol-2-yl]butyl}biphenyl-2-yl)carbamate,
(3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-2H-1,2,3-benzotriazol-2-yl]butyl}biphenyl-2-yl)carbamate,
trans-4-aminocyclohexyl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, (3R)-1-azabicyclo[2.2.2]oct-3-yl(5-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate,
(3R)-1-azabicyclo[2.2.2]oct-3-yl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate,
trans-4-aminocyclohexyl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate,
(3R)-1-azabicyclo[2.2.2]oct-3-yl(4-{4-[6-({[(2R)-2-hydroxy-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate,
trans-4-aminocyclohexyl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate,
trans-4-aminocyclohexyl(4-{4-[5-({[(2R)-2-hydroxy-2-(8-hydroxy-2-oxo-1,2-dihydroquinolin-5-yl)ethyl]amino}methyl)-1H-indol-1-yl]butyl}biphenyl-2-yl)carbamate,
(3R)-1-azabicyclo[2.2.2]oct-3-yl(4-{4-[6-(2-{[(2R)-2-hydroxy-2-(8-hydroxy-2-oxo-1,2-dihydroquinolin-5-yl)ethyl]amino}ethyl)-2-oxo-1,3-benzoxazol-3(2H)-yl]butyl}biphenyl-2-yl)carbamate,
trans-4-aminocyclohexyl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate,
(3R)-1-azabicyclo[2.2.2]oct-3-yl(4-{3-[6-(2-{[(2R)-2-hydroxy-2-(8-hydroxy-2-oxo-1,2-dihydroquinolin-5-yl)ethyl]amino}ethyl)-2-oxo-1,3-benzoxazol-3(2H)-yl]propyl}biphenyl-2-yl)carbamate,
(3R)-1-azabicyclo[2.2.2]oct-3-yl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate,
trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate,
trans-4-aminocyclohexyl{4-[(6-{[(2R)-2-hydroxy-2-(8-hydroxy-2-oxo-1,2-dihydroquinolin-5-yl)ethyl]amino}hexyl)oxy]biphenyl-2-yl}carbamate,
trans-4-aminocyclohexyl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate,
trans-4-aminocyclohexyl(4-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}biphenyl-2-yl)carbamate,
trans-4-aminocyclohexyl[5-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
trans-4-aminocyclohexyl[4-(5-{[4-({[(2R)-2-hydroxy-2-(8-hydroxy-2-oxo-1,2-dihydroquinolin-5-yl)ethyl]amino}methyl)phenyl]amino}-5-oxopentyl)biphenyl-2-yl]carbamate,
trans-4-aminocyclohexyl[4-(4-{[4-(2-{[(2R)-2-hydroxy-2-(8-hydroxy-2-oxo-1,2-dihydroquinolin-5-yl)ethyl]amino}ethyl)phenyl]amino}-4-oxobutyl)biphenyl-2-yl]carbamate,
trans-4-aminocyclohexyl(4-{4-[6-({[(2R)-2-hydroxy-2-(8-hydroxy-2-oxo-1,2-dihydroquinolin-5-yl)ethyl]amino}methyl)-5-methoxy-2-oxo-1,3-benzoxazol-3(2H)-yl]butyl}biphenyl-2-yl)carbamate,
trans-4-[methyl(3-phenylpropyl)amino]cyclohexyl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
trans-4-aminocyclohexyl[4-(3-{[4-({[(2R)-2-hydroxy-2-(8-hydroxy-2-oxo-1,2-dihydroquinolin-5-yl)ethyl]amino}methyl)phenyl]amino}-3-oxopropyl)biphenyl-2-yl]carbamate,
(3R)-1-azabicyclo[2.2.2]oct-3-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
trans-4-aminocyclohexyl(4-{[4-({[(2R)-2-hydroxy-2-(8-hydroxy-2-oxo-1,2-dihydroquinolin-5-yl)ethyl]amino}methyl)phenyl](methyl)amino]-4-oxobutyl}biphenyl-2-yl)carbamate,
trans-4-aminocyclohexyl[4-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)biphenyl-2-yl]carbamate,
trans-4-aminocyclohexyl[4-(4-{[4-(2-{[(2R)-2-hydroxy-2-(8-hydroxy-2-oxo-1,2-dihydroquinolin-5-yl)ethyl]amino}propyl)phenyl]amino}-4-oxobutyl)biphenyl-2-yl]carbamate,
trans-4-aminocyclohexyl(4-{4-[(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}biphenyl-2-yl)carbamate,
trans-4-aminocyclohexyl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]-propyl}biphenyl-2-yl)carbamate,
trans-4-amino-1-methylcyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)biphenyl-2-yl]carbamate,
trans-4-amino-1-methylcyclohexyl[4-(3-{[trans-4-({[(2R)-2-hydroxy-2-(8-hydroxy-2-oxo-1,2-dihydroquinolin-5-yl)ethyl]amino}methyl)cyclohexyl]amino}-3-oxopropyl)biphenyl-2-yl]carbamate,
1-azabicyclo[2.2.2]oct-4-yl[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)biphenyl-2-yl]carbamate,
trans-4-aminocyclohexyl(4-{2-[{[2-chloro-4-({[(2R)-2-hydroxy-2-(8-hydroxy-2-oxo-1,2-dihydroquinolin-5-yl)ethyl]amino}methyl)-5methoxyphenoxy]acetyl}(methyl)amino]ethyl}biphenyl-2-yl)carbamate,
trans-4-aminocyclohexyl(4-{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}biphenyl-2-yl)carbamate,
trans-4-aminocyclohexyl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate,
trans-4-aminocyclohexyl[4-(4-{[trans-3-({[(2R)-2-hydroxy-2-(8-hydroxy-2-oxo-1,2-dihydroquinolin-5-yl)ethyl]amino}methyl)cyclobutyl]amino}-4-oxobutyl)biphenyl-2-yl]carbamate, trans-4-aminocyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)biphenyl-2-yl]carbamate, trans-4-aminocyclohexyl[4-(3-{4-[4-({[(2R)-2-hydroxy-2-(8-hydroxy-2-oxo-1,2-dihydroquinolin-5-yl)ethyl]amino}methyl)phenoxy]phenyl}propyl)biphenyl-2-yl]carbamate, trans-4-aminocyclohexyl[4-(4-{[4-({[(2R)-2-hydroxy-2-(8-hydroxy-2-oxo-1,2-dihydroquinolin-5-yl)ethyl]amino}methyl)benzyl]amino}-4-oxobutyl)biphenyl-2-yl]carbamate, trans-4-aminocyclohexyl[4-(4-{[5-({[(2R)-2-hydroxy-2-(8-hydroxy-2-oxo-1,2-dihydroquinolin-5-yl)ethyl]amino}methyl)pyridin-2-yl]amino}-4-oxobutyl)biphenyl-2-yl]carbamate, trans-4-[hexyl(methyl)amino]cyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate, trans-4-aminocyclohexyl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)biphenyl-2-yl]carbamate, Trans-4-aminocyclohexyl(4-(3-(Trans-4-(((((2R)-2-hydroxy-2-(8-hydroxy-2-oxo-1,2-dihydroquinolin-5-yl)ethyl)amino)methyl)cyclohexanecarboxamido)propyl)-biphenyl-2-yl)carbamate, trans-4-aminocyclohexyl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)amino]propyl}biphenyl-2-yl)carbamate, trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate, 1-azabicyclo[2.2.2]oct-4-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl] Carbamate, trans-4-aminocyclohexyl(4-{3-[({[trans-4-({[(2R)-2-hydroxy-2-(8-hydroxy-2-oxo-1,2-dihydroquinolin-5-yl)ethyl]amino}methyl)cyclohexyl]oxy}acetyl)(methyl)amino]propyl}biphenyl-2-yl)carbamate, 1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate trans-4-aminocyclohexyl[4-{4-[5-({[(2R)-2-hydroxy-2-(8-hydroxy-2-oxo-1,2-dihydroquinolin-5-yl)ethyl]amino}methyl)-1H-benzimidazol-1-yl]butyl}biphenyl-2-yl)carbamate, trans-4-amino-1-methylcyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate, 1-azabicyclo[2.2.2]oct-4-yl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino propyl}biphenyl-2-yl)carbamate, 1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate and 1-azabicyclo[2.2.2]oct-4-yl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)biphenyl-2-yl]carbamate, and pharmaceutically acceptable salts and deuterated derivates thereof.

Of particular interest are the compounds:

(3R)-1-azabicyclo[2.2.2]oct-3-yl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate, (3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-indol-1-yl]propyl}biphenyl-2-yl)carbamate, (3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, (3R)-1-azabicyclo[2.2.2]oct-3-yl(4-{4-[3-({[(2R)-2-hydroxy-2-(8-hydroxy-2-oxo-1,2-dihydroquinolin-5-yl)ethyl]amino}methyl)phenoxy]butyl}biphenyl-2-yl)carbamate, (3R)-1-azabicyclo[2.2.2]oct-3-yl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2,3,4-tetrahydroquinolin-5-yl)ethyl]amino}methyl)-1,3-benzoxazol-2-yl]butyl}biphenyl-2-yl)carbamate, (3R)-1-azabicyclo[2.2.2]oct-3-yl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]-propyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-1H-indol-1-yl]butyl}biphenyl-2-yl)carbamate, (3R)-1-azabicyclo[2.2.2]oct-3-yl(4-{3-[4-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-2H-1,2,3-benzotriazol-2-yl]butyl}biphenyl-2-yl)carbamate, trans-4-aminocyclohexyl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, trans-4-aminocyclohexyl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate, (3R)-1-azabicyclo[2.2.2]oct-3-yl(4-{4-[6-({[(2R)-2-hydroxy-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate, (3R)-1-azabicyclo[2.2.2]oct-3-yl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate, trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate, trans-4-aminocyclohexyl(4-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}biphenyl-2-yl)carbamate,
trans-4-aminocyclohexyl(4-{4-[6-({[(2R)-2-hydroxy-2-(8-hydroxy-2-oxo-1,2-dihydroquinolin-5-yl)ethyl]amino}methyl)-5-methoxy-2-oxo-1,3-benzoxazol-3(2H)-yl]butyl}biphenyl-2-yl)carbamate,
(3R)-1-azabicyclo[2.2.2]oct-3-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
trans-4-aminocyclohexyl[4-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)biphenyl-2-yl]carbamate,
trans-4-aminocyclohexyl[4-(4-{[4-(2-{[(2R)-2-hydroxy-2-(8-hydroxy-2-oxo-1,2-dihydroquinolin-5-yl)ethyl]amino}propyl)phenyl]amino}-4-oxobutyl)biphenyl-2-yl]carbamate,
trans-4-aminocyclohexyl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]-propyl}biphenyl-2-yl)carbamate,
trans-4-aminocyclohexyl(4-{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}biphenyl-2-yl)carbamate,
trans-4-aminocyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)biphenyl-2-yl]carbamate,
trans-4-aminocyclohexyl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)biphenyl-2-yl]carbamate,
Trans-4-aminocyclohexyl(4-(3-(trans-4-((((2R)-2-hydroxy-2-(8-hydroxy-2-oxo-1,2-dihydroquinolin-5-yl)ethyl)amino)methyl)cyclohexanecarboxamido)propyl)-biphenyl-2-yl)carbamate,
trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate,
1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate,
1-azabicyclo[2.2.2]oct-4-yl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]propyl}biphenyl-2-yl)carbamate, and
1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate,
and pharmaceutically acceptable salts and deuterated derivates thereof.

The invention is also directed to a compound of the invention as described herein for use in the treatment of the human or animal body by therapy.

According to another embodiment the present invention covers pharmaceutical compositions comprising at least a compound of the invention, as hereinabove described, in admixture with pharmaceutically acceptable diluents or carriers.

In an embodiment of the present invention the pharmaceutical composition further comprises a therapeutically effective amount of one or more other therapeutic agents, in particular one or more drugs selected from the group consisting of corticosteroids, and PDE4 inhibitors.

It is also an embodiment of the present invention that the pharmaceutical composition is formulated for administration by inhalation.

The compounds of the present invention as hereinabove defined may also be combined with one or more other therapeutic agents, in particular one or more drugs selected from the group consisting of corticosteroids and PDE4 inhibitors, for simultaneous, separate or sequential use in the treatment of the human or animal body.

The invention is also directed to compounds of the present invention for use in the treatment of a pathological condition or disease associated with both β2 adrenergic receptor and muscarinic receptor activities such as a pulmonary disease. In particular the pulmonary disease is asthma or chronic obstructive pulmonary disease.

The pathological condition or disease can also be applied within the scope of the present invention to the treatment of a disease or condition selected from the group consisting of pre-term labor, glaucoma, neurological disorders, cardiac disorders, and inflammation, urological disorders such as urinary incontinence and gastrointestinal disorders such as irritable bowel syndrome or spastic colitis.

The invention is also directed to the use of compounds of the present invention for the manufacture of a medicament for the treatment of pathological condition or disease associated with one or both β2 adrenergic receptor and muscarinic receptor activities such as a pulmonary disease, in particular asthma or chronic obstructive pulmonary disease, pre-term labor, glaucoma, neurological disorders, cardiac disorders, inflammation, urological disorders and gastrointestinal disorders, preferably, asthma and chronic obstructive pulmonary disease.

The invention is also directed to a method of treating these diseases, which comprises administering a therapeutically effective amount of a pharmaceutical composition comprising a dual β2 adrenergic receptor agonists and muscarinic receptor antagonists according to the present invention. The method further comprises administering a therapeutically effective amount of one or more other therapeutic agent selected from the group consisting of a corticosteroid and a PDE4 inhibitor.

The invention is also directed to a method of modulating the activity of a β2 adrenergic and/or a M3 receptor, the method comprising stimulating a β2 adrenergic receptor and/or blocking a M3 receptor with a modulatory amount of compounds of the present invention.

The term "therapeutically effective amount" refers to an amount sufficient to effect treatment when administered to a patient in need of treatment.

The term "treatment" as used herein refers to the treatment of a disease or medical condition in a human patient which includes:
 (a) preventing the disease or medical condition from occurring, i.e., prophylactic treatment of a patient;
 (b) ameliorating the disease or medical condition, i.e., causing regression of the disease or medical condition in a patient;
 (c) suppressing the disease or medical condition, i.e., slowing the development of the disease or medical condition in a patient; or
 (d) alleviating the symptoms of the disease or medical condition in a patient.

The phrase "disease or condition associated with β2 adrenergic receptor and muscarinic activities" includes all disease states and/or conditions that are acknowledged now, or that are found in the future, to be associated with both β2 adrenergic receptor and muscarinic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), GI ulcers, spastic colitis (see, for ex., U.S. Pat. No. 4,556,653); urinary-tract disorders such as urinary incontinence (see, for ex., J. Med. Chem., 2005, 48, 6597-6606), pollakiuria; motion sickness and vagally induced sinus bradycardia.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given. Other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

One of the most convenient route for the preparation of compounds of formula (I) is depicted in Scheme 1.

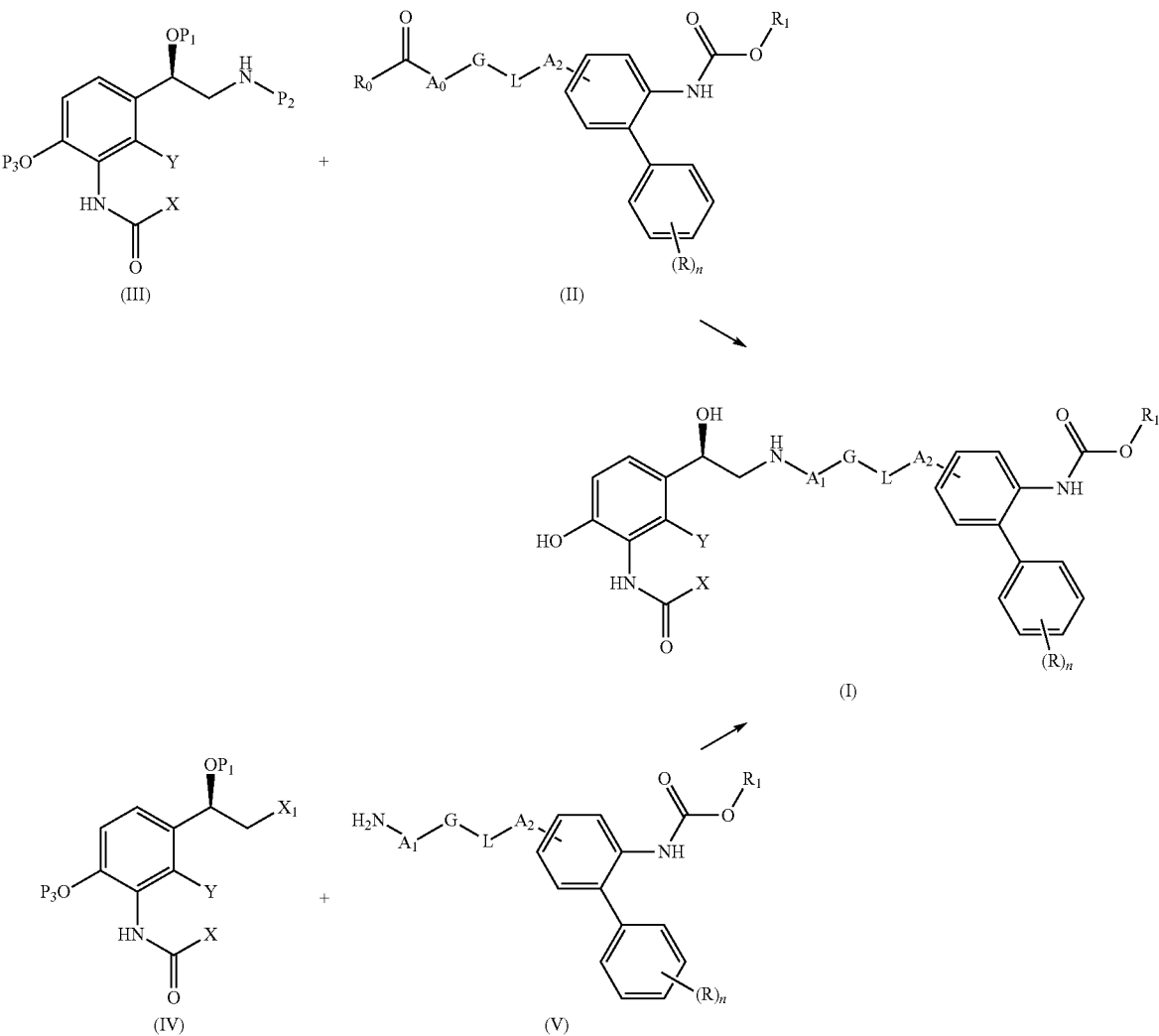

Scheme 1

Compounds of formula (I) may be prepared by reacting intermediates of formula (II) wherein $A_0$ represents a group that together with the adjacent methylene newly formed affords the $A_1$ group, being $R_0$ hydrogen or lower alkyl group, with intermediates of formula (III) wherein $X_1$ represents a leaving group such as a halogen atom, $P_1$ and $P_3$ independently represent a hydrogen atom or a oxygen-protecting group such as a silyl or benzyl ether and $P_2$ represents a hydrogen atom or a nitrogen-protecting group such as for example a benzyl group. This reaction is best carried out in a solvent or mixture of solvents like THF, methanol, dichloromethane or DMSO at a temperature between 0° C. and 60° C. using a hydride like sodium borohydride or sodium triacetoxyborohydride as reducing agent.

Alternatively, compounds of formula (I) may also be prepared by reacting intermediates of formula (V) with intermediates of formula (IV) wherein $X_1$, $P_1$ and $P_3$ have the same meaning as disclosed above, following the same synthetic procedure; and subsequently removing whichever protecting group present in the intermediate to provide a compound of formula (I). Such deprotection processes involve, for example, a desilylation process, by using tri-ethylamine trihydrofluoride, TBAF, hydrogen chloride or other acidic reagents in an inert solvent like THF in a range of temperatures between 0° C. and 50° C. The deprotection could also be carried out by a debenzylation process, for example, by hydrogenating the compound in the presence of a catalyst such as palladium on charcoal in an inert solvent like ethanol or THF or a mixture of solvents. This reaction is typically carried out at a hydrogen pressure between 10 and 60 psi and in a range of temperatures between room temperature and 50° C.

Intermediates of formula (II) may be prepared as depicted in Scheme 2, starting from known biphenylamine compounds (VI) trough subsequent conversion to isocyanates (VII) (using acylating agents like diphosgene) and carbamates (VIII) by treatment with an optionally protected amino alcohol (IX). The bromocarbamates (VIII) are then coupled to an olefinic fragment (X) via, for ex., a Heck reaction, carried out in the presence of a palladium salt, a phosphine and a base, for ex., palladium acetate, tri-o-tolylphosphine and diisopropylethylamine in a solvent like acetonitrile or THF in a range of temperatures between room temperature and 120° C.

Scheme 2

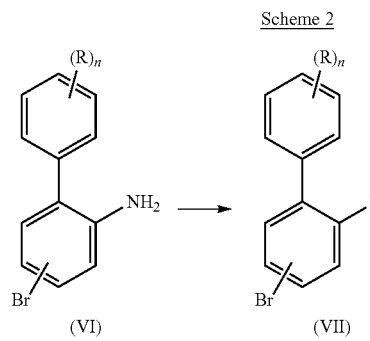

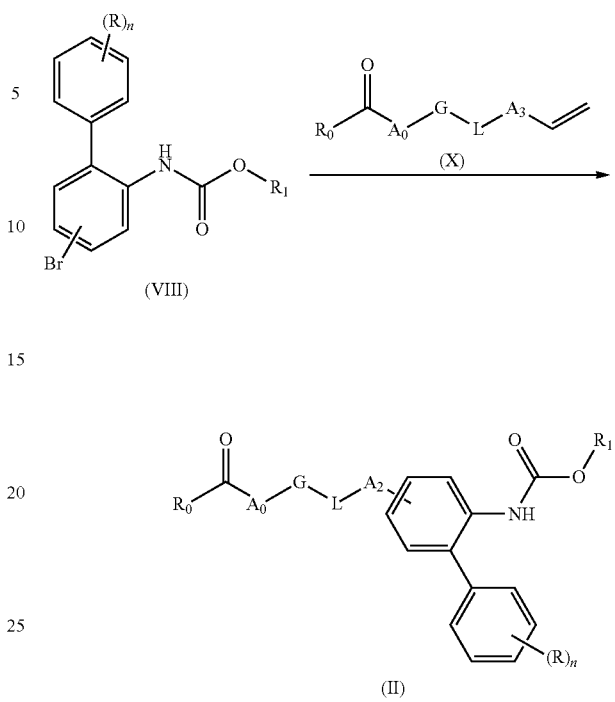

In the particular case of $R_0$ being a hydrogen atom with $A_1$=—$CH_2$— and G an aryl group, the corresponding intermediates (XIII) (having $A_2$ a number of methylene groups equal to that of $A_3$ plus 2) could also be prepared starting from the corresponding nitriles (XII) by coupling to the bromo derivatives (VIII) in a similar way as described previously and then converting the intermediates (XII) to the aldehydes (XIII) by reduction, for ex., with NiAl alloy in formic acid at a temperature between 50° C. and 100° C., as shown in Scheme 3:

Scheme 3

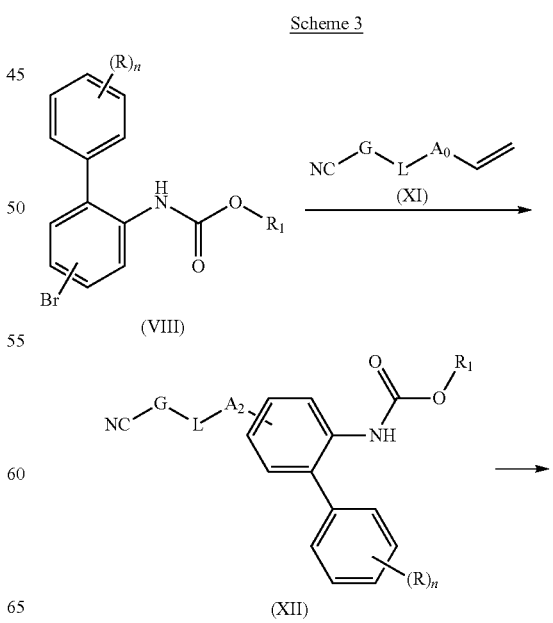

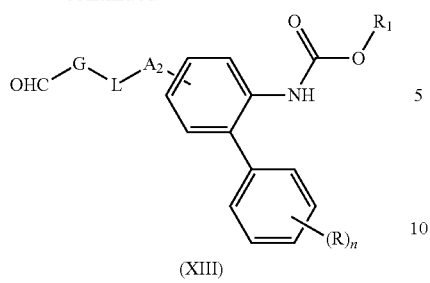

(XIII)

Still in other particular cases when G represents an aryl group and L the amide —NHCO— or carbamate —NHCOO— functionalities it is possible to prepare the intermediates (II) by building the G-L bond in the last step as disclosed in Schemes 4 and 5:

Scheme 4

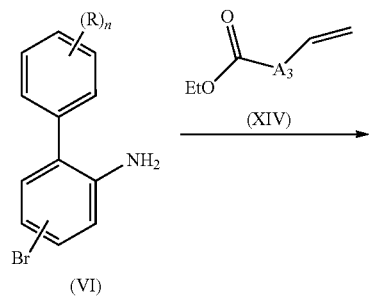

(XV)

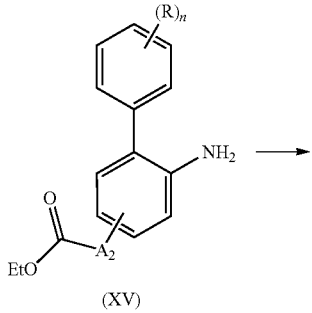

(XVI)

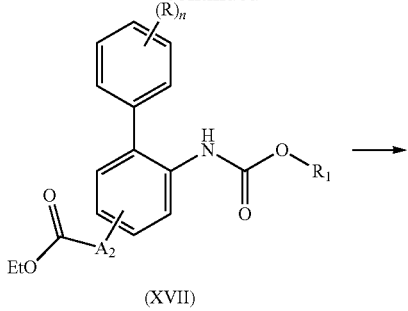

(XVII)

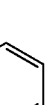

(XVIII)

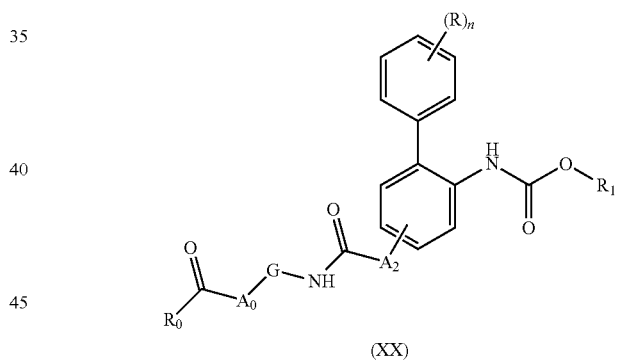

(XX)

By a similar coupling process as described above for compounds (II) followed by a hydrogenation of the carbon-carbon double bond—catalysed by palladium or palladium hydroxide—it is possible to access to intermediates (XV), being $A_2$ and $A_3$ as defined earlier. The amines (XV) are then readily converted to the carbamates (XVII) through the isocyanates (XVI) according to the process described above for the preparation of intermediates (VIII). After hydrolysis of the esters (XVII) to the carboxylic acids (XVIII), carried out by the usual methods as treatment with aqueous alkali, a coupling step with an amine (XIX) follows to give intermediates (XX). This process is catalysed by a coupling agent such as HATU and a tertiary amine as diisopropyl ethyl amine, in a solvent like THF or methylene chloride at a temperature between room temperature and the reflux temperature of the solvent. $R_1$ stands for the -$A_0$-CO—$R_0$ group or a rest that could revert to it through some simple transformation (for ex., a deprotection of a silylated alcohol plus an oxidation step to the carbonyl group).

Scheme 5

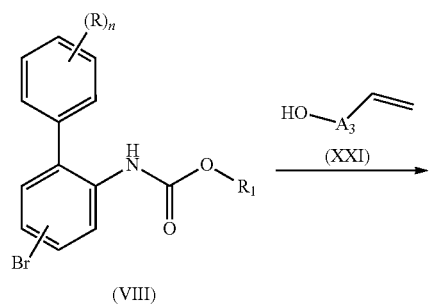

(VIII)

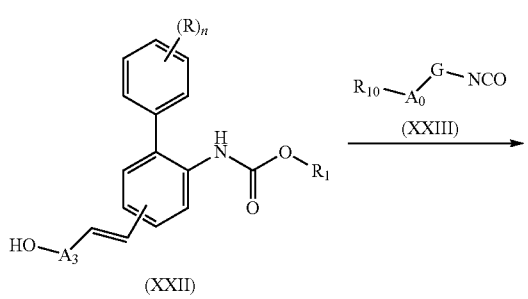

(XXII)

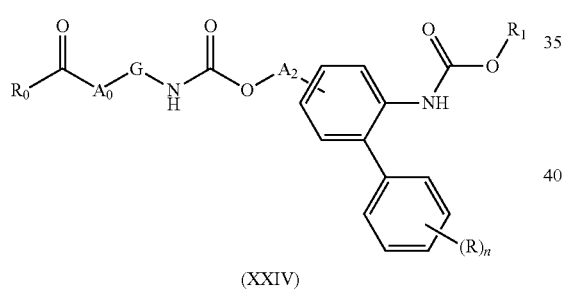

(XXIV)

Scheme 6

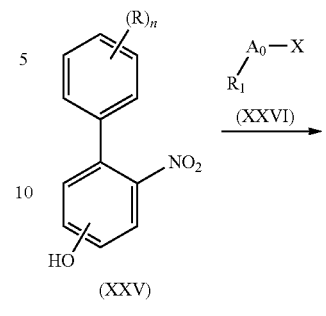

(XXV)

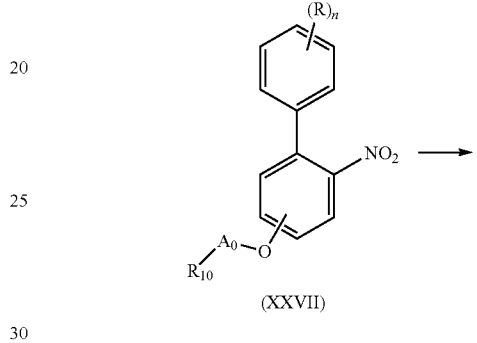

(XXVII)

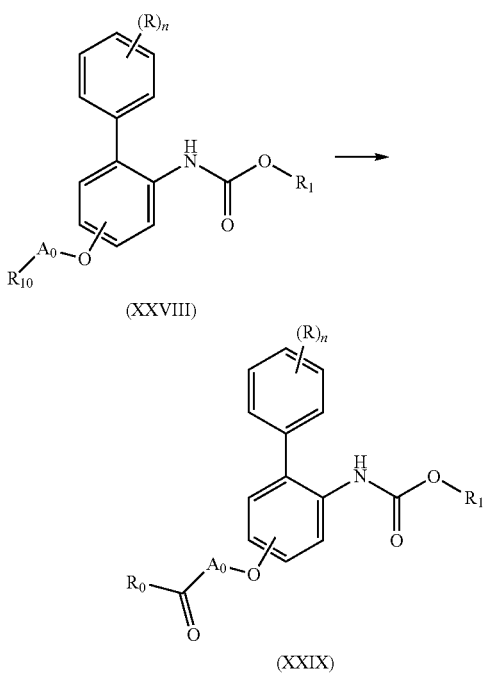

(XXVIII)

(XXIX)

Alcohols (XXII) are easily prepared from intermediates (VIII) via a coupling reaction Heck-type using the same conditions as described above for the synthesis of intermediates (II). By reaction of (XXII) with isocyanates (XXIII) carbamates (XXIV) are obtained using a variety of inert solvents or with no solvent at all, in a range of temperatures from room temperature to 150° C. Here $R_{10}$ has the same meaning as in intermediates (XIX) described above.

In the case of $A_2$ and G being direct bonds and L an oxygen atom it is possible to prepare the corresponding intermediates (XXIX) trough the process depicted in Scheme 6. By direct alkylation of the known phenols (XXV) with derivatives (XXVI) (being X a leaving group) in the presence of a base like an alkali carbonate or a tertiary amine intermediates (XXVII) are prepared (being $R_1$ as defined above). Compounds (XXVII) are in turn converted to carbamates (XXVIII) through subsequent reduction to anilines, conversion to isocyanates and reaction with alcohols as described in Scheme 2. After some deprotection and/or oxidation steps, intermediates (XXIX) are easily obtained.

Finally, intermediates (V) from Scheme 2 can be prepared, inter alia, as depicted in Scheme 7, by coupling of shown intermediates (VIII) with compounds (XXX) in a Heck-type mode as described earlier to give protected amines (XXXI), being $A_3$ as defined previously and $P_4$ an amino-protecting group. By subsequent deprotection (ex., hydrolysis of a BOC group in acidic medium) compounds (V) are thus synthesized.

Scheme 7

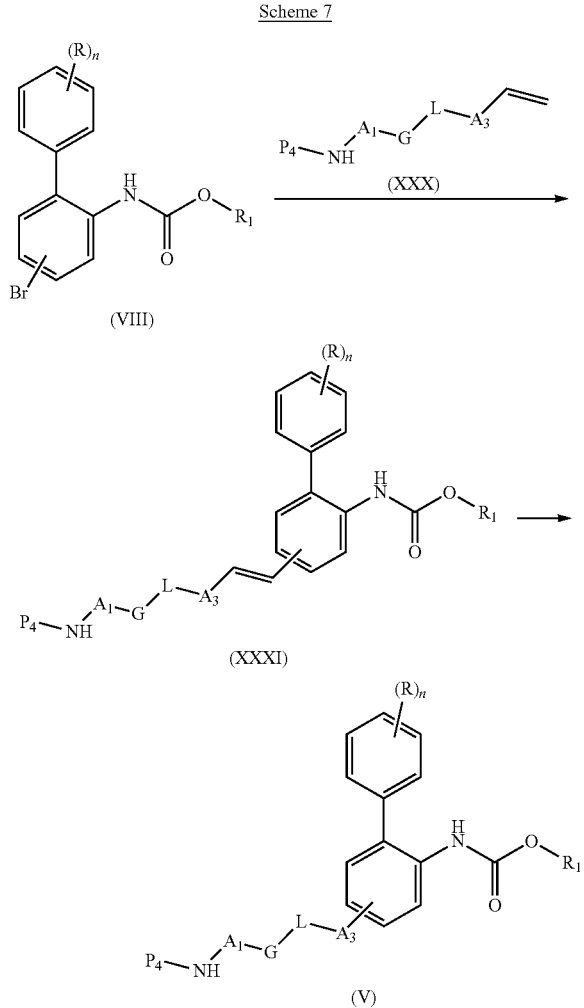

EXAMPLES

General

Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 μm) with the solvent system indicated or using preparative HPLC conditions (see bellow description of two systems used). Spectroscopic data were recorded on a Varian Gemini 300 spectrometer. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector.

HPLC System 1:

C-18 reverse phase column silica from MERK, water/acetonitrile (without buffer) as eluents using a gradient from 0% to 100%.

Intermediate 1

3-allyl-2-oxo-2,3-dihydro-1,3-benzoxazole-6-carbonitrile

To a solution of 2-oxo-2,3-dihydrobenzo[d]oxazole-6-carbonitrile (210 mg, 1.31 mmol, that product was synthesized by a mixture of 6-bromo-1,3-benzoxazol-2(3H)-one (2 g; 9.34 mmol) and copper (I) cyanide (1.42 g; 15.86 mmol) in 6 ml DMF, heated at 150° C. under nitrogen atmosphere for 22 hr. After cooling to room temperature, a solution of 1.55 g (31.6 mmol) of sodium cyanide in 32 ml water is added followed by 1 hr stirring. The system is extracted thoroughly with ethyl acetate, washed with brine, dried and concentrated in vacuum) in acetonitrile (4 mL) was added potassium carbonate (362 mg, 2.62 mmol) and potassium iodide (43 mg, 0.26 mmol) in a sealed tub. Then 3-bromoprop-1-ene (0.9 mL, 10.4 mmol) was added to the reaction. The mixture was stirred overnight at 70° C. The solid residue was filtrated through Celite. The solvent of the filtrate was removed under reduced pressure and the crude obtained was treated with ether giving a solid (150 mg, 57% yield), which was used in the next step without further purification.

LRMS (m/z): 201 (M+1)+.

Intermediate 2

3-allyl-2-oxo-2,3-dihydro-1,3-benzoxazole-6-carbaldehyde

To a solution of 3-allyl-2-oxo-2,3-dihydro-1,3-benzoxazole-6-carbonitrile (Intermediate 1; 150 mg, 0.75 mmol) in 1.64 mL of a solution of Formic Acid 75% was added Niquel-Aluminium (121.9 mg, 1.42 mmol). The mixture was stirred overnight at 75° C. The solids were removed by filtration through Celite and the solvent was removed under reduced pressure. The crude obtained was treated with ether giving a solid (140 mg; 92% yield), which was used in the next step without further purification.

LRMS (m/z): 204 (M+1)+.

Intermediate 3

(4-bromobiphenyl-2-yl)amine

To a solution of 5-bromo-2-iodoaniline (500 mg, 2.01 mmol) in dioxane (20 mL) was added potassium carbonate 4M (1.68 mL). The mixture was purged into nitrogen. Phenylboronic acid (250 mg, 2.01 mmol) and norbornylphosphino Pd II (50 mg) were added and the reaction was stirred for 3 hours at 110° C. The solvent was removed under reduced pressure and the crude was purified by column chromatography with silica gel, eluting with a mixture of hexane/ether to give the title compound as a solid (220 mg, 53%).

LRMS (m/z): 249 (M+1)+.

Intermediate 4

4-bromo-2-isocyanatobiphenyl

To a solution of triphosgene (143.4 mg; 0.48 mmol) in 1 mL of toluene was added drop wise at 0° C. a solution of (4-bromobiphenyl-2-yl)amine (Intermediate 3; 300 mg, 1.21 mmol) in 10 mL of toluene. Once the addition is finished triethylamine (0.325 mL, 2.42 mmol) was added drop wise.

The reaction mixture was stirred for 2 hours at room temperature. Cold pentane was added into the reaction mixture. The mixture was filtrated and the pentane of the filtrate was reduced under reduced pressure giving the title compound in solution of toluene, which was used in the next step without further manipulation.

LRMS (m/z): 289 (M+16)+; (aliquot in MeOH and detection of methylic ester).

Intermediate 5

(3R)-1-azabicyclo[2.2.2]oct-3-yl(4-bromobiphenyl-2-yl)carbamate

To a solution of Sodium (R)-quinuclidin-3-ol (3.61 g, 24.1 mmol), previously formed reflux-ing sodium with (R)-quinuclidin-3-ol at 125° C. for 4 hours, in 10 mL of toluene was added 4-bromo-2-isocyanatobiphenyl (6.63 g, 21.1 mmol). The mixture was stirred 2 hours at 120° C. The solvent was removed under reduced pressure and the crude was partitioned between ethyl acetate and hydrogen chloride 2N. The aqueous phase was neutralized and extracted with chloroform twice. The organic phase was dried, filtered and evaporated, giving the title compound as a solid (4.7 g, 48%), which was used in the next step without further purification.

LRMS (m/z): 402; 403 (M+1/M+2)+

Intermediate 6

(3R)-1-azabicyclo[2.2.2]oct-3-yl{4-[(1E)-3-(6-formyl-2-oxo-1,3-benzoxazol-3(2H)-yl)prop-1-en-1-yl]biphenyl-2-yl}carbamate To a mixture of (3R)-1-azabicyclo[2.2.2]oct-3-yl(4-bromobiphenyl-2-yl)carbamate (Intermediate 5; 400 mg, 1 mmol) and 3-allyl-2-oxo-2,3-dihydro-1,3-benzoxazole-6-carbaldehyde (Intermediate 2; 203 mg, 1 mmol) in acetonitrile (3 mL) in a sealed tub were added tri-o-tolylphosphine (304 mg, 1 mmol) and N,N-Diisopropylethylamine (0.34 mL, 2 mmol). The mixture was degassed under Argon during 5 minutes. Then palladium acetate (112 mg, 0.5 mmol) was added and the reaction mixture was stirred at 90° C. for 6 hours. The crude was filtrated and the filtrate was evaporated to dryness. The crude obtained was purified by column chromatography with silica gel, eluting with a mixture of chloroform:methanol:ammonium (40:4:0.2) to give the title compound as an oil (258 mg, 49%).

LRMS (m/z): 524 (M+1)+

Intermediate 7

(3R)-1-azabicyclo[2.2.2]oct-3-yl(4-{(1E)-3-[6-({[(2R)-2-{[tert-butyl(dimethyl) silyl]oxy}-2-(8-hydroxy-2-oxo-1,2-dihydroquinolin-5-yl)ethyl]amino}methyl)-2-oxo-1,3-benzoxazol-3(2H)-yl]prop-1-en-1-yl}biphenyl-2-yl)carbamate To a mixture of (3R)-1-azabicyclo[2.2.2]oct-3-yl{4-[(1E)-3-(6-formyl-2-oxo-1,3-benzoxazol-3(2H)-yl)prop-1-en-1-yl]biphenyl-2-yl}carbamate (258 mg, 0.44 mmol) and 5-((1R)-2-amino-1-{[tert-butyl(dimethyl)-silyl]oxy}ethyl)-8-hydroxyquinolin-2(1H)-one acetate (175 mg, 0.44 mmol) (prepared according to preparation 8 from US20060035931) in 10 mL of methanol was added DIEA (0.116 mL, 0.97 mmol) and sodium triacetoxyborohydride (282 mg, 1.33 mmol). The mixture was stirred overnight at room temperature. The solvent was removed under reduced pressure and the crude obtained was suspended in chloroform, the solid was filtrated and the solvent was evaporated. The crude obtained was purified by column chromatography with silica gel, eluting with a mixture of chloroform:methanol:ammonium (40:4:0.2) to give the title compound as a solid (255 mg, 60%).

LRMS (m/z): 843 (M+1)+

Intermediate 8

(3R)-1-azabicyclo[2.2.2]oct-3-yl(4-{3-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate To a solution of (3R)-1-azabicyclo[2.2.2]oct-3-yl (4-{(1E)-3-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]prop-1-en-1-yl}biphenyl-2-yl)carbamate (Intermediate 7; 79 mg, 0.06 mmol) in methanol (2 mL) was added ammonium formate (77 mg, 1.22 mmol) and palladium hydroxide (8 mg, 0.06 mmol). The reaction mixture was stirred for 2 hours at 80° C. The crude was filtrated and the solvent removed under reduced pressure. The crude obtained was partitioned between ethyl acetate and sodium bicarbonate. The organic phase was washed with water, dried, filtrated and the solvent was removed under reduced pressure, giving the title compound as a solid (10 mg, 13%), which was used in the final step without further purification.

LRMS (m/z): 845 (M+1)+

Example 1

(3R)-1-azabicyclo[2.2.2]oct-3-yl(4-{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate dihydrofluoride To a solution of (3R)-1-azabicyclo[2.2.2]oct-3-yl(4-{3-[6-({[(2R)-2-{[tert-butyl(dimethyl)silyl]oxy}-2-(8-hydroxy-2-oxo-1,2-dihydroquinolin-5-yl)ethyl]amino}-methyl)-2-oxo-1,3-benzoxazol-3(2H)-yl]propyl}biphenyl-2-yl)carbamate (10 mg, 0.01 mmol) in tetrahydrofurane (2 mL) was added triethylamine trihydrofluoride (18 μL, 0.11 mmol). The mixture was stirred overnight at room temperature. The solvent was removed and the residue was treated with acetonitrile giving a white solid as a title compound (8 mg, 58%).

LRMS (m/z): 730 (M+1)+

1H NMR (300 MHz, dmso) δ 8.75 (s, 1H), 8.18 (d, 10.0 Hz, 1H), 7.56-7.01 (m, 10H), 6.93 (s, 1H), 6.49 (d, J=10.0 Hz, 1H), 5.20 (bs, 1H), 4.60 (bs, 1H), 3.91 (m, 4H), 3.03-2.64 (m, 8H), 1.97 (m, 3H), 1.67 (s, 4H), 1.12 (m, 3H).

Intermediate 9 tert-butyl {2-[4-(but-3-en-1-yloxy)phenyl]ethyl}carbamate

To a solution of tert-butyl[2-(4-hydroxyphenyl)ethyl]carbamate (Intermediate 20 described in the patent WO2009/068177 A1; 1.7 g, 7.29 mmol) in dimethylformamide (15 mL) was added 4-bromobut-1-ene (0.88 mL, 8.67 mmol)

and potassium carbonate (1.21 g, 8.75 mmol). The mixture was stirred at 60° C. overnight. The solvent was removed under reduced pressure and the crude obtained was purified by column chromatography with silica gel, eluting with a mixture of hexane:ether to give the title compound as an oil (680 mg, 16%).

LRMS (m/z): 292 (M+1)+

Intermediate 10

(3R)-1-azabicyclo[2.2.2]oct-3-yl{4-[(1E)-4-(4-{2-[(tert-butoxycarbonyl)amino]ethyl}-phenoxy)but-1-en-1-yl]biphenyl-2-yl}carbamate Obtained as a solid (26 mg, 39%) from tert-butyl {2-[4-(but-3-en-1-yloxy)phenyl]-ethyl}carbamate (27 mg, 0.09 mmol), (3R)-1-azabicyclo[2.2.2]oct-3-yl(4-bromobiphenyl-2-yl)carbamate (Intermediate 5; 37 mg, 0.09 mmol), tri-o-tolylphosphine (40 mg, 0.13 mmol), N,N-Diisopropylethylamine (25 µL, 0.14 mmol) and palladium acetate (16 mg, 0.07 mmol) following the experimental procedure as described for Intermediate 6. The crude obtained was purified by column chromatography with silica gel, eluting with a mixture of chloroform:methanol:ammonium (40:4:0.2).

LRMS (m/z): 612 (M+1)+

Intermediate 11

(3R)-1-azabicyclo[2.2.2]oct-3-yl{4-[4-(4-{2-[(tert-butoxycarbonyl)amino]ethyl}-phenoxy)butyl]biphenyl-2-yl}carbamate Obtained as a solid (367 mg, 71%) from (3R)-1-azabicyclo[2.2.2]oct-3-yl{4-[(1E)-4-(4-{2-[(tert-butoxycarbonyl)amino]ethyl}phenoxy)but-1-en-1-yl]biphenyl-2-yl}carbamate (Inter-mediate 10; 490 mg, 0.8 mmol), ammonium formate (404 mg, 6.41 mmol) and palladium hydroxide (112 mg, 0.8 mmol) following the experimental procedure as described for Inter-mediate 8, the crude obtained was used without further purification.

LRMS (m/z): 614 (M+1)+

Intermediate 12

(3R)-1-azabicyclo[2.2.2]oct-3-yl(4-{4-[4-(2-aminoethyl)phenoxy]butyl}biphenyl-2-yl)carbamate (3R)-1-azabicyclo[2.2.2]oct-3-yl{4-[4-(4-{2-[(tert-butoxycarbonyl)amino]ethyl}phenoxy)butyl]biphenyl-2-yl}carbamate (Intermediate 11; 367 mg, 0.6 mmol) was dissolved in 6 mL of hydrogen chloride 4M in dioxane. The mixture was stirred for 2 hours at room temperature. The solvent was removed under reduced pressure and the crude obtained was purified by column chromatography with silica gel, eluting with a mixture of chloroform:methanol:ammonium (40:8:1) to give the title compound as a solid (255 mg, 83%).

LRMS (m/z): 514 (M+1)+

Intermediate 13

(3R)-1-azabicyclo[2.2.2]oct-3-yl{4-[4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}-phenoxy)-butyl]biphenyl-2-yl}carbamate To a solution of (3R)-1-azabicyclo[2.2.2]oct-3-yl(4-{4-[4-(2-aminoethyl)phenoxy]butyl}-biphenyl-2-yl)carbamate (Intermediate 12; 255 mg, 0.43 mmol) in dimethylacetamide (4 mL) was added 8-(benzyloxy)-5-((1R)-2-bromo-1-{[tert-butyl(dimethyl)silyl]oxy}ethyl)-quinolin-2(1H)-one (US20040059116) (212 mg, 0.43 mmol), sodium bicarbonate (109 mg, 1.3 mmol) and sodium iodine (98 mg, 0.65 mmol). The mixture was stirred at 80° C. for 24 hours. Water was poured into the reaction mixture and the solid was collected by filtration. The crude obtained was purified by column chromatography with silica gel, eluting with a mixture of chloroform:methanol:ammonium (40:4:0.2) to give the title compound as a solid (132 mg, 33%).

LRMS (m/z): 922 (M+1)+

Intermediate 14

(3R)-1-azabicyclo[2.2.2]oct-3-yl(4-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]butyl}-biphenyl-2-yl)carbamate (3R)-1-azabicyclo[2.2.2]oct-3-yl{4-[4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)butyl]biphenyl-2-yl}carbamate (17 mg, 0.02 mmol) was dissolved in acetic acid (2 mL) and submitted to an H-Cube® Continuous-flow Hydrogenation Reactor. Conditions used: Pressure: Full H2, Flow 1 mL/min, $T^\alpha$ 40° C.

The solvent was removed under reduced pressure obtaining the diacetate salt of the title compound (10 mg, 62%).

LRMS (m/z): 832 (M+1)+

Example 2

(3R)-1-azabicyclo[2.2.2]oct-3-yl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)-carbamate di-hydrofluoride Obtained as a white solid dihydrofluoride salt (24 mg, 56%) from (3R)-1-azabicyclo[2.2.2]oct-3-yl(4-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]butyl}biphenyl-2-yl)carbamate (45 mg, 0.05 mmol) and triethylamine trihydrofluoride (44 µL, 0.27 mmol) following the ex-perimental procedure as described for Example 1.

LRMS (m/z): 716 (M+1)+

1H NMR (300 MHz, dmso) δ 8.68 (s, 1H), 8.20 (d, J=9.7 Hz, 1H), 7.45-7.27 (m, 4H), 7.22 (d, J=3.5 Hz, 2H), 7.17-7.03 (m, 3H), 6.93 (d, J=8.4 Hz, 1H), 6.84 (d, J=8.4 Hz, 2H), 6.52 (d, J=9.7 Hz, 1H), 5.17 (s, 1H), 4.50 (s, 1H), 3.96 (s, 1H), 2.86 (bs, 3H), 2.67 (s, 7H), 2.46-2.33 (m, 2H), 1.82 (bs, 1H), 1.74 (bs, 3H), 1.58 (bs, 2H), 1.47 (bs, 2H), 1.29 (bs, 2H).

Intermediate 15 trans-4-(methyltert-butylamino)cyclohexyl(4-bromo-biphenyl-2-yl)carbamate

To a solution of 4-bromo-2-isocyanatobiphenyl (Intermediate 4; 227 mg 0.91 mmol) in 3 mL of anhydridous toluene was added a solution of tert-butyl(trans-4-hydroxycyclohexyl)methylcarbamate methyl hidroxi(di-2-thienyl)acetate (Intermediate 3 from WO2011/141180A1; 278 mg, 1.21 mmol) in 5 mL of anhydrous toluene. The reaction mixture was stirred at 75° C. for 36 hours. The solvent was removed under reduced pressure and the crude obtained was purified by column chromatography with silica gel, eluting with a mixture of Hexane:Ether to give the title compound as a white solid (305 mg, 66%).

LRMS (m/z): 504 (M+1)+

Intermediate 16

4-(allylamino)-3-nitrobenzonitrile

To a solution of 4-amino-3-nitrobenzonitrile (5 g, 0.03 mol) in 12 mL of dimethylacetamide was added 3-bromoprop-1-ene (2.67 mL, 0.03 mol) and potassium carbonate (21.1 g, 0.153 mol). The reaction mixture was stirred for 4 hours at 75° C. Water was added and the organic phase was extracted twice with ether. The organic phase was dried, filtered and the solvent was removed under reduced pressure. The crude obtained was crystallized with petroleum ether giving the title compound as an oil (5.8 g, 93%).

LRMS (m/z): 204 (M+1)+

Intermediate 17

4-(allylamino)-3-aminobenzonitrile

To a solution of 4-(allylamino)-3-nitrobenzonitrile (Intermediate 16; 140 mg, 0.69 mmol) in ethanol (8 mL) was added Tin(II)chloride (777 mg, 3.44 mmol). The reaction mixture was stirred for 12 h at 90° C. The solution was basified by sodium hydroxide 8N and the solu-tion obtained was filtrated through Celite. The filtrate was extracted twice with ethyl ace-tate, the organic layer was dried, filtered and the solvent was removed under reduced pressure. The title compound was obtained as a solid (94 mg, 79%).

LRMS (m/z): 174 (M+1)+

Intermediate 18

1-allyl-1H-1,2,3-benzotriazole-5-carbonitrile

To a suspension of 4-(allylamino)-3-aminobenzonitrile (Intermediate 17, 1.5 g, 0.008 mol) in hydrogen chloride (14.7 mL, 4N) was added at 0° C. and drop wise a solution of sodium nitrite (0.9 g, 0.012 mol) in water (7 mL). The reaction mixture was stirred overnight at room temperature. Water was added into the mixture and the organics were extracted with dichloromethane. The organic layer was dried, filtered and the solvent was removed under reduced pressure. The crude obtained was purified by column chromatography with silica gel, eluting with a mixture of Dichloromethane:Ethanol (9:1) to give the title compound as a solid (1.2 g, 75%).

LRMS (m/z): 185 (M+1)+

Intermediate 19 trans-4-(methyltert-butylamino)cyclohexyl{4-[(1E)-3-(5-cyano-1H-1,2,3-benzotriazol-1-yl)prop-1-en-1-yl]biphenyl-2-yl}carbamate Obtained as a solid (132 mg, 84%) from trans-4-(methyltert-butylamino)cyclohexyl(4-bromobiphenyl-2-yl)carbamate (Intermediate 15; 250 mg, 0.5 mmol), 1-allyl-1H-1,2,3-benzotriazole-5-carbonitrile (Intermediate 18; 91 mg, 0.49 mmol), tri-o-tolylphosphine (151 mg, 0.5 mmol), palladium acetate (55 mg, 0.24 mmol) and N,N-Diisopropylethylamine (0.17 mL, 0.99 mmol) following the experimental procedure as described for Intermediate 6 and the crude obtained was purified by column chromatography with silica gel, eluting with a mixture of Hexane:Ether.

LRMS (m/z): 607 (M+1)+

Intermediate 20 trans-4-(methyltert-butylamino)cyclohexyl{4-[3-(5-cyano-1H-1,2,3-benzotriazol-1-yl)propyl]biphenyl-2-yl}carbamate Obtained as a white solid (110 mg, 81%) from trans-4-(methyltert-butylamino)cyclohexyl {4-[(1E)-3-(5-cyano-1H-1,2,3-benzotriazol-1-yl)prop-1-en-1-yl]biphenyl-2-yl}carbamate (In-termediate 19; 132 mg, 0.22 mmol), palladium hydroxide (7 mg, 0.05 mmol) and ammonium formate (109 mg, 1.73 mmol) following the experimental procedure as described for Inter-mediate 8. The crude obtained was purified by column chromatography with silica gel, eluting with a mixture of Hexane:Ether.

LRMS (m/z): 609 (M+1)+

Intermediate 21 trans-4-(methylamino)cyclohexyl{4-[3-(5-cyano-1H-1,2,3-benzotriazol-1-yl)propyl]biphenyl-2-yl}carbamate A solution of trans-4-(methyltert-butylamino)cyclohexyl{4-[3-(5-cyano-1H-1,2,3-benzotriazol-1-yl)propyl]biphenyl-2-yl}carbamate (Intermediate 20; 35 mg, 0.06 mmol) in 3 mL of hydrogen chloride (4N in dioxane) was stirred for 2 hours at room temperature. The solvent was removed under reduced pressure and the crude obtained was treated with ether giving a white solid as the title compound (29 mg, 90%), which was used in the next step without further purification.

LRMS (m/z): 509 (M+1)+

Intermediate 22 trans-4-(methylamino)cyclohexyl{4-[3-(5-formyl-1H-1,2,3-benzotriazol-1-yl)propyl]biphenyl-2-yl}carbamate Obtained as a solid (110 mg whit 60% of purity by HPLC, 73%) from trans-4-(methylamino)cyclohexyl{4-[3-(5-cyano-1H-1,2,3-benzotriazol-1-yl)propyl]biphenyl-2-yl}carbamate (Intermediate 21; 96 mg, 0.17 mmol), Formic Acid 75% and Niquel-Aluminium (15 mg, 0.17 mmol) following the experimental procedure as described for In-termediate 2. The crude obtained was used in the next step without further manipulation.

LRMS (m/z): 512 (M+1)+

Intermediate 23 trans-4-(methylamino)cyclohexyl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]propyl}biphenyl-2-yl)carbamate Obtained as a solid (20 mg, 24%) from trans-4-(methylamino)cyclohexyl{4-[3-(5-formyl-1H-1,2,3-benzotriazol-1-yl)propyl]biphenyl-2-yl}carbamate (90 mg, 0.1 mmol), -((1R)-2-amino-1-{[tert-butyl(dimethyl)-silyl]oxy}ethyl)-8-hydroxyquinolin-2(1H)-one acetate (39 mg, 0.1 mmol) (prepared according to preparation 8 from US20060035931), DIEA (26µ, 0.15 mmol) and sodium triacetoxyborohydride (63 mg, 0.3 mmol) following the experimental procedure as described for Intermediate 7. The crude obtained was purified by column chromatography in reverse phase using as eluents water and acetonitrile.

LRMS (m/z): 831 (M+1)+

Example 3 trans-4-(methylamino)cyclohexyl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl] propyl}biphenyl-2-yl)carbamate dihydrofluoride Obtained as a white solid (3 mg, 37%) from trans-4-(methylamino)cyclohexyl(4-{3-[5-({[(2R)-2-{[tert-butyl (dimethyl)silyl]oxy}-2-(8-hydroxy-2-oxo-1,2-dihydroquinolin-5-yl)ethyl]amino}methyl)-1H-1,2,3-benzotriazol-1-yl]propyl}biphenyl-2-yl)carbamate (Inter-mediate 23; 10 mg, 0.01 mmol) and triethylamine trihydrofluoride (10 µL, 0.06 mmol) follow-ing the experimental procedure as described for Example 1.

LRMS (m/z): 716 (M+1)+

1H NMR (300 MHz, cd3od) δ 8.30 (d, J=9.8 Hz, 1H), 8.12 (s, 1H), 7.90 (s, 1H), 7.83 (d, J=8.7 Hz, 1H), 7.69 (s, 1H), 7.46-7.29 (m, 2H), 7.24 (d, J=8.0 Hz, 1H), 7.18 (d, J=7.9 Hz, 1H), 7.09 (bs, 1H), 6.99 (d, J=8.3 Hz, 1H), 6.59 (d, J=9.5 Hz, 1H), 5.38 (bs, 1H), 4.61 (s, 2H), 4.56-4.41 (m, 1H), 4.34 (s, 1H), 3.56-3.41 (m, 2H), 3.26-3.04 (m, 3H), 2.68 (bs, 2H), 2.41 (s, 2H), 2.07 (m, 3H), 1.41 (s, 2H).

Intermediate 24

1-allyl-1H-1,2,3-benzotriazole-5-carbaldehyde

Obtained as a solid (0.45 g, 35%) from 1-allyl-1H-1,2,3-benzotriazole-5-carbonitrile (Inter-mediate 18; 1 g, 0.005 mol), Formic Acid 75 and Niquel-Aluminium (0.72 g, 0.008 mol) fol-lowing the experimental procedure as described for Intermediate 2. The crude obtained was purified by column chromatography with silica gel, eluting with a mixture of Hexane:Ether.

LRMS (m/z): 188 (M+1)+

Intermediate 25

(3R)-1-azabicyclo[2.2.2]oct-3-yl{4-[(1E)-3-(5-formyl-1H-1,2,3-benzotriazol-1-yl)prop-1-en-1-yl] biphenyl-2-yl}carbamate Obtained as a solid (165 mg, 58%) from (3R)-1-azabicyclo[2.2.2]oct-3-yl(4-bromobiphenyl-2-yl)carbamate (Inter-mediate 5; 200 mg, 0.39 mmol), 1-allyl-1H-1,2,3-benzotriazole-5-carbaldehyde (Intermediate 24; 180 mg, 0.48 mmol), tri-o-tolylphosphine (120 mg, 0.39 mmol), N,N-Diisopropylethylamine (0.13 mL, 0.79 mmol) and palladium ace-tate (65 mg, 0.20 mmol) following the experimental procedure as described for Intermediate 6. The crude obtained was purified by column chromatography with silica gel, eluting with a mixture of chloroform:methanol:ammonium (40:8:1)

LRMS (m/z): 508 (M+1)+

Intermediate 26

(3R)-1-azabicyclo[2.2.2]oct-3-yl(4-{(1E)-3-[5-({[(2R)-2-{[tert-butyl(dimethyl)silyl]-oxy}-2-(8-hydroxy-2-oxo-1,2-dihydroquinolin-5-yl)ethyl] amino}methyl)-1H-1,2,3-benzotriazol-1-yl]prop-1-en-1-yl}biphenyl-2-yl)carbamate Obtained as a foam (113 mg, 51%) from (3R)-1-azabicyclo[2.2.2]oct-3-yl{4-[(1E)-3-(5-formyl-1H-1,2,3-benzotriazol-1-yl)prop-1-en-1-yl]biphenyl-2-yl}carbamate (Intermediate 25; 165 mg, 0.23 mmol), 5-((1R)-2-amino-1-{[tert-butyl(dimethyl)-silyl]oxy}ethyl)-8-hydroxyquinolin-2(1H)-one acetate (76 mg, 0.23 mmol) (prepared according to preparation 8 from US20060035931), DIEA (60 µL, 0.34 mmol) and sodium triacetoxyborohydride (144 mg, 0.38 mmol) following the experimental procedure as described for Intermediate 7. The crude obtained was purified by column chromatography with silica gel, eluting with a mixture of chloroform:methanol:ammonium (40:8:1)

LRMS (m/z): 827 (M+1)+

Intermediate 27

(3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]propyl}biphenyl-2-yl) carbamate Obtained as a yellow solid (85 mg, 85%) from (3R)-1-azabicyclo[2.2.2]oct-3-yl(4-{(1E)-3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]prop-1-en-1-yl}biphenyl-2-yl)carbamate (Intermediate 26; 113 mg, 0.12 mmol), ammonium formate (143 mg, 2.32 mmol) and palla-dium hydroxide (14 mg, 0.1 mmol) following the experimental procedure as described for Intermediate 8. The crude obtained was used in the next step without further purification.

LRMS (m/z): 829 (M+1)+

Example 4

(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl] propyl}biphenyl-2-yl)carbamate dihydrofluoride Obtained as a white solid (57 mg, 88%) from (3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl] propyl}biphenyl-2-yl)carbamate (85 mg, 0.08 mmol) and triethylamine trihydrofluoride (83 µL, 0.51 mmol) following the experimental procedure as described for Example 1.

LRMS (m/z): 754 (M+1)+

1H NMR (300 MHz, dmso) δ 8.70 (s, 1H), 8.13 (d, J=9.8 Hz, 1H), 7.99 (s, 1H), 7.83 (d, J=8.3 Hz, 1H), 7.57 (d, J=8.0 Hz, 1H), 7.39 (bs, 3H), 7.22 (s, 1H), 7.10 (bs, 2H), 6.90 (d, J=8.1 Hz, 1H), 6.43 (d, J=9.5 Hz, 1H), 5.13 (s, 1H), 4.74 (s, 1H), 4.52 (s, 1H), 3.98 (s, 2H), 2.68 (bs, 6H), 2.25 (s, 3H), 1.84 (s, 2H), 1.59 (s, 4H), 1.32 (s, 2H).

Intermediate 28

1-allyl-2-oxo-2,3-dihydro-1H-benzimidazole-5-carbonitrile

To a solution of 4-(allylamino)-3-aminobenzonitrile (Intermediate 17; 97 mg, 0.54 mmol) in dichloromethane (10 mL) was added triphosgene (80 mg, 0.27 mmol) and triethylamine (0.113 mL, 0.81 mmol). The reaction mixture was stirred at room temperature overnight. The organic layer was washed with water and bicarbonate, dried, filtered and the solvent was removed under reduced pressure. The title compound was obtained as a gum (90 mg, 66%), and it was used in the next step without further manipulation.
LRMS (m/z): 201 (M+1)+

Intermediate 29

1-allyl-2-oxo-2,3-dihydro-1H-benzimidazole-5-carbaldehyde

Obtained as a solid (280 mg, 25%) from 1-allyl-2-oxo-2,3-dihydro-1H-benzimidazole-5-carbonitrile (Intermediate 28; 600 mg, 0.003 mol), formic acid 75% and niquel aluminium (283 mg, 0.003 mol) following the experimental procedure as described for Intermediate 2. The crude obtained was purified by column chromatography with silica gel, eluting with a mixture of Hexane:ethanol
LRMS (m/z): 203 (M+1)+

Intermediate 30

(3R)-1-azabicyclo[2.2.2]oct-3-yl{4-[(1E)-3-(5-formyl-2-oxo-2,3-dihydro-1H-benzimidazol-1-yl)prop-1-en-1-yl]biphenyl-2-yl}carbamate Obtained as a solid (590 mg, 65%) from 1-allyl-2-oxo-2,3-dihydro-1H-benzimidazole-5-carbaldehyde (Intermediate 29; 280 mg, 1.38 mmol), (3R)-1-azabicyclo[2.2.2]oct-3-yl(4-bromobiphenyl-2-yl)carbamate (Intermediate 5; 650 mg, 1.62 mmol), tri-o-tolylphosphine (120 mg, 0.39 mmol), N,N-Diisopropylethylamine (0.13 mL, 0.79 mmol) and palladium acetate (65 mg, 0.20 mmol) following the experimental procedure as described for Intermediate 6. The crude obtained was purified by column chromatography with silica gel, eluting with a mixture of chloroform:methanol:ammonium (40:8:1).
LRMS (m/z): 523 (M+1)+

Intermediate 31

(3R)-1-azabicyclo[2.2.2]oct-3-yl(4-{(1E)-3-[5-({[(2R)-2-{[tert-butyl(dimethyl)silyl]-oxy}-2-(8-hydroxy-2-oxo-1,2-dihydroquinolin-5-yl)ethyl]amino}methyl)-2-oxo-2,3-dihydro-1H-benzimida-zol-1-yl]prop-1-en-1-yl}biphenyl-2-yl)carbamate Obtained as a solid (416 mg, 52%) from (3R)-1-azabicyclo[2.2.2]oct-3-yl{4-[(1E)-3-(5-formyl-2-oxo-2,3-dihydro-1H-benzimidazol-1-yl)prop-1-en-1-yl]biphenyl-2-yl}carbamate (Intermediate 30, 590 mg, 0.9 mmol), 5-((1R)-2-amino-1-{[tert-butyl(dimethyl)-silyl]oxy}ethyl)-8-hydroxyquinolin-2(1H)-one acetate (400 mg, 1.01 mmol) (prepared according to preparation 8 from US20060035931), DIEA (0.137 mL, 0.26 mmol) and sodium triacetoxyborohydride (700 mg, 3.3 mmol) follow-ing the experimental procedure as de-scribed for Intermediate 7. The crude obtained was purified by column chromatography with silica gel, eluting with a mixture of chloroform:methanol:ammonium (40:8:1)
LRMS (m/z): 842 (M+1)+

Intermediate 32

(3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-2,3-dihydro-1H-benzimidazol-1-yl]propyl}biphenyl-2-yl)carbamate Obtained as a solid (194 mg, 49%) from (3R)-1-azabicyclo[2.2.2]oct-3-yl(4-{(1E)-3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-2,3-dihydro-1H-benzimidazol-1-yl]prop-1-en-1-yl}biphenyl-2-yl)carbamate (Intermediate 31; 415 mg, 0.417 mmol), ammonium formate (570 mg, 9.04 mmol) and palladium hydroxide (45 mg, 0.32 mmol) following the experimental proce-dure as described for Intermediate 8. The crude obtained was used in the next step with-out further purification.
LRMS (m/z): 844 (M+1)+

Example 5

(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}biphenyl-2-yl)carbamate dihydrofluoride Obtained as a white solid (123 mg, 62%) from (3R)-1-azabicyclo[2.2.2]oct-3-yl(4-{3-[5-({[(2R)-2-{tert-butyl(dimethyl)silyl]oxy}-2-(8-hydroxy-2-oxo-1,2-dihydroquinolin-5-yl)ethyl]amino}methyl)-2-oxo-2,3-dihydro-1H-benzimidazol-1-yl]propyl}biphenyl-2-yl)carbamate (198 mg, 0.23 mmol) and triethylamine trihydrofluoride (187 μL, 1.17 mmol) following the experimental procedure as described for Example 1.
LRMS (m/z): 769 (M+1)+
1H NMR (300 MHz, dmso) δ 10.88 (s, 1H), 8.67 (s, 1H), 8.10 (d, J=10.0 Hz, 1H), 7.36 (bs, 4H), 7.27-6.80 (m, 8H), 6.47 (d, J=9.8 Hz, 1H), 5.11 (bs, 1H), 4.50 (bs, 1H), 3.60 (s, 2H), 3.04 (s, 2H), 2.80-2.55 (m, 7H), 2.42 (s, 2H), 1.95 (s, 2H), 1.78 (bs, 2H), 1.56 (s, 2H), 1.46 (s, 2H), 1.30 (s, 1H).

Intermediate 33

1-allyl-1H-indole-5-carbaldehyde

To a solution of 1H-indole-5-carbaldehyde (200 mg, 1.38 mmol) in dimethylformamide (2 mL) was added at 0° C. sodium hydride (61 mg, 2.54 mmol) and the mixture was allowed to stirred for 30 minutes at 0° C. Then 3-bromoprop-1-ene (0.180 mL, 2.08 mmol) was added into the reaction mixture. The reaction was stirred overnight at room temperature. Water was added and the organics were extracted with hexane. The organic layer was dried, filtered and the solvent was removed under reduced pressure giving the title com-pound as an oil (251 mg, 92%), which was used in the next step without further purification.
LRMS (m/z): 186 (M+1)+

Intermediate 34

(3R)-1-azabicyclo[2.2.2]oct-3-yl{4-[(1E)-3-(5-formyl-1H-indol-1-yl)prop-1-en-1-yl]biphenyl-2-yl}carbamate Obtained as a solid (278 mg, 78%) from 1-allyl-1H-indole-5-carbaldehyde (Intermediate 33; 110 mg, 0.59 mmol), (3R)-1-azabicyclo[2.2.2]oct-3-yl(4-bromobiphenyl-2-yl)carbamate (Intermediate 5; 300 mg, 0.59 mmol), tri-o-tolylphosphine (180 mg, 0.59 mmol), N,N-Diisopropylethylamine (0.2 mL, 1.15 mmol) and palladium acetate (65 mg, 0.20 mmol) fol-lowing the experimental procedure as described for Intermediate 6. The crude obtained was purified by column chromatography with silica gel, eluting with a mixture of chloro-form:methanol:ammonium (40:8:1).
LRMS (m/z): 506 (M+1)+

Intermediate 35

(3R)-1-azabicyclo[2.2.2]oct-3-yl(4-{(1E)-3-[5-({[(2R)-2-{[tert-butyl(dimethyl)silyl]-oxy}-2-(8-hydroxy-2-oxo-1,2-dihydroquinolin-5-yl)ethyl]amino}methyl)-1H-indol-1-yl]prop-1-en-1-yl}biphenyl-2-yl)carbamate Obtained as a solid (164 mg, 38%) from (3R)-1-azabicyclo[2.2.2]oct-3-yl{4-[(1E)-3-(5-formyl-1H-indol-1-yl)prop-1-en-1-yl]biphenyl-2-yl}carbamate (275 mg, 0.47 mmol), 5-((1R)-2-amino-1-{[tert-butyl(dimethyl)-silyl]oxy}ethyl)-8-hydroxyquinolin-2(1H)-one acetate (188 mg, 0.48 mmol) (prepared according to preparation 8 from US20060035931), DIEA (0.13 mL, 0.75 mmol) and sodium triacetoxyborohydride (300 mg, 1.42 mmol) following the experimental procedure as described for Intermediate 7. The crude obtained was purified by column chromatography with silica gel, eluting with a mixture of chloro-form:methanol:ammonium (40:4:0.2)
LRMS (m/z): 825 (M+1)+

Intermediate 36

(3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]propyl}biphenyl-2-yl)carbamate Obtained as a solid (123 mg, 47%) from (3R)-1-azabicyclo[2.2.2]oct-3-yl(4-{(1E)-3-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]prop-1-en-1-yl}biphenyl-2-yl)carbamate (287 mg, 0.31 mmol), ammonium formate (197 mg, 3.12 mmol) and palladium hydroxide (23 mg, 0.16 mmol) following the experimental procedure as described for Intermediate 8. The crude obtained was purified by column chromatography with silica gel, eluting with a mix-ture of chloroform:methanol:ammonium (40:4:0.2)
LRMS (m/z): 827 (M+1)+

Example 6

(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-indol-1-yl]propyl}biphenyl-2-yl)carbamate dihydrofluoride Obtained as a solid (56 mg, 52%) from (3R)-1-azabicyclo[2.2.2]oct-3-yl(4-{3-[5-({[(2R)-2-{[tert-butyl(dimethyl)si-lyl]oxy}-2-(8-hydroxy-2-oxo-1,2-dihydroquinolin-5-yl)ethyl]-amino}methyl)-1H-indol-1-yl]propyl}biphenyl-2-yl)carbamate (123 mg, 0.15 mmol) and triethylamine trihydrofluoride (187 μL, 1.17 mmol) following the experimental procedure as described for Example 1.
LRMS (m/z): 712 (M+1)+
1H NMR (300 MHz, dmso) δ 8.83 (s, 1H), 8.23 (d, J=9.9 Hz, 1H), 7.67 (bs1H), 7.73-7.42 (m, 5H), 7.41-7.17 (m, 4H), 7.08 (bs, 2H), 6.62-6.47 (m, 2H), 6.45 (d, J=9.98 Hz, 1H), 5.30 (bs, 1H), 4.65 (bs, 1H), 4.37-4.34 (m, 2H), 4.10 (bs, 2H), 3.20 (bs, 2H), 2.93 (s, 1H), 2.79 (bs, 3H), 2.57-2.28 (m, 2H), 1.98 (bs, 2H), 1.72 (bs, 4H), 1.43 (bs, 2H), 1.19 (bs, 2H).

Intermediate 37

3-but-3-en-1-yl-2-oxo-2,3-dihydro-1,3-benzoxazole-6-carbonitrile

To a solution of 2-oxo-2,3-dihydrobenzo[d]oxazole-6-carbonitrile (see experimental in In-termediate 1; 1.2 g, 0.0075 mol) in dimethylformamide (10 mL) was added 4-bromobut-1-ene (1.21 g, 0.009 mol) and potassium carbonate (1.24 g, 0.009 mol). The reaction mixture was stirred at 60° C. for 3 hours. The crude was filtered and the filtrate was evaporated. The crude obtained was treated with ether and hexane, giving a solid which was filtered. The solid obtained (1.02 g, 63%) was the desired product and it was used in the next step without further purification.
LRMS (m/z): 215 (M+1)+

Intermediate 38

3-but-3-en-1-yl-2-oxo-2,3-dihydro-1,3-benzoxazole-6-carbaldehyde

Obtained as a solid (280 mg, 22%) from 3-but-3-en-1-yl-2-oxo-2,3-dihydro-1,3-benzoxazole-6-carbonitrile (Intermediate 37; 1 g, 0.004 mol), Formic Acid 75% and Niquel-Aluminium (440 mg, 0.005 mol) following the experimental procedure as described for In-termediate 2. The crude obtained was purified by column chromatography with silica gel, eluting with a mixture of Hexane:dicloromethane.
LRMS (m/z): 218 (M+1)+

Intermediate 39

(3R)-1-azabicyclo[2.2.2]oct-3-yl{4-[(1E)-4-(6-formyl-2-oxo-1,3-benzoxazol-3(2H)-yl)but-1-en-1-yl]biphenyl-2-yl}carbamate Obtained as a foam (650 mg, 83%) from 3-but-3-en-1-yl-2-oxo-2,3-dihydro-1,3-benzoxazole-6-carbaldehyde (Intermediate 38; 270 mg, 1 mmol) (3R)-1-azabicyclo[2.2.2]oct-3-yl(4-bromobiphenyl-2-yl)carbamate (Intermediate 5; 270 mg, 1.25 mmol), tri-o-tolylphosphine (303 mg, 1 mmol), N,N-Diisopropylethylamine (0.347 mL, 2 mmol) and palladium acetate (164 mg, 0.5 mmol) following the experimental procedure as described for Intermediate 6. The crude obtained was purified by column chromatography with silica gel, eluting with a mixture of chloroform:methanol:ammonium (40:8:1).

LRMS (m/z): 538 (M+1)+

Intermediate 40

(3R)-1-azabicyclo[2.2.2]oct-3-yl(4-{(1E)-4-[6-({[(2R)-2-{[tert-butyl(dimethyl) silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate Obtained as a solid (200 mg, 23%) from (3R)-1-azabicyclo[2.2.2]oct-3-yl{4-[(1E)-4-(6-formyl-2-oxo-1,3-benzoxazol-3(2H)-yl)but-1-en-1-yl]biphenyl-2-yl}carbamate (Intermediate 39; 650 mg, 1.21 mmol, 5-((1R)-2-amino-1-{[tert-butyl(dimethyl)-silyl]oxy}ethyl)-8-hydroxyquinolin-2(1H)-one acetate (331 mg, 0.99 mmol) (prepared according to prepara-tion 8 from US20060035931), DIEA (0.25 mL, 1.49 mmol) and sodium triacetoxyboro-hydride (630 mg, 2.97 mmol) following the experimental procedure as described for Inter-mediate 7. The crude obtained was purified by column chromatography with silica gel, eluting with a mixture of chloroform:methanol:ammonium (40:4: 0.2)

LRMS (m/z): 857 (M+1)+

Intermediate 41

(3R)-1-azabicyclo[2.2.2]oct-3-yl(4-{(1E)-4-[6-({[(2R)-2-{[tert-butyl(dimethyl) silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate Obtained as a solid (200 mg, 84%) from (3R)-1-azabicyclo[2.2.2]oct-3-yl(4-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate (Intermediate 40; 200 mg, 0.23 mmol), ammonium formate (294 mg, 4.67 mmol) and palladium hydroxide (26 mg, 0.19 mmol) following the experimental proce-dure as described for Intermediate 8. The crude obtained was used in the next step with-out further purification.

LRMS (m/z): 859 (M+1)+

Example 7

(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate dihydrofluoride Obtained as a solid (95 mg, 55%) from (3R)-1-azabicyclo[2.2.2]oct-3-yl(4-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate (Intermediate 41; 200 mg, 0.23 mmol) and triethylamine trihydrofluoride (186 μL, 1.17 mmol) following the experimental procedure as described for Example 1.

LRMS (m/z): 744 (M+1)+

1H NMR (300 MHz, dmso) δ 8.64 (s, 1H), 8.14 (bs, 1H), 7.5-7.1 (m 11H), 6.90 (s, 1H), 6.47 (bs, 1H), 5.05 (bs, 1H), 4.47 (bs, 1H), 4.01-3.8 (m, 5H), 3.15-2.86 (m, 2H), 2.63 (s, 4H), 2.41-2.21 (m, 1H), 2.07 (s, 2H), 1.67 (bs, 5H), 1.17 (bs, 4H).

Intermediate 42 benzyl(trans-4-hydroxycyclohexyl)carbamate

Obtained as a white solid (5.27 g, 84%) from trans-4-aminocyclohexanol (3.8 g, 0.025 mol), benzyl chloroformiate (3.9 mL, 0.027 mL) and sodium carbonate (5.8 g, 0.054 mol) following the experimental procedure as described in J. Med. Chem., 1987, 30, 2, 313. The crude ob-tained was used in the next step without further purification.

LRMS (m/z): 250 (M+1)+

Intermediate 43 trans-4-benzyl-aminocyclohexyl(4-bromobiphenyl-2-yl)carbamate

To a solution of 4-bromo-2-isocyanatobiphenyl (1.88 g, 0.007 mol) in toluene (5 mL) was added benzyl(trans-4-hydroxycyclohexyl)carbamate (Intermediate 42; 2.27 g, 0.009 mol) in toluene (20 mL). The reaction mixture was stirred for 7 hours at 90° C. The solvent was removed under reduced pressure giving an oil, which was purified by column chromatog-raphy with silica gel, eluting with a mixture of Hexane:ether. The title compound was ob-tained as a white solid (1.7 g, 47%)

LRMS (m/z): 524 (M+1)+

Intermediate 44 trans-4-benzylaminocyclohexyl{4-[(1E)-3-(5-formyl-1H-1,2,3-benzotriazol-1-yl)prop-1-en-1-yl]biphenyl-2-yl}carbamate Obtained as a solid (500 mg, 59%) from trans-4-tert-butylaminocyclohexyl(4-bromobiphenyl-2-yl)carbamate (Intermediate 43; 700 mg, 1.34 mmol), 1-allyl-1H-1,2,3-benzotriazole-5-carbaldehyde (Intermediate 24; 455 mg, 1.34 mmol), tri-o-tolylphosphine (407 mg, 1.34 mmol), N,N-Diisopropylethylamine (0.46 mL, 2.67 mmol) and pal-ladium ace-tate (221 mg, 0.67 mmol) following the experi-mental procedure as described for Intermedi-ate 6. The crude obtained was purified by column chromatography with silica gel, eluting with a mixture of Hexane:ether.

LRMS (m/z): 630 (M+1)+

Intermediate 45 trans-4-benzylaminocyclohexyl(4-{(1E)-3-[5-({[(2R)-2-{[tert-butyl(dimethyl)silyl]-oxy}-2-(8-hydroxy-2-oxo-1,2-dihydroquinolin-5-yl)ethyl]amino}methyl)-1H-1,2,3-benzotriazol-1-yl]prop-1-en-1-yl}biphenyl-2-yl)carbamate Obtained as a solid (150 mg, 20%) from trans-4-tert-butylaminocyclohexyl{4-[(1E)-3-(5-formyl-1H-1,2,3-benzotriazol-1-yl)prop-1-en-1-yl]biphenyl-2-yl}carbamate (Intermediate 44; 500 mg, 0.79 mmol), 5-((1R)-2-amino-1-{[tert-butyl(dimethyl)-silyl]oxy}ethyl)-8-hydroxyquinolin-2(1H)-one acetate (265 mg, 0.79 mmol) (prepared according to prepara-tion 8 from US20060035931), DIEA (0.2 mL, 1.19 mmol) and sodium triacetoxyborohydride (505 mg, 2.38 mmol) following the experimental procedure as described for Intermediate 7. The crude obtained was purified by column chromatography with silica gel, eluting with a mixture of chloroform:methanol:ammonium (40:4:0.2)
LRMS (m/z): 949 (M+1)+

Intermediate 46 trans-4-aminocyclohexyl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]propyl}biphenyl-2-yl)carbamate Obtained as a solid (150 mg, 99%) from trans-4-benzylaminocyclohexyl(4-{(1E)-3-[5-({[(2R)-2-{[tert-butyl(dimethyl)silyl]oxy}-2-(8-hydroxy-2-oxo-1,2-dihydroquinolin-5-yl)-ethyl]-amino}methyl)-1H-1,2,3-benzotriazol-1-yl]prop-1-en-1-yl}biphenyl-2-yl)carbamate (150 mg, 0.16 mmol), ammonium formate (199 mg, 3.16 mmol) and palladium hydroxide (18 mg, 0.13 mmol) following the experimental procedure as described for Intermediate 8. The crude obtained was used in the next step without further purification.
LRMS (m/z): 817 (M+1)+

Example 8 trans-4-aminocyclohexyl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate dihydrofluoride Obtained as a white solid (23 mg, 17%) from trans-4-aminocyclohexyl(4-{3-[5-({[(2R)-2-{[tert-butyl(dimethyl)silyl]oxy}-2-(8-hydroxy-2-oxo-1,2-dihydroquinolin-5-yl)ethyl]amino}-methyl)-1H-1,2,3-benzotriazol-1-yl]propyl}biphenyl-2-yl)carbamate (150 mg, 0.18 mmol) and triethylamine trihydrofluoride (186 µL, 1.17 mmol) following the experimen-tal procedure as described for Example 1. The crude obtained was purified by reversed phase using as eluents Methanol and Water.
LRMS (m/z): 702 (M+1)+
1H NMR (300 MHz, cd3od) δ 8.28 (d, J=9.8 Hz, 1H), 8.10 (s, 1H), 7.81 (d, J=8.4 Hz, 1H), 7.65 (d, J=8.7 Hz, 1H), 7.47-7.26 (m, 6H), 7.20 (dd, J=20.7, 8.0 Hz, 2H), 7.03 (dd, J=20.4, 7.8 Hz, 2H), 6.58 (d, J=9.9 Hz, 1H), 5.36 (s, 1H), 4.79 (s, 2H), 4.49 (s, 1H), 4.31 (s, 2H), 3.34 (s, 2H), 3.10 (bs, 2H), 2.77-2.60 (m, 2H), 2.39 (s, 2H), 2.00 (bs, 2H), 1.55-1.22 (m, 4H).

Intermediate 47

3-(but-3-en-1-yloxy)benzaldehyde

To a solution of 3-hydroxybenzaldehyde (2.5 g, 0.02 mol) in dimethylacetamide (20 mL) was added 4-bromobut-1-ene (2.19 mL, 0.022 mol) and cesium carbonate (10 g, 0.03 mol). The mixture was stirred at 60° C. for 48 hours in a sealed tub. The precipitate was filtrated and washed with ethyl acetate. The organic layer was washed with water and the organic sol-vent was removed under reduced pressure. The crude obtained was purified by column chromatography with silica gel, eluting with a mixture of hexane:ether, and the title com-pound was obtained as a solid (2.1 g, 58%).
LRMS (m/z): 177 (M+1)+

Intermediate 48

(3R)-1-azabicyclo[2.2.2]oct-3-yl{4-[(1E)-4-(3-formylphenoxyl)but-1-en-1-yl]biphenyl-2-yl}carbamate Obtained as a solid (207 mg, 88%) from 3-(but-3-en-1-yloxy)benzaldehyde (Intermediate 47; 79 mg, 0.45 mmol), (3R)-1-azabicyclo[2.2.2]oct-3-yl(4-bromobiphenyl-2-yl)carbamate (Intermediate 5; 225 mg, 0.56 mmol), tri-o-tolylphosphine (136 mg, 0.45 mmol), N,N-Diisopropylethylamine (156 µL, 0.9 mmol) and palladium acetate (74 mg, 0.22 mmol) following the experimental procedure as described for intermediate 6. The crude obtained was purified by column chromatography with silica gel, eluting with a mixture of chloroform:methanol:ammonium (40:4:0.2).
LRMS (m/z): 497 (M+1)+

Intermediate 49

(3R)-1-azabicyclo[2.2.2]oct-3-yl(4-{(1E)-4-[3-({[(2R)-2-{[tert-butyl(dimethyl)silyl]oxy}-2-(8-hydroxy-2-oxo-1,2-dihydroquinolin-5-yl)ethyl]amino}methyl)phenoxy]but-1-en-1-yl}biphenyl-2-yl)carbamate Obtained as a solid (160 mg, 41%) from (3R)-1-azabicyclo[2.2.2]oct-3-yl{4-[(1E)-4-(3-formylphenoxyl)but-1-en-1-yl]biphenyl-2-yl}carbamate (Intermediate 48; 207 mg, 0.42 mmol), 5-((1R)-2-amino-1-{[tert-butyl(dimethyl)-silyl]oxy}ethyl)-8-hydroxyquinolin-2(1H)-one acetate (139 mg, 0.42 mmol) (prepared according to preparation 8 from US20060035931), DIEA (0.1 mL, 0.63 mmol) and sodium triacetoxyborohydride (265 mg, 1.25 mmol) following the experimental procedure as described for Intermediate 7. The crude obtained was purified by column chromatography with silica gel, eluting with a mix-ture of chloroform:methanol:ammonium (40:4:0.2)
LRMS (m/z): 816 (M+1)+

Intermediate 50

(3R)-1-azabicyclo[2.2.2]oct-3-yl(4-{3-[({[(2R)-2-{[tert-butyl(dimethyl)silyl]oxy}-2-(8-hydroxy-2-oxo-1,2-dihydroquinolin-5-yl)ethyl]amino}methyl)phenoxy]butyl}biphenyl-2-yl)carbamate Obtained as a solid (53 mg, 33%) from (3R)-1-azabicyclo[2.2.2]oct-3-yl(4-{(1E)-4-[3-({[(2R)-2-{[tert-butyl(dimethyl)silyl]oxy}-2-(8-hydroxy-2-oxo-1,2-dihydroquinolin-5-yl)ethyl]amino}methyl)phenoxy]but-1-en-1-yl}biphenyl-2-yl)carbamate (Intermediate 49; 160 mg, 0.2 mmol), ammonium formate (217 mg, 3.45 mmol) and palladium hydroxide (19 mg, 0.14 mmol) following the experimental procedure as described for Intermediate 8. The crude obtained was purified by column chromatography with silica gel, eluting with a mixture of chloroform:methanol:ammonium (40:4:0.2)
LRMS (m/z): 818 (M+1)+

Example 9

(3R)-1-azabicyclo[2.2.2]oct-3-yl(4-{3-[({[(2R)-2-hydroxy-2-(8-hydroxy-2-oxo-1,2-dihydroquinolin-5-yl)ethyl]amino}methyl)phenoxy]butyl}biphenyl-2-yl)carbamate dihydrofluoride Obtained as a yellow solid (31 mg, 63%) from (3R)-1-azabicyclo[2.2.2]oct-3-yl(4-{3-[({[(2R)-2-{[tert-butyl(dimethyl)silyl]oxy}-2-(8-hydroxy-2-oxo-1,2-dihydroquinolin-5-yl)ethyl]amino}methyl)phenoxy]butyl}biphenyl-2-yl)carbamate (Intermediate 50; 54 mg, 0.07 mmol) and triethylamine trihydrofluoride (53 μL, 0.33 mmol) following the experimental procedure as described for Example 1.

LRMS (m/z): 703 (M+1)+

1H NMR (300 MHz, dmso) δ 8.66 (s, 1H), 8.11 (d, J=9.5 Hz, 1H), 7.38 (m, 5H), 7.20 (bs, 3H), 7.06 (d, J=8.1 Hz, 2H), 6.90 (d, J=9.3 Hz, 2H), 6.80 (s, 1H), 6.46 (d, J=9.1 Hz, 1H), 5.08 (s, 1H), 4.50 (s, 1H), 3.96 (s, 2H), 3.74 (s, 2H), 3.12-2.95 (m, 2H), 2.67 (bs, 5H), 2.08 (bs, 1H), 1.75 (s, 3H), 1.57 (bs, 2H), 1.46 (s, 1H), 1.29 (s, 1H), 1.09 (s, 1H)

Intermediate 51

4-(but-3-en-1-yloxy)benzaldehyde

To a solution of 4-hydroxybenzaldehyde (2 g, 0.016 mol) in dimethylformamide (14 mL) was added 4-bromobut-1-ene (2.4 mL, 0.024 mol) and potassium carbonate (3.7 g, 0.026 mol). The reaction mixture was stirred for 20 hours at 60° C. Water was added into the reaction and the crude was extracted with ethyl acetate. The organic layer was washed several times with water. The organics were dried, filtered and the solvent was removed under reduced pressure giving a solid (1.97 g, 68%) as the title compound, which was used in the next step without further purification.

LRMS (m/z): 177 (M+1)+

Intermediate 52

(3R)-1-azabicyclo[2.2.2]oct-3-yl{4-[(1E)-4-(4-formylphenoxy)but-1-en-1-yl]biphenyl-2-yl}carbamate Obtained as an oil (207 mg, 65%) from 4-(but-3-en-1-yloxy)benzaldehyde (Intermediate 51; 99 mg, 0.56 mg), (3R)-1-azabicyclo[2.2.2]oct-3-yl(4-bromobiphenyl-2-yl)carbamate (Intermediate 5; 225 mg, 0.45 mmol), tri-o-tolylphosphine (170 mg, 0.56 mmol), N,N-Diisopropylethylamine (195 μL, 1.12 mmol) and palladium acetate (63 mg, 0.28 mmol) following the experimental procedure as described for intermediate 6. The crude obtained was purified by column chromatography with silica gel, eluting with a mixture of chloroform:methanol:ammonium (40:4:0.2).

LRMS (m/z): 497 (M+1)+

Intermediate 53

(3R)-1-azabicyclo[2.2.2]oct-3-yl(4-{(1E)-4-[4-({[(2R)-2-{[tert-butyl(dimethyl) silyl]oxy}-2-(8-hydroxy-2-oxo-1,2-dihydroquinolin-5-yl)ethyl]amino}methyl)phenoxy]but-1-en-1-yl}biphenyl-2-yl)carbamate Obtained as a solid (96 mg, 24%) from (3R)-1-azabicyclo[2.2.2]oct-3-yl{4-[(1E)-4-(4-formylphenoxy)but-1-en-1-yl]biphenyl-2-yl}carbamate (Intermediate 52; 205 mg, 0.41 mmol), 5-((1R)-2-amino-1-{[tert-butyl(dimethyl)-silyl]oxy}ethyl)-8-hydroxyquinolin-2(1H)-one acetate (207 mg, 0.37 mmol) (prepared according to preparation 8 from US20060035931), DIEA (0.1 mL, 0.62 mmol) and sodium triacetoxyborohydride (263 mg, 1.24 mmol) following the experimental procedure as described for Intermediate 7. The crude obtained was purified by column chromatography with silica gel, eluting with a mix-ture of chloroform: methanol:ammonium (40:4:0.2)

LRMS (m/z): 816 (M+1)+

Intermediate 54

(3R)-1-azabicyclo[2.2.2]oct-3-yl(4-{4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]butyl}biphenyl-2-yl)carbamate Obtained as a solid (70 mg, 48%) from (3R)-1-azabicyclo[2.2.2]oct-3-yl(4-{(1E)-4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]but-1-en-1-yl}biphenyl-2-yl)carbamate (Intermediate 53; 96 mg, 0.09 mmol), ammonium formate (56 mg, 0.89 mmol) and palladium hydroxide (11 mg, 0.08 mmol) following the experimental procedure as described for Intermediate 8.

LRMS (m/z): 818 (M+1)+

Example 10

(3R)-1-azabicyclo[2.2.2]oct-3-yl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate Obtained as a solid (8 mg, 27%) from (3R)-1-azabicyclo[2.2.2]oct-3-yl(4-{4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]butyl}biphenyl-2-yl)carbamate (Intermediate 54; 70 mg, 0.04 mmol) and triethylamine trihydrofluoride (35 μL, 0.21 mmol) following the experimental procedure as described for Example 1. The crude obtained was purified by column chro-matography with silica gel, eluting with a mixture of chloroform:methanol:ammonium (40:4:0.2)

LRMS (m/z): 703 (M+1)+

1H NMR (300 MHz, cd3od) δ 8.23 (d, J=8.9 Hz, 1H), 7.31 (bs, 5H), 7.18-7.16 (m, 5H), 6.91-6.89 (m, 4H), 6.58 (d, J=9.0 Hz, 1H), 5.19 (s, 1H), 4.64 (s, 1H), 3.98 (s, 2H), 3.75-3.71 (m, 6H), 3.60 (s, 1H), 3.12 (s, 1H), 2.73 (s, 6H), 2.56 (s, 1H), 1.63-1.04 (m, 5H).

Intermediate 55 tert-butyl[2-(4-hydroxyphenyl)ethyl]carbamate

To a solution of 4-(2-aminoethyl)phenol (2 g, 0.014 mol) in a mixture of water and dioxane (30 mL/15 mL) was added potassium carbonate (2 g, 0.014 mol). The mixture was cooled to 0° C. and a solution of di-tert-butyl dicarbonate (3.18 g, 0.014 mol) in dioxane (15 mL) was added drop wise. The mixture was stirred for 1.5 h at room temperature. The crude was partitioned between ethyl acetate and water, and the organic layer was washed with bi-carbonate and brine. The organics were dried, filtered and the solvent was removed under reduced pressure giving the title compound as a white solid (3.3 g, 99%), which was used in the next step without further purification.

LRMS (m/z): 238 (M+1)+

Intermediate 56 tert-butyl {2-[4-(but-3-en-1-yloxy)phenyl]ethyl}carbamate

Obtained as an oil (680 mg, 16%) from tert-butyl[2-(4-hydroxyphenyl)ethyl]carbamate (In-termediate 55; 1.73 g, 0.007 mol), 4-bromobut-1-ene (0.88 mL, 0.008 mol) and potassium carbonate (1.21 g, 0.008 mol) following the experimental procedure as described for Inter-mediate 51 and the crude obtained was purified by column chromatography with silica gel, eluting with a mixture of Hexane: Ether.

LRMS (m/z): 292 (M+1)+

Intermediate 57 trans-4-tert-butylaminocyclohexyl{4-[(1E)-4-(4-{2-[(tert-butoxycarbonyl)amino]ethyl}phenoxy)but-1-en-1-yl]biphenyl-2-yl}carbamate Obtained as a solid (246 mg, 50%) from tert-butyl {2-[4-(but-3-en-1-yloxy)phenyl]ethyl}carbamate (194 mg, 0.67 mmol), trans-4-benzyl-aminocyclohexyl(4-bromobiphenyl-2-yl)carbamate (Intermediate 43; 350 mg, 0.67 mmol), tri-o-tolylphosphine (203 mg, 0.67 mmol), N,N-Diisopropyl-ethylamine (233 µL, 1.34 mmol) and palladium acetate (110 mg, 0.33 mmol) following the experimental procedure as described for intermediate 6. The crude obtained was purified by column chromatography with silica gel, eluting with a mixture of chloroform:ethanol LRMS (m/z): 734 (M+1)+

Intermediate 58 trans-4-tert-butylaminocyclohexyl(4-{(1E)-4-[4-(2-aminoethyl)phenoxy]but-1-en-1-yl}biphenyl-2-yl)carbamate To a solution of trans-4-tert-butylaminocyclohexyl{4-[(1E)-4-(4-{2-[(tert-butoxycarbonyl)amino]ethyl}phenoxy)but-1-en-1-yl]biphenyl-2-yl}carbamate (Intermediate 57; 240 mg, 0.33 mmol) was added hydrogen chloride 4N in dioxane (2.04 mL, 8.18 mmol). The mixture was stirred for 2 hours at room temperature. The solvent was removed under re-duced pressure and the crude obtained was purified by column chromatography with silica gel, eluting with a mixture of chloroform:methanol:ammonium (40:4:0.2). The title com-pound was obtained as solid (135 mg, 65%).

LRMS (m/z): 634 (M+1)+

Intermediate 59 trans-4-tert-butylaminocyclohexyl{4-[(1E)-4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)but-1-en-1-yl]biphenyl-2-yl}carbamate Obtained as a solid (145 m, 75%) from trans-4-tert-butylaminocyclohexyl(4-{(1E)-4-[4-(2-aminoethyl)phenoxy]but-1-en-1-yl}biphenyl-2-yl)carbamate (100 mg, 0.16 mmol), 8-(benzyloxy)-5-((1R)-2-bromo-1-{[tert-butyl(dimethyl)silyl]oxy}ethyl)quinolin-2(1H)-one (US20040059116) (77 mg, 0.16 mmol), sodium bicarbonate (39 mg, 0.47 mmol) and sodium iodine (35 mg, 0.24 mmol) following the experimental procedure as described for Interme-diate 13 and the crude obtained was used in the next step without further purification.

LRMS (m/z): 1042 (M+1)+

Intermediate 60 trans-4-aminocyclohexyl(4-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]butyl}biphenyl-2-yl)carbamate trans-4-tert-butylaminocyclohexyl{4-[(1E)-4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)but-1-en-1-yl]biphenyl-2-yl}carbamate (Intermediate 59; 16 mg) was dissolved in MeOH (2 mL) and submitted to submitted twice to an H-Cube® Continu-ous-flow Hydrogenation Reactor. Conditions used: Pressure: Full H2, Flow 1 mL/min, $T^a$ 35° C. The solvent was removed under reduced pressure and the title compound was obtained as a solid (5 mg, 33%), which was used in the final step without further manipulation.

LRMS (m/z): 820 (M+1)+

Example 11 trans-4-aminocyclohexyl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate dihydrofluoride Obtained as a white solid (4 mg, 84%) from trans-4-aminocyclohexyl(4-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]butyl}biphenyl-2-yl)carbamate (Intermediate 60; 5 mg, 33%) and triethylamine trihydrofluoride (6 µL, 0.04 mmol) following the experi-mental procedure as described for Example 1.

LRMS (m/z): 705 (M+1)+

1H NMR (300 MHz, dmso) δ 8.55 (bs, 1H), 7.34-7.33 (m, 7H), 7.04-7.02 (m, 4H), 6.86 (bs, 3H), 6.42 (bs, 1H), 5.41 (bs, 1H), 4.44-4.22 (m, 1H), 3.95 (s, 1H), 2.82-2.70 (m, 6H), 2.10-1.65 (m, 4H), 1.22 (bs, 4H), 1.07 (bs, 4H), 0.98-0.65 (m, 3H).

Intermediate 61 methyl 3-amino-4-hydroxybenzoate

Hydrogen chloride (1.25M in Methanol, 100 mL) was placed in a reactor at 0° C. Then 3-amino-4-hydroxybenzoic acid (5 g, 0.032 mol) was added in portions. The reaction mixture was stirred 5 minutes at 0° C. and 24 hours at room temperature. The solvent was removed under reduced pres-sure and the crude was partitioned between ethyl acetate and satu-rated bicarbonate. The organics layer were combined, dried, filtered and the solvent was removed under reduced pressure to obtain the title compound as a solid (5.38 g, 98%), which was used in the next step without further purification.

LRMS (m/z): 168 (M+1)+

Intermediate 62 methyl 2-but-3-en-1-yl-1,3-benzoxazole-5-carboxylate

A round-bottomed flask fitted with stir bar was charged with methyl 3-amino-4-hydroxybenzoate (498 mg, 2.98 mmol) in xylenes (15 mL). Triethylamine (0.46 mL, 3.3 mmol) and pyridine 4-methylbenzenesulfonate (256 mg, 1.02 mmol) were added suc-cessively, and the mixture was stirred 5 min until (almost) complete dissolution of the starting materials. Pent-4-enoyl chloride (0.35 mL, 3.3 mmol) was added drop wise to the cooled (ice/water bath) mixture, and then stirred at room temperature for 1 h. After having performed the first step, the flask is coupled to a Dean-Stark condenser system, and the mixture is heated at reflux overnight (T display=170° C.). The mixture is diluted with ethyl acetate, washed with saturated bicarbonate, the aqueous layer was extracted with ethyl acetate, and com-bined organic layers were washed with brine, dried over MgSO4, filtered and concentrated to give 540 mg (70%) of a brown solid, which was used in the next step without further purification.

LRMS (m/z): 232 (M+1)+

Intermediate 63

(2-but-3-en-1-yl-1,3-benzoxazol-5-yl)methanol

A round-bottomed flask fitted with stir bar was charged with methyl 2-but-3-en-1-yl-1,3-benzoxazole-5-carboxylate (Intermediate 62; 540 mg, 2.34 mmol) in 10 mL anhydrous tet-rahydrofurane and under Argon atmosphere. The mixture was cooled with an ice/water bath and lithium aluminium hydride was added cautiously. The solution is stirred at 0° C. for 30 min, and then a further 30 min at rt. The reaction is quenched by sequentially addi-tion of n:n:3n (where n is the LiAlH4 mass), that is 100 μL H2O:100 μL NaOH 4N:300 μL H2O, and then is stirred 15 min at rt. The solid formed is filtered and the resulting solution is concentrated under reduced pressure to give 450 mg (90%) of a dark brown oil, which was used in the next step without further purification.

LRMS (m/z): 204 (M+1)+

Intermediate 64

2-but-3-en-1-yl-1,3-benzoxazole-5-carbaldehyde

A round-bottomed flask fitted with stir bar was charged with (2-but-3-en-1-yl-1,3-benzoxazol-5-yl)methanol (Inter-mediate 63; 430 mg, 2.12 mmol) in wet DCM. Dess-Martin periodinane (1.03 g, 2.44 mmol) was added portion wise and the mixture stirred at room temperature for 30 minutes. The reaction was quenched by addition of saturated bicarbonate (little bubbling) and thiosulfate solutions, and diluted with DCM. The organic layer was washed with more bicarbonate solution (twice), brine, dried over MgSO4, filtered and concentrated. The residue was purified by usual column chromatography (Ethyl acetate in hexanes gradient, 0-10-25-40%) to give 300 mg (67%) as a brown oil.

LRMS (m/z): 202 (M+1)+

Intermediate 65

(3R)-1-azabicyclo[2.2.2]oct-3-yl{4-[(1E)-4-(5-formyl-1,3-benzoxazol-2-yl)but-1-en-1-yl]biphenyl-2-yl}carbamate Obtained as an orange gum (287 mg, 81%) from 2-but-3-en-1-yl-1,3-benzoxazole-5-carbaldehyde (Intermediate 64; 150 mg, 0.75 mmol), (3R)-1-azabicyclo[2.2.2]oct-3-yl (4-bromobiphenyl-2-yl)carbamate (Intermediate 5; 300 mg, 0.75 mmol), tri-o-tolylphosphine (226 mg, 0.74 mmol), N,N-Diisopropylethylamine (260 μL, 1.49 mmol) and pal-ladium acetate (84 mg, 0.37 mmol) following the experi-mental procedure as described for intermediate 6. The crude obtained was purified by column chromatography with silica gel, eluting with a mixture of chloroform:methanol:ammo-nium (40:4:0.2).

LRMS (m/z): 522 (M+1)+

Intermediate 66

(3R)-1-azabicyclo[2.2.2]oct-3-yl(4-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-1,3-benzoxazol-2-yl]but-1-en-1-yl}biphenyl-2-yl)carbamate Obtained as a solid (240 mg, 28%) from (3R)-1-azabicy-clo[2.2.2]oct-3-yl{4-[(1E)-4-(5-formyl-1,3-benzoxazol-2-yl]but-1-en-1-yl]biphenyl-2-yl}carbamate (Intermediate 65; 418 mg, 0.8 mmol), 5-((1R)-2-amino-1-{[tert-butyl(dim-ethyl)-silyl]oxy}ethyl)-8-hydroxyquinolin-2(1H)-one acetate (316 mg, 0.80 mmol) (prepared according to pre-para-tion 8 from US20060035931) and sodium triacetoxy-borohydride (510 mg, 2.41 mmol) fol-lowing the experi-mental procedure as described for Intermediate 7. The crude obtained was purified by column chromatography with silica gel, eluting with a mixture of chloro-form:methanol:ammo-nium (40:4:0.2)

LRMS (m/z): 841 (M+1)+

Intermediate 67

(3R)-1-azabicyclo[2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1,3-benzoxazol-2-yl]butyl}biphenyl-2-yl)carbamate A round-bottomed flask fitted with stir bar was charged with (3R)-1-azabicyclo[2.2.2]oct-3-yl(4-{(1E)-4-[5-({[(2R)-2-{[tert-butyl(dimethyl)silyl]oxy}-2-(8-hy-droxy-2-oxo-1,2-dihydroquinolin-5-yl)ethyl]amino}methyl)-1,3-benzoxazol-2-yl]but-1-en-1-yl}biphenyl-2-yl)carbamate (Intermediate 66; 137 mg, 0.16 mmol) in MeOH (5 mL) The flask was filled with Argon, and then Pd/C (145 mg, 0.14 mmol) was added employing an Argon cone stream to avoid solvent ignition. The flask was coupled with a quick-fit T-adaptor with one outlet to the hydrogen balloon and the other to the vacuum line. The flask was emptied by connecting it to the vacuum and then filled with hydrogen. This operation was repeated twice. The mixture was stirred vigorously at room temperature for 1.5 h. A further 40 mg of Pd/C were added employing the previously described procedure. The mixture was vigor-ously stirred at room temperature for 1 h. The Pd/C was filtered off and the solution con-centrated under reduced pressure. The solid was again dissolved in 5 mL MeOH and 71 mg of Pd/C were added. The mixture is stirred at room temperature for 5.5 h. The solid was filtered through a Celite pad and concentrated under reduced pressure to give 50 mg of a dark green/brown oil/gum. The residue was purified by column chromatography using as eluents CHCl3—MeOH—NH4OH 40:2:0.2 to give the title compound as a pale yellow gum (12 mg, 7%).

LRMS (m/z): 843 (M+1)+

Example 12

(3R)-1-azabicyclo[2.2.2]oct-3-yl(4-{4-[5-({[(2R)-2-hydroxy-2-(8-hydroxy-2-oxo-1,2,3,4-tetrahydroqui-nolin-5-yl)ethyl]amino}methyl)-1,3-benzoxazol-2-yl]butyl}biphenyl-2-yl)carbamate dihydrofluoride Obtained as solid (8 mg, 80%) from (3R)-1-azabicyclo [2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1,3-benzoxazol-2-yl]butyl}biphenyl-2-yl)carbamate (Intermediate 67; 12 mg, 0.01 mmo) and triethylamine trihydrofluoride (25 µL, 0.15 mmol) following the experimental procedure as described for Example 1.

LRMS (m/z): 730 (M+1)+

1H NMR (300 MHz, cd3od) δ 7.76 (s, 1H), 7.63 (d, J=8.4 Hz, 1H), 7.50-7.29 (m, 5H), 7.23 (d, J=7.7 Hz, 1H), 7.18-6.98 (m, 3H), 6.80-6.68 (m, 2H), 4.23 (s, 1H), 3.37-3.33 (m, 5H), 3.30-3.26 (m, 5H), 3.16-2.89 (m, 5H), 2.83-2.67 (m, 2H), 2.62-2.42 (m, 2H), 2.12 (s, 1H), 2.07-1.86 (m, 3H), 1.80 (bs, 2H), 1.44-1.22 (m, 2H), 1.23-1.05 (m, 1H).

Intermediate 68 tert-butyl {2-[3-(benzyloxy)phenyl]ethyl}carbamate

To a solution of 2-(3-(benzyloxy)phenyl)ethanamine (500 mg, 2.2 mmol) in dioxane (25 mL) was added at 0° C. a solution of sodium hydroxide (88 mg, 2.2 mmol) in water (2 mL). Then a solution of di-tert-butyl dicarbonate (488 mg, 2.24 mmol) in dioxane (5 mL) was added drop wise. The reaction mixture was stirred at 0° C. for 1 hour and 4 hours at room temperature. The solvent was removed under reduced pressure and the crude obtained was partitioned between ethyl acetate and water. The organic layer was dried, filtered and the solvent was removed under reduced pressure. The residue obtained was purified by column chroma-tography eluting with Hexane:ethyl acetate (15:1) to give the title compound as a solid (329 mg, 45%).

LRMS (m/z): 328 (M+1)+

Intermediate 69 tert-butyl[2-(3-hydroxyphenyl)ethyl]carbamate

A round-bottomed flask fitted with stir bar was charged with tert-butyl {2-[3-(benzyloxy)phenyl]ethyl}carbamate (Intermediate 68; 1.43 g, 0.004 mol) in MeOH (50 mL) The flask was filled with Argon, and then Pd/C (143 mg, 0.001 mol) was added employing an Argon cone stream to avoid solvent ignition. The flask was coupled with a quick-fit T-adaptor with one outlet to the hydrogen balloon and the other to the vacuum line. The flask was emptied by connecting it to the vacuum and then filled with hydrogen. This op-eration was repeated twice. The reaction mixture was stirred overnight at room tempera-ture. The solid was filtered through a Celite pad and concentrated under reduced pressure to give the title compound as a white solid (980 mg, 98%).

LRMS (m/z): 238 (M+1)+

Intermediate 70 tert-butyl {2-[3-(allyloxy)phenyl]ethyl}carbamate

To a suspension of tert-butyl[2-(3-hydroxyphenyl)ethyl] carbamate (500 mg, 2.11 mol) in acetonitrile (5 mL) was added potassium carbonate (437 mg, 3.16 mmol) and 3-bromoprop-1-ene (0.22 mL, 2.54 mmol). The reaction mixture was stirred overnight at room temperature. The solvent was removed under reduced pressure and the crude was partitioned between ether and water. The organic layer was washed with further water, dried, filtered and evaporated, giving a crude which was purified by column chromatography with silica gel, eluting with a mixture of hexane:ether.

The title compound was obtained as a gum (488 mg, 83%).

LRMS (m/z): 278 (M+1)+

Intermediate 71

(3R)-1-azabicyclo[2.2.2]oct-3-yl{4-[(1E)-3-(3-{2-[(tert-butoxycarbonyl)amino]ethyl}phenoxy)prop-1-en-1-yl]biphenyl-2-yl}carbamate Obtained as a solid (125 mg, 28%) from tert-butyl {2-[3-(allyloxy)phenyl]ethyl}carbamate (207 mf, 0.75 mmol), (3R)-1-azabicyclo[2.2.2]oct-3-yl(4-bromobiphenyl-2-yl)carbamate (Intermediate 5; 300 mg, 0.75 mmol), tri-o-tolylphosphine (227 mg, 0.75 mmol), N,N-Diisopropylethylamine (261 µL, 1.49 mmol) and palladium acetate (84 mg, 0.37 mmol) following the experimental procedure as described for intermediate 6. The crude obtained was purified by column chromatography with silica gel, eluting with a mixture of chloroform:methanol:ammonium (40:4:0.2).

LRMS (m/z): 598 (M+1)+

Intermediate 72

(3R)-1-azabicyclo[2.2.2]oct-3-yl{4-[3-(3-{2-[(tert-butoxycarbonyl)amino]ethyl}phenoxy)propyl]biphenyl-2-yl}carbamate Obtained as a solid (161 mg, 53%) from (3R)-1-azabicyclo[2.2.2]oct-3-yl{4-[(1E)-3-(3-{2-[(tert-butoxycarbonyl)amino]ethyl}phenoxy)prop-1-en-1-yl]biphenyl-2-yl}carbamate (Inter-mediate 71; 300 mg, 0.5 mmol) following the experimental procedure as described for Intermediate 60. The crude obtained was used in the next step without further purification.

LRMS (m/z): 600 (M+1)+

Intermediate 73

(3R)-1-azabicyclo[2.2.2]oct-3-yl(4-{3-[3-(2-aminoethyl)phenoxy]propyl}biphenyl-2-yl)carbamate Obtained as a solid (82 mg, 61%) from (3R)-1-azabicyclo[2.2.2]oct-3-yl{4-[3-(3-{2-[(tert-butoxycarbonyl)amino]ethyl}phenoxy)propyl]biphenyl-2-yl}carbamate (Intermediate 72; 161 mg, 0.27 mmol) and hydrogen chloride (4M in dioxane, 1.5 mL) following the experimental procedure as described for Intermediate 58. The crude obtained was purified by column chromatography with silica gel, eluting with a mixture of chloroform:methanol:ammonium (40:4:0.2).

LRMS (m/z): 500 (M+1)+

Intermediate 74

(3R)-1-azabicyclo[2.2.2]oct-3-yl{4-[3-(3-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)propyl]biphenyl-2-yl}carbamate Obtained as a solid (52 mg, 34%) from (3R)-1-azabicyclo[2.2.2]oct-3-yl(4-{3-[3-(2-aminoethyl)phenoxy]propyl}biphenyl-2-yl)carbamate (Intermediate 73; 84 mg, 0.17 mmol), 8-(benzyloxy)-5-((1R)-2-bromo-1-{[tert-butyl(dimethyl)silyl]oxy}ethyl)quinolin-2(1H)-one (US20040059116) (82 mg, 0.17 mmol), sodium bicarbonate (42 mg, 0.50 mmol) and sodium iodine (38 mg, 0.24 mmol) following the experimental procedure as described for Intermediate 13 and the crude obtained was purified by column chromatography with silica gel, eluting with a mixture of chloroform:methanol:ammonium (40:4:0.2).

LRMS (m/z): 908 (M+1)+

Intermediate 75

(3R)-1-azabicyclo[2.2.2]oct-3-yl(4-{3-[3-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]propyl}biphenyl-2-yl)carbamate A solution of (3R)-1-azabicyclo[2.2.2]oct-3-yl{4-[3-(3-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy) propyl]biphenyl-2-yl}carbamate (52 mg, 0.06 mmol) in methanol (3 mL) was submitted tree times to an H-Cube® Continuous-flow Hydrogenation Reactor. Conditions used: Pressure: Full H2, Flow 1 mL/min, T$^a$ 60° C. The solvent was removed under reduced pressure and the title compound was obtained as a solid (23 mg, 49%), which was used in the final step without further manipulation.

LRMS (m/z): 818 (M+1)+

Example 13

(3R)-1-azabicyclo[2.2.2]oct-3-yl(4-{3-[3-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate dihydrofluoride Obtained as a solid (11 mg, 55%) from (3R)-1-azabicyclo[2.2.2]oct-3-yl(4-{3-[3-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]propyl}biphenyl-2-yl)carbamate (23 mg, 0.03 mmol) and triethylamine trihydrofluoride (100 µL, 0.61 mmol) following the experimental procedure as described for Example 1.

LRMS (m/z): 703 (M+1)+

1H NMR (300 MHz, dmso) δ 8.72 (s, 1H), 8.15 (d, J=9.9 Hz, 1H), 7.56 (bs, 1H), 7.46-7.28 (m, 5H), 7.29-7.04 (m, 3H), 6.95 bs, 1H), 6.83 (s, 2H), 6.56 (d, J=9.9 Hz, 1H), 5.27-5.14 (m, 1H), 4.54 (s, 1H), 3.99 (s, 1H), 3.21-3.03 (m, 2H), 3.02-2.89 (m, 2H), 2.75 (bs, 4H), 2.36 (s, 1H), 2.27 (s, 1H), 2.18 (s, 1H), 2.07-2.05 (m, 4H), 1.88 (d, J=15.4 Hz, 1H), 1.57 (s, 3H), 1.35 (s, 2H), 1.11 (s, 1H).

Intermediate 76

(3R)-1-azabicyclo[2.2.2]oct-3-yl{4-[(1E)-3-hydroxyprop-1-en-1-yl]biphenyl-2-yl}carbamate Obtained as a gum (282 mg, 32%) from prop-2-en-1-ol (168 mg, 2.89 mmol), (3R)-1-azabicyclo[2.2.2]oct-3-yl(4-bromobiphenyl-2-yl)carbamate (Intermediate 5; 658 mg, 1.64 mmol), tri-o-tolylphosphine (300 mg, 0.99 mmol), N,N-Diisopropylethylamine (572 µL, 3.28 mmol) and palladium acetate (110 mg, 0.49 mmol) following the experimental procedure as described for intermediate 6. The crude obtained was purified by column chromatography with silica gel, eluting with a mixture of chloroform:methanol:ammonium (40:4:0.2).

LRMS (m/z): 379 (M+1)+

Intermediate 77

(3R)-1-azabicyclo[2.2.2]oct-3-yl[4-(3-hydroxypropyl)biphenyl-2-yl]carbamate

A solution of (3R)-1-azabicyclo[2.2.2]oct-3-yl{4-[(1E)-3-hydroxyprop-1-en-1-yl]biphenyl-2-yl}carbamate (Intermediate 76; 282 mg, 0.75 mmol) in acid acetic (10 mL) was submitted tree times to an H-Cube® Continuous-flow Hydrogenation Reactor. Conditions used: Pressure: Full H2, Flow 1 mL/min, T$^a$ 30° C. The solvent was removed under reduced pres-sure and the title compound was obtained as a solid (79 mg, 62%), which was used in the final step without further manipulation.

LRMS (m/z): 381 (M+1)+

Intermediate 78

(3R)-1-azabicyclo[2.2.2]oct-3-yl(4-{3-[({[4-({[tert-butyl(dimethyl)silyl]oxy}methyl)-2-chloro-5-methoxyphenyl]amino}carbonyl)oxy]propyl}biphenyl-2-yl)carbamate To a solution of (3R)-1-azabicyclo[2.2.2]oct-3-yl[4-(3-hydroxypropyl)biphenyl-2-yl]carbamate (Intermediate 77; 20 mg, 0.05 mmol) and diisopropylethylenediamine (18 µL, 0.1 mmol) in tetrahydrofurane (5 mL) was a added a solution of tert-butyl[(5-chloro-4-isocyanato-2-methoxybenzyl)oxy] dimethylsilane (Intermediate 59 WO2011/141180A1; 30 mg, 0.09 mmol) in tetrahydrofurane (5 mL). The reaction mixture was stirred overnight at 80° C. The solvent was removed under reduced pressure and the crude obtained was purified by column chromatography with silica gel, eluting with a mixture of chloroform:methanol:ammonium (40:4:0.2). The title compound was obtained as a solid (9.9 mg, 26%).

LRMS (m/z): 709 (M+1)+

Intermediate 79

(3R)-1-azabicyclo[2.2.2]oct-3-yl(4-{3-[({[2-chloro-4-(hydroxymethyl)-5-methoxyphenyl]amino}carbonyl)oxy]propyl}biphenyl-2-yl)carbamate To a solution of (3R)-1-azabicyclo[2.2.2]oct-3-yl(4-{3-[({[4-({[tert-butyl(dimethyl)silyl]oxy}methyl)-2-chloro-5-methoxyphenyl]amino}carbonyl)oxy]propyl}biphenyl-2-yl)carbamate (Intermediate 78; 9.9 mg, 0.01 mmol) in tetrahydrofurane (5 mL) was added triethylamine trihydrofluoride (14 µL, 0.09 mmol). The reaction mixture was stirred at room temperature 24 hours. The solvent was removed under reduced pressure. The crude obtained was treated with ace-tonitrile to obtain the title compound as a gum (4 mg, 48%), and it was used in the next step without further manipulation.

LRMS (m/z): 595 (M+1)+

Intermediate 80

(3R)-1-azabicyclo[2.2.2]oct-3-yl{4-[3-({[(2-chloro-4-formyl-5-methoxyphenyl)amino]carbonyl}oxy)propyl]biphenyl-2-yl}carbamate Obtained as a foam (37 mg, 63%) from (3R)-1-azabicyclo[2.2.2]oct-3-yl(4-{3-[({[2-chloro-4-(hydroxymethyl)-5- methoxyphenyl]amino}carbonyl)oxy]propyl}biphenyl-2-yl)carbamate (Intermediate 79; 50 mg, 0.08 mmol) and Dess-Martin periodinane (39 mg, 0.09 mmol) fol-lowing the experimental procedure as described for Intermediate 64. The crude obtained was used in the next step without further purification.

LRMS (m/z): 593 (M+1)+

Intermediate 81

(3R)-1-azabicyclo[2.2.2]oct-3-yl(4-{3-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]propyl}biphenyl-2-yl)carbamate Obtained as a solid (74 mg, 62%) from (3R)-1-azabicyclo[2.2.2]oct-3-yl{4-[3-({[(2-chloro-4-formyl-5-methoxyphenyl)amino]carbonyl}oxy)propyl]biphenyl-2-yl}carbamate (Intermediate 80; 37 mg, 0.06 mmol), 5-((1R)-2-amino-1-{[tert-butyl(dimethyl)-silyl]oxy}ethyl)-8-hydroxyquinolin-2(1H)-one acetate (25 mg, 0.07 mmol) (prepared according to preparation 8 from US20060035931) and sodium triacetoxyborohydride (40 mg, 0.19 mmol) following the experimental procedure as described for Intermediate 7. The crude obtained was used in the final step without further purification.

LRMS (m/z): 911 (M+1)+

Example 14

(3R)-1-azabicyclo[2.2.2]oct-3-yl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]propyl}biphenyl-2-yl)carbamate dihydrofluoride Obtained as a solid (6 mg, 24%) from (3R)-1-azabicyclo[2.2.2]oct-3-yl(4-{3-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]propyl}biphenyl-2-yl)carbamate (Intermediate 81; 56 mg, 0.03 mmol) and triethylamine trihydrofluoride (83 µL, 0.5 mmol) following the experimental procedure as described for Example 1. The crude obtained was purified by column chromatography in reverse phase using as eluents water and acetonitrile.

LRMS (m/z): 797 (M+1)+

1H NMR (300 MHz, cd3od) δ 8.17 (d, J=9.7 Hz, 1H), 7.46 (s, 1H), 7.43-7.23 (m, 5H), 7.22-7.12 (m, 4H), 7.09 (bs, 1H), 6.90 (d, J=8.1 Hz, 1H), 6.53 (d, J=9.8 Hz, 1H), 5.10 (s, 1H), 4.60-4.53 (m, 1H), 4.25 (d, J=7.3 Hz, 1H), 4.15 (s, 1H), 3.69 (t, J=6.7 Hz, 2H), 3.15 (s, 2H), 2.86-2.60 (m, 4H), 2.00 (bs, 2H), 1.89 (bs, 2H), 1.82 (bs, 2H), 1.67 b (s, 1H), 1.53 (bs, 1H), 1.37 (bs, 1H), 1.26 (d, J=24.5 Hz, 2H).

Intermediate 82

1-but-3-en-1-yl-1H-indole-5-carbaldehyde

To a solution of 1H-indole-5-carbaldehyde (500 mg, 3.44 mmol) in dimethylformamide (5 mL) was added at 0° C. sodium hydride (124 mg, 5.17 mmol) and the solution was stirred for some minutes. Then 4-bromobut-1-ene (0.524 mL, 5.16 mmol) was added into the solu-tion and the mixture was stirred at room temperature overnight. Water was poured into the mixture and the crude was extracted with chloroform. The organic layer was washed sev-eral times with water, dried, filtered and the solvent was removed under reduced pressure to give the title compound as an oil (510 mg, 59%), which was used in the next step with-out further purification.

LRMS (m/z): 200 (M+1)+

Intermediate 83

(3R)-1-azabicyclo[2.2.2]oct-3-yl{4-[(1E)-4-(5-formyl-1H-indol-1-yl)but-1-en-1-yl]biphenyl-2-yl}carbamate Obtained as a foam (320 mg, 94%) from 1-but-3-en-1-yl-1H-indole-5-carbaldehyde (217 mg, 0.76 mmol), (3R)-1-azabicyclo[2.2.2]oct-3-yl(4-bromobiphenyl-2-yl)carbamate (Intermediate 5; 250 mg, 0.62 mmol), tri-o-tolylphosphine (150 mg, 0.49 mmol), N,N-Diisopropylethylamine (300 µL, 1.72 mmol) and palladium acetate (29 mg, 0.13 mmol) following the experimental procedure as described for intermediate 6. The crude obtained was purified by column chromatography with silica gel, eluting with a mixture of chloroform:methanol:ammonium (40:4:0.2).

LRMS (m/z): 520 (M+1)+

Intermediate 84

(3R)-1-azabicyclo[2.2.2]oct-3-yl(4-{(1E)-4-[5-({[(2R)-2-{[tert-butyl(dimethyl) silyl]oxy}-2-(8-hydroxy-2-oxo-1,2-dihydroquinolin-5-yl)ethyl]amino}methyl)-1H-indol-1-yl]but-1-en-1-yl}biphenyl-2-yl)carbamate Obtained as a foam (185 mg, 25%) from (3R)-1-azabicyclo[2.2.2]oct-3-yl{4-[(1E)-4-(5-formyl-1H-indol-1-yl)but-1-en-1-yl]biphenyl-2-yl}carbamate (Intermediate 83; 320 mg, 0.62 mmol), 5-((1R)-2-amino-1-{[tert-butyl(dimethyl)-silyl]oxy}ethyl)-8-hydroxyquinolin-2(1H)-one acetate (278 mg, 0.70 mmol) (prepared according to preparation 8 from US20060035931) and sodium triacetoxyborohydride (449 mg, 2.12 mmol) following the experimental procedure as described for Intermediate 7. The crude obtained was purified by column chromatography with silica gel, eluting with a mixture of chloroform:methanol:ammonium (40:4:0.2).

LRMS (m/z): 839 (M+1)+

Intermediate 85

(3R)-1-azabicyclo[2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]butyl}biphenyl-2-yl)carbamate Obtained as a solid diacetate salt (123 mg, 77%) from (3R)-1-azabicyclo[2.2.2]oct-3-yl(4-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]but-1-en-1-yl}biphenyl-2-yl)carbamate (Intermediate 84; 160 mg, 0.19 mmol) following the experimental procedure as described for Intermediate 77 and the crude obtained was used in the final step without further purification.

LRMS (m/z): 841 (M+1)+

Example 15

(3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-1H-indol-1-yl]butyl}biphenyl-2-yl)carbamate dihydrofluoride Obtained as a white solid (49 mg, 27%) from (3R)-1-azabicyclo[2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]butyl}biphenyl-2-yl)carbamate (Intermediate 85; 225 m, 0.23 mmol) and triethylamine trihydrofluoride (162 µL, 0.99 mmol) following the ex-perimental procedure as described for Example 1.

LRMS (m/z): 726 (M+1)+

1H NMR (300 MHz, dmso) δ 8.83 (s, 1H), 8.23 (d, J=9.9 Hz, 1H), 7.69 (s, 1H), 7.66-7.40 (m, 5H), 7.41-7.15 (m, 4H), 7.08 (bs, 2H), 6.75-6.64 (m, 1H), 6.56 (d, J=9.8 Hz, 1H), 5.30 (s, 1H), 4.65 (s, 1H), 4.37 (d, J=6.6 Hz, 2H), 4.10 (s, 2H), 3.20 (s, 2H), 2.93 (s, 2H), 2.79 (d, J=7.2 Hz, 3H), 1.98 (s, 2H), 1.72 (s, 4H), 1.43 (bs, 2H), 1.14 (bs, 1H), 1.00 (s, 1H).

Intermediate 86

3-but-3-en-1-yl-2-oxo-2,3-dihydro-1,3-benzothiazole-6-carbaldehyde

To a solution of 2-oxo-2,3-dihydrobenzo[d]thiazole-6-carbaldehyde (120 mg, 0.67 mmol) in a mixture of acetonitrile:tetrhydrofurane (5:2) was added 4-bromobut-1-ene (361 mg, 2.68 mmol), potassium iodide (22 m, 0.13 mmol) and potassium carbonate (185 mg, 1.34 mmol). The reaction mixture was stirred for 4 hours at 70° C. The mixture was filtered and the solvent was removed under reduced pressure. The crude obtained was purified by column chromatography with silica gel, eluting with a mixture of Hexane:Ether.

LRMS (m/z): 234 (M+1)+

Intermediate 87

(3R)-1-azabicyclo[2.2.2]oct-3-yl{4-[(1E)-4-(6-formyl-2-oxo-1,3-benzothiazol-3(2H)-yl)but-1-en-1-yl]biphenyl-2-yl}carbamate Obtained as a foam (114 mg, 55%) from 3-but-3-en-1-yl-2-oxo-2,3-dihydro-1,3-benzothiazole-6-carbaldehyde (87 mg, 0.37 mmol), (3R)-1-azabicyclo[2.2.2]oct-3-yl(4-bromobiphenyl-2-yl)carbamate (Intermediate 5; 150 mg, 0.37 mmol), tri-o-tolylphosphine (114 mg, 0.37 mmol), N,N-Diisopropylethylamine (130 µL, 0.75 mmol) and palladium acetate (49 mg, 0.15 mmol) following the experimental procedure as described for intermediate 6. The crude obtained was purified by column chromatography with silica gel, eluting with a mixture of chloroform:methanol:ammonium (40:4:0.2).

LRMS (m/z): 554 (M+1)+

Intermediate 88

(3R)-1-azabicyclo[2.2.2]oct-3-yl(4-{(1E)-4-[6-({[(2R)-2-{[tert-butyl(dimethyl) silyl]oxy}-2-(8-hydroxy-2-oxo-1,2-dihydroquinolin-5-yl)ethyl]amino}methyl)-2-oxo-1,3-benzothiazol-3(2H)-yl]but-1-en-1-yl}biphenyl-2-yl)carbamate Obtained as a foam (168 mg, 79%) from (3R)-1-azabicyclo[2.2.2]oct-3-yl{4-[(1E)-4-(6-formyl-2-oxo-1,3-benzothiazol-3(2H)-yl)but-1-en-1-yl]biphenyl-2-yl}carbamate (Intermedi-ate 87; 114 mg, 0.21 mmol), 5-((1R)-2-amino-1-{[tert-butyl(dimethyl)-silyl]oxy}ethyl)-8-hydroxyquinolin-2(1H)-one acetate (69 mg, 0.21 mmol) (prepared according to preparation 8 from US20060035931), sodium triacetoxyborohydride (131 mg, 0.62 mmol) and diisopropylethylenamine (0.054 mL, 0.31 mmol) following the experimental procedure as described for Intermediate 7. The crude obtained was used in the next step without further purifica-tion.

LRMS (m/z): 873 (M+1)+

Intermediate 89

(3R)-1-azabicyclo[2.2.2]oct-3-yl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzothiazol-3(2H)-yl]butyl}biphenyl-2-yl)carbamate Obtained as a foam (83 mg, 23%) from (3R)-1-azabicyclo[2.2.2]oct-3-yl(4-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzothiazol-3(2H)-yl]but-1-en-1-yl}biphenyl-2-yl)carbamate (Intermediate 88; 200 mg, 0.23 mmol) following the experimental procedure as described for Intermediate 77. The crude obtained was used in the final step without further manipulation.

LRMS (m/z): 875 (M+1)+

Example 16

(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzothiazol-3(2H)-yl]butyl}biphenyl-2-yl)carbamate dihydrofluoride Obtained as a white solid (8.4 mg, 11%) from (3R)-1-azabicyclo[2.2.2]oct-3-yl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzothiazol-3(2H)-yl]butyl}biphenyl-2-yl)carbamate (In-termediate 89; 83 mg, 0.09 mol) and triethylamine trihydrofluoride (42 µL, 0.26 mmol) follow-ing the experimental procedure as described for Example 1 and the crude obtained was purified by column chromatography in reversed phase, eluting with a mixture of methanol and water.

LRMS (m/z): 760 (M+1)+

1H NMR (300 MHz, cd3od) δ 8.26 (d, J=9.8 Hz, 1H), 7.57 (d, J=15.1 Hz, 1H), 7.38 (d, J=5.1 Hz, 5H), 7.29-7.13 (m, 4H), 7.12 (s, 1H), 6.99 (bs 2H), 6.61 (d, J=9.8 Hz, 1H), 5.31 (s, 1H), 4.76-4.59 (m, 2H), 4.07 (d, J=10.4 Hz, 2H), 3.67-3.53 (m, 1H), 3.45 (s, 1H), 3.33 (d, J=8.1 Hz, 1H), 3.23-2.95 (m, 3H), 2.68 (d, J=12.8 Hz, 1H), 2.07-2.05 (m 4H), 1.77 (s, 3H), 1.26 (bs, 4H), 1.25-1.07 (m, 2H).

Intermediate 90 tert-butyl {2-[4-(allyloxy)phenyl]ethyl}carbamate

Obtained as a solid (291 mg, 62%) from tert-butyl[2-(4-hydroxyphenyl)ethyl]carbamate (Intermediate 20 described in the patent WO2009/068177 A1; 400 mg, 1.69 mmol), 3-bromoprop-1-ene (0.29 mL, 3.37 mmol) and potassium carbonate (466 mg, 3.37 mmol) fol-lowing the experimental procedure as described for Intermediate 6. The crude obtained was purified by column chromatography with silica gel, eluting with a mixture of Hexane:Ether.
LRMS (m/z): 278 (M+1)+

Intermediate 91

(3R)-1-azabicyclo[2.2.2]oct-3-yl{4-[(1E)-3-(4-{2-[(tert-butoxycarbonyl)amino]ethyl}phenoxy)prop-1-en-1-yl]biphenyl-2-yl}carbamate Obtained as a solid (105 mg, 28%) from tert-butyl {2-[4-(allyloxy)phenyl]ethyl}carbamate (Intermediate 90; 173 mg, 0.62 mmol), (3R)-1-azabicyclo[2.2.2]oct-3-yl(4-bromobiphenyl-2-yl)carbamate (Intermediate 5; 250 mg, 0.62 mmol), tri-o-tolylphosphine (190 mg, 0.62 mmol), N,N-Diisopropylethylamine (220 µL, 1.26 mmol) and palladium acetate (70 mg, 0.31 mmol) following the experimental procedure as described for intermediate 6. The crude obtained was purified by column chromatography with silica gel, eluting with a mixture of chloroform:methanol:ammonium (40:4:0.2).
LRMS (m/z): 598 (M+1)+

Intermediate 92

(3R)-1-azabicyclo[2.2.2]oct-3-yl{4-[3-(4-{2-[(tert-butoxycarbonyl)amino]ethyl}phenoxy)propyl]biphenyl-2-yl}carbamate Obtained as a foam (150 mg, 68%) from (3R)-1-azabicyclo[2.2.2]oct-3-yl{4-[(1E)-3-(4-{2-[(tert-butoxycarbonyl)amino]ethyl}phenoxy)prop-1-en-1-yl]biphenyl-2-yl}carbamate (Inter-mediate 91; 220 mg, 0.37 mmol) and palladium on charcoal (10%; 44 mg, 0.04 mmol) follow-ing the experimental procedure as described for Intermediate 67. The crude obtained was used in the next step without further purification.
LRMS (m/z): 600 (M+1)+

Intermediate 93

(3R)-1-azabicyclo[2.2.2]oct-3-yl(4-{3-[4-(2-aminoethyl)phenoxy]propyl}biphenyl-2-yl)carbamate Obtained as a gum (51 mg, 41%) from (3R)-1-azabicyclo[2.2.2]oct-3-yl{4-[3-(4-{2-[(tert-butoxycarbonyl)amino]ethyl}phenoxy)propyl]biphenyl-2-yl}carbamate (Intermediate 92; 150 mg, 0.25 mol) and hydrogen chloride (4M in dioxane, 1.5 mL, 6 mmol) following the experimental procedure as described for Intermediate 58. The crude obtained was purified by column chromatography with silica gel, eluting with a mixture of chloroform:methanol:ammonium (40:4:0.2).
LRMS (m/z): 500 (M+1)+

Intermediate 94

(3R)-1-azabicyclo[2.2.2]oct-3-yl{4-[3-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)propyl]biphenyl-2-yl}carbamate Obtained as a solid (20 mg, 21%) from (3R)-1-azabicyclo[2.2.2]oct-3-yl(4-{3-[4-(2-aminoethyl)phenoxy]propyl}biphenyl-2-yl)carbamate (Intermediate 93; 50 mg, 0.1 mmol), 8-(benzyloxy)-5-((1R)-2-bromo-1-{[tert-butyl(dimethyl)silyl]oxy}ethyl)quinolin-2(1H)-one (US20040059116) (50 mg, 0.1 mmol), sodium bicarbonate (26 mg, 0.31 mmol) and sodium iodine (23 mg, 0.15 mmol) following the experimental procedure as described for Intermediate 13. The crude obtained was purified by column chromatography with silica gel, eluting with a mixture of chloroform:methanol:ammonium (40:4:0.2).
LRMS (m/z): 908 (M+1)+

Intermediate 95

(3R)-1-azabicyclo[2.2.2]oct-3-yl(4-{3-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]propyl}biphenyl-2-yl)carbamate A solution of (3R)-1-azabicyclo[2.2.2]oct-3-yl{4-[3-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)propyl]biphenyl-2-yl}carbamate (Intermediate 94; 20 mg, 0.02 mmol) in acetic acid (8 mL) was submitted once to an H-Cube® Continuous-flow Hydrogenation Reactor. Conditions used: Pressure: 20 bars, Flow 1 mL/min, $T^\alpha$ 40° C. The solvent was removed under reduced pressure and the title com-pound was obtained as a solid (16 mg, 88%), which was used in the final step without fur-ther manipulation.
LRMS (m/z): 818 (M+1)+

Example 17

(3R)-1-azabicyclo[2.2.2]oct-3-yl(4-{3-[4-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate dihydrofluoride Obtained as a white solid (5 mg, 40%) from (3R)-1-azabicyclo[2.2.2]oct-3-yl(4-{3-[4-(2-{[(2R)-2-{[tert-butyl(dimethyl)silyl]oxy}-2-(8-hydroxy-2-oxo-1,2-dihydroquinolin-5-yl)ethyl]amino}ethyl)phenoxy]propyl}biphenyl-2-yl)carbamate (Intermediate 95; 16 mg, 0.05 mmol) and triethylamine trihydrofluoride (14 µL, 0.09 mmol) following the experimental procedure as described for Example 1.
LRMS (m/z): 703 (M+1)+
1H NMR (300 MHz, cd3od) δ 8.34 (d, J=9.5 Hz, 1H), 7.97 (bs, 2H), 7.38 (bs, 6H), 7.14-7.12 (m, 4H), 6.95 (d, J=8.1 Hz, 1H), 6.83 (d, J=8.2 Hz, 1H), 6.65 (d, J=10.0 Hz, 1H), 5.20 (bs, 1H), 3.98 (bs, 2H), 3.58-3.43 (m, 2H), 2.97 (bs, 3H), 2.84-2.70 (m, 4H), 2.62-2.46 (m, 2H), 2.06 (bs 3H), 1.94 (s, 1H), 1.89 (s, 1H), 1.77-1.66 (m, 1H), 1.64-1.50 (m, 2H), 1.39 (s, 2H), 1.28 (s, 1H).

Intermediate 96 methyl 2-but-3-en-1-yl-1,3-benzoxazole-6-carboxylate

Obtained as a brown oil (1.32 g, 86%) from methyl 4-amino-3-hydroxybenzoate (1 g, 5.98 mmol), triethylamine (0.92 mL, 6.6 mmol), pyridine 4-methylbenzenesulfonate (0.45 g, 1.79 mmol), pent-4-enoyl chloride (0.7 mL, 6.32 mmol) following the experimental procedure as described for Intermediate 62 and the crude obtained was used in the next step without further purification.

LRMS (m/z): 232 (M+1)+

Intermediate 97

(2-but-3-en-1-yl-1,3-benzoxazol-6-yl)methanol

Obtained as a dark brown oil (311 mg, 47%) from methyl 2-but-3-en-1-yl-1,3-benzoxazole-6-carboxylate (646 mg, 2.79 mmol) following the experimental procedure as described for Intermediate 63 and the crude obtained was used in the next step without further purifica-tion.

LRMS (m/z): 204 (M+1)+

Intermediate 98

2-but-3-en-1-yl-1,3-benzoxazole-6-carbaldehyde

Obtained as a brown oil (294 mg, 86%) from (2-but-3-en-1-yl-1,3-benzoxazol-6-yl)methanol (311 mg, 1.53 mmol) and Dess-Martin periodinane (746 mg, 1.76 mmol) following the experimental procedure as described for Intermediate 64. The crude obtained was purified by column chromatography with silica gel, eluting with a mixture of Ethyl acetate:Hexane.

LRMS (m/z): 202 (M+1)+

Intermediate 99

(3R)-1-azabicyclo[2.2.2]oct-3-yl{4-[(1E)-4-(6-formyl-1,3-benzoxazol-2-yl)but-1-en-1-yl]biphenyl-2-yl}carbamate Obtained as an orange gum (280 mg, 68%) from 2-but-3-en-1-yl-1,3-benzoxazole-6-carbaldehyde (Intermediate 98; 150 mg, 0.75 mmol), (3R)-1-azabicyclo[2.2.2]oct-3-yl (4-bromobiphenyl-2-yl)carbamate (Intermediate 5; 300 mg, 0.75 mmol), tri-o-tolylphosphine (227 mg, 0.75 mmol), N,N-Diisopropylethylamine (0.26 mL, 1.49 mmol) and palladium acetate (84 mg, 0.37 mmol) following the experimental procedure as described for intermediate 6. The crude obtained was purified by column chromatography with silica gel, eluting with a mixture of chloroform:methanol:ammonium (40:4:0.2).

LRMS (m/z): 522 (M+1)+

Intermediate 100

(3R)-1-azabicyclo[2.2.2]oct-3-yl(4-{(1E)-4-[6-({[(2R)-2-{[tert-butyl(dimethyl) silyl]oxy}-2-(8-hydroxy-2-oxo-1,2-dihydroquinolin-5-yl)ethyl]amino}methyl)-1,3-benzoxazol-2-yl]but-1-en-1-yl}biphenyl-2-yl)carbamate Obtained as a yellow/orange gum (262 mg, 29%) from (3R)-1-azabicyclo[2.2.2]oct-3-yl {4-[(1E)-4-(6-formyl-1,3-benzoxazol-2-yl)but-1-en-1-yl]biphenyl-2-yl}carbamate (280 mg, 0.54 mmol), 5-((1R)-2-amino-1-{[tert-butyl(dimethyl)-silyl]oxy}ethyl)-8-hydroxyquinolin-2(1H)-one acetate (212 mg, 0.54 mmol) (prepared according to preparation 8 from US20060035931) and sodium triacetoxyborohydride (341 mg, 1.61 mmol) following the experimental procedure as described for Intermediate 7. The crude obtained was used in the next step without further purification.

LRMS (m/z): 841 (M+1)+

Intermediate 101

(3R)-1-azabicyclo[2.2.2]oct-3-yl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-1,3-benzoxazol-2-yl]butyl}biphenyl-2-yl)carbamate Obtained as a gum (50 mg, 96%) from (3R)-1-azabicyclo [2.2.2]oct-3-yl(4-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-1,3-benzoxazol-2-yl]but-1-en-1-yl}biphenyl-2-yl)carbamate (Inter-mediate 100; 132 mg, 0.08 mmol) following the experimental procedure as described for Intermediate 77 and the crude obtained was used in the next step without further purifica-tion.

LRMS (m/z): 843 (M+1)+

Example 18

(3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-1,3-benzoxazol-2-yl] butyl}biphenyl-2-yl)carbamate Obtained as a solid (3 mg, 4%) from (3R)-1-azabicyclo [2.2.2]oct-3-yl(4-{4-[6-({[(2R)-2-{[tert-butyl(dimethyl)silyl]oxy}-2-(8-hydroxy-2-oxo-1,2-dihydroquinolin-5-yl) ethyl]amino}methyl)-1,3-benzoxazol-2-yl]butyl}biphenyl-2-yl)carbamate (Intermediate 101; 160 mg, 0.09 mmol) and triethylamine trihydrofluoride (14 µL, 0.09 mmol) following the experimental procedure as described for Example 1. The crude obtained was purified by column chromatography with silica gel, eluting with a mixture of chloroform:methanol:ammonium (40:4:0.2).

LRMS (m/z): 728 (M+1)+

1H NMR (300 MHz, cd3od) δ 8.26 (d, J=9.9 Hz, 1H), 7.64 (d, J=8.5 Hz, 1H), 7.52-7.27 (m, 6H), 7.18-7.05 (m, 5H), 6.99 (d, J=8.1 Hz, 1H), 6.59 (d, J=9.8 Hz, 1H), 5.37-5.25 (m, 1H), 4.19 (s, 1H), 3.64-3.50 (m, 1H), 3.25-2.95 (m, 4H), 2.77 (dd, J=25.9, 18.3 Hz, 3H), 2.15 (s, 1H), 1.95-1.9 (m, 5H), 1.80 (bs, 4H), 1.31 (bs, 4H), 1.22-1.07 (m, 2H).

Intermediate 102 ethyl 1H-1,2,3-benzotriazole-5-carboxylate

To a solution of 1H-benzo[d][1,2,3]triazole-5-carboxylic acid (5 g, 0.03 mol) in ethanol (60 mL) was added sulphuric acid (7.35 mL, 0.13 mol). The reaction mixture was stirred at 90° C. for 8 hours. The solvent was removed and the crude was basified until pH 7-8 then extracted with ethyl acetate. The organic layer was dried, filtered and the solvent was re-moved under reduced pressure giving the title compound as a white solid (5 g, 85%), which was used in the next step without further purification.

LRMS (m/z): 192 (M+1)+

Intermediate 103 ethyl 2-but-3-en-1-yl-2H-1,2,3-benzotriazole-5-carboxylate

Obtained as a foam (2.5 g, 39%) from ethyl 1H-1,2,3-benzotriazole-5-carboxylate (Intermediate 102; 5 g, 0.026 mol), 4-bromobut-1-ene (3.19 mL, 0.031 mol) and potassium carbonate (7.23 g, 0.052 mol) following the experimental procedure as described for Intermediate 51. The crude obtained was purified by column chromatography with silica gel, eluting with a mixture of hexane:ether.

LRMS (m/z): 246 (M+1)+

Intermediate 104

(2-but-3-en-1-yl-2H-1,2,3-benzotriazol-5-yl)methanol

Obtained as an oil (1.5 g, 90%) from ethyl 2-but-3-en-1-yl-2H-1,2,3-benzotriazole-5-carboxylate (Intermediate 103; 2 g, 0.008 mol) and lithium aluminium hydride (370 mg, 0.009 mol) following the experimental procedure as described for Intermediate 63 and the crude obtained was used in the next step without further purification.

LRMS (m/z): 204 (M+1)+

Intermediate 105

2-but-3-en-1-yl-2H-1,2,3-benzotriazole-5-carbaldehyde

Obtained as an oil (300 mg, 32%) from (2-but-3-en-1-yl-2H-1,2,3-benzotriazol-5-yl)methanol (Intermediate 104; 750 mg, 3.69 mmol) and Dess-Martin periodinane (1.72 g, 4.06 mmol) following the experimental procedure as described for Intermediate 64 and the crude obtained was used in the next step without further purification.

LRMS (m/z): 202 (M+1)+

Intermediate 106

(3R)-1-azabicyclo[2.2.2]oct-3-yl{4-[(1E)-4-(5-formyl-2H-1,2,3-benzotriazol-2-yl)but-1-en-1-yl]biphenyl-2-yl}carbamate Obtained as a solid (345 mg, 76%) from 2-but-3-en-1-yl-2H-1,2,3-benzotriazole-5-carbaldehyde (Intermediate 105; 219 mg, 1.09 mmol), (3R)-1-azabicyclo[2.2.2]oct-3-yl(4-bromobiphenyl-2-yl)carbamate (Intermediate 5; 350 mg, 0.87 mmol), tri-o-tolylphosphine (265 mg, 0.87 mmol), N,N-Diisopropylethylamine (0.304 mL, 1.74 mmol) and palladium acetate (144 mg, 0.44 mmol) following the experimental procedure as described for intermediate 6. The crude obtained was purified by column chromatography with silica gel, eluting with a mixture of chloroform:methanol:ammonium (40:4:0.2).

LRMS (m/z): 522 (M+1)+

Intermediate 107

(3R)-1-azabicyclo[2.2.2]oct-3-yl(4-{(1E)-4-[5-({[(2R)-2-{[tert-butyl(dimethyl) silyl]oxy}-2-(8-hydroxy-2-oxo-1,2-dihydroquinolin-5-yl)ethyl]amino}methyl)-2H-1,2,3-benzotriazol-2-yl]but-1-en-1-yl}biphenyl-2-yl)carbamate Obtained as a solid (244 mg, 44%) from (3R)-1-azabicyclo[2.2.2]oct-3-yl{4-[(1E)-4-(5-formyl-2H-1,2,3-benzotriazol-2-yl)but-1-en-1-yl]biphenyl-2-yl}carbamate (Intermediate 106; 345 mg, 0.66 mmol), 5-((1R)-2-amino-1-{[tert-butyl(dimethyl)-silyl]oxy}ethyl)-8-hydroxyquinolin-2(1H)-one acetate (221 mg, 0.66 mmol) (prepared according to preparation 8 from US20060035931), sodium triacetoxyborohydride (420 mg, 1.98 mmol) and isopropyl ethylene diamine (173 μL, 1.74 mmol) following the experimental procedure as described for Intermediate 7. The crude obtained was purified by column chromatography with silica gel, eluting with a mixture of chloroform:methanol:ammonium (40:4:0.2).

LRMS (m/z): 841 (M+1)+

Intermediate 108

(3R)-1-azabicyclo[2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-2H-1,2,3-benzotriazol-2-yl]butyl}biphenyl-2-yl)carbamate Obtained as a diacetate salt (239 mg, 84%) from (3R)-1-azabicyclo[2.2.2]oct-3-yl(4-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-2H-1,2,3-benzotriazol-2-yl]but-1-en-1-yl}biphenyl-2-yl)carbamate (Intermediate 107; 240 mg, 0.29 mmol) following the experimental procedure as described for Intermediate 77. The crude obtained was used in the final step without further purifica-tion.

LRMS (m/z): 843 (M+1)+

Example 19

(3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-2H-1,2,3-benzotriazol-2-yl]butyl}biphenyl-2-yl)carbamate Obtained as a solid (60 mg, 26%) from (3R)-1-azabicyclo[2.2.2]oct-3-yl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-2H-1,2,3-benzotriazol-2-yl]butyl}biphenyl-2-yl)carbamate (Intermediate 108; 242 mg, 0.29 mmol) and triethylamine trihydrofluoride (230 μL, 1.44 mmol) following the experimental procedure as described for Example 1. The crude obtained was purified by column chromatography with silica gel, eluting with a mixture of chloroform:methanol:ammonium (40:4:0.2).

LRMS (m/z): 728 (M+1)+

1H NMR (400 MHz, dmso) δ 8.56 (s, 1H), 8.09 (d, J=9.9 Hz, 1H), 7.80 (d, J=9.0 Hz, 1H), 7.75 (s, 1H), 7.41-7.23 (m, 6H), 7.16 (t, J=6.1 Hz, 2H), 7.07 (d, J=7.8 Hz, 1H), 7.03 (d, J=8.2 Hz, 1H), 6.87 (d, J=8.1 Hz, 1H), 6.39 (d, J=9.9 Hz, 1H), 5.04 (dd, J=7.8, 4.4 Hz, 1H), 4.73 (t, J=7.0 Hz, 2H), 4.44 (s, 1H), 3.85 (s, 2H), 2.97 (d, J=14.6 Hz, 3H), 2.65-2.63

(m, 8H), 2.30 (s, 1H), 2.08-1.97 (m, 2H), 1.73 (s, 1H), 1.61-1.51 (m, 2H), 1.39 (s, 1H), 1.28-1.13 (m, 1H).

Intermediate 109 trans-4-tert-butylaminocyclohexyl{4-[4-(6-formyl-2-oxo-1,3-benzoxazol-3(2H)-yl)butyl]biphenyl-2-yl}carbamate Obtained as a solid (233 mg, 60%) from 3-but-3-en-1-yl-2-oxo-2,3-dihydro-1,3-benzoxazole-6-carbaldehyde (Intermediate 38; 150 mg, 0.69 mmol), trans-4-benzyl-aminocyclohexyl(4-bromobiphenyl-2-yl)carbamate (Intermediate 43; 300 mg, 0.57 mmol), tri-o-tolylphosphine (174 mg, 0.57 mmol), N,N-Diisopropylethylamine (0.199 mL, 1.15 mmol) and palladium acetate (95 mg, 0.29 mmol) following the experimental procedure as described for intermediate 6. The crude obtained was purified by column chromatography with silica gel, eluting with a mixture of Hexane:Ether.
LRMS (m/z): 662 (M+1)+

Intermediate 110 trans-4-tert-butylaminocyclohexyl(4-{(1E)-4-[6-({[(2R)-2-{[tert-butyl(dimethyl) silyl]oxy}-2-(8-hydroxy-2-oxo-1,2-dihydroquinolin-5-yl)ethyl] amino}methyl)-2-oxo-1,3-benzoxazol-3(2H)-yl]but-1-en-1-yl}biphenyl-2-yl)carbamate Obtained as an oil (50 mg, 69%) from trans-4-tert-butylaminocyclohexyl{4-[4-(6-formyl-2-oxo-1,3-benzoxazol-3(2H)-yl)butyl]biphenyl-2-yl}carbamate (Intermediate 109; 358 mg, 0.54 mol), 5-((1R)-2-amino-1-{[tert-butyl (dimethyl)-silyl]oxy}ethyl)-8-hydroxyquinolin-2(1H)-one acetate (163 mg, 0.49 mmol) (prepared according to preparation 8 from US20060035931) and sodium triacetoxyborohydride (575 mg, 2.71 mmol) following the experimental procedure as described for Intermediate 7. The crude obtained was used in the next step without further purification.
LRMS (m/z): 979 (M+1)+

Intermediate 111 trans-4-aminocyclohexyl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate Obtained as a foam (130 mg, 92%) from trans-4-tert-butylaminocyclohexyl(4-{(1E)-4-[6-({[(2R)-2-{[tert-butyl (dimethyl)silyl]oxy}-2-(8-hydroxy-2-oxo-1,2-dihydroquinolin-5-yl)ethyl]amino}methyl)-2-oxo-1,3-benzoxazol-3 (2H)-yl]but-1-en-1-yl}biphenyl-2-yl)carbamate
(Intermediate 110; 140 mg, 0.14 mmol) following the experimental procedure as described for Intermediate 77 and the crude obtained was used in the next step without further purification.
LRMS (m/z): 847 (M+1)+

Example 20 trans-4-aminocyclohexyl(4-{4-[6-({[(2R)-2-hydroxy-2-(8-hydroxy-2-oxo-1,2-dihydroquinolin-5-yl) ethyl]amino}methyl)-2-oxo-1,3-benzoxazol-3(2H)-yl]butyl}biphenyl-2-yl)carbamate dihydrofluoride Obtained as a solid (21 mg, 35%) from trans-4-aminocyclohexyl(4-{4-[6-({[(2R)-2-{[tert-butyl(dimethyl)silyl] oxy}-2-(8-hydroxy-2-oxo-1,2-dihydroquinolin-5-yl)ethyl] amino}methyl)-2-oxo-1,3-benzoxazol-3(2H)-yl] butyl}biphenyl-2-yl)carbamate (Intermediate 111; 70 mg, 0.08 mmol) and triethylamine trihydrofluoride (230 μL, 1.44 mmol) following the experimen-tal procedure as described for Example 1.
LRMS (m/z): 732 (M+1)+
1H NMR (300 MHz, dmso) δ 8.55 (s, 1H), 8.12 (d, J=9.9 Hz, 1H), 7.46-7.26 (m, 6H), 7.13-7.09 (m, 5H), 6.87 (d, J=8.3 Hz, 1H), 6.44 (d, J=9.9 Hz, 1H), 5.04 (s, 1H), 4.32 (s, 1H), 3.84 (s, 2H), 3.75 (s, 2H), 2.82 (s, 1H), 2.63 (bs, 4H), 2.08 (bs, 3H), 1.85-1.7 (m, 4H), 1.60 (s, 2H), 1.26 (s, 3H).

Intermediate 112

(5-bromobiphenyl-2-yl)amine

To a solution of biphenyl-2-amine (2.5 g, 0.015 mol) in dimethylformamide (5 mL) was added at 0° C. a solution of N-bromosuccinimide (3.16 g, 0.018 mol) in dimethylformamide (4 mL). The reaction mixture was stirred at 0° C. for 1 hour. Water was poured into the mixture and the crude was extracted with ethyl acetate. The organic layer was washed with water, dried, filtered and the solvent was removed under reduced pressure. The crude obtained was purified by column chromatography with silica gel, eluting with a mixture of Hexane:Ether, giving the title compound as an orange solid (2.6 g, 71%).
LRMS (m/z): 249 (M+1)+

Intermediate 113

5-bromo-2-isocyanatobiphenyl

Obtained as a solution in toluene (550 mg, 98%) from (5-bromobiphenyl-2-yl)amine (Inter-mediate 112; 500 mg, 2.02 mmol), triphosgene (239 mg, 0.81 mmol) and triethylamine (0.56 mL, 4.04 mmol) following the experimental procedure as described for Intermediate 4.
LRMS (m/z): 289 (M+16)+; (aliquot in MeOH and detection of methylic ester).

Intermediate 114

(3R)-1-azabicyclo[2.2.2]oct-3-yl(5-bromobiphenyl-2-yl)carbamate

Obtained as a solid (1.29 g, 37%) from 5-bromo-2-isocyanatobiphenyl (Intermediate 113; 1.88 g, 6.8 mmol) and sodium (R)-quinuclidin-3-ol (1 g, 6.7 mmol) following the experimental procedure as described for Intermediate 5 and the crude obtained was used in the next step without further purification.
LRMS (m/z): 402; 403 (M+1/M+2)+

Intermediate 115

(3R)-1-azabicyclo[2.2.2]oct-3-yl{5-[(1E)-4-(4-{2-[(tert-butoxycarbonyl)amino]ethyl}phenoxy)but-1-en-1-yl]biphenyl-2-yl}carbamate Obtained as a foam (1.29 g, 50%) from (3R)-1-azabicyclo [2.2.2]oct-3-yl(5-bromobiphenyl-2-yl)carbamate (Intermediate 114; 450 mg, 1.12 mmol), tert-butyl {2-[4-(but-3-en-1-yloxy)phenyl]ethyl}carbamate (Intermediate 9; 326 mg, 1.12 mmol), tri-o-tolylphosphine (341 mg, 1.12 mmol), N,N-Diisopropylethylamine (0.39 mL, 2.23 mmol) and palladium acetate (125 mg, 0.56 mmol) following the experimental procedure as described for intermediate 6. The crude obtained was purified by column chromatography with silica gel, eluting with a mixture of chloroform:methanol:ammonium (40:4:0.2).

LRMS (m/z): 612 (M+1)+

Intermediate 116

(3R)-1-azabicyclo[2.2.2]oct-3-yl(5-{(1E)-4-[4-(2-aminoethyl)phenoxy]but-1-en-1-yl}biphenyl-2-yl) carbamate Obtained as solid (120 mg, 65%) from (3R)-1-azabicyclo[2.2.2]oct-3-yl{5-[(1E)-4-(4-{2-[(tert-butoxycarbonyl)amino]ethyl}phenoxy)but-1-en-1-yl]biphenyl-2-yl}carbamate (Inter-mediate 115; 130 mg, 0.21 mmol) and hydrogen chloride (2M in diethyl ether, 1.59 mL) following the experimental procedure as described for Intermediate 58 and the crude obtained was used in the next step without further purification.

LRMS (m/z): 512 (M+1)+

Intermediate 117

(3R)-1-azabicyclo[2.2.2]oct-3-yl{5-[(1E)-4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy) but-1-en-1-yl]biphenyl-2-yl}carbamate Obtained as solid (92 mg, 7%) from (3R)-1-azabicyclo[2.2.2]oct-3-yl(5-{(1E)-4-[4-(2-aminoethyl)phenoxy]but-1-en-1-yl}biphenyl-2-yl)carbamate (Intermediate 116; 120 mg, 0.23 mmol), 8-(benzyloxy)-5-((1R)-2-bromo-1-{[tert-butyl(dimethyl)silyl]oxy}ethyl) quinolin-2(1H)-one (US20040059116) (66 mg, 0.14 mmol), sodium bicarbonate (69 mg, 0.82 mmol) and sodium iodide (61 mg, 0.41 mmol) following the experimental procedure as described for Intermediate 13. The crude obtained was used in the next step without further purifica-tion.

LRMS (m/z): 920 (M+1)+

Intermediate 118

(3R)-1-azabicyclo[2.2.2]oct-3-yl(5-{4-[4-(2-{[(2R)-2-{[tert-butyl(dimethyl)silyl]oxy}-2-(8-hydroxy-2-oxo-1,2-dihydroquinolin-5-yl)ethyl]amino}ethyl) phenoxy]butyl}biphenyl-2-yl)carbamate Obtained as a solid (46 mg, 68%) from (3R)-1-azabicyclo[2.2.2]oct-3-yl{5-[(1E)-4-(4-{2-[((2R)-2-[8-(benzyloxy)-2-oxo-1,2-dihydroquinolin-5-yl]-2-{[tert-butyl(dimethyl)silyl]oxy}ethyl)amino]ethyl}phenoxy)but-1-en-1-yl]biphenyl-2-yl}carbamate (Intermediate 117; 71 mg, 0.08 mmol) following the experimental procedure as described for Intermediate 77 and the crude obtained was used in the final step without further manipulation.

LRMS (m/z): 832 (M+1)+

Example 21

(3R)-1-azabicyclo[2.2.2]oct-3-yl(5-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate dihydrofluoride Obtained as solid (25 mg, 68%) from (3R)-1-azabicyclo[2.2.2]oct-3-yl(5-{4-[4-(2-{[(2R)-2-{[tert-butyl(dimethyl) silyl]oxy}-2-(8-hydroxy-2-oxo-1,2-dihydroquinolin-5-yl) ethyl]amino}ethyl)phenoxy]butyl}biphenyl-2-yl)carbamate (Intermediate 118; 46 mg, 68%) and triethylamine trihydrofluoride (39 μL, 0.24 mmol) following the experimental pro-cedure as described for Example 1.

LRMS (m/z): 717 (M+1)+

1H NMR (300 MHz, dmso) δ 8.67 (s, 1H), 8.18 (bs, 1H), 7.38 (s, 5H), 7.29-7.12 (m, 3H), 7.07 (bs, 2H), 6.93 (bs, 1H), 6.82 (d, J=7.5 Hz, 1H), 6.50 (bs, 1H), 5.16 (s, 1H), 4.49 (s, 1H), 3.94 (bs, 2H), 3.03 (bs, 2H), 2.84 (bs, 4H), 2.67 (s, 4H), 2.08 (bs, 2H), 1.76-1.6 (m, 4H), 1.57 (s, 1H), 1.46 (bs, 2H), 1.29 (bs, 2H), 1.02 (bs, 2H).

Intermediate 119

(3R)-1-azabicyclo[2.2.2]oct-3-yl{5-[(1E)-4-(6-formyl-2-oxo-1,3-benzoxazol-3(2H)-yl)but-1-en-1-yl]biphenyl-2-yl}carbamate Obtained as a foam (480 mg, 53%) from (3R)-1-azabicyclo[2.2.2]oct-3-yl(5-bromobiphenyl-2-yl)carbamate (Intermediate 114; 554 mg, 1.38 mmol), 3-but-3-en-1-yl-2-oxo-2,3-dihydro-1,3-benzoxazole-6-carbaldehyde (Intermediate 38; 300 mg, 1.38 mmol), tri-o-tolylphosphine (336 mg, 1.1 mmol), N,N-Diisopropylethylamine (0.48 mL, 2.76 mmol) and palladium acetate (124 mg, 0.37 mmol) following the experimental procedure as described for inter-mediate 6. The crude obtained was purified by column chromatography with silica gel, eluting with a mixture of chloroform:methanol:ammonium (40:4:0.2).

LRMS (m/z): 538 (M+1)+

Intermediate 120

(3R)-1-azabicyclo[2.2.2]oct-3-yl(5-{(1E)-4-[6-({[(2R)-2-{[tert-butyl(dimethyl) silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate Obtained as solid (316 mg, 51%) from (3R)-1-azabicyclo[2.2.2]oct-3-yl{5-[(1E)-4-(6-formyl-2-oxo-1,3-benzoxazol-3(2H)-yl)but-1-en-1-yl]biphenyl-2-yl}carbamate (Intermediate 119; 170 mg, 0.43 mmol), 5-((1R)-2-amino-1-{[tert-butyl(dimethyl)-silyl]oxy}ethyl)-8-hydroxyquinolin-2(1H)-one acetate (321 mg, 0.54 mmol) (prepared according to prepara-tion 8 from US20060035931) and sodium triacetoxyborohydride (274 mg, 1.29 mmol) fol-lowing the experimental procedure as described for Intermediate 7. The crude obtained was used in the next step without further purification.

LRMS (m/z): 979 (M+1)+

Intermediate 121

(3R)-1-azabicyclo[2.2.2]oct-3-yl(5-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl) carbamate Obtained as a solid (138 mg, 39%) from (3R)-1-azabicyclo[2.2.2]oct-3-yl(5-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]but-1-en-1-yl}biphenyl-2-yl)carbamate (Intermediate 120; 316 mg, 0.37 mmol) following the experimental procedure as described for Intermediate 67. The crude obtained was purified by column chromatography with silica gel, eluting with a mixture of chloroform:methanol:ammonium (40:4:0.2).

LRMS (m/z): 859 (M+1)+

Example 22

(3R)-1-azabicyclo[2.2.2]oct-3-yl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate Obtained as a yellow solid (28 mg, 42%) from (3R)-1-azabicyclo[2.2.2]oct-3-yl(5-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate (Intermediate 121; 77 mg, 0.09 mmol) and triethylamine trihydrofluoride (73 µL, 0.45 mmol) following the experimental procedure as described for Example 1. The crude obtained was purified by column chromatography with silica gel, eluting with a mixture of chloroform:methanol:ammonium (40:4:0.2).

LRMS (m/z): 744 (M+1)+
1H NMR (300 MHz, cd3od) δ 8.28 (d, J=9.8 Hz, 1H), 7.41-7.30 (m, 5H), 7.24 (bs, 2H), 7.15-7.05 (m, 5H), 6.92 (d, J=8.2 Hz, 1H), 6.57 (d, J=9.7 Hz, 1H), 5.17 (s, 1H), 4.66-4.56 (m, 1H), 3.88 (bs, 2H), 3.82 (bs, 2H), 3.22 (bs, 2H), 3.06 (bs, 2H), 2.99 (s, 1H), 2.92-2.64 (m, 3H), 1.96-1.63 (m, 3H), 1.57 (s, 1H), 1.40 (s, 1H), 1.37-1.22 (m, 3H), 1.15 (bs, 2H), 0.89 (s, 1H).

Intermediate 122 ethyl 4-(2-aminobiphenyl-4-yl)butanoate

To a solution of (4-bromobiphenyl-2-yl)amine (Intermediate 3; 941 mg, 3.79 mmol) in tetra-hydrofurane (10 mL) was added palladium acetate (9 mg, 0.04 mmol) and 2-diciclohexylamino-2',6'-dimethoxy-1,1'-biphenyl (31 mg, 0.08 mmol). Then (4-ethoxy-4-oxobutyl)zinc(II) bromide (9.1 mL, 4.55 mmol) was added drop wise under argon atmosphere. The reaction mixture was stirred overnight at room temperature. Ethyl ether was added into the mixture and the organics were extracted with hexane. The organic layer was washed with water, dried, filtered and the solvent was removed under reduced pres-sure giving the title compound as an orange oil (1.04 g, 97%), which was used in the next step without further purification.

LRMS (m/z): 284 (M+1)+

Intermediate 123 ethyl 4-(2-(((((trans)-4-(((benzyloxy)carbonyl)amino)cyclohexyl)oxy)carbonyl)amino)-[1,1'-biphenyl]-4-yl)butanoate To a solution of triphosgene (0.4 g, 1.35 mmol) in dichloromethane (20 mL) was added drop wise at 0° C. a solution of ethyl 4-(2-aminobiphenyl-4-yl)butanoate (Intermediate 122; 1.04 g, 3.67 mmol), once the addition is finished triethylamine (1.02 mL, 7.32 mmol) was added. The mixture was stirred 2 hours at room temperature. The solvent was partially removed under reduced pressure without heating and hexane was added to precipitate the salts, the mixture was filtered and the filtrate was evaporated. The corresponding iso-cyanate was dissolved in tetrahydrofurane (10 mL) and was added into a solution of benzyl (trans-4-hydroxycyclohexyl)carbamate (Intermediate 42; 0.96 g, 3.85 mmol) in tetrahydrofurane (5 mL). The mixture was stirred for 24 hours at 70° C. The solvent was removed under reduced pressure and the crude obtained was purified by column chromatography with silica gel, eluting with a mixture of hexane:ether, giving the title compound as a solid (1.39 g, 68%).

LRMS (m/z): 559 (M+1)+

Intermediate 124

4-(2-(((((trans)-4-(((benzyloxy)carbonyl)amino)cyclohexyl)oxy)carbonyl)amino)-[1,1'-biphenyl]-4-yl)butanoic acid To a solution of ethyl 4-(2-(((((trans)-4-(((benzyloxy)carbonyl)amino)cyclohexyl)oxy) carbonyl)amino)-[1,1'-biphenyl]-4-yl)butanoate (Intermediate 123; 394 mg, 0.71 mmol) in tetrahydrofurane (10 mL) was added sodium hydroxide (2M, 2 mL). The reaction mixture was stirred overnight at room tempera-ture. The solvent was removed under reduced pressure and the crude obtained was di-luted with water and acidified by hydrogen chloride 2N until pH 2-3. Then the crude was ex-tracted with diethyl ether. The organic layer was dried, filtered and the solvent was removed under reduced pressure giving the title compound as a white solid (370 mg, 90%).

LRMS (m/z): 531 (M+1)+

Intermediate 125 trans-4-(((benzyloxy)carbonyl)amino)cyclohexyl(4-(4-((4-formylphenyl)amino)-4-oxobutyl)-[1,1'-biphenyl]-2-yl)carbamate To a solution of 4-(2-(((((trans)-4-(((benzyloxy)carbonyl)amino)cyclohexyl)oxy) carbonyl)amino)-[1,1'-biphenyl]-4-yl)butanoic acid (Intermediate 124; 378 mg, 0.32 mmol) was added 4-aminobenzaldehyde (80 mg, 0.66 mmol) and diisopropylethylenediamine (0.32 mL, 1.86 mmol) under nitrogen atmosphere. Then HATU (306 mg, 0.80 mmol) was added. The reaction mixture was stirred at room temperature overnight. The solvent was removed under reduced pressure and the crude was partitioned between chloroform and water, the organic layer was washed with water several times, dried, filtered and the solvent was removed under reduced pressure. The crude obtained was purified by column chromatography with silica gel, eluting with a mixture of hexane:ether, giving the title compound as a solid (198 mg, 50%).

LRMS (m/z): 634 (M+1)+

Intermediate 126 trans-4-(((benzyloxy)carbonyl)amino)cyclohexyl(4-(4-((4-((((R)-2-((tert-butyldimethylsilyl)oxy)-2-(8-hydroxy-2-oxo-1,2-dihydroquinolin-5-yl)ethyl)amino)methyl)phenyl)amino)-4-oxobutyl)-[1,1'-biphenyl]-2-yl)carbamate Obtained as solid (250 mg, 98%) from trans-4-(((benzyloxy)carbonyl)amino)cyclohexyl(4-(4-((4-formylphenyl)amino)-4-oxobutyl)-[1,1'-biphenyl]-2-yl)carbamate (Intermediate 125; 198 mg, 0.31 mmol), 5-((1R)-2-amino-1-{[tert-butyl(dimethyl)-silyl]oxy}ethyl)-8-hydroxyquinolin-2(1H)-one acetate (105 mg, 0.27 mmol) (prepared according to prepara-tion 8 from US20060035931) and sodium triacetoxyborohydride (199 mg, 0.92 mmol) fol-lowing the experimental procedure as described for Intermediate 7. The crude obtained was used in the next step without further purification.

LRMS (m/z): 953 (M+1)+

Intermediate 127 trans-4-aminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate Obtained as solid (338 mg, 88%) from trans-4-(((benzyloxy)carbonyl)amino)cyclohexyl(4-(4-((4-(((((R)-2-((tert-butyldimethylsilyl)oxy)-2-(8-hydroxy-2-oxo-1,2-dihydroquinolin-5-yl)ethyl)amino)methyl)phenyl)amino)-4-oxobutyl)-[1,1'-biphenyl]-2-yl)carbamate (Intermediate 126; 418 mg, 0.44 mmol) following the experimental pro-cedure as described for In-termediate 77 and the crude obtained was used in the next step without further purification.

LRMS (m/z): 819 (M+1)+

Example 23 trans-4-aminocyclohexyl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate dihydrofluoride Obtained as a white solid (140 mg, 56%) from trans-4-aminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate (Intermediate 127; 338 mg, 0.34 mmol) and triethylamine trihydrofluoride (276 µL, 1.69 mmol) follow-ing the experimental procedure as described for Example 1.

LRMS (m/z): 704 (M+1)+

1H NMR (300 MHz, dmso) δ 8.55 (s, 1H), 8.06 (d, J=10.3 Hz, 1H), 7.52 (d, J=8.3 Hz, 1H), 7.45-7.26 (m, 5H), 7.27-7.10 (m, 5H), 7.03 (d, J=8.2 Hz, 1H), 6.87 (s, 1H), 6.44 (d, J=10.0 Hz, 1H), 5.02 (bs, 1H), 4.68-4.53 (m, 2H), 4.4-4.3 (m, 4H), 3.68 (s, 1H), 2.73 (s, 3H), 2.59 (bs, 4H), 2.34 (s, 6H), 1.87 (bs, 4H), 1.80 (bs, 4H), 1.20-1.1 (m, 4H).

Intermediate 128

2-oxo-2,3-dihydro-1,3-benzoxazole-5-carbonitrile

A mixture of 5-bromobenzo[d]oxazol-2(3H)-one (1 g, 4.67 mmol) and copper (I) cyanide (0.71 g, 7.93 mmol) in 3 ml DMF is heated at 150° C. under nitrogen atmosphere for 22 hr. After cooling to room temperature, a solution of 1.55 g (31.6 mmol) of sodium cyanide in 32 ml water is added followed by 1 hr stirring. The system is extracted thoroughly with ethyl acetate, washed with brine, dried and concentrated in vacuum to provide 1.04 of the crude mix-ture, which was carried out forward without further purification.

LRMS (m/z): 161 (M+1)+

Intermediate 129

2-oxo-2,3-dihydro-1,3-benzoxazole-5-carbaldehyde

Obtained as a yellow solid (1.05 g, 82%) from 2-oxo-2,3-dihydro-1,3-benzoxazole-5-carbonitrile (Intermediate 128; 1.09 g, 6.81 mmol) and Niquel-Aluminium (121.9 mg, 1.42 mmol) following the experimental procedure as described for Intermediate 2. The crude obtained was used in the next step without further manipulation.

LRMS (m/z): 164 (M+1)+

Intermediate 130

3-allyl-2-oxo-2,3-dihydro-1,3-benzoxazole-5-carbal-dehyde

Obtained as an oil (580 mg, 39%) from 2-oxo-2,3-dihydro-1,3-benzoxazole-5-carbaldehyde (Intermediate 129; 1.19 g, 0.007 mol), potassium carbonate (2.02 g, 0.014 mmol), potassium iodide (240 mg, 1.46 mmol) and 3-bro-moprop-1-ene (1.98 mL, 0.022 mol) following the experi-mental procedure as described for Intermediate 129. The crude obtained was purified by column chromatography with silica gel, eluting with a mixture of hexane:ether.

LRMS (m/z): 204 (M+1)+

Intermediate 131

(3R)-1-azabicyclo[2.2.2]oct-3-yl{4-[(1E)-3-(5-formyl-2-oxo-1,3-benzoxazol-3(2H)-yl)prop-1-en-1-yl]biphenyl-2-yl}carbamate Obtained as a solid (542 mg, 90%) from 3-allyl-2-oxo-2,3-dihydro-1,3-benzoxazole-5-carbaldehyde (Intermediate 130; 200 mg, 0.98 mmol), (3R)-1-azabicyclo[2.2.2]oct-3-yl (4-bromobiphenyl-2-yl)carbamate (Intermediate 5; 400 mg, 1 mmol), tri-o-tolylphosphine (303 mg, 1 mmol), N,N-Diisopropylethylamine (0.347 mL, 1.99 mmol) and palla-dium acetate (165 mg, 0.5 mmol) following the experimen-tal procedure as described for intermediate 6. The crude obtained was purified by column chromatography with silica gel, eluting with a mixture of chloroform:methanol:ammo-nium (40:4:0.2).

LRMS (m/z): 553 (M+1)+

Intermediate 132

(3R)-1-azabicyclo[2.2.2]oct-3-yl(4-{(1E)-3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]prop-1-en-1-yl}biphenyl-2-yl)carbamate Obtained as a foam (750 mg, 94%) from (3R)-1-azabi-cyclo[2.2.2]oct-3-yl{4-[(1E)-3-(5-formyl-2-oxo-1,3-benzo-xazol-3(2H)-yl)prop-1-en-1-yl]biphenyl-2-yl}carbamate (Intermedi-ate 131; 552 mg, 1.05 mmol), 5-((1R)-2-amino-1-{[tert-butyl(dimethyl)-silyl]oxy}ethyl)-8-hydroxyquino-lin-2(1H)-one acetate (374 mg, 0.95 mmol) (prepared according to prepara-tion 8 from US20060035931) and sodium triacetoxyborohydride (670 mg, 3.16 mmol) fol-lowing the experimental procedure as described for Inter-mediate 7. The crude obtained was used in the next step without further purification.

LRMS (m/z): 843 (M+1)+

Intermediate 133

(3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate Obtained as a foam (28 mg, 14%) from (3R)-1-azabicyclo[2.2.2]oct-3-yl(4-{(1E)-3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]prop-1-en-1-yl}biphenyl-2-yl)carbamate (Intermediate 132; 200 mg, 0.24 mmol) and palladium on charcoal (10%, 20 mg) following the experimental procedure as described for Intermediate 67. The crude obtained was purified by column chromatography with silica gel, eluting with a mixture of chloroform:methanol:ammonium (40:4:0.2).

LRMS (m/z): 845 (M+1)+

Example 24

(3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate dihydrofluoride Obtained as a solid (20 mg, 92%) from (3R)-1-azabicyclo[2.2.2]oct-3-yl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate (Intermediate 133; 28 mg, 0.03 mmol) and triethylamine trihydrofluoride (30 µL, 0.18 mmol) following the experimental procedure as described for Example 1.

LRMS (m/z): 730 (M+1)+

1H NMR (300 MHz, cd3od) δ 8.27 (d, J=9.9 Hz, 1H), 7.47-7.26 (m, 6H), 7.23-7.03 (m, 6H), 6.95 (d, J=7.8 Hz, 1H), 6.58 (d, J=9.6 Hz, 1H), 5.22 (s, 1H), 4.71 (s, 2H), 3.92 (s, 2H), 2.99 (s, 1H), 2.97-2.77 (m, 3H), 2.75 (s, 2H), 2.16 (s, 2H), 2.00 (s, 1H), 1.84 (bs 3H), 1.58 (bs 3H), 1.28 (s, 1H), 1.15 (bs, 2H).

Intermediate 134

(3R)-1-azabicyclo[2.2.2]oct-3-yl(4-{(1E)-4-[6-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-2-oxo-1,3-benzoxazol-3(2H)-yl]but-1-en-1-yl}biphenyl-2-yl)carbamate Obtained as a yellow foam (256 mg, 67%) from 8-[(R)-2-amino-1-(tert-butyl-dimethyl-silanoxy)-ethyl-5-hydroxy-4H-benzo[1,4]oxazin-3-one (preparation described in WO2008149110 intermediate 65; 123 mg, 0.36 mmol), (3R)-1-azabicyclo[2.2.2]oct-3-yl {4-[(1E)-4-(6-formyl-2-oxo-1,3-benzoxazol-3(2H)-yl)but-1-en-1-yl]biphenyl-2-yl}carbamate (Intermediate 39; 210 mg, 0.33 mmol and sodium triacetoxyborohydride (231 mg, 1.09 mmol) following the experimental procedure as described for Intermediate 7. The crude obtained was purified by column chromatography with silica gel, eluting with a mixture of chloroform:methanol:ammonium (40:4:0.2).

LRMS (m/z): 861 (M+1)+

Intermediate 135

(3R)-1-azabicyclo[2.2.2]oct-3-yl(4-{4-[6-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate Obtained as a yellow solid (218 mg, 60%) from (3R)-1-azabicyclo[2.2.2]oct-3-yl(4-{(1E)-4-[6-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-2-oxo-1,3-benzoxazol-3(2H)-yl]but-1-en-1-yl}biphenyl-2-yl)carbamate (Intermediate 134; 256 mg, 0.3 mmol) following the experimental procedure as described for Intermediate 77 and the crude obtained was used in the next step without further purification.

LRMS (m/z): 863 (M+1)+

Example 25

(3R)-1-azabicyclo[2.2.2]oct-3-yl(4-{4-[6-({[(2R)-2-hydroxy-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate dihydrofluoride Obtained as a white solid (64 mg, 48%) from (3R)-1-azabicyclo[2.2.2]oct-3-yl(4-{4-[6-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate (Intermediate 135; 218 mg, 0.18 mmol) and triethylamine trihydrofluoride (30 µL, 0.18 mmol) following the experimental procedure as described for Example 1. The crude obtained was purified by column chromatography in reversed phase using as eluents Acetonitrile and Methanol.

LRMS (m/z): 745 (M+1)+

1H NMR (300 MHz, dmso) δ 9.96 (s, 1H), 8.74 (s, 1H), 7.48-7.16 (m, 10H), 7.12 (bs, 1H), 6.86 (d, J=8.5 Hz, 1H), 6.51 (d, J=8.4 Hz, 1H), 4.98-4.91 (m, 1H), 4.56 (s, 1H), 4.45 (s, 2H), 3.94 (s, 2H), 3.86 (t, J=6.5 Hz, 2H), 3.18 (d, J=12.0 Hz, 2H), 2.88-2.69 (m, 4H), 2.63 (bs, 2H), 1.90 (d, J=5.6 Hz, 1H), 1.74 (d, J=6.5 Hz, 2H), 1.62 (d, J=6.1 Hz, 4H), 1.40 (s, 2H).

Intermediate 136 trans-4-(((benzyloxy)carbonyl)amino)cyclohexyl(4-((E)-3-(5-formyl-2-oxobenzo[d]oxazol-3(2H)-yl)prop-1-enyl)-[1,1'-biphenyl]-2-yl)carbamate Obtained as a foam (250 mg, 81%) from 3-allyl-2-oxo-2,3-dihydro-1,3-benzoxazole-5-carbaldehyde (Intermediate 130; 100 mg, 0.49 mmol), trans-4-benzylaminocyclohexyl (4-bromobiphenyl-2-yl)carbamate (Intermediate 43; 250 mg, 0.48 mmol), tri-o-tolylphosphine (150 mg, 0.49 mmol), N,N-Diisopropylethylamine (0.166 mL, 0.95 mmol) and palladium acetate (82 mg, 0.25 mmol) following the experimental procedure as described for intermediate 6. The crude obtained was purified by column chromatography with silica gel, eluting with a mixture of Hexane:Ether:Ethanol.

LRMS (m/z): 646 (M+1)+

Intermediate 137 trans-4-(((benzyloxy)carbonyl)amino)cyclohexyl(4-((E)-3-(5-((((R)-2-((tert-butyldimethylsilyl)oxy)-2-(8-hydroxy-2-oxo-1,2-dihydroquinolin-5-yl)ethyl)amino)methyl)-2-oxobenzo[d]oxazol-3(2H)-yl)prop-1-enyl)-[1,1'-biphenyl]-2-yl)carbamate Obtained as a yellow solid (331 mg, 89%) from trans-4-(((benzyloxy)carbonyl)amino)cyclohexyl(4-((E)-3-(5-formyl-2-oxobenzo[d]oxazol-3(2H)-yl)prop-1-enyl)-[1,1'-biphenyl]-2-yl)carbamate (Intermediate 136; 250 mg, 0.39 mmol), 5-((1R)-2-amino-1-{[tert-butyl(dimethyl)-silyl]oxy}ethyl)-8-hydroxyquinolin-2(1H)-one acetate (160 mg, 0.41 mmol) (prepared according to preparation 8 from US20060035931) and so-dium triacetoxyborohydride (250 mg, 1.118 mmol) following the experimental procedure as described for Intermediate 7. The crude obtained was used in the next step without further purification.

LRMS (m/z): 965 (M+1)+

Intermediate 138 trans-4-aminocyclohexyl(4-{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}biphenyl-2-yl) carbamate Obtained as foam (128 mg, 45%) from trans-4-(((benzyloxy)carbonyl)amino)cyclohexyl(4-((E)-3-(5-((((R)-2-((tert-butyldimethylsilyl)oxy)-2-(8-hydroxy-2-oxo-1,2-dihydroquinolin-5-yl)ethyl)amino)methyl)-2-oxobenzo[d]oxazol-3(2H)-yl)prop-1-enyl)-[1,1'-biphenyl]-2-yl)carbamate (Intermediate 137; 331 mg, 0.34 mmol) following the experimental procedure as described for Intermediate 77. The crude obtained was purified by column chromatography with silica gel, eluting with a mixture of Hexane:Ether:Ethanol.

LRMS (m/z): 833 (M+1)+

Example 26 trans-4-aminocyclohexyl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate dihydrofluoride Obtained as a white solid (100 mg, 90%) from trans-4-aminocyclohexyl(4-{3-[5-({[(2R)-2-{[tert-butyl(dimethyl) silyl]oxy}-2-(8-hydroxy-2-oxo-1,2-dihydroquinolin-5-yl) ethyl]amino}methyl)-2-oxo-1,3-benzoxazol-3(2H)-yl] propyl}biphenyl-2-yl)carbamate (Intermediate 138; 128 mg, 0.15 mmol) and triethylamine trihydrofluoride (125 μL, 0.77 mmol) following the experimental procedure as described for Example 1.

LRMS (m/z): 718 (M+1)+

1H NMR (300 MHz, dmso) δ 8.57 (s, 1H), 8.12 (d, J=10.0 Hz, 1H), 7.45-7.28 (m, 2H), 7.28-6.99 (m, 6H), 6.88 (d, J=8.1 Hz, 1H), 6.44 (d, J=9.9 Hz, 1H), 5.07 (s, 1H), 4.31 (s, 1H), 3.85 (s, 1H), 3.77 (bs, 2H), 2.7-2.65 (m, 4H), 2.44 (t, J=7.1 Hz, 2H), 2.27 (bs, 2H), 2.01 (bs, 1H), 1.80 (bs, 3H), 1.23 (bs, 2H).

Intermediate 139

1-but-3-en-1-yl-1H-indole-5-carbaldehyde

Obtained as an oil (510 mg, 59%) from 1H-indole-5-carbaldehyde (500 mg, 3.44 mmol), 4-bromobut-1-ene (0.524 mL, 5.16 mmol) and sodium hydride (60%, 124 mg, 5.17 mmol) following the experimental procedure as described for Intermediate 33. The crude obtained was used in the next step without further purification.

LRMS (m/z): 200 (M+1)+

Intermediate 140 trans-4-(((benzyloxy)carbonyl)amino)cyclohexyl(4-((E)-4-(5-formyl-1H-indol-1-yl)but-1-enyl)-[1,1'-biphenyl]-2-yl)carbamate Obtained as a foam (232 mg, 51%) from 1-but-3-en-1-yl-1H-indole-5-carbaldehyde (Intermediate 139; 159 mg, 0.8 mmol), trans-4-benzylaminocyclohexyl(4-bromobiphenyl-2-yl)carbamate (Intermediate 43; 350 mg, 0.67 mmol), tri-o-tolylphosphine (203 mg, 0.67 mmol), N,N-Diisopropylethylamine (0.233 mL, 1.34 mmol) and palladium acetate (110 mg, 0.33 mmol) following the experimental procedure as described for intermediate 6. The crude obtained was purified by column chromatography with silica gel, eluting with a mixture of Hexane:Ether:Ethanol.

LRMS (m/z): 646 (M+1)+

Intermediate 141 trans-4-(((benzyloxy)carbonyl)amino)cyclohexyl(4-((E)-4-(5-((((R)-2-((tert-butyldimethylsilyl)oxy)-2-(8-hydroxy-2-oxo-1,2-dihydroquinolin-5-yl)ethyl) amino)methyl)-1H-indol-1-yl)but-1-enyl)-[1,1'-biphenyl]-2-yl)carbamate Obtained as a solid (173 mg, 50%) from trans-4-(((benzyloxy)carbonyl)amino)cyclohexyl(4-((E)-4-(5-formyl-1H-indol-1-yl)but-1-enyl)-[1,1'-biphenyl]-2-yl)carbamate (Intermediate 140; 232 mg, 0.36 mmol), 5-((1R)-2-amino-1-{[tert-butyl(dimethyl)-silyl]oxy}ethyl)-8-hydroxyquinolin-2(1H)-one acetate (121 mg, 0.36 mmol) (prepared according to preparation 8 from US20060035931) and sodium triacetoxyborohydride (383 mg, 1.81 mmol) following the experimental procedure as described for Intermediate 7. The crude obtained was purified by column chromatography with silica gel, eluting with a mixture of Hexane:Ether:Ethanol.

LRMS (m/z): 961 (M+1)+

Intermediate 142 trans-4-aminocyclohexyl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]butyl}biphenyl-2-yl)carbamate Obtained as solid (120 mg, 77%) from trans-4-(((benzyloxy)carbonyl)amino)cyclohexyl(4-((E)-4-(5-((((R)-2-((tert-butyldimethylsilyl)oxy)-2-(8-hydroxy-2-oxo-1,2-dihydroquinolin-5-yl)ethyl)amino)methyl)-1H-indol-1-yl)but-1-enyl)-[1,1'-biphenyl]-2-yl)carbamate (Intermediate 141; 170 mg, 0.18 mmol) following the experimental procedure as described for Intermediate 77 and the crude obtained was used in the final step without further purification.

LRMS (m/z): 829 (M+1)+

Example 27 trans-4-aminocyclohexyl(4-{4-[5-({[(2R)-2-hydroxy-2-(8-hydroxy-2-oxo-1,2-dihydroquinolin-5-yl) ethyl]amino}methyl)-1H-indol-1-yl]butyl}biphenyl-2-yl)carbamate Obtained as a solid (42 mg, 41%) from trans-4-aminocyclohexyl(4-{4-[5-({[(2R)-2-{[tert-butyl(dimethyl)silyl] oxy}-2-(8-hydroxy-2-oxo-1,2-dihydroquinolin-5-yl)ethyl] amino}methyl)-1H-indol-1-yl]butyl}biphenyl-2-yl) carbamate (Intermediate 142; 120 mg, 0.14 mmol) and triethylamine trihydrofluoride (116 μL, 0.72 mmol) following the experimental procedure as described for Example 1. The crude obtained was purified by column chromatography with silica gel, eluting with a mixture of chloroform:methanol:ammonium (40:4:0.2).

LRMS (m/z): 714 (M+1)+

1H NMR (300 MHz, dmso) δ 8.06 (d, J=9.9 Hz, 1H), 7.45-7.3 (m, 7H), 7.17 (bs, 3H), 7.06 (bs, 3H), 6.86 (d, J=8.2 Hz, 1H), 6.39 (d, J=9.9 Hz, 1H), 6.35 (d, J=3.0 Hz, 1H), 5.04 (s, 1H), 4.32 (s, 2H), 4.21-4.1 (m, 4H), 3.78 b (s, H), 3.17 (bs, 2H), 2.76-2.54 (m, 3H), 1.88-1.66 (m, 4H), 1.53 (s, 2H), 1.39-1.10 (m, 3H).

Intermediate 143

3-but-3-en-1-yl-6-[(E)-2-methoxyvinyl]-1,3-benzoxazol-2(3H)-one

To a solution of (methoxymethyl)triphenylphosphonium chloride (5 g, 0.014 mol) in anhydrous tetrahydrofurane (25 mL) was added drop wise at 0° C. a solution of Lithium bis(trimethylsilyl)amide (1M in toluene, 15 mL). The mixture was stirred for 30 minutes and then a solution of 3-but-3-en-1-yl-2-oxo-2,3-dihydro-1,3-benzoxazole-6-carbaldehyde (Intermediate 38; 1.26 gm 0.005 mol) in anhydrous tetrahydrofurane (25 mL) was added into the mixture and it was allowed to stir for 30 minutes at 0° C. and 20 hours at room temperature. A saturated solution of Ammonium chloride was poured into the mixture and the organics were extracted with ethyl acetate, dried, filtered and the solvent was removed under reduced pressure. The crude obtained was purified by column chromatography with silica gel, eluting with a mixture of hexane:ether giving the title compound as a solid (0.68 g, 48%).

LRMS (m/z): 246 (M+1)+

Intermediate 144

(3R)-1-azabicyclo[2.2.2]oct-3-yl(4-{(1E)-4-[6-[(E)-2-methoxyvinyl]-2-oxo-1,3-benzoxazol-3(2H)-yl]but-1-en-1-yl}biphenyl-2-yl)carbamate Obtained as a yellow foam (557 mg, 66%) from 3-but-3-en-1-yl-6-[(E)-2-methoxyvinyl]-1,3-benzoxazol-2(3H)-one (Intermediate 143; 367 mg, 1.5 mmol), (3R)-1-azabicyclo[2.2.2]oct-3-yl(4-bromobiphenyl-2-yl)carbamate (Intermediate 5; 600 mg, 1.5 mmol), tri-o-tolylphosphine (364 mg, 1.2 mmol), N,N-Diisopropylethylamine (0.521 mL, 2.99 mmol) and palladium acetate (134 mg, 0.4 mmol) following the experimental procedure as described for intermediate 6. The crude obtained was purified by column chromatography with silica gel, eluting with a mixture of chloroform:methanol:ammonium (40:4:0.2).

LRMS (m/z): 566 (M+1)+

Intermediate 145

(3R)-1-azabicyclo[2.2.2]oct-3-yl(4-{(1E)-4-[2-oxo-6-(2-oxoethyl)-1,3-benzoxazol-3(2H)-yl]but-1-en-1-yl}biphenyl-2-yl)carbamate To a solution of (3R)-1-azabicyclo[2.2.2]oct-3-yl (4-{(1E)-4-[6-[(E)-2-methoxyvinyl]-2-oxo-1,3-benzoxazol-3(2H)-yl]but-1-en-1-yl}biphenyl-2-yl)carbamate (Intermediate 144; 100 mg, 0.18 mmol) in dioxane (1 mL) was added hydrogen chloride (4M in dioxane, 0.11 mL, 0.44 mmol). The mixture was stirred for 30 minutes and then a cool saturated solution of bicarbonate was poured into the mixture and the organics were extracted with ethyl acetate. The organic layer was washed with bicarbonate 4%, dried, filtered and the solvent was removed under reduced pressure. The title compound was obtained (85 mg, 81%), which was used in the next step without further purification.

LRMS (m/z): 568/584 (M+16/M+32)+

Intermediate 146

(3R)-1-azabicyclo[2.2.2]oct-3-yl(4-{(1E)-4-[6-(2-{[(2R)-2-{[tert-butyl(dimethyl) silyl]oxy}-2-(8-hydroxy-2-oxo-1,2-dihydroquinolin-5-yl)ethyl] amino}ethyl)-2-oxo-1,3-benzoxazol-3(2H)-yl]but-1-en-1-yl}biphenyl-2-yl)carbamate To a solution of (3R)-1-azabicyclo[2.2.2]oct-3-yl (4-{(1E)-4-[2-oxo-6-(2-oxoethyl)-1,3-benzoxazol-3(2H)-yl]but-1-en-1-yl}biphenyl-2-yl)carbamate (Intermediate 145; 85 mg, 0.14 mmol) in dichloromethane (4 mL) was added 5-((1R)-2-amino-1-{[tert-butyl(dimethyl)-silyl]oxy}ethyl)-8-hydroxyquinolin-2(1H)-one acetate (55 mg, 0.14 mmol) (prepared according to preparation 8 from US20060035931) and methanol was added until complete dissolution of the mixture, then sodium cianoborohydride (0.4 mmol) was added. The reaction is stirred overnight at room temperature. The solvent was removed under reduced pressure and the crude obtained was treated with chloroform giving a foam as the title compound (102 mg, 45%), which was used in the next step without further purification.

LRMS (m/z): 871 (M+1)+

Intermediate 147

(3R)-1-azabicyclo[2.2.2]oct-3-yl(4-{4-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]butyl}biphenyl-2-yl) carbamate Obtained as a crude mixture (76 mg) which was taken into the final step without purification, from (3R)-1-azabicyclo [2.2.2]oct-3-yl(4-{(1E)-4-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl] but-1-en-1-yl}biphenyl-2-yl)carbamate (56 mg, 0.04 mmol) following the experimental procedure as described for Intermediate 77.

LRMS (m/z): 873 (M+1)+

Example 28

(3R)-1-azabicyclo[2.2.2]oct-3-yl(4-{4-[6-(2-{[(2R)-2-hydroxy-2-(8-hydroxy-2-oxo-1,2-dihydroquinolin-5-yl)ethyl]amino}ethyl)-2-oxo-1,3-benzoxazol-3 (2H)-yl]butyl}biphenyl-2-yl)carbamate dihydrofluoride Obtained as a white solid (33 mg, 21%) from (3R)-1-azabicyclo[2.2.2]oct-3-yl(4-{4-[6-(2-{[(2R)-2-{[tert-butyl (dimethyl)silyl]oxy}-2-(8-hydroxy-2-oxo-1,2-dihydroquinolin-5-yl)ethyl]amino}ethyl)-2-oxo-1,3-benzoxazol-3 (2H)-yl]butyl}biphenyl-2-yl)carbamate (Intermediate 147; 400 mg, 0.2 mmol) and triethylamine trihydrofluoride (116 μL, 0.72 mmol) following the experimental procedure as described for Example 1. The crude obtained was purified by column chromatography in reversed phase using as eluents Acetonitrile and Methanol.

LRMS (m/z): 758 (M+1)+

1H NMR (300 MHz, dmso) δ 8.64 (s, 1H), 8.16 (d, J=9.9 Hz, 1H), 7.45-7.27 (m, 4H), 7.20 (bs, 3H), 7.18-7.0 (m, 3H), 6.92 (d, J=8.0 Hz, 2H), 6.49 (d, J=9.9 Hz, 1H), 5.01 (bs, 1H), 4.45 (bs, 1H), 3.84 (bs, 2H), 3.04-2.91 (m, 2H), 2.73 b (s, 2H), 2.63 (bs, 2H), 2.57 (bs, 1H), 2.44 (bs, 2H), 1.76 (bs, 3H), 1.61 (bs, 3H), 1.4-1.3 (m, 4H), 1.31-1.24 (m, 4H).

Intermediate 148

2-oxo-3-pent-4-en-1-yl-2,3-dihydro-1,3-benzoxazole-6-carbaldehyde

Obtained as a solid (460 mg, 65%) from 2-oxo-2,3-dihydrobenzo[d]oxazole-6-carbaldehyde (500 mg, 3.07 mmol), 5-bromopent-1-ene (2.28 g, 0.015 mol) and potassium carbonate (423 mg, 3.07 mmol) following the experimental procedure as described for Intermediate 9. The crude obtained was purified by column chromatography with silica gel, eluting with a mixture of Hexane:Ether.
LRMS (m/z): 232 (M+1)+

Intermediate 149 trans-4-(((benzyloxy)carbonyl)amino)cyclohexyl(4-((E)-5-(6-formyl-2-oxobenzo[d]oxazol-3(2H)-yl)pent-1-enyl)-[1,1'-biphenyl]-2-yl)carbamate Obtained as a solid (221 mg, 49%) from 2-oxo-3-pent-4-en-1-yl-2,3-dihydro-1,3-benzoxazole-6-carbaldehyde (Intermediate 148; 170 mg, 0.74 mmol), trans-4-benzylaminocyclohexyl(4-bromobiphenyl-2-yl)carbamate (Intermediate 43; 350 mg, 0.67 mmol), tri-o-tolylphosphine (203 mg, 0.67 mmol), N,N-Diisopropylethylamine (0.233 mL, 1.34 mmol) and palladium acetate (75 mg, 0.33 mmol) following the experimental procedure as described for intermediate 6. The crude obtained was purified by column chromatography with silica gel, eluting with a mixture of Hexane:Ether:Ethanol.
LRMS (m/z): 674 (M+1)+

Intermediate 150 trans-4-(((benzyloxy)carbonyl)amino)cyclohexyl(4-((E)-5-(6-((((R)-2-((tert-butyldimethylsilyl)oxy)-2-(8-hydroxy-2-oxo-1,2-dihydroquinolin-5-yl)ethyl)amino)methyl)-2-oxobenzo[d]oxazol-3(2H)-yl)pent-1-enyl)-[1,1'-biphenyl]-2-yl)carbamate Obtained as a foam (147 mg, 45%) from trans-4-(((benzyloxy)carbonyl)amino)cyclohexyl(4-((E)-5-(6-formyl-2-oxobenzo[d]oxazol-3(2H)-yl)pent-1-enyl)-[1,1'-biphenyl]-2-yl)carbamate (Intermediate 146; 221 mg, 0.33 mmol), 5-((1R)-2-amino-1-{[tert-butyl(dimethyl)-silyl]oxy}ethyl)-8-hydroxyquinolin-2(1H)-one acetate (110 mg, 0.33 mmol) (prepared according to preparation 8 from US20060035931) and sodium triacetoxyborohydride (347 mg, 1.64 mmol) following the experimental procedure as described for Intermediate 7. The crude obtained was purified by column chromatography with silica gel, eluting with a mixture of Hexane:Ether:Ethanol.
LRMS (m/z): 993 (M+1)+

Intermediate 151 trans-4-aminocyclohexyl(4-{5-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate Obtained as a foam (51 mg, 42%) from trans-4-(((benzyloxy)carbonyl)amino)cyclohexyl(4-((E)-5-(6-((((R)-2-((tert-butyldimethylsilyl)oxy)-2-(8-hydroxy-2-oxo-1,2-dihydroquinolin-5-yl)ethyl)amino)methyl)-2-oxobenzo[d]oxazol-3(2H)-yl)pent-1-enyl)-[1,1'-biphenyl]-2-yl)carbamate (Intermediate 150; 140 mg, 0.14 mmol) in Methanol following the experimental procedure as described for Intermediate 77 and the crude obtained was used in the final step without further purification.
LRMS (m/z): 861 (M+1)+

Example 29 trans-4-aminocyclohexyl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate dihydrofluoride Obtained as white solid (30 mg, 38%) from trans-4-aminocyclohexyl(4-{5-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate (Intermediate 151; 51 mg, 0.06 mmol) and triethylamine trihydrofluoride (48 μL, 0.3 mmol) following the experimental procedure as described for Example 1.
LRMS (m/z): 746 (M+1)+
1H NMR (300 MHz, dmso) δ 8.55 (s, 1H), 8.11 (d, J=9.3 Hz, 1H), 7.4-7.2 (m, 4H), 7.18-7.0 (m, 6H), 6.89 (s, 2H), 6.44 (d, J=10.0 Hz, 1H), 5.04 (s, 1H), 4.32 (s, 1H), 3.75 (bs, 3H), 2.08 (bs, 6H), 1.71 (d, J=69.8 Hz, 8H), 1.26 (bs, 6H).

Intermediate 152

3-allyl-6-[(E)-2-methoxyvinyl]-1,3-benzoxazol-2(3H)-one

Obtained as a foam (148 mg, 27%) from 3-allyl-2-oxo-2,3-dihydro-1,3-benzoxazole-6-carbaldehyde (Intermediate 2; 485 mg, 2.39 mmol), (methoxymethyl)triphenylphosphonium chloride (4.1 g, 0.012 mmol) and Lithium bis(trimethylsilyl)amide (1M in toluene, 12 mL) following the experimental procedure as described for Intermediate 143.
LRMS (m/z): 232 (M+1)+

Intermediate 153

(3R)-1-azabicyclo[2.2.2]oct-3-yl(4-{(1E)-3-[6-[(E)-2-methoxyvinyl]-2-oxo-1,3-benzoxazol-3(2H)-yl]prop-1-en-1-yl}biphenyl-2-yl)carbamate Obtained as a foam (308 mg, 80%) from 3-allyl-6-[(E)-2-methoxyvinyl]-1,3-benzoxazol-2(3H)-one (Intermediate 152; 148 mg, 0.64 mmol), (3R)-1-azabicyclo[2.2.2]oct-3-yl (4-bromobiphenyl-2-yl)carbamate (Intermediate 5; 257 mg, 0.64 mmol), tri-o-tolylphosphine (156 mg, 0.51 mmol), N,N-Diisopropylethylamine (0.223 mL, 1.28 mmol) and palladium acetate (85 mg, 0.26 mmol) following the experimental procedure as described for intermediate 6. The crude obtained was purified by column chromatography with silica gel, eluting with a mixture of chloroform:methanol:ammonium (40:4:0.2).
LRMS (m/z): 552 (M+1)+

Intermediate 154

(3R)-1-azabicyclo[2.2.2]oct-3-yl(4-{(1E)-3-[2-oxo-6-(2-oxoethyl)-1,3-benzoxazol-3(2H)-yl]prop-1-en-1-yl}biphenyl-2-yl)carbamate The crude mixture obtained (209 mg) in the previous preparation was used in the next step without further manipulation and it was obtained from (3R)-1-azabicyclo[2.2.2]oct-3-yl(4-{(1E)-3-[6-[(E)-2-methoxyvinyl]-2-oxo-1,3-benzoxazol-3(2H)-yl]prop-1-en-1-yl}biphenyl-2-yl)carbamate (Intermediate 153; 200 mg, 0.36 mmol) and hydrogen chloride (4M in dioxane, 0.185 mL) following the experimental procedure as described for Intermediate 145.

LRMS (m/z): 538 (M+1)+

Intermediate 155

(3R)-1-azabicyclo[2.2.2]oct-3-yl(4-{(1E)-3-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]prop-1-en-1-yl}biphenyl-2-yl)carbamate Obtained as a foam (40 mg, 14%) from (3R)-1-azabicyclo[2.2.2]oct-3-yl(4-{(1E)-3-[2-oxo-6-(2-oxoethyl)-1,3-benzoxazol-3(2H)-yl]prop-1-en-1-yl}biphenyl-2-yl)carbamate (Intermediate 154; 92 mg, 0.16 mmol), 5-((1R)-2-amino-1-{[tert-butyl(dimethyl)-silyl]oxy}ethyl)-8-hydroxyquinolin-2(1H)-one acetate (63 mg, 0.16 mmol) (prepared according to preparation 8 from US20060035931) and sodium cianoborohydride (25 mg, 0.4 mmol) following the experimental procedure as described for Intermediate 146 and the crude obtained was purified by column chromatography with silica gel, eluting with a mixture of chloroform:methanol:ammonium (40:4:0.2).

LRMS (m/z): 857 (M+1)+

Intermediate 156

(3R)-1-azabicyclo[2.2.2]oct-3-yl(4-{3-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]propyl}biphenyl-2-yl)carbamate Obtained as a diacetate salt (83 mg, 40%) from (3R)-1-azabicyclo[2.2.2]oct-3-yl(4-{(1E)-3-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]prop-1-en-1-yl}biphenyl-2-yl)carbamate (Intermediate 155; 370 mg, 0.22 mmol) and palladium on charcoal (10%; 30 mg) in a mixture of methanol:acid acetic (2:1) following the experimental procedure as described for Intermediate 67. The crude obtained was purified by column chromatography in reversed phase using as eluents Acetonitrile and Methanol.

LRMS (m/z): 859 (M+1)+

Example 30

(3R)-1-azabicyclo[2.2.2]oct-3-yl(4-{3-[6-(2-{[(2R)-2-2-hydroxy-2-(8-hydroxy-2-oxo-1,2-dihydroquinolin-5-yl)ethyl]amino}ethyl)-2-oxo-1,3-benzoxazol-3(2H)-yl]propyl}biphenyl-2-yl)carbamate dihydrofluoride Obtained as a white solid (66 mg, 93%) from (3R)-1-azabicyclo[2.2.2]oct-3-yl(4-{3-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]propyl}biphenyl-2-yl)carbamate (Intermediate 156; 83 mg, 0.08 mmol) and triethylamine trihydrofluoride (45 µL, 0.28 mmol) following the experimental procedure as described for Example 1.

LRMS (m/z): 744 (M+1)+

1H NMR (300 MHz, dmso) δ 8.69 (s, 1H), 8.17 (d, J=9.8 Hz, 1H), 7.42-7.3 (m, 5H), 7.19 (dd, J=20.1, 8.1 Hz, 5H), 7.11-7.04 (m, 2H), 6.91 (d, J=8.0 Hz, 1H), 6.51 (d, J=9.7 Hz, 1H), 5.12 (s, 1H), 4.49 (s, 1H), 3.05 (bs, 2H), 2.89 (bs, 2H), 2.81 (bs, 4H), 2.66 (m, 6H), 2.37 (bs, 2H), 2.03 (d, J=7.0 Hz, 2H), 1.56 (bs, 2H), 1.46 (bs, 2H), 1.27 (bs, 2H).

Intermediate 157

(3R)-1-azabicyclo[2.2.2]oct-3-yl{4-[(1E)-5-(6-formyl-2-oxo-1,3-benzoxazol-3(2H)-yl)pent-1-en-1-yl]biphenyl-2-yl}carbamate Obtained as a foam (244 mg, 81%) from 2-oxo-3-pent-4-en-1-yl-2,3-dihydro-1,3-benzoxazole-6-carbaldehyde (Intermediate 148; 120 mg, 0.52 mmol), (3R)-1-azabicyclo[2.2.2]oct-3-yl(4-bromobiphenyl-2-yl)carbamate (Intermediate 5; 220 mg, 0.5 mmol), tri-o-tolylphosphine (150 mg, 0.49 mmol), N,N-Diisopropylethylamine (0.175 mL, 1 mmol) and palladium acetate (55 mg, 0.24 mmol) following the experimental procedure as described for intermediate 6. The crude obtained was purified by column chromatography with silica gel, eluting with a mixture of chloroform:methanol:ammonium (40:4:0.2).

LRMS (m/z): 552 (M+1)+

Intermediate 158

(3R)-1-azabicyclo[2.2.2]oct-3-yl(4-{(1E)-5-[6-({[(2R)-2-{[tert-butyl(dimethyl)silyl]-oxy}-2-(8-hydroxy-2-oxo-1,2-dihydroquinolin-5-yl)ethyl]amino}methyl)-2-oxo-1,3-benzoxazol-3(2H)-yl]pent-1-en-1-yl}biphenyl-2-yl)carbamate Obtained as solid (262 mg, 50%) from (3R)-1-azabicyclo[2.2.2]oct-3-yl{4-[(1E)-5-(6-formyl-2-oxo-1,3-benzoxazol-3(2H)-yl)pent-1-en-1-yl]biphenyl-2-yl}carbamate (Intermediate 157; 244 mg, 0.44 mmol), 5-((1R)-2-amino-1-{[tert-butyl(dimethyl)-silyl]oxy}ethyl)-8-hydroxyquinolin-2(1H)-one acetate (190 mg, 0.48 mmol) (prepared according to preparation 8 from US20060035931) and sodium triacetoxyborohydride (285 mg, 1.34 mmol) following the experimental procedure as described for Intermediate 7. The crude obtained was purified by column chromatography with silica gel, eluting with a mixture of chloroform:methanol:ammonium (40:4:0.2).

LRMS (m/z): 871 (M+1)+

Intermediate 159

(3R)-1-azabicyclo[2.2.2]oct-3-yl(4-{5-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate Obtained as a diacetate salt (158 mg, 53%) from (3R)-1-azabicyclo[2.2.2]oct-3-yl(4-{(1E)-5-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]pent-1-en-1-yl}-biphenyl-2-yl)carbamate (Intermediate 158; 262 mg, 0.3 mmol) and palladium on charcoal (10%, 35 mg) following the experimental procedure as described for Intermediate 67. The crude obtained was purified by column chromatography with silica gel, eluting with a mixture of chloroform:methanol:ammonium (40:4:0.2).

LRMS (m/z): 873 (M+1)+

Example 31

(3R)-1-azabicyclo[2.2.2]oct-3-yl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3 (2H)-yl]pentyl}biphenyl-2-yl)carbamate dihydrofluoride Obtained as a white solid (124 mg, 99%) from (3R)-1-azabicyclo[2.2.2]oct-3-yl(4-{5-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate (Intermediate 159; 155 mg, 0.16 mmol) and triethylamine trihydrofluoride (80 μL, 0.49 mmol) following the experimental procedure as described for Example 1.

LRMS (m/z): 758 (M+1)+

1H NMR (300 MHz, dmso) δ 8.69 (s, 1H), 8.11 (d, J=10.0 Hz, 1H), 7.45-7.27 (m, 6H), 7.27-7.13 (m, 4H), 7.12-7.02 (m, 2H), 6.90 (d, J=8.1 Hz, 1H), 6.46 (d, J=9.9 Hz, 1H), 5.12-5.05 (m, 1H), 4.50 (s, 1H), 3.81 (bs, 4H), 3.08 (dd, J=13.9, 8.3 Hz, 2H), 2.67 (dd, J=10.1, 7.7 Hz, 6H), 2.57 (t, J=7.4 Hz, 2H), 2.42 (d, J=14.1 Hz, 2H), 1.66-1.53 (m, 4H), 1.48 (s, 2H), 1.35 (s, 3H).

Intermediate 160 trans-4-(benzyloxy)carbonylaminocyclohexyl[4-(4-{[4-({[tert-butyl(dimethyl)silyl]oxy}methyl)-2-chloro-5-methoxyphenyl]amino}-4-oxobutyl)biphenyl-2-yl]carbamate Obtained as a white solid (99 mg, 83%) from 4-(2-(((((trans)-4-(((benzyloxy)carbonyl)amino)cyclohexyl)oxy)carbonyl)amino)-[1,1'-biphenyl]-4-yl)butanoic acid (Intermediate 124; 78 mg, 0.15 mmol), 4-((tert-butyldimethylsilyloxy)methyl)-2-chloro-5-methoxyaniline (Intermediate 39 WO2011/141180A1; 50 mg, 0.17 mmol), diisopropylethylenediamine (77 μL, 0.44 mmol) and HATU (73 mg, 0.19 mmol) following the experimental procedure as described for Intermediate 125 and the crude obtained was used in the next step without further purification.

LRMS (m/z): 683 (tropilic cation)+

Intermediate 161 trans-4-(benzyloxy)carbonylaminocyclohexyl[4-(4-{[2-chloro-4-(hydroxymethyl)-5-methoxyphenyl]amino}-4-oxobutyl)biphenyl-2-yl]carbamate To a solution of trans-4-(benzyloxy)carbonylaminocyclohexyl[4-(4-{[4-({[tert-butyl(dimethyl)silyl]oxy}methyl)-2-chloro-5-methoxyphenyl]amino}-4-oxobutyl)biphenyl-2-yl]carbamate (Intermediate 160; 99 mg, 0.12 mmol) in anhydrous tetrahydrofurane (1 mL) was added triethylamine trihydrofluoride (100 μL, 0.61 mmol). The reaction mixture was stirred overnight at room temperature. The solvent was removed under reduced pressure and the crude obtained was partitioned between methylene chloride and bicarbonate 4%. The organic layer was washed with water and brine, dried, filtered and the solvent was removed under reduced pressure giving the title compound as a foam (78 mg, 91%), which was used in the next step without further purification.

LRMS (m/z): 701 (M+1)+

Intermediate 162 trans-4-(benzyloxy)carbonylaminocyclohexyl(4-{4-[(2-chloro-4-formyl-5-methoxyphenyl)amino]-4-oxobutyl}biphenyl-2-yl)carbamate Obtained as a foam (81 mg, 80%) from trans-4-(benzyloxy)carbonylaminocyclohexyl[4-(4-{[2-chloro-4-(hydroxymethyl)-5-methoxyphenyl]amino}-4-oxobutyl)biphenyl-2-yl]carbamate (Intermediate 161; 78 mg, 0.11 mmol) and Dess-Martin periodinane (57 mg, 0.13 mmol) following the experimental procedure as described for Intermediate 64 and the crude obtained was used in the next step without further purification.

LRMS (m/z): 699 (M+1)+

Intermediate 163 trans-4-(benzyloxy)carbonylaminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate Obtained as a white solid (30 mg, 25%) from trans-4-(benzyloxy)carbonylaminocyclohexyl(4-{4-[(2-chloro-4-formyl-5-methoxyphenyl)-amino]-4-oxobutyl}-biphenyl-2-yl)-carbamate (Intermediate 162; 81 mg, 0.12 mmol), 5-((1R)-2-amino-1-{[tert-butyl(dimethyl)-silyl]oxy}ethyl)-8-hydroxyquinolin-2(1H)-one acetate (46 mg, 0.12 mmol) (prepared according to preparation 8 from US20060035931) and sodium triacetoxyborohydride (74 mg, 0.35 mmol) following the experimental procedure as described for Intermediate 7. The crude obtained was purified by column chromatography with silica gel, eluting with a mixture of Hexane:Ethyl ether:Ethanol.

LRMS (m/z): 508 (M/2)+

Intermediate 164 trans-4-aminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl] carbamate Obtained as a yellow solid (22 mg, 84%) from trans-4-(benzyloxy)carbonylaminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate (Intermediate 163; 30 mg, 0.03 mmol) and palladium on charcoal (10%; 3 mg) following the experimental procedure as described for Intermediate 67, and the crude obtained was used in the final step without further manipulation.

LRMS (m/z): 883 (M+1)+

Example 32 trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate dihydrofluoride Obtained as a solid (17 mg, 80%) from trans-4-aminocyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate (Intermediate 164; 20 mg, 0.02 mmol) and triethylamine trihydrofluoride (80 µL, 0.49 mmol) following the experimental procedure as described for Example 1.

LRMS (m/z): 769 (M+1)+

1H NMR (300 MHz, dmso) δ 9.52 (s, 1H), 8.96 (s, 1H), 8.22 (d, J=10.0 Hz, 1H), 7.67 (s, 1H), 7.53 (s, 1H), 7.50-7.06 (m, 10H), 7.02 (t, J=6.1 Hz, 1H), 6.55 (d, J=9.9 Hz, 1H), 5.48 (d, J=7.1 Hz, 1H), 4.33 (s, 1H), 4.17 (d, J=5.1 Hz, 2H), 3.80 (s, 3H), 2.99 (d, J=10.3 Hz, 4H), 2.74-2.57 (m, 2H), 2.04-1.71 (m, 4H), 1.49-1.15 (m, 4H).

Intermediate 165

2-nitrobiphenyl-4-ol

To a solution of 4-iodo-3-nitrophenol (1 g, 0.0037 mol) in dioxane (10 mL) was added potassium carbonate (2 g, 0.014 mol) and phenyl boronic acid (0.6 g, 0.0049 mol), the mixture was placed under nitrogen atmosphere and then norbornylphosphino Pd II (0.11 g, 0.002 mol) was added into the reaction mixture, which was stirred for 2 hours at 90° C. The mixture was filtered through Celite and the solvent was removed under reduced pressure. The crude was partitioned between ethyl acetate and water, the organic layer was washed with brine, dried, filtered and the solvent was removed under reduced pressure giving the title compound as a solid (890 mg, 95%), which was used in the next step without further purification.

LRMS (m/z): 216 (M+1)+

Intermediate 166 tert-butyl(dimethyl)({6-[(2-nitrobiphenyl-4-yl)oxy]hexyl}oxy)silane

To a solution of 2-nitrobiphenyl-4-ol (Intermediate 165; 890 mg, 3.64 mmol) was added (6-bromohexyloxy)(tert-butyl)dimethylsilane (1.6 mg, 5.7 mmol) and potassium carbonate (760 mg, 5.5 mmol). The mixture was stirred at 70° C. during 2 hours. Ethyl acetate was added into the mixture and the organic layer was washed several times with water, dried, filtered and the solvent was removed under reduced pressure. The crude obtained was purified by column chromatography with silica gel, eluting with a mixture of Hexane:Ethyl ether, giving the title compound as a solid (1.5 g, 93%).

LRMS (m/z): 430 (M+1)+

Intermediate 167

{4-[(6-{[tert-butyl(dimethyl)silyl]oxy}hexyl)oxy]biphenyl-2-yl}amine

To a solution of tert-butyl(dimethyl)({6-[(2-nitrobiphenyl-4-yl)oxy]hexyl}oxy)silane (Intermediate 166; 3.53 g, 0.008 mol) in methanol (20 mL) was added palladium on charcoal (10%, 0.1 g). The reaction mixture was submitted to a hydrogenation with a hydrogen balloon overnight at room temperature. The catalyst was removed by filtration through Celite and the solvent was removed under reduced pressure giving the title compound an oil (1.52 g, 46%), which was used in the next step without further purification.

LRMS (m/z): 400 (M+1)+

Intermediate 168 tert-butyl({6-[(2-isocyanatobiphenyl-4-yl)oxy]hexyl}oxy)dimethylsilane

Obtained as a solution of toluene (4.2 mL, 400 mg; 93%) from {4-[(6-{[tert-butyl(dimethyl)silyl]oxy}hexyl)oxy]biphenyl-2-yl}amine (Intermediate 167; 400 mg, 1 mmol), triphosgene (120 mg, 0.4 mmol) and triethylamine (279 µL, 2 mmol) following the experimental procedure as described for Intermediate 4 and the crude obtained was used as a solution of the title compound in toluene.

LRMS (m/z): 426 (M+1)+

Intermediate 169 trans-4-(((benzyloxy)carbonyl)amino)cyclohexyl(4-((6-((tert-butyldimethylsilyl)oxy)hexyl)oxy)-[1,1'-biphenyl]-2-yl)carbamate Obtained as a solid (117 mg, 37%) from benzyl(trans-4-hydroxycyclohexyl)carbamate (117 mg, 0.47 mmol) and tert-butyl({6-[(2-isocyanatobiphenyl-4-yl)oxy]hexyl}oxy)-dimethylsilane (200 mg, 0.47 mmol) following the experimental procedure as described for Intermediate 43 and the crude obtained was purified by column chromatography with silica gel, eluting with a mixture of Hexane:Ethyl ether:Ethanol.

LRMS (m/z): 675 (M+1)+

Intermediate 170 trans-4-(((benzyloxy)carbonyl)amino)cyclohexyl(4-((6-hydroxyhexyl)oxy)-[1,1'-biphenyl]-2-yl)carbamate Obtained as a foam (103 mg, 98%) from trans-4-(((benzyloxy)carbonyl)amino)-cyclohexyl(4-((6-((tert-butyldimethylsilyl)oxy)hexyl)oxy)-[1,1'-biphenyl]-2-yl)carbamate (Intermediate 169; 120 mg, 0.18 mmol) and triethylamine trihydrofluoride (80 µL, 0.49 mmol) following the experimental procedure as described for Example 1. The crude obtained was used in the next step without further purification.

LRMS (m/z): 561 (M+1)+

Intermediate 171 trans-4-(((benzyloxy)carbonyl)amino)cyclohexyl(4-((6-oxohexyl)oxy)-[1,1'-biphenyl]-2-yl)carbamate Obtained as a foam (83 mg, 98%) from trans-4-(((benzyloxy)carbonyl)amino)cyclohexyl(4-((6-hydroxyhexyl)oxy)-[1,1'-biphenyl]-2-yl)carbamate (Intermediate 170; 120 mg, 0.18 mmol) and Dess-Martin periodinane (63 mg, 0.15 mmol) following the experimental procedure as described for Intermediate 64 and the crude obtained was used in the next step without further purification.

LRMS (m/z): 559 (M+1)+

Intermediate 172 trans-4-(((benzyloxy)carbonyl)amino)cyclohexyl(4-((6-(((R)-2-((tert-butyldimethyl-silyl)oxy)-2-(8-hydroxy-2-oxo-1,2-dihydroquinolin-5-yl)ethyl)amino)hexyl)oxy)-[1,1'-biphenyl]-2-yl)carbamate Obtained as a solid (30 mg, 58%) from trans-4-(((benzyloxy)carbonyl)amino)cyclohexyl(4-((6-oxohexyl)oxy)-[1,1'-biphenyl]-2-yl)carbamate (Intermediate 171; 20 mg, 0.04 mmol), 5-((1R)-2-amino-1-{[tert-butyl(dimethyl)-silyl]oxy}ethyl)-8-hydroxyquinolin-2(1H)-one acetate (14 mg, 0.04 mmol) (prepared according to preparation 8 from US20060035931) and sodium triacetoxyborohydride (40 mg, 0.19 mmol) following the experimental procedure as described for Intermediate 7. The crude mixture was used in the next step without further purification.

LRMS (m/z): 879 (M+1)

Intermediate 173 trans-4-aminocyclohexyl{4-[(6-{[(2R)-2-{[tert-butyl(dimethyl)silyl]oxy}-2-(8-hydroxy-2-oxo-1,2-dihydroquinolin-5-yl)ethyl]amino}hexyl)oxy]biphenyl-2-yl}carbamate Obtained as a foam (30 mg, 41%) from trans-4-(((benzyloxy)carbonyl)amino)cyclohexyl(4-((6-(((R)-2-((tert-butyldimethylsilyl)oxy)-2-(8-hydroxy-2-oxo-1,2-dihydroquinolin-5-yl)ethyl)amino)hexyl)oxy)-[1,1'-biphenyl]-2-yl)carbamate (Intermediate 172; 81 mg, 0.09 mmol) following the experimental procedure as described for Intermediate 77 but using as a solvent methanol instead of acetic acid. The crude obtained was used in the next step without further purification.

LRMS (m/z): 744 (M+1)

Example 33 trans-4-aminocyclohexyl{4-[(6-{[(2R)-2-hydroxy-2-(8-hydroxy-2-oxo-1,2-dihydroquinolin-5-yl)ethyl]amino}hexyl)oxy]biphenyl-2-yl}carbamate dihydrofluoride Obtained as a solid (18 mg, 71%) from trans-4-aminocyclohexyl{4-[(6-{[(2R)-2-{[tert-butyl(dimethyl)silyl]oxy}-2-(8-hydroxy-2-oxo-1,2-dihydroquinolin-5-yl)ethyl]amino}hexyl)-oxy]biphenyl-2-yl}carbamate (Intermediate 173; 30 mg, 0.04 mmol) and triethylamine trihydrofluoride (80 µL, 0.49 mmol) following the experimental procedure as described for Example 1.

LRMS (m/z): 629 (M+1)+

1H NMR (300 MHz, cd3od) δ 8.36 (d, J=9.7 Hz, 1H), 7.79 (s, 1H), 7.41 (bs, 2H), 7.45-7.25 (m, 4H), 7.17 (d, J=8.5 Hz, 1H), 7.03 (d, J=7.9 Hz, 1H), 6.77 (d, J=8.2 Hz, 1H), 6.70 (d, J=9.6 Hz, 1H), 5.38 (s, 1H), 4.91 (bs, 1H), 4.54 (bs, 1H), 4.04 (bs, 2H), 3.18 (d, J=6.9 Hz, 2H), 3.06 (bs, 2H), 2.04 (bs, 4H), 1.83 (bs, 4H), 1.46 (bs, 6H), 1.36-1.26 (m, 2H).

Intermediate 174 tert-butyl(trans-4-hydroxycyclohexyl)carbamate

To a solution of trans-4-aminocyclohexanol (15 g, 0.13 mol) in acetonitrile (250 mL) was added in portions di-tert-butyldicarbonate (31 g, 0.14 mol). The mixture was stirred at room temperature overnight. The solid was filtered and washed with Hexane/Ethyl Acetate, obtaining the title compound as a white solid (23.7 g, 84%), which was used in the next step without further purification.

1H NMR (300 MHz, cdcl3) δ 4.35 (bs, 1H), 3.60 (t, J=10.5 Hz, 1H), 3.42 (bs, 1H), 2.05-1.78 (m, 4H), 1.60 (s, 2H), 1.42 (s, 9H), 1.38-1.26 (m, 2H), 1.26-1.06 (m, 2H).

Intermediate 175 trans-4-tert-butylaminocyclohexyl(5-bromobiphenyl-2-yl)carbamate

Obtained as a white solid (890 mg, 85%) from 5-bromo-2-isocyanatobiphenyl (Intermediate 113; 552 mg, 2.01 mmol) and tert-butyl(trans-4-hydroxycyclohexyl)-carbamate (Intermediate 174; 433 mg, 2.01 mmol) following the experimental procedure as described for Intermediate 43 and the crude obtained was used in the next step without further purification.

LRMS (m/z): 490 (M+1)+

Intermediate 176 trans-4-tert-butylaminocyclohexyl{5-[(1E)-4-(6-formyl-2-oxo-1,3-benzoxazol-3(2H)-yl)but-1-en-1-yl]biphenyl-2-yl}carbamate Obtained as a yellow foam (235 mg, 33%) from trans-4-tert-butylaminocyclohexyl(5-bromobiphenyl-2-yl)carbamate (Intermediate 175; 530 mg, 1.08 mmol), 3-but-3-en-1-yl-2-oxo-2,3-dihydro-1,3-benzoxazole-6-carbaldehyde (Intermediate 38; 235 mg, 1.08 mmol), tri-o-tolylphosphine (263 mg, 0.86 mmol), N,N-Diisopropylethylamine (0.377 mL, 2.16 mmol) and palladium acetate (69 mg, 0.31 mmol) following the experimental procedure as described for intermediate 6. The crude obtained was purified by column chromatography with silica gel, eluting with a mixture of hexane:ether:ethanol.

LRMS (m/z): 626 (M+1)+

Intermediate 177 trans-4-tert-butylaminocyclohexyl(5-{4-[6-({[(2R)-2-{[tert-butyl(dimethyl)silyl]-oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate Obtained as a pale yellow solid (179 mg, 50%) from trans-4-tert-butylaminocyclohexyl {5-[(1E)-4-(6-formyl-2-oxo-1,3-benzoxazol-3(2H)-yl)but-1-en-1-yl]biphenyl-2-yl}carbamate (Intermediate 176; 230 mg, 0.37 mmol), 5-((1R)-2-amino-1-{[tert-butyl(dimethyl)-silyl]oxy}ethyl)-8-hydroxyquinolin-2(1H)-one acetate (145 mg, 0.37 mmol) (prepared according to preparation 8 from US20060035931) and sodium triacetoxyborohydride (234 mg, 1.1 mmol) following the experimental procedure as described for Intermediate 7. The crude obtained was purified by column chromatography with silica gel, eluting with a mixture of hexane:ether:ethanol.

LRMS (m/z): 945 (M+1)+

Intermediate 178 trans-4-tert-butylaminocyclohexyl(5-{4-[6-({[(2R)-2-{[tert-butyl(dimethyl)silyl]-oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl) carbamate Obtained as a foam (129 mg, 69%) from trans-4-tert-butylaminocyclohexyl(5-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate (Intermediate 177; 174 mg, 0.18 mmol) and palladium on charcoal (10%, 20 mg) following the experimental procedure as described for Intermediate 67 and the crude mixture obtained was used in the final step without further purification.

LRMS (m/z): 947 (M+1)+

Example 34 trans-4-aminocyclohexyl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate dihydrochloride Obtained as a white solid (19 mg, 33%) from trans-4-tert-butylaminocyclohexyl(5-{4-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate (Intermediate 178; 74 mg, 0.08 mmol) and hydrogen chloride (4N in dioxane; 3 mL) following the experimental procedure as described for Intermediate 21. The crude obtained was purified by column chromatography in reversed phase using as eluents Acetonitrile and Methanol.

LRMS (m/z): 732 (M+1)+

1H NMR (300 MHz, dmso) δ 8.52 (s, 1H), 8.12 (d, J=10.0 Hz, 1H), 7.45-7.26 (m, 5H), 7.27-7.08 (m, 5H), 7.05 (d, J=8.3 Hz, 1H), 6.90 (d, J=8.1 Hz, 1H), 6.45 (d, J=9.9 Hz, 1H), 5.04 (bs, 1H), 4.32 (bs, 2H), 4.12 (bs, 2H), 3.83 (bs, 2H), 3.73 (bs, 2H), 3.17 (bs, 4H), 2.63 (bs, 2H), 2.44 (bs, 2H), 1.77 (bs, 4H), 1.23 (bs, 4H).

Intermediate 179

4-(but-3-en-1-ylamino)-3-nitrobenzonitrile

Obtained as a yellow solid (2 g, 67%) from 4-amino-3-nitrobenzonitrile (2.5 g, 0.015 mol), 4-bromobut-1-ene (1.33 mL, 0.014 mol) and potassium carbonate (10.5 g, 0.076 mol) following the experimental procedure as described for Intermediate 9 and the crude obtained was purified by column chromatography with silica gel, eluting with a mixture of hexane:ether.

LRMS (m/z): 218 (M+1)+

Intermediate 180

3-amino-4-(but-3-en-1-ylamino)benzonitrile

To a solution of 4-(but-3-en-1-ylamino)-3-nitrobenzonitrile (Intermediate 179; 2 g, 0.009 mol) in ethanol (20 mL) was added Tin(II)chloride (11.1 g, 0.049 mol). The reaction mixture was stirred at 90° C. for 4 hours. The solvent was partially removed and sodium hydroxide was added to precipitate salts, which were filtrated. The solvent was removed under reduced pressure to give the title compound (1.6 g, 92%), which was used in the next step without further purification.

LRMS (m/z): 188 (M+1)+

Intermediate 181

1-but-3-en-1-yl-1H-1,2,3-benzotriazole-5-carbonitrile 3-amino-4-(but-3-en-1-ylamino)benzonitrile (Intermediate 180; 1 g, 5.34 mmol) was dissolved in hydrogen chloride (5N, 9.6 mL). The reaction mixture was cooled to 0° C. and a solution of sodium nitrite (0.55 g, 8.01 mmol) in water (20 mL) was added. The reaction mixture was stirred for 2 hours at room temperature. Water was added into the mixture and the crude was extracted with chloroform. The solvent was removed under reduced pressure and the crude obtained was crystallized with pentane giving the title compound as a solid (0.84 g, 79%).

LRMS (m/z): 199 (M+1)+

Intermediate 182

1-but-3-en-1-yl-1H-1,2,3-benzotriazole-5-carbaldehyde

Obtained as an oil (167 mg, 33%) from 1-but-3-en-1-yl-1H-1,2,3-benzotriazole-5-carbonitrile (Intermediate 181; 350 mg, 1.77 mmol) in formic acid 80% and Niquel-aluminium (391 mg, 4.4 mmol) following the experimental procedure as described for Intermediate 2 and the crude was purified by column chromatography with silica gel, eluting with a mixture of hexane:ether.

LRMS (m/z): 202 (M+1)+

Intermediate 183 trans-4-tert-butylaminocyclohexyl(4-bromobiphenyl-2-yl)carbamate

Obtained as a solid (1.2 g, 64%) from 4-bromo-2-isocyanatobiphenyl (Intermediate 4; 1.05 g, 3.83 mmol) and tert-butyl(trans-4-hydroxycyclohexyl)carbamate (Intermediate 174; 0.82 g, 3.83 mmol) following the experimental procedure as described for Intermediate 43 and the crude obtained was used in the next step without further purification.

LRMS (m/z): 490 (M+1)+

Intermediate 184 trans-4-tert-butylaminocyclohexyl{4-[(1E)-4-(5-formyl-1H-1,2,3-benzotriazol-1-yl)but-1-en-1-yl]biphenyl-2-yl}carbamate Obtained as a yellow foam (130 mg, 42%) from trans-4-tert-butylaminocyclohexyl(4-bromobiphenyl-2-yl)carbamate (Intermediate 183; 250 mg, 0.51 mmol), 1-but-3-en-1-yl-1H-1,2,3-benzotriazole-5-carbaldehyde (Intermediate 182; 161 mg, 0.8 mmol), tri-o-tolylphosphine (155 mg, 0.51 mmol), N,N-Diisopropylethylamine (0.177 mL, 1.02 mmol) and palladium acetate (57 mg, 0.25 mmol) following the experimental procedure as described for intermediate 6. The crude obtained was purified by column chromatography with silica gel, eluting with a mixture of hexane:ether:ethanol.

LRMS (m/z): 610 (M+1)+

Intermediate 185 trans-4-tert-butylaminocyclohexyl(4-{(1E)-4-[5-({[(2R)-2-{[tert-butyl(dimethyl)-silyl]oxy}-2-(8-hydroxy-2-oxo-1,2-dihydroquinolin-5-yl)ethyl]amino}methyl)-1H-1,2,3-benzotriazol-1-yl]but-1-en-1-yl}biphenyl-2-yl)carbamate Obtained as a solid (81 mg, 41%) from trans-4-tert-butylaminocyclohexyl{4-[(1E)-4-(5-formyl-1H-1,2,3-benzotriazol-1-yl)but-1-en-1-yl]biphenyl-2-yl}carbamate (Intermediate 184; 130 mg, 0.21 mmol), 5-((1R)-2-amino-1-{[tert-butyl(dimethyl)-silyl]oxy}ethyl)-8-hydroxyquinolin-2(1H)-one acetate (145 mg, 0.37 mmol) (prepared according to preparation 8 from US20060035931) and sodium triacetoxyborohydride (234 mg, 1.1 mmol) following the experimental procedure as described for Intermediate 7. The crude obtained was purified by column chromatography with silica gel, eluting with a mixture of hexane:ether:ethanol.

LRMS (m/z): 929 (M+1)+

Intermediate 186 trans-4-tert-butylaminocyclohexyl(4-{4-[5-({[(2R)-2-{[tert-butyl(dimethyl)silyl]-oxy}-2-(8-hydroxy-2-oxo-1,2-dihydroquinolin-5-yl)ethyl]amino}methyl)-1H-1,2,3-benzotriazol-1-yl]butyl}biphenyl-2-yl)carbamate Obtained as solid (74 mg, 73%) from trans-4-tert-butylaminocyclohexyl(4-{(1E)-4-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]but-1-en-1-yl}biphenyl-2-yl)carbamate (Intermediate 185; 85 mg, 0.09 mmol) and palladium on charcoal (10%, 10 mg) following the experimental procedure as described for Intermediate 67 and the crude obtained was used in the next step without further purification.

LRMS (m/z): 931 (M+1)+

Example 35 trans-4-aminocyclohexyl(4-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}biphenyl-2-yl)carbamate Obtained as solid (8 mg, 12%) from trans-4-tert-butylaminocyclohexyl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]butyl}biphenyl-2-yl)carbamate (Intermediate 186; 85 mg, 0.09 mmol) and hydrogen chloride (4N in dioxane; 5 mL) following the experimental procedure as described for Intermediate 21. The crude obtained was purified by column chromatography with silica gel, eluting with a mixture of chloroform:methanol:ammonium (40:4:0.2).

LRMS (m/z): 716 (M+1)+

1H NMR (300 MHz, cd3od) δ 8.25 (d, J=9.8 Hz, 1H), 7.91 (d, J=7.3 Hz, 1H), 7.68 (d, J=8.5 Hz, 1H), 7.51 (d, J=8.5 Hz, 1H), 7.44-7.27 (m, 5H), 7.14 (bs, 2H), 6.99 (d, J=7.7 Hz, 1H), 6.94-6.86 (m, 1H), 6.55-6.48 (m, 1H), 5.23-5.16 (m, 1H), 4.75 (dd, J=14.0, 7.2 Hz, 2H), 4.45 (s, 1H), 3.97 (s, 1H), 3.84 (dd, J=10.5, 7.8 Hz, 1H), 3.65-3.54 (m, 1H), 2.95-2.72 (m, 2H), 2.66 (s, 1H), 2.12-1.99 (m, 2H), 1.91 (d, J=5.5 Hz, 2H), 1.67 (d, J=7.0 Hz, 2H), 1.43-1.22 (m, 5H).

Intermediate 187 ethyl 4-(6-aminobiphenyl-3-yl)butanoate

Obtained as an orange oil (1 g, 87%) from (5-bromobiphenyl-2-yl)amine (Intermediate 112; 1 g, 4.03 mmol), palladium acetate (9.05 mg, 0.04 mmol), 2-diciclohexylamino-2',6'-dimethoxy-1,1'-biphenyl (33 mg, 0.08 mmol) and (4-ethoxy-4-oxobutyl)zinc(II) bromide (9.67 mL, 4.84 mmol) following the experimental procedure as described for Intermediate 122 and the crude obtained was used in the next step without further purification.

LRMS (m/z): 284 (M+1)+

Intermediate 188 ethyl 4-(6-{[({trans-4-[(tert-butoxycarbonyl)amino]cyclohexyl}oxy)carbonyl]amino}biphenyl-3-yl)butanoate Obtained as a solid (0.94 g, 51%) from ethyl 4-(6-aminobiphenyl-3-yl)butanoate (Intermediate 187; 1 g, 3.53 mmol), tert-butyl(trans-4-hydroxycyclohexyl)carbamate (Intermediate 174; 0.8 g, 3.71 mmol), triphosgene (0.42 g, 1.41 mmol) and triethylamine (0.983 mL, 7.05 mmol) following the experimental procedure as described for Intermediate 123 and the crude obtained was purified by column chromatography with silica gel, eluting with a mixture of hexane:ether:ethanol.

LRMS (m/z): 525 (M+1)+

Intermediate 189

4-(6-{[({trans-4-[(tert-butoxycarbonyl)amino]cyclohexyl}oxy) carbonyl]amino}-biphenyl-3-yl)butanoic acid Obtained as a solid (880 mg, 98%) from ethyl 4-(6-{[({trans-4-[(tert-butoxycarbonyl)-amino]cyclohexyl}oxy)carbonyl]amino}biphenyl-3-yl)butanoate (Intermediate 188; 940 mg, 1.79 mmol) and sodium hydroxide (2N, 4.48 mL) following the experimental procedure as described for Intermediate 124 and the crude obtained was used in the next step without further purification.

LRMS (m/z): 497 (M+1)+

Intermediate 190 tert-butyl-trans-4-aminocyclohexyl(5-{4-[(4-formylphenyl)amino]-4-oxobutyl}-biphenyl-2-yl)carbamate Obtained as a solid (740 mg, 69%) from 4-(6-{[({trans-4-[(tert-butoxycarbonyl)amino]-cyclohexyl}oxy)carbonyl]amino}biphenyl-3-yl)butanoic acid (Intermediate 189; 880 mg, 1.77 mmol), 4-aminobenzaldehyde (236 mg, 1.95 mmol), diisopropylethylenediamine (0.925 mL, 5.32 mmol) and HATU (1 g, 2.66 mmol) following the experimental procedure as described for Intermediate 125 and the crude obtained was used in the next step without further purification.

LRMS (m/z): 600 (M+1)+

Intermediate 191 tert-butyl-trans-4-aminocyclohexyl[5-(4-{[4-({[(2R)-2-{[tert-butyl(dimethyl)silyl]-oxy}-2-(8-hydroxy-2-oxo-1,2-dihydroquinolin-5-yl)ethyl]amino}methyl)phenyl]-amino}-4-oxobutyl)biphenyl-2-yl]carbamate Obtained as a solid (770 mg, 68%) from tert-butyl-trans-4-aminocyclohexyl(5-{4-[(4-formylphenyl)amino]-4-oxobutyl}biphenyl-2-yl)carbamate (Intermediate 190; 740 mg, 1.23 mmol), 5-((1R)-2-amino-1-{[tert-butyl(dimethyl)silyl]oxy}ethyl)-8-hydroxyquinolin-2(1H)-one acetate (413 mg, 1.23 mmol) (prepared according to preparation 8 from US20060035931) and sodium triacetoxyborohydride (784 mg, 3.7 mmol) following the experimental procedure as described for Intermediate 7. The crude obtained was purified by column chromatography with silica gel, eluting with a mixture of hexane:ether:ethanol.

LRMS (m/z): 919 (M+1)+

Example 36 trans-4-aminocyclohexyl[5-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate Obtained as a white solid (110 mg, 18%) from tert-butyl-trans-4-aminocyclohexyl[5-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate (Intermediate 191; 770 mg, 0.84 mmol) and hydrogen chloride (8N in dioxane, 8 mL) following the experimental procedure as described for Intermediate 21 and the crude obtained was purified by column chromatography with silica gel, eluting with a mixture of chloroform:methanol:ammonium (40:4:0.2).

LRMS (m/z): 704 (M+1)+

1H NMR (400 MHz, dmso) δ 8.56 (s, 1H), 8.09 (d, J=10.2 Hz, 1H), 7.50 (d, J=8.3 Hz, 2H), 7.35 (t, J=28.1 Hz, 5H), 7.20 (dd, J=25.0, 16.9 Hz, 4H), 7.04 (d, J=8.4 Hz, 1H), 6.90 (d, J=8.0 Hz, 1H), 6.45 (d, J=9.8 Hz, 1H), 5.04 (s, 1H), 4.33 (s, 2H), 2.69 (d, J=20.4 Hz, 3H), 2.64 (s, 5H), 2.33 (s, 2H), 1.91 (s, 2H), 1.79 (s, 4H), 1.21 (s, 4H).

Intermediate 192 methyl(4E)-5-(2-{[({trans-4-[(tert-butoxycarbonyl)amino]cyclohexyl}oxy)-carbonyl]amino}biphenyl-4-yl)pent-4-enoate Obtained as a solid (0.57 g, 44%) from trans-4-tert-butylaminocyclohexyl(4-bromobiphenyl-2-yl)carbamate (Intermediate 183; 1.2 g, 2.45 mmol), methyl pent-4-enoate (0.36 mL, 2.94 mmol), tri-o-tolylphosphine (0.8 g, 2.63 mmol), N,N-Diisopropylethylamine (0.85 mL, 4.88 mmol) and palladium acetate (280 mg, 1.25 mmol) following the experimental procedure as described for intermediate 6. The crude obtained was purified by column chromatography with silica gel, eluting with a mixture of hexane:ether.

LRMS (m/z): 523 (M+1)+

Intermediate 193

(4E)-5-(2-{[({trans-4-[(tert-butoxycarbonyl)amino]cyclohexyl}oxy) carbonyl]amino}biphenyl-4-yl)pent-4-enoic acid Obtained as a solid (599 mg, 97%) from methyl(4E)-5-(2-{[({trans-4-[(tert-butoxycarbonyl)amino]cyclohexyl}oxy)carbonyl]amino}biphenyl-4-yl)pent-4-enoate (Intermediate 192; 570 mg, 1.09 mmol) and sodium hydroxide (2N, 4.5 mL) following the experimental procedure as described for Intermediate 124 and the crude obtained was used in the next step without further purification.

LRMS (m/z): 509 (M+1)+

Intermediate 194 trans-4-aminocyclohexyl(4-{(1E)-5-[(4-formylphenyl)amino]-5-oxopent-1-en-1-yl}biphenyl-2-yl)carbamate Obtained as a solid (400 mg, 88%) from (4E)-5-(2-{[({trans-4-[(tert-butoxycarbonyl)-amino]cyclohexyl}oxy)carbonyl]amino}biphenyl-4-yl)pent-4-enoic acid (Intermediate 193; 300 mg, 0.59 mmol), 4-aminobenzaldehyde (80 mg, 0.66 mmol), diisopropylethylenediamine (0.31 mL, 1.78 mmol) and HATU (340 mg, 0.89 mmol) following the experimental procedure as described for Intermediate 125 and the crude obtained was used in the next step without further purification.

LRMS (m/z): 612 (M+1)+

Intermediate 195 trans-4-aminocyclohexyl[4-((1E)-5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopent-1-en-1-yl)biphenyl-2-yl]carbamate Obtained as a solid (60 mg, 12%) from trans-4-aminocyclohexyl(4-{(1E)-5-[(4-formylphenyl)amino]-5-oxopent-1-en-1-yl}biphenyl-2-yl)carbamate (Intermediate 194; 400 mg, 0.52 mmol), 5-((1R)-2-amino-1-{[tert-butyl(dimethyl)silyl]oxy}ethyl)-8-hydroxyquinolin-2(1H)-one acetate (175 mg, 0.52 mmol) (prepared according to preparation 8 from US20060035931) and sodium triacetoxyborohydride (333 mg, 1.57 mmol) following the experimental procedure as described for Intermediate 7. The crude obtained was purified by column chromatography with silica gel twice, first, eluting with a mixture of hexane:ether:ethanol and second, in reversed phase using as eluents Acetonitrile and Methanol.

LRMS (m/z): 931 (M+1)+

Intermediate 196 trans-4-aminocyclohexyl[4-(5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopentyl)biphenyl-2-yl]carbamate Obtained as a crude mixture (60 mg) from trans-4-aminocyclohexyl[4-((1E)-5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopent-1-en-1-yl)biphenyl-2-yl]carbamate (Intermediate 195; 60 mg, 0.06 mmol) and palladium on charcoal (10%, 10 mg) following the experimental procedure as described for Intermediate 67 and the crude mixture obtained was taken forward without purification.

LRMS (m/z): 933 (M+1)+

Example 37 trans-4-aminocyclohexyl[4-(5-{[4-({[(2R)-2-hydroxy-2-(8-hydroxy-2-oxo-1,2-dihydroquinolin-5-yl)ethyl]amino}methyl)phenyl]amino}-5-oxopentyl)biphenyl-2-yl]carbamate dihydrochloride Obtained as a white salt (55 mg, 97%) from trans-4-aminocyclohexyl[4-(5-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-5-oxopentyl)biphenyl-2-yl]carbamate (Intermediate 196; 65 mg, 0.07 mmol) and hydrogen chloride (4M in dioxane, 2 mL) following the experimental procedure as described for Intermediate 21.

LRMS (m/z): 718 (M+1)+

1H NMR (400 MHz, dmso) δ 8.12 (d, J=10.0 Hz, 1H), 7.92 (bs, 3H), 7.60 (bs, 2H), 7.48-7.25 (m, 5H), 7.14 (bs, 3H), 6.96 (bs, 1H), 6.53 (d, J=9.8, Hz 1H), 5.43-5.32 (m, 1H), 4.29 b (s, 1H), 4.11 (bs, 2H), 3.24 (bs, 4H), 2.96 (bs, 2H), 2.60 (bs, 2H), 2.34 (bs, 2H), 1.87 (bs, 3H), 1.61 (bs, 3H), 1.21 (bs, 3H).

Intermediate 197

N-benzyl-trans-4-aminocyclohexyl(4-{4-[(4-{2-[((2R)-2-[8-(benzyloxy)-2-oxo-1,2-dihydroquinolin-5-yl]-2-{[tert-butyl(dimethyl)silyl]oxy}ethyl)-tert-butylamino]ethyl}phenyl)carbamateamino]-4-oxobutyl}biphenyl-2-yl)carbamate Obtained as a solid (124 mg, 50%) from 4-(2-(((((trans)-4-(((benzyloxy)carbonyl)amino)-cyclohexyl)oxy)carbonyl)amino)-[1,1'-biphenyl]-4-yl)butanoic acid (Intermediate 124; 85 mg, 0.16 mmol), tert-butyl[2-(4-aminophenyl)ethyl]((2R)-2-[8-(benzyloxy)-2-oxo-1,2-dihydroquinolin-5-yl]-2-{[tert-butyl(dimethyl)silyl]oxy}ethyl)carbamate (Intermediate 121 from WO2009106351A1; 101 mg, 0.16 mmol), diisopropylethylenediamine (55 µL, 0.32 mmol) and HATU (132 mg, 0.35 mmol) following the experimental procedure as described for Intermediate 125. The crude obtained was purified by column chromatography with silica gel, eluting with a mixture of chloroform:methanol:ammonium (40:4:0.2).

LRMS (m/z): 579 (M/2)

Example 38 trans-4-aminocyclohexyl[4-(4-{[4-(2-{[(2R)-2-hydroxy-2-(8-hydroxy-2-oxo-1,2-dihydroquinolin-5-yl)ethyl]amino}ethyl)phenyl]amino}-4-oxobutyl)biphenyl-2-yl]carbamate dihydrochloride To a solution of N-benzyl-trans-4-aminocyclohexyl(4-{4-[(4-{2-[((2R)-2-[8-(benzyloxy)-2-oxo-1,2-dihydroquinolin-5-yl]-2-{[tert-butyl(dimethyl)silyl]oxy}ethyl)-tert-butylamino]-ethyl}phenyl)carbamateamino]-4-oxobutyl}biphenyl-2-yl)carbamate (Intermediate 197; 125 mg, 0.08 mmol) was added hydrogen chloride (5N, 165 µL) and the reaction mixture was stirred for 5 hours, then hydrogen chloride (4M in dioxane, 420 µL) was added. The mixture was stirred overnight at room temperature. The solvent was removed under reduced pressure and the crude obtained was dissolved with a mixture of Acetic Acid and Methanol (2:1) and palladium on charcoal (10%) was added. The reaction mixture was submitted to hydrogen with a balloon and it was stirred 24 h at room temperature. The catalyst was filtered through Celite and the solvent was removed under reduced pressure to afford a crude, which was treated with hydrogen chloride (4M in dioxane; 2 mL) and stirred 24 h at room temperature. The solvent was removed under reduced pressure and the crude obtained was purified by column chromatography with silica gel in reversed phase using as eluents Acetonitrile and Methanol. The title compound was obtained as a yellow foam (61 mg, 30%)

LRMS (m/z): 718 (M+1)+

1H NMR (300 MHz, dmso) δ 8.59 (s, 1H), 8.24 (d, J=10.0 Hz, 1H), 8.00 (s, 2H), 7.56 (d, J=8.6 Hz, 1H), 7.4-7.3 (m, 5H), 7.26-7.08 (m, 2H), 7.01 (d, J=8.1 Hz, 1H), 6.57 (d, J=10.0 Hz, 1H), 5.42 (s, 1H), 4.34 (bs, 2H), 3.17 (bs, 2H), 3.04-2.71 (m, 5H), 2.48-2.26 (m, 6H), 2.06-1.74 (m, 3H), 1.33 (bs, 4H).

Intermediate 198

2-amino-4-methoxyphenol

To a solution of 4-methoxy-2-nitrophenol (5 g, 0.029 mol) in methanol (250 mL) was added palladium on charcoal (10%, 0.5 g). The mixture was submitted to a H2 balloon over weekend at room temperature. The catalyst was filtered through Celite and the solvent was removed under reduced pressure giving the title compound as a yellow solid (4.85 g, 93%).

LRMS (m/z): 140 (M+1)+

Intermediate 199

5-methoxy-1,3-benzoxazol-2(3H)-one

A mixture of 2-amino-4-methoxyphenol (Intermediate 198; 4.8 g, 0.027 mol) and urea (2.65 g, 0.044 mol) was heated at 180° C. during 2 hours. Hydrogen chloride 1N (70 mL) was poured into the mixture and the crude was extracted with Ethyl Acetate, the organic layer was washed with water and brine, dried, filtered and the solvent was removed under reduced pressure giving the title compound as a solid (4.5 g, 99%).

LRMS (m/z): 166 (M+1)+

Intermediate 200

6-bromo-5-methoxy-1,3-benzoxazol-2(3H)-one

To a solution of 5-methoxy-1,3-benzoxazol-2(3H)-one (Intermediate 199; 4.5 g, 0.027 mol) in acetic acid (16 mL) was added drop wise at 15° C. acid bromide (33% in acetic acid; 12.5 mL, 0.069 mol) and hydrogen peroxide (3.6 mL, 0.035 mol). The mixture was stirred at room temperature 2 hours. Water was poured into the mixture and the crude was extracted with ethyl acetate. The solvent was removed under reduced pressure, giving the title compound as a solid (5.5 g, 82%).

LRMS (m/z): 245 (M+1)+

Intermediate 201

5-methoxy-2-oxo-2,3-dihydro-1,3-benzoxazole-6-carbaldehyde

To a solution of 6-bromo-5-methoxy-1,3-benzoxazol-2 (3H)-one (Intermediate 200; 1 g, 4.1 mmol) in anhydrous tetrahydrofurane (10 mL) was added drop wise at −78° C. Methyl magnesium bromide 3M in diethyl ether (1.5 mL, 4.5 mmol), then was slowly added 35 mL of anhydrous tetrahydrofurane. Once the temperature was −78° C. again, tert-butyl lithium (1.7M in pentane, 8.7 mL, 14.7 mmol) was added into the mixture. After some minutes dimethylformamide (1.9 mL, 24.4 mmol) was added and the reaction mixture was stirred 3 hours at room temperature. Water was slowly added into the mixture and tetrahydrofurane was partially evaporated. Ethyl acetate was added and the organic layer was washed with water, dried, filtered and evaporated to dryness. The crude obtained was purified by column chromatography with silica gel, eluting with a mixture of hexane:ether giving the title compound as a solid (310 mg, 39%).

LRMS (m/z): 194 (M+1)+

Intermediate 202

3-but-3-en-1-yl-5-methoxy-2-oxo-2,3-dihydro-1,3-benzoxazole-6-carbaldehyde

Obtained as foam (267 mg, 68%) from 5-methoxy-2-oxo-2,3-dihydro-1,3-benzoxazole-6-carbaldehyde (Intermediate 201; 307 mg, 1.59 mmol), 4-bromobut-1-ene (200 µL, 1.97 mmol) and potassium carbonate (220 mg, 1.59 mmol) following the experimental procedure as described for Intermediate 9. The crude obtained was purified by column chromatography with silica gel, eluting with a mixture of hexane:ether.

LRMS (m/z): 248 (M+1)+

Intermediate 203

N-benzylcarbamate-trans-4-aminocyclohexyl{4-[(1E)-4-(6-formyl-5-methoxy-2-oxo-1,3-benzoxazol-3(2H)-yl)but-1-en-1-yl]biphenyl-2-yl}carbamate Obtained as foam (194 mg, 69%) from trans-4-benzylaminocyclohexyl(4-bromobiphenyl-2-yl)carbamate (Intermediate 43; 540 mg, 1.03 mmol), 3-but-3-en-1-yl-5-methoxy-2-oxo-2,3-dihydro-1,3-benzoxazole-6-carbaldehyde (Intermediate 202; 267 mg, 1.08 mmol), tri-o-tolylphosphine (314 mg, 1.03 mmol), N,N-Diisopropylethylamine (0.360 mL, 2.07 mmol) and palladium acetate (115 mg, 0.51 mmol) following the experimental procedure as described for intermediate 6. The crude obtained was purified by column chromatography with silica gel, eluting with a mixture of hexane:ether.

LRMS (m/z): 690 (M+1)+

Intermediate 204

N-benzylcarbamate-trans-4-aminocyclohexyl (4-{(1E)-4-[6-({[(2R)-2-{[tert-butyl(dimethyl)silyl]oxy}-2-(8-hydroxy-2-oxo-1,2-dihydroquinolin-5-yl)ethyl]-amino}methyl)-5-methoxy-2-oxo-1,3-benzoxazol-3(2H)-yl]but-1-en-1-yl}biphenyl-2-yl)carbamate Obtained as a solid (328 mg, 61%) from N-benzylcarbamate-trans-4-aminocyclohexyl {4-[(1E)-4-(6-formyl-5-methoxy-2-oxo-1,3-benzoxazol-3(2H)-yl)but-1-en-1-yl]biphenyl-2-yl}carbamate (Intermediate 203; 369 mg, 0.53 mmol), 5-((1R)-2-amino-1-{[tert-butyl(dimethyl)-silyl]oxy}ethyl)-8-hydroxyquinolin-2(1H)-one acetate (211 mg, 0.54 mmol) (prepared according to preparation 8 from US20060035931) and sodium triacetoxyborohydride (345 mg, 1.63 mmol) following the experimental procedure as described for Intermediate 7. The crude obtained was purified by column chromatography with silica gel in reversed phase using as eluents Acetonitrile and Methanol.

LRMS (m/z): 504 (M/2)

Intermediate 205 trans-4-aminocyclohexyl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-5-methoxy-2-oxo-1,3-benzoxazol-3(2H)-yl]butyl}biphenyl-2-yl)carbamate Obtained as a foam (214 mg, 75%) from N-benzylcarbamate-trans-4-aminocyclohexyl(4-{(1E)-4-[6-({[(2R)-2-{[tert-butyl(dimethyl)silyl]oxy}-2-(8-hydroxy-2-oxo-1,2-dihydroquinolin-5-yl)ethyl]amino}methyl)-5-methoxy-2-oxo-1,3-benzoxazol-3(2H)-yl]but-1-en-1-yl}biphenyl-2-yl)carbamate (Intermediate 204; 328 mg, 0.33 mmol) and palladium on charcoal (10%, 80 mg) following the experimental procedure as described for Intermediate 67 and the crude obtained was purified by column chromatography with silica gel, eluting with a mixture of chloroform:methanol:ammonium (40:4:0.2).

LRMS (m/z): 877 (M+1)+

Example 39 trans-4-aminocyclohexyl(4-{4-[6-({[(2R)-2-hydroxy-2-(8-hydroxy-2-oxo-1,2-dihydroquinolin-5-yl)ethyl]amino}methyl)-5-methoxy-2-oxo-1,3-benzoxazol-3(2H)-yl]butyl}biphenyl-2-yl)carbamate dihydrofluoride Obtained as a white solid (180 mg, 92%) from trans-4-aminocyclohexyl(4-{4-[6-({[(2R)-2-{[tert-butyl(dimethyl)silyl]oxy}-2-(8-hydroxy-2-oxo-1,2-dihydroquinolin-5-yl)ethyl]amino}methyl)-5-methoxy-2-oxo-1,3-benzoxazol-3 (2H)-yl]butyl}biphenyl-2-yl)carbamate (Intermediate 205; 214 mg, 0.24 mmol) and triethylamine trihydrofluoride (140 µL, 0.86 mmol) following the experimental procedure as described for Example 1.

LRMS (m/z): 762 (M+1)+

1H NMR (300 MHz, cd3od) δ 8.25 (d, J=9.6 Hz, 1H), 7.48-7.28 (m, 6H), 7.27-7.11 (m, 2H), 7.11-6.91 (m, 4H), 6.62 (d, J=9.7 Hz, 1H), 5.39 (bs, 1H), 4.48 (bs, 1H), 4.29 (bs, 2H), 3.92 (bs, 3H), 3.19 (bs, 2H), 3.06 (bs, 2H), 2.72 (bs, 2H), 2.01 (bs, 3H), 1.86 (bs, 2H), 1.73 (bs, 4H), 1.5-1.4 (m, 4H).

Intermediate 206 trans-4-[methyl(3-phenylpropyl)amino]cyclohexanol

Obtained as an oil (1.3 g, 97%) from trans-4-(methylamino)cyclohexanol (0.7 g, 5.42 mmol), 3-phenylpropanal (0.78 mL, 5.92 mmol) and sodium triacetoxyborohydride (344 mg, 1.63 mmol) following the experimental procedure as described for Intermediate 7 and the crude obtained was used in the next step without further purification.

LRMS (m/z): 248 (M+1)+

Intermediate 207 ethyl 4-(2-{[({trans-4-[methyl(3-phenylpropyl)amino]cyclohexyl}oxy)carbonyl]amino}biphenyl-4-yl)butanoate Obtained as a foam (350 mg, 16%) from ethyl 4-(2-aminobiphenyl-4-yl)butanoate (Intermediate 122; 1 g, 3.53 mmol), trans-4-[methyl(3-phenylpropyl)amino]cyclohexanol (Intermediate 206; 0.87 g, 3.53 mmol), triphosgene (0.42 g, 1.41 mmol) and triethylamine (0.98 mL, 7.05 mmol) following the experimental procedure as described for Intermediate 123 and the crude obtained was purified by column chromatography with silica gel, eluting with a mixture of hexane:ether:ethanol.

LRMS (m/z): 557 (M+1)+

Intermediate 208

4-(2-{[({trans-4-[methyl(3-phenylpropyl)amino]cyclohexyl}oxy)carbonyl]amino}biphenyl-4-yl)butanoic acid Obtained as a solid (330 mg, 98%) from ethyl 4-(2-{[({trans-4-[methyl(3-phenylpropyl)amino]cyclohexyl}oxy)carbonyl]amino}biphenyl-4-yl)butanoate (Intermediate 207; 350 mg, 0.63 mg) and lithium hydroxide monohydrate (79 mg, 1.89 mmol) following the experimental procedure as described for Intermediate 124 and the crude obtained was used in the next step without further purification.

LRMS (m/z): 529 (M+1)+

Intermediate 209 trans-4-[methyl(3-phenylpropyl)amino]cyclohexyl (4-{4-[(4-formylphenyl)amino]-4-oxobutyl}biphenyl-2-yl)carbamate Obtained as an oil (143 mg, 36%) from 4-(2-{[({trans-4-[methyl(3-phenylpropyl)amino]cyclohexyl}oxy)carbonyl]amino}biphenyl-4-yl)butanoic acid (Intermediate 208; 330 mg, 0.62 mmol), 4-aminobenzaldehyde (83 mg, 0.69 mmol), diisopropylethylenediamine (0.326 mL, 1.87 mmol) and HATU (356 mg, 0.94 mmol) following the experimental procedure as described for Intermediate 125 and the crude obtained was used in the next step without further purification.

LRMS (m/z): 632 (M+1)+

Intermediate 210 trans-4-[methyl(3-phenylpropyl)amino]cyclohexyl [4-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate Obtained as a solid (70 mg, 33%) from trans-4-[methyl(3-phenylpropyl)amino]cyclohexyl(4-{4-[(4-formylphenyl)amino]-4-oxobutyl}biphenyl-2-yl)carbamate (Intermediate 209; 141 mg, 0.22 mmol), 5-((1R)-2-amino-1-{[tert-butyl(dimethyl)-silyl]oxy}ethyl)-8-hydroxyquinolin-2(1H)-one acetate (211 mg, 0.54 mmol) (prepared according to preparation 8 from US20060035931) and sodium triacetoxyborohydride (345 mg, 1.63 mmol) following the experimental procedure as described for Intermediate 7. The crude obtained was purified by column chromatography with silica gel, eluting with a mixture of chloroform:methanol:ammonium (40:4:0.2).

LRMS (m/z): 951 (M+1)+

Example 40 trans-4-[methyl(3-phenylpropyl)amino]cyclohexyl [4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate dihydrofluoride Obtained as a white solid (13 mg, 21%) from trans-4-[methyl(3-phenylpropyl)amino]cyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate (Intermediate 210; 70 mg, 0.07 mmol) and triethylamine trihydrofluoride (60 µL, 0.37 mmol) following the experimental procedure as described for Example 1 and the crude obtained was purified by column chromatography in reversed phase using as eluents Acetonitrile and Methanol.

LRMS (m/z): 877 (M+1)+

1H NMR (300 MHz, cd3od) δ 8.24 (d, J=9.8 Hz, 1H), 7.52 (d, J=8.4 Hz, 4H), 7.48-7.08 (m, 14H), 6.94 (d, J=8.1 Hz, 1H), 6.59 (d, J=9.8 Hz, 1H), 5.20 (bs, 1H), 4.42 (bs, 2H), 3.80 (bs, 2H), 2.93-2.68 (m, 4H), 2.52 (ddd, J=29.8, 18.3, 7.5 Hz, 6H), 2.26 (s, 3H), 2.04 (bs, 2H), 1.97 (s, 2H), 1.80 (bs, 4H), 1.31 (d, J=9.5 Hz, 4H).

Intermediate 211 methyl(2E)-3-(4-chloro-3-nitrophenyl)acrylate

To a solution of (E)-3-(4-chloro-3-nitrophenyl)acrylic acid (1 g, 4.39 mmol) in a mixture of methanol/anhydrous dichloromethane (8 mL-4 mL) was added at −78° C. tionyl chloride (200 µL, 2.75 mmol) and the mixture was stirred for 4.5 h at 45° C. The solvent was removed under reduced pressure giving the title compound as a yellow solid (1.05 g, 99%), which was used in the next step without further purification.

LRMS (m/z): 242 (M+1)+

Intermediate 212 methyl(2E)-3-(2-nitrobiphenyl-4-yl)acrylate

To a solution of methyl(2E)-3-(4-chloro-3-nitrophenyl)acrylate (Intermediate 211; 1.05 g, 4.35 mmol) in dioxane (40 mL) was added under nitrogen atmosphere phenylboronic acid (1.06 g, 8.69 mmol), cesium carbonate (2M, 6.6 mL, 13.2 mmol) and [1,1'-Bis(diphenilphosfine)-ferrocene]diclhoropaladium(II) (dichloromethane complex; 192 mg, 0.22 mmol). The reaction mixture was stirred 4 h at 80° C. The catalyst was filtrated through Celite and the solvent was removed under reduced pressure. The crude obtained was purified by column chromatography with silica gel, eluting with a mixture of Ethyl acetate:Hexane to obtain the title compound as a solid (1.3 g, 98%).

LRMS (m/z): 284 (M+1)+

Intermediate 213 methyl 3-(2-aminobiphenyl-4-yl)propanoate

To a solution of methyl(2E)-3-(2-nitrobiphenyl-4-yl)acrylate (Intermediate 212; 1.3 g, 4.73 mmol) in methanol (15 mL) was added palladium on charcoal (10%, 500 mg). The crude mixture was submitted under an H2 balloon 2.5 h at room temperature. The catalyst was filtered through Celite and the solvent was removed under reduced pressure. The crude obtained was purified by column chromatography with silica gel, eluting with a mixture of Hexane:Ether to obtain the title compound as a solid (714 mg, 59%).
LRMS (m/z): 256 (M+1)+

Intermediate 214 methyl 3-(2-isocyanatobiphenyl-4-yl)propanoate

Obtained as a solid (764 mg, 97%) from methyl 3-(2-aminobiphenyl-4-yl)propanoate (Intermediate 213; 710 mg, 2.78 mmol), triphosgene (330 mg, 1.11 mmol) and triethylamine (0.77 mL, 5.56 mmol) following the experimental procedure as described for Intermediate 4 and the crude obtained was used in the next step without further manipulation.
LRMS (m/z): 281 (M+16; HPLC aliquot with MeOH).

Intermediate 215 methyl 3-(2-{[({trans-4-[(tert-butoxycarbonyl)amino]cyclohexyl}oxy)carbonyl]-amino}biphenyl-4-yl)propanoate Obtained as a solid (1.1 g, 85%) from tert-butyl(trans-4-hydroxycyclohexyl)carbamate (640 mg, 2.97 mmol) and methyl 3-(2-isocyanatobiphenyl-4-yl)propanoate (Intermediate 214; 710 mg, 2.7 mmol) following the experimental procedure as described for Intermediate 123. The crude obtained was purified by column chromatography with silica gel, eluting with a mixture of Hexane:Ether.
LRMS (m/z): 497 (M+1)+

Intermediate 216

3-(2-{[({trans-4-[(tert-butoxycarbonyl)amino]cyclohexyl}oxy)carbonyl]amino}-biphenyl-4-yl)propanoic acid Obtained as a solid (1.07 g, 96%) from methyl 3-(2-{[({trans-4-[(tert-butoxycarbonyl)amino]cyclohexyl}oxy)carbonyl]amino}biphenyl-4-yl)propanoate (Intermediate 215; 1.1 g, 2.3 mmol) and lithium hydroxide (290 mg, 6.91 mmol) following the experimental procedure as described for Intermediate 124 and the crude obtained was used in the next step without further purification.
LRMS (m/z): 483 (M+1)+

Intermediate 217 tert-butyl-trans-4-aminocyclohexyl[4-(3-{[4-(hydroxymethyl)phenyl]amino}-3-oxopropyl)biphenyl-2-yl]carbamate Obtained as a foam (470 mg) from 3-(2-{[({trans-4-[(tert-butoxycarbonyl)amino]-cyclohexyl}oxy)carbonyl]amino}biphenyl-4-yl)propanoic acid (Intermediate 216; 300 mg, 0.62 mmol), (4-aminophenyl)methanol (92 mg, 0.75 mmol), diisopropylethylenediamine (0.33 mL, 1.89 mmol) and HATU (307 mg, 0.81 mmol) following the experimental procedure as described for Intermediate 125 and the crude obtained was taken forward without purification.
LRMS (m/z): 588 (M+1)+

Intermediate 218 tert-butyl-trans-4-aminocyclohexyl(4-{3-[(4-formylphenyl)amino]-3-oxopropyl}-biphenyl-2-yl)carbamate To a solution of tert-butyl-trans-4-aminocyclohexyl[4-(3-{[4-(hydroxymethyl)phenyl]-amino}-3-oxopropyl)biphenyl-2-yl]carbamate (Intermediate 217; 365 mg, 0.62 mmol) in chloroform (6 mL) was added activated manganese oxide (430 mg, 4.95 mmol). The reaction mixture was stirred overnight at 45° C. The mixture was filtered and the solvent was removed under reduced pressure giving the title compound as an orange foam (390 mg, 96%), which was used in the next step without further purification.
LRMS (m/z): 586 (M+1)+

Intermediate 219 trans-4-aminocyclohexyl[4-(3-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-3-oxopropyl)biphenyl-2-yl]carbamate Obtained as a grey solid (518 mg, 95%) from tert-butyl-trans-4-aminocyclohexyl(4-{3-[(4-formylphenyl)amino]-3-oxopropyl}biphenyl-2-yl)carbamate (Intermediate 218; 390 mg, 0.6 mmol), 5-((1R)-2-amino-1-{[tert-butyl(dimethyl)-silyl]oxy}ethyl)-8-hydroxyquinolin-2(1H)-one acetate (250 mg, 0.63 mmol) (prepared according to preparation 8 from US20060035931) and sodium triacetoxyborohydride (385 mg, 1.82 mmol) following the experimental procedure as described for Intermediate 7. The crude obtained was purified by column chromatography with silica gel, eluting with a mixture of chloroform:methanol:ammonium (40:4:0.2).
LRMS (m/z): 905 (M+1)+

Example 41 trans-4-aminocyclohexyl[4-(3-{[4-({[(2R)-2-hydroxy-2-(8-hydroxy-2-oxo-1,2-dihydroquinolin-5-yl)ethyl]amino}methyl)phenyl]amino}-3-oxopropyl)biphenyl-2-yl]carbamate dihydrochloride Obtained as a yellow solid (380 mg, 84%) from trans-4-aminocyclohexyl[4-(3-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-3-oxopropyl)biphenyl-2-yl]carbamate (Intermediate 219; 515 mg, 0.57 mmol) and hydrogen chloride (4M in dioxane, 5 mL) following the experimental procedure as described for Intermediate 21.
LRMS (m/z): 690 (M+1)+
1H NMR (300 MHz, dmso) δ 10.52 (bs, 1H), 10.26 (s, 1H), 9.77 (bs, 1H), 9.10 (bs, 1H), 8.65 (s, 1H), 8.23 (d, J=9.9 Hz, 1H), 8.12 (bs, 2H), 7.65 (d, J=8.4 Hz, 1H), 7.50 (d, J=8.5 Hz, 1H), 7.46-7.16 (m, 6H), 7.12 (d, J=8.2 Hz, 1H), 7.00 (d, J=8.2 Hz, 1H), 6.53 (d, J=9.9 Hz, 1H), 5.50 (d, J=8.5 Hz, 1H), 4.32 (bs, 2H), 4.14 (bs, 2H), 3.07-2.80 (m, 4H), 2.69 (t, J=7.4 Hz, 2H), 1.86 (d, J=31.8 Hz, 4H), 1.50-1.12 (m, 4H).

Intermediate 220 ethyl 4-[2-({[(3R)-1-azabicyclo[2.2.2]oct-3-yloxy] carbonyl}amino)biphenyl-4-yl]butanoate Obtained as an oil (503 mg) from ethyl 4-(2-aminobiphenyl-4-yl)butanoate (Intermediate 122; 300 mg, 1.06 mmol), (R)-quinuclidin-3-ol (135 mg, 1.06 mmol), triphosgene (126 mg, 0.42 mmol) and triethylamine (0.3 mL, 2.16 mmol) following the experimental procedure as described for Intermediate 123 and the crude obtained was used in the next step without further purification.

LRMS (m/z): 437 (M+1)+

Intermediate 221

4-[2-({[(3R)-1-azabicyclo[2.2.2]oct-3-yloxy] carbonyl}amino)biphenyl-4-yl]butanoic acid Obtained as a yellow-orange solid (608 mg) from ethyl 4-[2-({[(3R)-1-azabicyclo-[2.2.2]oct-3-yloxy] carbonyl}amino)biphenyl-4-yl]butanoate (Intermediate 220; 503 mg, 1.04 mmol) and lithium hydroxide monohydrate (130 mg, 3.1 mmol) following the experimental procedure as described for Intermediate 124 and the crude obtained was taken forward without further manipulation.

LRMS (m/z): 409 (M+1)+

Intermediate 222

(3R)-1-azabicyclo[2.2.2]oct-3-yl(4-{4-[(4-formylphenyl)amino]-4-oxobutyl}-biphenyl-2-yl)carbamate To a solution of 4-[2-({[(3R)-1-azabicyclo[2.2.2]oct-3-yloxy]carbonyl}amino)biphenyl-4-yl]butanoic acid (Intermediate 221; 360 mg, 0.75 mmol) in dichloromethane (5 mL) was added under nitrogen atmosphere oxalyl chloride (100 µL, 1.15 mmol) and a drop of dimethylformamide. The reaction mixture was stirred overnight at room temperature. Solvent was removed under reduced pressure and the crude (319 mg, 0.66 mmol) was taken into the next step without further manipulation. It was dissolved in dichloromethane (5 mL) and 4-aminobenzaldehyde (115 mg, 0.95 mmol) and triethylamine (0.24 mL, 1.72 mmol) were added into the mixture. The reaction was stirred overnight at room temperature and 6 hours at 45° C. The solvent was removed under reduced pressure and the crude obtained was purified by column chromatography with silica gel, eluting with a mixture of chloroform:methanol:ammonium (40:4:0.2), giving the title compound as a solid (22 mg, 4%).

LRMS (m/z): 512 (M+1)+

Intermediate 223

(3R)-1-azabicyclo[2.2.2]oct-3-yl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl) phenyl]amino}-4-oxobutyl)biphenyl-2-yl]carbamate Obtained as a yellow solid (17 mg, 40%) from (3R)-1-azabicyclo[2.2.2]oct-3-yl(4-{4-[(4-formylphenyl)amino]-4-oxobutyl}biphenyl-2-yl)carbamate (Intermediate 222; 22 mg, 0.03 mmol), 5-((1R)-2-amino-1-{[tert-butyl(dimethyl)silyl]oxy}ethyl)-8-hydroxyquinolin-2(1H)-one acetate (16 mg, 0.04 mmol) (prepared according to preparation 8 from US20060035931) and sodium triacetoxyborohydride (30 mg, 0.14 mmol) following the experimental procedure as described for Intermediate 7. The crude obtained was purified by column chromatography with silica gel, eluting with a mixture of chloroform:methanol:ammonium (40:4:0.2).

LRMS (m/z): 831 (M+1)+

Example 42

(3R)-1-azabicyclo[2.2.2]oct-3-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl) biphenyl-2-yl]carbamate dihydrofluoride Obtained as a white solid (4 mg, 40%) from (3R)-1-azabicyclo[2.2.2]oct-3-yl[4-(4-{[4-({[(2R)-2-{[tert-butyl (dimethyl)silyl]oxy}-2-(8-hydroxy-2-oxo-1,2-dihydroquinolin-5-yl)ethyl]amino}methyl)phenyl]amino}-4-oxobutyl) biphenyl-2-yl]carbamate (Intermediate 223; 17 mg, 0.01 mmol) and triethylamine trihydrofluoride (25 µL, 0.15 mmol) following the experimental procedure as described for Example 1 and the crude obtained was purified by column chromatography in reversed phase using as eluents Acetonitrile and Methanol.

LRMS (m/z): 716 (M+1)+

1H NMR (300 MHz, cd3od) δ 8.25 (d, J=10.0 Hz, 1H), 7.69-7.54 (m, 2H), 7.42-7.25 (m, 7H), 7.22 (bs, 2H), 7.01 (t, J=7.8 Hz, 2H), 6.62 (d, J=9.8 Hz, 1H), 5.33 (bs, 1H), 4.68 (bs, 1H), 4.12 (bs, 1H), 3.51-3.32 (m, 2H), 3.12 (bs, 4H), 2.86 (bs, 1H), 2.74 (t, J=7.4 Hz, 2H), 2.44 (t, J=7.4 Hz, 2H), 2.20-1.84 (m, 3H), 1.72 (d, J=38.8 Hz, 2H), 1.31 (d, J=13.5 Hz, 2H), 0.88 (d, J=9.2 Hz, 2H).

Intermediate 224

4-[(tert-butoxycarbonyl)amino]benzoic acid

To a solution of 4-aminobenzoic acid (1 g, 7.29 mmol) in a mixture of dioxane:water (20 mL:10 mL) was added sodium hydroxide (2M, 35 mL). The mixture was stirred until complete dissolution and then it was added di-tert-butyl dicarbonate (3.18 g, 14.57 mmol) at 0° C. The reaction mixture was stirred 24 hours at room temperature. The solvent was removed under reduced pressure and the crude was acidified with hydrogen chloride 5N. The precipitate obtained was filtered and washed with water to obtain the title compound as a white solid (1.23 g, 71%).

LRMS (m/z): 238 (M+1)+

Intermediate 225

[4-(methylamino)phenyl]methanol

To a solution of 4-[(tert-butoxycarbonyl)amino]benzoic acid (Intermediate 224; 500 mg, 2.11 mmol) in tetrahydrofurane (20 mL) was added slowly lithium aluminium hydride (450 mg, 11.86 mmol). The reaction mixture was refluxed for 1.5 hours. Hydride was destroyed and the solvent was removed under reduced pressure giving a crude, which was purified by reversed phase using as eluents Acetonitrile and Methanol. The title compound was obtained as an oil (159 mg, 55%).

LRMS (m/z): 139 (M+1)+

Intermediate 226 tert-butyl-trans-4-aminocyclohexyl(4-{4-[[4-(hydroxymethyl)phenyl](methyl)-amino]-4-oxobutyl}biphenyl-2-yl)carbamate Obtained as a foam (78 mg, 15%) from [4-(methylamino)phenyl]methanol (130 mg, 0.95 mmol), 4-(2-{[({trans-4-[(tert-butoxycarbonyl)amino]cyclohexyl}oxy)carbonyl]amino}biphenyl-4-yl)butanoic acid (synthesized as Intermediate 189; 400 mg, 0.81 mmol), diisopropylethylenediamine (0.421 mL, 2.42 mmol) and HATU (613 mg, 1.61 mmol) following the experimental procedure as described for Intermediate 125 and the crude obtained was purified by column chromatography with silica gel, eluting with a mixture of Hexane:Ether.

LRMS (m/z): 616 (M+1)+

Intermediate 227 trans-4-aminocyclohexyl(4-{4-[(4-formylphenyl)(methyl)amino]-4-oxobutyl}-biphenyl-2-yl)carbamate Obtained as a foam (66 mg, 85%) from tert-butyl-trans-4-aminocyclohexyl(4-{4-[[4-(hydroxymethyl)phenyl](methyl)amino]-4-oxobutyl}biphenyl-2-yl)carbamate (Intermediate 226; 78 mg, 0.13 mmol) and manganese oxide (110 mg, 1.27 mmol) following the experi-mental procedure as described for Intermediate 218 and the crude obtained was used in the next step without further purification.

LRMS (m/z): 614 (M+1)+

Intermediate 228 tert-butyl-trans-4-aminocyclohexyl(4-{4-[[4-({[(2R)-2-{[tert-butyl(dimethyl)silyl]-oxy}-2-(8-hydroxy-2-oxo-1,2-dihydroquinolin-5-yl)ethyl]amino}methyl)phenyl]-(methyl)amino]-4-oxobutyl}biphenyl-2-yl)carbamate Obtained as a solid (16 mg, 16%) from trans-4-aminocyclohexyl(4-{4-[(4-formylphenyl)(methyl)amino]-4-oxobutyl}biphenyl-2-yl)carbamate (Intermediate 227; 66 mg, 0.11 mmol), 5-((1R)-2-amino-1-{[tert-butyl(dimethyl)silyl]oxy}ethyl)-8-hydroxyquinolin-2(1H)-one acetate (36 mg, 0.11 mmol) (prepared according to preparation 8 from US20060035931), sodium cianoborohydride (17 mg, 0.27 mmol) and diethylethylenamine (19 µL, 0.11 mmol) following the experimental procedure as described for Intermediate 7. The crude obtained was purified by column chromatography with silica gel, eluting with a mixture of chloroform:methanol (9:1).

LRMS (m/z): 933 (M+1)+

Example 43 trans-4-aminocyclohexyl(4-{4-[[4-({[(2R)-2-hydroxy-2-(8-hydroxy-2-oxo-1,2-dihydroquinolin-5-yl)ethyl]amino}methyl)phenyl](methyl)amino]-4-oxobutyl}-biphenyl-2-yl)carbamate dihydrochloride Obtained as white solid (10 mg, 81%) from tert-butyl-trans-4-aminocyclohexyl(4-{4-[[4-({[(2R)-2-{[tert-butyl(dimethyl)silyl]oxy}-2-(8-hydroxy-2-oxo-1,2-dihydroquinolin-5-yl)ethyl]amino}methyl)phenyl](methyl)amino]-4-oxobutyl}biphenyl-2-yl)carbamate (Inter-mediate 228; 16 mg, 0.02 mmol) and hydrogen chloride (4M in dioxane, 1 mL) following the ex-perimental procedure as described for Intermediate 21.

LRMS (m/z): 718 (M+1)+

1H NMR (300 MHz, dmso) δ 10.52 (bs, 1H), 9.70 (bs, 1H), 9.18 (bs, 1H), 8.62 (s, 1H), 8.21 (d, J=9.9 Hz, 1H), 7.98 (s, 1H), 7.63 (d, J=8.1 Hz, 1H), 7.51-7.22 (m, 6H), 7.22-7.07 (m, 3H), 6.99 (d, J=8.2 Hz, 1H), 6.55 (d, J=9.7 Hz, 1H), 5.49 (d, J=8.7 Hz, 1H), 4.33 (s, 1H), 4.23 (s, 2H), 3.54 (d, J=14.8 Hz, 4H), 3.18 (s, 2H), 2.92 (d, J=20.2 Hz, 4H), 2.04 (d, J=31.0 Hz, 2H), 2.01-1.59 (m, 4H), 1.5-1.02 (m, 4H).

Intermediate 229 ethyl trans-4-aminocyclohexanecarboxylate

Hydrogen chloride (7 mL) was added to a suspension of the (1r,4r)-4-aminocyclohexanecarboxylic acid hydrochloride (6.32 g, 0.035 mol) in Ethanol (100 mL) and the mixture was stirred and heated to 60° C. and left overnight. The mixture was evaporated in vacuum, azeotroping the water with further Ethanol and finally toluene to give the title product as a white solid (7.2 g, 98%).

1H NMR (300 MHz, dmso) δ 4.05 (q, J=7.1 Hz, 2H), 2.95 (bs, 1H), 2.30-2.15 (m, 1H), 2.02-1.88 (m, 4H), 1.43-1.28 (m, 4H), 1.22-1.13 (t, J=6.9 Hz, 3H).

Intermediate 230

(trans-4-aminocyclohexyl)methanol

A suspension of ethyl trans-4-aminocyclohexanecarboxylate (Intermediate 229; 7.2 g, 0.034 mol) in tetrahydrofurane (200 mL) was added in rough portions at 0° C. to lithium aluminium hydride (1M in tetrahydrofurane) and stirred 1 h at 0° C., the ice bath was removed and the mixture was stirred at room temperature overnight. The stirred mixture was cooled in an ice bath and very carefully water (6.9 mL), 15% NaOH (21 mL) and water (21 mL) were added slowly. After stirring 30 minutes at room temperature the mixture was filtered through a thin layer (1 cm) of Celite and the filter cake was washed with tetrahydrofurane. The combined filtrate and washings were evaporated to give a white solid as the title compound (4.4 g, 99%).

1H NMR (300 MHz, dmso) δ 3.18 (d, J=6.3 Hz, 2H), 2.42 (m, 1H), 1.79-1.60 (m, 4H), 1.30-1.13 (m, 1H), 1.05-0.72 (m, 4H).

Intermediate 231 trans-4-aminocyclohexyl[4-(4-{[trans-4-(hydroxymethyl)cyclohexyl]amino}-4-oxobutyl)biphenyl-2-yl]carbamate Obtained as an oil (455 mg, 92%) from (trans-4-aminocyclohexyl)methanol (Intermediate 230; 114 mg, 0.89 mmol), 4-(2-{[({trans-4-[(tert-butoxycarbonyl)amino]cyclohexyl}oxy)carbonyl]amino}biphenyl-4-yl)butanoic acid (synthesized as Intermediate 189; 400 mg, 0.81 mmol), diisopropylethylenediamine (0.421 mL, 2.42 mmol) and HATU (613 mg, 1.61 mmol) following the experimental procedure as described for Intermediate 125 and the crude obtained was taken forward to the next step without purification.

LRMS (m/z): 608 (M+1)+

Intermediate 232 trans-4-aminocyclohexyl(4-{4-[(trans-4-formylcyclohexyl)amino]-4-oxobutyl}-biphenyl-2-yl)carbamate Obtained as an oil (525 mg, 85%) from trans-4-aminocyclohexyl[4-(4-{[trans-4-(hydroxymethyl)cyclohexyl]amino}-4-oxobutyl)biphenyl-2-yl]carbamate (Intermediate 231; 550 mg, 0.9 mmol) and Dess-Martin periodinane (422 mg, 0.99 mmol) following the experimental procedure as described for Intermediate 64.

LRMS (m/z): 606 (M+1)+

Intermediate 233 trans-4-aminocyclohexyl[4-(4-{[trans-4-({[(2R)-2-{[tert-butyl(dimethyl)silyl]oxy}-2-(8-hydroxy-2-oxo-1,2-dihydroquinolin-5-yl)ethyl]amino}methyl)cyclohexyl]-amino}-4-oxobutyl)biphenyl-2-yl]carbamate Obtained as a yellow solid (246 mg, 34%) from trans-4-aminocyclohexyl(4-{4-[(trans-4-formylcyclohexyl)amino]-4-oxobutyl}biphenyl-2-yl)carbamate (Intermediate 232; 525 mg, 0.87 mmol), 5-((1R)-2-amino-1-{[tert-butyl(dimethyl)-silyl]oxy}ethyl)-8-hydroxyquinolin-2(1H)-one acetate (260 mg, 0.78 mmol) (prepared according to preparation 8 from US20060035931) and sodium triacetoxyborohydride (826 mg, 3.9 mmol) following the experimental procedure as described for Intermediate 7. The crude obtained was purified by column chromatography with silica gel, eluting with a mixture of chloroform:methanol (9:1).

LRMS (m/z): 925 (M+1)+

Example 44 trans-4-aminocyclohexyl[4-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)biphenyl-2-yl]carbamate dihydrochloride Obtained as a white solid (125 mg, 66%) from trans-4-aminocyclohexyl[4-(4-{[trans-4-({[(2R)-2-{[tert-butyl(dimethyl)silyl]oxy}-2-(8-hydroxy-2-oxo-1,2-dihydroquinolin-5-yl)ethyl]amino}methyl)cyclohexyl]amino}-4-oxobutyl)biphenyl-2-yl]carbamate (Intermediate 233; 245 mg, 0.27 mmol) and hydrogen chloride (4M in dioxane; 3.31 mL) following the experimental procedure as described for Intermediate 21.

LRMS (m/z): 710 (M+1)+

1H NMR (300 MHz, dmso) δ 8.68 (s, 1H), 8.32 (d, J=10.0 Hz, 1H), 8.03 (s, 2H), 7.78 (d, J=7.8 Hz, 1H), 7.41 (m, 4H), 7.30-7.13 (m, 3H), 7.04 (d, J=8.2 Hz, 1H), 6.61 (d, J=10.0 Hz, 1H), 5.51 (d, J=9.3 Hz, 1H), 4.38 (bs, 2H), 3.58-3.52 (m, 2H), 3.04 (bs, 3H), 2.89 (bs, 2H), 2.61 (bs, 2H), 2.12 (bs, 4H), 1.90 (m, 6H), 1.50-1.26 (m, 4H), 1.13 (m, 4H).

Intermediate 234

1-(4-nitrophenyl)propan-2-ol

To solution of 1-(4-nitrophenyl)propan-2-one (500 mg, 2.79 mmol) in methanol (9 mL) was added in portions at 0° C. sodium borohydride (106 mg, 2.8 mmol). The reaction mixture was stirred at room temperature for 1 hour. The solvent was removed under reduced pressure at room temperature and the crude obtained was partitioned between ether and water. The organic layer was washed with ammonium chloride, dried, filtered and the solvent was removed under reduced pressure giving the title compound as a solid (500 mg, 98%).

LRMS (m/z): 182 (M+1)+

Intermediate 235

1-(4-aminophenyl)propan-2-ol

To a solution of 1-(4-nitrophenyl)propan-2-ol (Intermediate 234; 500 mg, 2.76 mmol) in ethanol was added palladium on charcoal (10%, 30 mg). The mixture was submitted to a H2 balloon pressure during 2 hours. The catalyst was filtered trough celite and the filtrate was evaporated giving a crude, which was the desired compound (412 mg, 98%).

LRMS (m/z): 152 (M+1)+

Intermediate 236 tert-butyl-trans-4-aminocyclohexyl[4-(4-{[4-(2-hydroxypropyl)phenyl]amino}-4-oxobutyl)biphenyl-2-yl]carbamate Obtained as a foam (305 mg, 98%) from 1-(4-aminophenyl)propan-2-ol (Intermediate 235; 74 mg, 0.79 mmol), 4-(2-{[({trans-4-[(tert-butoxycarbonyl)amino]cyclohexyl}oxy) carbonyl]amino}biphenyl-4-yl)butanoic acid (syn-thesized as Intermediate 189; 200 mg, 0.4 mmol), diisopropylethylenediamine (0.21 mL, 1.21 mmol) and HATU (199 mg, 0.52 mmol) following the experimental procedure as de-scribed for Intermediate 125 and the crude obtained was used in the next step without further purification.

LRMS (m/z): 630 (M+1)+

Intermediate 237 tert-butyl-trans-4-aminocyclohexyl[4-(4-oxo-4-{[4-(2-oxopropyl)phenyl]amino}-butyl)biphenyl-2-yl]carbamate Obtained as an oil (275 mg, 97%) from tert-butyl-trans-4-aminocyclohexyl[4-(4-{[4-(2-hydroxypropyl)phenyl]amino}-4-oxobutyl)biphenyl-2-yl]carbamate (Intermediate 236; 254 mg, 0.4 mmol) and Dess-Martin periodinane (190 mg, 0.45 mmol) following the experi-mental procedure as described for Intermediate 64 and the crude obtained was used in the next step without further purification.

LRMS (m/z): 628 (M+1)+

Intermediate 238 tert-butyl-trans-4-aminocyclohexyl[4-(4-{[4-(2-{[(2R)-2-{[tert-butyl(dimethyl)-silyl]oxy}-2-(8-hydroxy-2-oxo-1,2-dihydroquinolin-5-yl)ethyl]amino}propyl)-phenyl]amino}-4-oxobutyl)biphenyl-2-yl]carbamate Obtained as a solid (127 mg, 33%) from tert-butyl-trans-4-aminocyclohexyl[4-(4-oxo-4-{[4-(2-oxopropyl)phenyl]amino}butyl)biphenyl-2-yl]carbamate (Intermediate 237; 253 mg, 0.4 mmol), 5-((1R)-2-amino-1-{[tert-butyl(dimethyl)-silyl]oxy}ethyl)-8-hydroxyquinolin-2(1H)-one acetate (170 mg, 0.43 mmol) (prepared according to preparation 8 from US20060035931) and sodium triacetoxyborohydride (275 mg, 1.3 mmol) following the experimental procedure as described for Intermediate 7. The crude obtained was purified by column chromatography with silica gel, eluting with a mixture of chloroform:methanol:ammonium (40:4:0.2).

LRMS (m/z): 947 (M+1)+

Example 45 trans-4-aminocyclohexyl[4-(4-{[4-(2-{[(2R)-2-hydroxy-2-(8-hydroxy-2-oxo-1,2-dihydroquinolin-5-yl)ethyl]amino}propyl)phenyl]amino}-4-oxobutyl)biphenyl-2-yl]carbamate dihydrochloride Obtained as a white solid (22 mg, 20%) from tert-butyl-trans-4-aminocyclohexyl[4-(4-{[4-(2-{[(2R)-2-{[tert-butyl(dimethyl)silyl]oxy}-2-(8-hydroxy-2-oxo-1,2-dihydroquinolin-5-yl)ethyl]amino}propyl)phenyl]amino}-4-oxobutyl)biphenyl-2-yl]carbamate (Intermediate 238; 127 mg, 0.13 mmol) and hydrogen chloride (4M in dioxane, 3.35 mL) following the experimental procedure as described for Intermediate 21 and the crude obtained was purified by reversed phase using as eluents Water and Methanol.

LRMS (m/z): 732 (M+1)+

1H NMR (300 MHz, cd3od) δ 8.40-8.30 (m, 1H), 7.54-7.29 (m, 8H), 7.26-7.06 (m, 5H), 6.97 (d, J=7.9 Hz, 1H), 6.66 (d, J=9.8 Hz, 1H), 5.27 (bs, 1H), 4.49 (bs, 1H), 3.18 (bs, 2H), 3.12-2.81 (m, 4H), 2.74 (bs, 4H), 2.42 (d, J=6.9 Hz, 2H), 2.03 (d, J=14.1 Hz, 4H), 1.4-1.25 (m, 4H), 1.16 (d, J=6.0 Hz, 3H).

Intermediate 239

5-(methylamino)pentanoic acid

To 1-methylpiperidin-2-one (3.8 g, 0.034 mol) was added hydrogen chloride (5N, 19 mL). The mixture was stirred over weekend at 150° C. The solvent was removed under reduced pressure at 50-60° C. giving a solid, which was treated with ether. The title compound was obtained as a white solid (5.08 g, 88%) and used in the next step without further purifica-tion.

LRMS (m/z): 132 (M+1)+

Intermediate 240

5-[(tert-butoxycarbonyl)(methyl)amino]pentanoic acid

To a solution of 5-(methylamino)pentanoic acid (Intermediate 239; 3.7 g, 0.022 mol) in di-oxane/water (60 mL, 2/1) was added sodium hydroxide (1N, 45 mL) and at 0° C. was added di-tert-butyl dicarbonate (5.4 g, 0.024 mol). The reaction mixture was stirred 10 minutes at 0° C. and overnight at room temperature. The organic solvent was removed and the aque-ous phase was acidified and extracted with ethyl acetate. The organic layer was washed with brine, dried, filtered and the solvent was removed under reduced pressure, obtaining an oil, which was treated with pentane at low temperature to achieve a white solid as a title compound (4.4 g, 80%)

LRMS (m/z): 230 (M+1)−

Intermediate 241 tert-butyl(5-{[4-(hydroxymethyl)phenyl]amino}-5-oxopentyl)methylcarbamate

To a solution of 5-[(tert-butoxycarbonyl)(methyl)amino]pentanoic acid (Intermediate 240; 1.4 g, 6.05 mmol) in dimethylformamide (10 mL) was added DIEA (3.14 mL, 18.1 mmol) and HATU (2.99 g, 7.87 mmol). The reaction mixture was stirred 1 hour at room temperature. Then (4-aminophenyl)methanol (820 mg, 6.6 mmol) was added into the mixture and it was stirred overnight at room temperature. The mixture was poured into 150 mL of water and extracted with ethyl acetate. The organic layer was washed with brine, dried, filtered, and the solvent was removed under reduced pressure giving a crude, which was purified by column chromatography with silica gel, eluting with a mixture of chloroform:hexane.

LRMS (m/z): 337 (M+1)+

Intermediate 242

N-[4-(hydroxymethyl)phenyl]-5-(methylamino)pentanamide

To a solution of tert-butyl(5-{[4-(hydroxymethyl)phenyl]amino}-5-oxopentyl)methylcarbamate (Intermediate 241; 812 mg, 2.41 mmol) in tetrahydrofurane (16 mL) was added hydrogen chloride (2.5N aqueous, 5.8 mL). The reaction mixture was stirred overnight at room temperature. Then 3 eq more of hydrogen chloride were added and the reac-tion was stirred 24 hours at room temperature. The aqueous phase was saturated with sodium bicarbonate and extracted with chloroform. The organic solvent was removed un-der reduced pressure giving the title compound as a solid (377 mg, 66%).

LRMS (m/z): 237 (M+1)+

Intermediate 243 tert-butyl-trans-4-aminocyclohexyl(4-{4-[(5-{[4-(hydroxymethyl)phenyl]amino}-5-oxopentyl)(methyl)amino]-4-oxobutyl}biphenyl-2-yl)carbamate Obtained as an oil (126 mg, 44%) from N-[4-(hydroxymethyl)phenyl]-5-(methylamino)pentanamide (Intermediate 242; 104 mg, 0.44 mmol), 4-(2-{[({trans-4-[(tert-butoxycarbonyl)amino]cyclohexyl}oxy)carbonyl]amino}biphenyl-4-yl)butanoic acid (synthesized as Intermediate 189; 200 mg, 0.4 mmol), DIEA (0.21 mL, 1.21 mmol) and HATU (229 mg, 0.60 mmol) following the experimental procedure as described for Intermediate 125 and the crude obtained was purified by column chromatography with silica gel, eluting with a mixture of chloroform:ethanol (9:1).

LRMS (m/z): 715 (M+1)+

Intermediate 244 tert-butyl-trans-4-aminocyclohexyl(4-{4-[{5-[(4-formylphenyl)amino]-5-oxopentyl}(methyl)amino]-4-oxobutyl}biphenyl-2-yl)carbamate Obtained as an oil (125 mg, 98%) from tert-butyl-trans-4-aminocyclohexyl(4-{4-[(5-{[4-(hydroxymethyl)phenyl]amino}-5-oxopentyl)(methyl)amino]-4-oxobutyl}biphenyl-2-yl)carbamate (Intermediate 243; 126 mg, 0.18 mmol) and

119

Dess-Martin periodinane (82 mg, 0.19 mmol) following the experimental procedure as described for Intermediate 64 and the crude obtained was used in the next step without further purification.

LRMS (m/z): 713 (M+1)+

Intermediate 245 tert-butyl-trans-4-aminocyclohexyl(4-{4-[(5-{[4-({[(2R)-2-{[tert-butyl(dimethyl-)silyl]oxy}-2-(8-hydroxy-2-oxo-1,2-dihydroquinolin-5-yl)ethyl]amino}methyl)-phenyl]amino}-5-oxopentyl)(methyl)amino]-4-oxobutyl}biphenyl-2-yl) carbamate Obtained as a solid (160 mg, 88%) from tert-butyl-trans-4-aminocyclohexyl(4-{4-[{5-[(4-formylphenyl)amino]-5-oxopentyl}(methyl)amino]-4-oxobutyl}biphenyl-2-yl)carbamate (In-termediate 244; 125 mg, 0.18 mmol), 5-((1R)-2-amino-1-{[tert-butyl(dimethyl)-silyl]oxy}ethyl)-8-hydroxyquinolin-2(1H)-one acetate (58 mg, 0.18 mmol) (prepared accord-ing to preparation 8 from US20060035931) and sodium triacetoxyborohydride (185 mg, 0.88 mmol) following the experimental procedure as described for Intermediate 7 and the crude obtained was used in the next step without further purification.

LRMS (m/z): 515 (M/2)+

Example 46 trans-4-aminocyclohexyl(4-{4-[(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}biphenyl-2-yl) carbamate dihydrochloride Obtained as a white solid (18 mg, 23%) from tert-butyl-trans-4-aminocyclohexyl(4-{4-[(5-{[4-({[(2R)-2-{[tert-butyl(dimethyl)silyl]oxy}-2-(8-hydroxy-2-oxo-1,2-dihydro-quinolin-5-yl)ethyl]amino}methyl)phenyl]amino}-5-oxopentyl)(methyl)amino]-4-oxobutyl}biphenyl-2-yl) carbamate (Intermediate 245; 100 mg, 0.1 mmol) and hydrogen chloride (4M in dioxane, 4.85 mL) following the experimental procedure as described for Intermediate 21 and the crude obtained was purified by reversed phase using as eluents Water and Methanol.

LRMS (m/z): 732 (M+1)+

1H NMR (300 MHz, dmso) δ 10.49 (d, J=9.2 Hz, 2H), 10.10 (d, J=13.0 Hz, 1H), 9.51 (s, 1H), 9.03 (s, 1H), 8.62 (s, 1H), 8.15 (d, J=10.0 Hz, 1H), 7.99 (bs, 3H), 7.63 (d, J=8.5 Hz, 2H), 7.54-7.27 (m, 6H), 7.27-7.04 (m, 4H), 6.98 (d, J=8.2 Hz, 1H), 6.53 (d, J=9.9 Hz, 1H), 6.15 (bs, 1H), 5.43 (d, J=9.0 Hz, 1H), 4.34 (s, 1H), 4.13 (s, 3H), 3.29 (s, 3H), 3.00 (d, J=14.7 Hz, 2H), 2.92 (s, 2H), 2.80 (bs, 2H), 2.66-2.55 (m, 4H), 2.53 (d, J=8.0 Hz, 2H), 2.31 (bs, 4H), 2.00-1.70 (m, 5H), 1.53 (bs, 4H), 1.42-1.17 (m, 4H).

Intermediate 246 methyl 5-chloro-4-hydroxy-2-methoxybenzoate

To solution of 4-amino-5-chloro-2-methoxybenzoic acid (10 g, 0.048 mol) in water (50 mL) was added HBF4 (48% in water, 16.2 mL, 0.12 mol) and acetyl chloride (2.24 mL, 0.031 mol) and the mixture was stirred for 1 hour at room temperature. The mixture was cooled to 0° C. to add drop wise sodium nitrite (3.76 g, 0.054 mol) in water (30 mL). The reaction was allowed to stirrer at 0° C. for 30 minutes. Then the solid was filtered and it was treated with Acid Acetic (500 mL). The mixture was heated at 100° C. for 1 hour. The mixture was cooled and it was stand without further manipulation overnight. The solvent was removed under reduced pressure and the crude obtained was partitioned between Ethyl acetate and Brine. The organic layer was dried, filtered and the solvent was removed under reduced pressure. The crude was treated with sodium hydroxide (150 mL) for 90 minutes at room temperature and overnight at 45° C. The crude was extracted with dichloromethane and purified over silica gel eluting with Dichloromethane/Ethanol (100/0 to 0/100) to give the title compound as a foam (1.1 g, 10%)

LRMS (m/z): 217 (M+1)+

Intermediate 247

2-chloro-4-(hydroxymethyl)-5-methoxyphenol

To a solution of methyl 5-chloro-4-hydroxy-2-methoxy-benzoate (Intermediate 246; 1.1 g, 5.08 mmol) in THF (30 mL) was added drop wise at 0° C. lithium aluminium hydride (1M in THF, 9.65 mL). The reaction mixture was stirred 10 minutes at 0° C., 1 hour at room temperature and 30 minutes at 65° C. The mixture was cooled at 0° C. and a saturated solution of L-Tartrate (100 mL) was added cautiously. Then Ethyl acetate was added and the mixture was stirred for 1 hour at room temperature. The organic layer was separated, dried, filtered and the solvent was removed under reduced pressure to give a crude, which was purified over silica gel eluting with Chloroform/Ethanol (100/0 to 0/100) to give the title compound as a foam (460 mg, 450%)

LRMS (m/z): 189 (M+1)+

Intermediate 248 ethyl[2-chloro-4-(hydroxymethyl)-5-methoxyphe-noxy]acetate

To a solution of 2-chloro-4-(hydroxymethyl)-5-methoxy-phenol (Intermediate 247; 459 mg, 2.43 mmol) in acetonitrile (5 mL) was added ethyl bromoacetate (0.26 mL, 2.43 mmol) and potassium carbonate (420 mg, 3.04 mmol) in a sealed tub. The mixture was stirred 2 hours at 90° C. The solid was filtrated, washed with acetonitrile and the solvent of the filtrate was removed under reduced pressure giving the title compound as a brown oil (640 mg, 85%), which was used in the next step without further purification.

LRMS (m/z): 275 (M+1)+

Intermediate 249

[2-chloro-4-(hydroxymethyl)-5-methoxyphenoxy] acetic acid

To a solution of ethyl[2-chloro-4-(hydroxymethyl)-5-methoxyphenoxy]acetate (Intermediate 248; 640 mg, 2.33 mmol) in THF (20 mL) was added water (20 mL) and lithium hydroxide (391 mg, 9.32 mmol). The reaction mixture was stirred for 1 hour at room temperature. The solvent was removed under reduced pressure and the aqueous phase was acidified until acid pH and then extracted with ethyl acetate. The organic layer was washed with brine, dried, filtered and the solvent was removed under reduced pressure to give the title compound as a red solid (550 mg, 95%), which was used in the next step without further purification.

LRMS (m/z): 247 (M+1)+

121

Intermediate 250 tert-butyl-trans-4-aminocyclohexyl[4-(3-hydroxypropyl)biphenyl-2-yl]carbamate

To a solution of methyl 3-(2-{[({trans-4-[(tert-butoxycarbonyl)amino]cyclohexyl}oxy) carbonyl]amino}biphenyl-4-yl)propanoate (Intermediate 215; 260 mg, 0.52 mmol) in tetrahydrofurane (7 mL) was added at −10° C. lithium boro-hydride (2.6 mL, 5.2 mmol). The reaction mixture was stirred 6 hours at room temperature. Ammonium chloride saturated was added into the mixture cautiously and with ethyl ace-tate was extracted. The organic layer was washed with water and brine, dried, filtered and the solvent was removed under reduced pressure to give the title compound as a foam (210 mg, 85%), which was used in the next step without further purification.

LRMS (m/z): 469 (M+1)+

Intermediate 251 tert-butyl-trans-4-aminocyclohexyl[4-(3-oxopropyl)biphenyl-2-yl]carbamate

Obtained as an oil (184 mg, 88%) from tert-butyl-trans-4-aminocyclohexyl[4-(3-hydroxypropyl)biphenyl-2-yl]carbamate (Intermediate 250; 210 mg, 0.45 mmol) and Dess-Martin periodinane (230 mg, 0.54 mmol) following the experimental procedure as described for Intermediate 64 and the crude obtained was used in the next step without further purification.

LRMS (m/z): 466 (M+1)+

Intermediate 252 tert-butyl-trans-4-aminocyclohexyl{4-[3-(methylamino)propyl]biphenyl-2-yl}carbamate To a solution of tert-butyl-trans-4-aminocyclohexyl[4-(3-oxopropyl)biphenyl-2-yl]carbamate (Intermediate 251; 210 mg, 0.45 mmol) in methanol (5 mL) was added methanamine (225 μL, 0.45 mmol) and DIEA (80 μL, 0.46 mmol). The solution was stirred for 30 minutes at room temperature and then sodiumcyanoborohydride (71 mg, 1.13 mmol) was added. The reaction mixture was stirred over weekend at room temperature. The solvent was removed and the crude obtained was treated with chloroform, the solid was filtered and the filtrate was evaporated giving a crude which was purified by column chromatography with silica gel, eluting with a mixture of chloroform:methanol:ammonium (40:4:0.2). The title compound was obtained as a foam (82 mg, 37%).

LRMS (m/z): 482 (M+1)+

Intermediate 253 tert-butyl-trans-4-aminocyclohexyl(4-{3-[{[2-chloro-4-(hydroxymethyl)-5-methoxyphenoxy]acetyl}(methyl)amino]propyl}biphenyl-2-yl)carbamate The title compound was obtained (22 mg, 18%) from tert-butyl-trans-4-aminocyclohexyl {4-[3-(methylamino)propyl]biphenyl-2-yl}carbamate (Intermediate 252; 82 mg, 0.17 mmol), [2-chloro-4-(hydroxymethyl)-5-methoxyphenoxy]acetic acid (Intermediate 249; 42 mg, 0.17 mmol), HBTU (65 mg, 0.17 mmol) and DIEA (120 μL, 0.69 mmol) following the experimental procedure as described for Intermediate 125 and the crude obtained was purified by column chromatography with silica gel, eluting with a mixture of hexane:ethyl acetate.

LRMS (m/z): 711 (M+1)+

Intermediate 254 tert-butyl-trans-4-aminocyclohexyl(4-{3-[[(2-chloro-4-formyl-5-methoxyphenoxy)-acetyl](methyl)amino]propyl}biphenyl-2-yl)carbamate Obtained as a yellow foam (22 mg, 90%) from tert-butyl-trans-4-aminocyclohexyl(4-{3-[{[2-chloro-4-(hydroxymethyl)-5-methoxyphenoxy]acetyl}(methyl)amino]propyl}biphenyl-2-yl)carbamate (Intermediate 253; 22 mg, 0.03 mmol) and manganese oxide (30 mg, 0.35 mmol) following the experimental procedure as described for Intermediate 218 and the crude obtained was used in the next step without further purification.

LRMS (m/z): 695 (M+1)+

Intermediate 255 tert-butyl-trans-4-aminocyclohexyl(4-{3-[{[4-({[(2R)-2-{[tert-butyl(dimethyl) silyl]oxy}-2-(8-hydroxy-2-oxo-1,2-dihydroquinolin-5-yl)ethyl]amino}methyl)-2-chloro-5-methoxyphenoxy]acetyl}(methyl)amino]propyl}biphenyl-2-yl)carbamate Obtained as a solid (12 mg, 37%) from tert-butyl-trans-4-aminocyclohexyl(4-{3-[[(2-chloro-4-formyl-5-methoxyphenoxy)acetyl](methyl)amino]propyl}biphenyl-2-yl)carbamate (Intermediate 254; 22 mg, 0.03 mmol), 5-((1R)-2-amino-1-{[tert-butyl(dimethyl)-silyl]oxy}ethyl)-8-hydroxyquinolin-2(1H)-one acetate (11 mg, 0.03 mmol) (prepared according to preparation 8 from US20060035931), sodium cyanoborohydride (5 mg, 0.08 mmol) and DIEA (6 μL, 0.03 mmol) following the experimental procedure as described for Intermediate 7 and the crude obtained was purified by column chromatography with silica gel, eluting with a mixture of chloroform:ethanol.

LRMS (m/z): 513 (M/2)+

Example 47 trans-4-aminocyclohexyl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)-amino]propyl}biphenyl-2-yl)carbamate dihydrochloride Obtained as white solid (7 mg, 73%) from tert-butyl-trans-4-aminocyclohexyl(4-{3-[{[4-({[(2R)-2-{[tert-butyl(dimethyl)silyl]oxy}-2-(8-hydroxy-2-oxo-1,2-dihydroquinolin-5-yl)-ethylamino}methyl)-2-chloro-5-methoxyphenoxy]acetyl}(methyl)amino]propyl}biphenyl-2-yl)carbamate (Intermediate 255; 12 mg, 0.01 mmol) and hydrogen chloride (4M in dioxane, 0.1 mL) following the experimental procedure as described for Intermediate 21.

LRMS (m/z): 813 (M+1)+

1H NMR (300 MHz, cd3od) δ 8.23 (d, J=9.8 Hz, 1H), 7.49-7.23 (m, 5H), 7.23-6.99 (m, 6H), 6.77 (s, 1H), 6.69 (d, J=10 Hz, 1H), 5.47-5.34 (bs, 1H), 5.01 (bs, 1H), 4.48 (bs, 1H), 4.20 (bs, 2H), 3.96-3.82 (m, 2H), 3.70 (bs, 2H), 3.51

(bs, 2H), 3.13 (d, J=20.5 Hz, 3H), 3.00 (bs, 2H), 2.72 (bs, 3H), 2.57 (bs, 2H), 1.97 (bs, 4H), 1.42 (bs, 4H).

Intermediate 256

Ethyl(4-bromo-3-nitrophenyl)acetate

A round-bottomed flask fitted with stir bar was charged with fuming nitric acid (10.5 mL, 0.25 mol) and was cooled at −10° C., ethyl(4-bromophenyl)acetate (4.00 g, 16.45 mmol) was added dropwise. After stirring for 1 h at −10° C., the reaction was poured onto ice, after stirring 30 min, chloroform was added. The organic layer was dried, filtered and the solvent was removed under reduced pressure to give 3.05 g (64%) of a yellow oil, which was used in the next step without further purification.

LRMS (m/z): 286, 288 (M−1, M+1)−

Intermediate 257

Ethyl(2-nitrobiphenyl-4-yl)acetate

To a solution of ethyl(4-bromo-3-nitrophenyl)acetate (Intermediate 256; 3.05 g, 10.59 mmol) in dioxane (8 mL) and (12 mL) was added under nitrogen atmosphere phenylboronic acid (1.55 g, 12.70 mmol), cesium carbonate (10.35 g, 31.76 mmol) and [1,1'-Bis(diphenilphosfine)-ferrocene]dichloropaladium(II) (dichloromethane complex; 0.26 g, 0.03 mmol). The reaction mixture was stirred 3 h at 80° C. The catalyst was filtrated through Celite and the solvent was removed under reduced pressure. The crude obtained was purified by column chromatography with silica gel, eluting with a mixture of Hexane:Diethyl ether to obtain the title compound as a yellow oil (2.39 g, 79%).

LRMS (m/z): 284 (M−1)−

Intermediate 258

Ethyl(2-aminobiphenyl-4-yl)acetate

Obtained (2.12 g, 99%) from ethyl(2-nitrobiphenyl-4-yl)acetate (Intermediate 257; 2.39 g, 8.38 mmol) and palladium on charcoal (10%, 250 mg) in EtOH following the experimental procedure as described for Intermediate 67. The crude obtained was purified by column chromatography with silica gel, eluting with a mixture of Ethyl acetate:Hexane.

LRMS (m/z): 256 (M+1)+

Intermediate 259 ethyl(2-isocyanatobiphenyl-4-yl)acetate

To a solution of triphosgene (0.60 g, 2.04 mmol) in dichloromethane (30 mL) was added drop wise at 0° C. a solution of ethyl(2-aminobiphenyl-4-yl)acetate (Intermediate 258; 1.30 g, 5.09 mmol) in dichloromethane (30 mL), once the addition is finished triethylamine (1.42 mL, 10.18 mmol) was added. The mixture was stirred 2 hours at room temperature. The solvent was partially removed under reduced pressure without heating and pentane was added to precipitate the salts, the mixture was filtered and the filtrate was evaporated to get the title compound which was used in the next step without further manipulation.

Intermediate 260 ethyl(2-{[({trans-4-[(tert-butoxycarbonyl)amino]cyclohexyl}oxy)carbonyl]amino}biphenyl-4-yl)acetate To a solution of ethyl(2-isocyanatobiphenyl-4-yl)acetate (Intermediate 259) in toluene (20 mL) was added tert-butyl (trans-4-hydroxycyclohexyl)carbamate (Intermediate 174; 1.10 g, 5.9 mmol). The mixture was stirred for 18 hours at 90° C. The solvent was removed under reduced pressure and the crude obtained was purified by column chromatography with silica gel, eluting with a mixture of hexane:ether, giving the title compound as a solid (1.12 g, 44%).

LRMS (m/z): 495 (M−1)−

Intermediate 261 trans-4-[(tert-butoxycarbonyl)amino]cyclohexyl[4-(2-hydroxyethyl)biphenyl-2-yl]-carbamate To a solution of ethyl(2-{[({trans-4-[(tert-butoxycarbonyl)amino]cyclohexyl}oxy) carbonyl]amino}biphenyl-4-yl)acetate (Intermediate 260; 1.0 g, 2.02 mmol) in THF (30 mL) was added drop wise at −5° C. lithium borohydride solution (2M in THF, 10.07 mL) and EtOH (4 mL). The reaction mixture was stirred 2 hours at room temperature. Ammonium chloride saturated was added into the mixture cautiously and with ethyl acetate was extracted. The organic layer was washed with water and brine, dried, filtered and the solvent was removed under reduced pressure to give the title compound (0.9 g, 98%), which was used in the next step without further purification.

LRMS (m/z): 453 (M−1)−

Intermediate 262

2-(2-{[({trans-4-[(tert-butoxycarbonyl)amino]cyclohexyl}oxy)carbonyl]amino}biphenyl-4-yl)ethyl methanesulfonate Methanesulfonyl chloride (56 μL, 0.72 mmol) was added dropwise to a solution of trans-4-[(tert-butoxycarbonyl)amino]cyclohexyl[4-(2-hydroxyethyl)biphenyl-2-yl]carbamate (Intermediate 261; 0.3 g, 0.66 mmol) and triethylamine (183 μL, 1.32 mmol) in dichloromethane at 0° C. The mixture was stirred for 2 hours at room temperature. The crude was partitioned between dichloromethane and sodium bicarbonate 4%, the organic layer was washed with brine, dried and the solvent was removed under reduced pressure to give the title compound as an off white solid (340 mg, 96%), which was used in the next step without further purification.

LRMS (m/z): 533 (M+1)+, 531 (M−1)−

Intermediate 263 trans-4-[(tert-butoxycarbonyl)amino]cyclohexyl{4-[2-(methylamino)ethyl]biphenyl-2-yl}carbamate Methylamine (1.70 mL, 3.40 mmol) was added to a solution of 2-(2-{[({trans-4-[(tert-butoxycarbonyl)amino]cyclohexyl}oxy)carbonyl]amino}biphenyl-4-yl)ethyl methanesulfonate (Intermediate 262; 351 mg, 0.64 mmol) in toluene, the mixture was stirred for 4 hours at 110° C. The solvent was removed under reduced pressure and the crude obtained was purified by column chromatography with silica gel, eluting with a mixture of chloroform:ethanol:ammonium (40:8:1) giving the title compound (0.30 mg, 97%).

LRMS (m/z): 469 (M+1)+, 467 (M−1)−

Intermediate 264 trans-4-[(tert-butoxycarbonyl)amino]cyclohexyl(4-{2-[{[2-chloro-4-(hydroxymethyl)-5-methoxyphenoxy]acetyl}(methyl)amino]ethyl}biphenyl-2-yl) carbamate The title compound was obtained (401 mg, 62%) from trans-4-[(tert-butoxycarbonyl)amino]cyclohexyl(4-{2-[{[2-chloro-4-(hydroxymethyl)-5-methoxyphenoxy]acetyl}(methyl)amino]ethyl}biphenyl-2-yl)carbamate (Intermediate 263; 305 mg, 0.65 mmol), [2-chloro-4-(hydroxymethyl)-5-methoxyphenoxy]acetic acid (Intermediate 249; 161 mg, 0.65 mmol), HBTU (247 mg, 0.65 mmol) and DIEA (454 µL, 2.61 mmol) following the experimental procedure as described for Intermediate 125 and the crude was used in the next step without further purification.

LRMS (m/z): 695 (M−1)−

Intermediate 265 trans-4-[(tert-butoxycarbonyl)amino]cyclohexyl(4-{2-[[(2-chloro-4-formyl-5-methoxyphenoxy)acetyl](methyl)amino]ethyl}biphenyl-2-yl)carbamate Obtained as a yellow foam (427 mg, 85%) from trans-4-[(tert-butoxycarbonyl)amino]cyclohexyl(4-{2-[{[2-chloro-4-(hydroxymethyl)-5-methoxyphenoxy]-acetyl}(methyl)amino]ethyl}biphenyl-2-yl)carbamate (Intermediate 264; 401 mg, 0.58 mmol) and manganese oxide (500 mg, 5.75 mmol) following the experimental procedure as described for Intermediate 218 and the crude obtained was used in the next step without further purification.

LRMS (m/z): 694 (M+1)+, 692 (M−1)−

Intermediate 266 trans-4-[(tert-butoxycarbonyl)amino]cyclohexyl(4-{2-[{[4-({[(2R)-2-{[tert-butyl(dimethyl) silyl]oxy}-2-(8-hydroxy-2-oxo-1,2-dihydroquinolin-5-yl)ethyl]amino}methyl)-2-chloro-5-methoxyphenoxy]acetyl}(methyl)amino]ethyl}biphenyl-2-yl)carbamate Obtained (236 mg, 38%) from trans-4-[(tert-butoxycarbonyl)amino]cyclohexyl(4-{2-[[(2-chloro-4-formyl-5-methoxyphenoxy)acetyl](methyl)amino]ethyl}biphenyl-2-yl)carbamate (Intermediate 265; 427 mg, 0.62 mmol), 5-((1R)-2-amino-1-{[tert-butyl(dimethyl)-silyl]oxy}ethyl)-8-hydroxyquinolin-2(1H)-one acetate (206 mg, 0.62 mmol) (prepared according to preparation 8 from US20060035931) and sodium triacetoxyborohydride (97 mg, 1.54 mmol) and DIEA (118 µL, 0.68 mmol) following the experimental procedure as described for Intermediate 146. The crude obtained was purified by column chromatography with silica gel, eluting with a mixture of chloroform:methanol (9:1).

LRMS (m/z): 508 (M/2)+

Example 48 trans-4-aminocyclohexyl(4-{2-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)-amino]ethyl}biphenyl-2-yl) carbamate dihydrochloride Obtained as a white solid (99 mg, 80%) from trans-4-[(tert-butoxycarbonyl)amino]cyclohexyl(4-{2-[{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)-amino]ethyl}biphenyl-2-yl)carbamate (Intermediate 266; 158 mg, 0.16 mmol) and hydrogen chloride (4N in dioxane; 0.5 mL) following the experimental procedure as described for Intermediate 21.

LRMS (m/z): 799 (M+1)+, 797 (M−1)−

1H NMR (400 MHz, dmso) δ 10.80 (s, 1H), 10.76 (s, 1H), 9.34 (bs, 1H), 9.06 (bs, 1H), 8.93 (d, J=7.6 Hz, 1H), 8.41 (d, J=9.9 Hz, 1H), 8.21 (bs, 3H), 7.82 (s, 1H), 7.65 (dd, J=11.8, 5.4 Hz, 2H), 7.60-7.54 (m, 3H), 7.52-7.44 (m, 1H), 7.38 (dd, J=8.8, 3.9 Hz, 1H), 7.24 (d, J=8.2 Hz, 1H), 6.97 (d, J=13.5 Hz, 1H), 6.82 (d, J=9.9 Hz, 1H), 6.44 (s, 1H), 5.65 (d, J=7.7 Hz, 1H), 5.32 (bs, 1H), 5.26 (bs, 1H), 4.58 (s, 1H), 4.36 (s, 2H), 4.06 (s, 3H), 4.03 (s, 2H), 3.92-3.73 (m, 2H), 3.66 (s, 3H), 3.25 (d, J=31.6 Hz, 2H), 2.15 (d, J=7.5 Hz, 2H), 2.07 (bs, 2H), 1.73-1.48 (m, 4H).

Intermediate 267

Tert-butyl[(5-chloro-4-isocyanato-2-methoxybenzyl)oxy]dimethylsilane

To a solution of 4-((tert-butyldimethylsilyloxy)methyl)-2-chloro-5-methoxyaniline (Intermediate 39 WO2011/141180A1; 300 mg, 0.9 mmol) in 4 mL of anhydrous dichloromethane at 0° C. was added dropwise a solution of triphosgene (108 mg; 0.36 mmol) in 5 mL of anhydrous dichloromethane.

Once the addition is finished triethylamine (280 uL, 2.01 mmol) was added dropwise. The reaction mixture was stirred for 2 hours at room temperature. The reaction mixture was concentrated under reduced pressure until half of the initial volume and 25 mL of pentane was added into the reaction mixture. The solid was filtrated and washed with more pentane and dried to get the title compound (307 mg, 79%).

Intermediate 268

Trans-4-[(tert-butoxycarbonyl)amino]cyclohexyl(4-{2-[({[4-({[tert-butyl(dimethyl) silyl]oxy}methyl)-2-chloro-5-methoxyphenyl]amino}carbonyl)oxy]ethyl}biphenyl-2-yl)carbamate To a solution of tert-butyl[(5-chloro-4-isocyanato-2-methoxybenzyl)oxy]dimethylsilane (Intermediate 267; 150 mg, 0.46 mmol) in toluene (5 mL) is added at 0° C. trans-4-[(tert-butoxycarbonyl)amino]cyclohexyl[4-(2-hydroxyethyl)biphenyl-2-yl]carbamate (Intermediate 261, 294 mmol, 0.55 mmol) and triehylamine (75 uL, 0.54 mmol) and the mixture is stirred at room temperature for 4 hours. The solvent was removed under reduced pressure and the crude was purified by column chromatography in reverse phase using as eluents water and acetonitrile, giving the title compound (170 mg, 47%).

Intermediate 269 trans-4-[(tert-butoxycarbonyl)amino]cyclohexyl(4-{2-[{[2-chloro-4-(hydroxy methyl)-5-methoxyphenoxy]acetyl}(methyl)amino]ethyl}biphenyl-2-yl) carbamate To a solution of trans-4-[(tert-butoxycarbonyl)amino]cyclohexyl(4-{2-[({[4-({[tert-butyl(dimethyl)silyl]oxy}methyl)-2-chloro-5-methoxyphenyl]amino}carbonyl)oxy]ethyl}biphenyl-2-yl)carbamate (Intermediate 268; 238 mg, 0.30 mmol) in tetrahydrofuran (8 mL) was added dropwise TBAF 1M in THF (304 uL, 0.3 mmol). The reaction mixture was stirred at room temperature for 1 hour. The solvent was removed under reduced pressure and the crude was partitioned between dichloromethane and water, the organic layer was washed with water several times, dried, filtered and the solvent was removed under reduced pressure. The crude obtained was used in the next step without further purification (200 mg, 98%).

Intermediate 270 trans-4-[(tert-butoxycarbonyl)amino]cyclohexyl(4-{2-[[(2-chloro-4-formyl-5-methoxy phenoxy)acetyl](methyl)amino]ethyl}biphenyl-2-yl)carbamate A round-bottomed flask fitted with stir bar was charged with trans-4-[(tert-butoxycarbonyl)amino]cyclohexyl(4-{2-[{[2-chloro-4-(hydroxymethyl)-5-methoxy phenoxy]acetyl}(methyl)amino]ethyl}biphenyl-2-yl)carbamate (Intermediate 269; 200 mg, 0.3 mmol) in DCM. Dess-Martin periodinane (139 mg, 0.33 mmol) was added portionwise and the mixture stirred at room temperature for 1 hour. The reaction was quenched by addition of saturated bicar-bonate (little bubbling) and diluted with DCM. The organic layer was washed with more bicarbonate solution (twice), brine, dried over MgSO4, filtered and concentrated. The residue was used in the next step without further purification (199 mg, 99%).

LRMS (m/z): 667 (M+1)+

Intermediate 271 trans-4-[(tert-butoxycarbonyl)amino]cyclohexyl(4-{2-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]ethyl}biphenyl-2-yl) carbamate To a mixture of trans-4-[(tert-butoxycarbonyl)amino]cyclohexyl(4-{2-[[(2-chloro-4-formyl-5-methoxyphenoxy)acetyl](methyl)amino]ethyl}biphenyl-2-yl)carbamate (Intermediate 270; 199 mg, 0.3 mmol) and 5-((1R)-2-amino-1-{[tert-butyl(dimethyl)-silyl]oxy}ethyl)-8-hydroxyquinolin-2(1H)-one acetate (99 mg, 0.3 mmol) (prepared according to preparation 8 from US20060035931) in 5 mL of DCE/methanol (4:1) sodium triacetoxyborohydride (474 mg, 2.22 mmol) was added. The mixture was stirred over a weekend at room temperature. The solvent was removed under reduced pressure and the crude was partitioned between ethyl acetate and water, the organic layer was washed with sodium bicarbonate solution and water, dried, filtered and the solvent was removed under reduced pressure. The crude obtained was used in the next step without further purification (160 mg, 54%).

Example 49 trans-4-aminocyclohexyl(4-{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}biphenyl-2-yl)carbamate dihydrochloride A solution trans-4-[(tert-butoxycarbonyl)amino]cyclohexyl(4-{2-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}carbonyl)oxy]ethyl}biphenyl-2-yl)carbamate (Intermediate 271; 110 mg, 0.11 mmol) in 2.8 mL of hydrogen chloride (4N in dioxane) was stirred for 3 hours at room temperature. The solvent was removed under reduced pressure and the crude obtained was treated with acetonitrile giving a white solid as the title compound (60 mg, 54%)

LRMS (m/z): 771 (M+1)+

1H NMR (400 MHz, dmso) δ 10.50 (bs, 1H), 9.20 (s, 1H), 8.87 (s, 1H), 8.67 (s, 1H), 8.15 (d, J=12.0 Hz, 1H), 8.01 (s, 2H), 7.60 (s, 1H), 7.48-7.16 (m, 10H), 7.11 (d, J=9.3 Hz, 1H), 6.97 (d, J=7.9 Hz, 1H), 6.54 (d, J=10.9 Hz, 1H), 5.41 (d, J=5.5 Hz, 1H), 4.32 (s, 3H), 4.15 (s, 2H), 3.77 (s, 3H), 2.96 (s, 6H), 1.84 (d, J=29.6 Hz, 4H), 1.45-1.16 (m, 4H).

Intermediate 272

4-(but-3-en-1-yloxy)benzaldehyde

To a solution of 4-hydroxybenzaldehyde (0.30 g, 2.46 mmol) in anhydrous DMF (3 mL) were added potassium carbonate (1.65 g, 12 mmol) and 4-bromobut-1-ene (1.08 mL, 11.1 mmol) and the reaction mixture was heated at 60° C. for 28 hr. After cooling to room temperature, water (30 mL) was added until complete dissolution of the solid. The aqueous phase was extracted with ether (3×20 mL) and the combined organic extracts were washed with water (30 mL) and brine (30 mL), dried with anhydrous sodium sulphate, filtered and concentrated to dryness to afford the title compound as a colorless oil (426 mg, 98%).

LRMS (m/z): 177 (M+1)+

Intermediate 273 trans-4-[(tert-butoxycarbonyl)amino]cyclohexyl{5-[(1E)-4-(4-formylphenoxyl)but-1-en-1-yl]biphenyl-2-yl}carbamate Obtained as a colorless oil (82 mg of an 80% purity, 22%) from trans-4-tert-butylaminocyclohexyl(5-bromobiphenyl-2-yl)carbamate (Intermediate 175, 250 mg, 0.51 mmol), 4-(but-3-en-1-yloxy)benzaldehyde (Intermediate 272, 99 mg, 0.56 mmol), tri-o-tolylphosphine (68 mg, 0.22 mmol), N,N-diisopropylethylamine (180 µL, 1.03 mmol) and palladium acetate (30 mg, 0.13 mmol) following the experimental procedure as described for Intermediate 6 using dioxane (3 mL) as solvent. The crude obtained was purified by column chromatography with silica gel, eluting with a mixture of hexane:ether.
LRMS (m/z): 585 (M+1)+

Intermediate 274 trans-4-[(tert-butoxycarbonyl)amino]cyclohexyl (5-{(1E)-4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]but-1-en-1-yl}biphenyl-2-yl)carbamate Obtained as a beige solid (66 mg, 66%) from trans-4-[(tert-butoxycarbonyl)amino]cyclohexyl{5-[(1E)-4-(4-formylphenoxyl)but-1-en-1-yl]biphenyl-2-yl}carbamate (Intermediate 273, 81 mg, 0.11 mmol), 5-((1R)-2-amino-1-{[tert-butyl(dimethyl)-silyl]oxy}ethyl)-8-hydroxyquinolin-2(1H)-one acetate (44 mg, 0.11 mmol) (prepared according to preparation 8 from US20060035931), and sodium triacetoxyborohydride (140 mg, 0.66 mmol) following the experimental procedure as described for Intermediate 7 without DIEA and using a mixture of methanol:tetrahydrofuran 1:1 as solvent (2 mL). The crude obtained was purified by column chromatography with silica gel, eluting with a mixture of chloroform and chloroform:methanol:ammonium hydroxide(40:4:0.2)
LRMS (m/z): 904 (M+1)+

Intermediate 275 trans-4-[(tert-butoxycarbonyl)amino]cyclohexyl(5-{4-[4-({[(2R)-2-{[tert-butyl-(dimethyl)silyl]oxy}-2-(8-hydroxy-2-oxo-1,2-dihydroquinolin-5-yl)ethyl]amino}-methyl)phenoxy]butyl}biphenyl-2-yl)carbamate To a solution of trans-4-[(tert-butoxycarbonyl)amino]cyclohexyl(5-{(1E)-4-[4-({[(2R)-2-{[tert-butyl(dimethyl)silyl]oxy}-2-(8-hydroxy-2-oxo-1,2-dihydroquinolin-5-yl)ethyl]amino}-methyl)phenoxy]but-1-en-1-yl}biphenyl-2-yl)carbamate (Intermediate 274, 66 mg, 0.07 mmol) in methanol (1.5 mL) was added palladium on carbon (10% palladium on carbon, 8.0 mg, 0.01 mmol) and the resulting suspension was purged with argon and then filled with hydrogen. The mixture was stirred at room temperature for 3 hr. The reaction mixture is then filtered, the solid washed with a mixture of chloroform:ethanol 1:1 and the filtrate is concentrated to dryness to afford the title compound as a colorless foam (70 mg, 100%)
LRMS (m/z): 906 (M+1)+

Example 50 trans-4-aminocyclohexyl(4-{5-[4-({[(2R)-2-hydroxy-2-(8-hydroxy-2-oxo-1,2-dihydroquinolin-5-yl)ethyl]amino}methyl)phenoxy]pentyl}biphenyl-2-yl)carbamate Obtained as white solid (40 mg of a 95% purity, 68%) from trans-4-[(tert-butoxycarbonyl)amino]cyclohexyl(5-{4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]butyl}biphenyl-2-yl)carbamate (Intermediate 275, 66 mg, 0.01 mmol) and hydrogen chloride (0.2 mL of a 4M solution in dioxane, 0.8 mmol) in tetrahydrofuran (1 mL), following the experimental procedure as described for Intermediate 21.

LRMS (m/z): 692 (M+1)+
1H NMR (300 MHz, dmso) δ 10.48 (bs, 2H), 9.59 (bs, 1H), 9.01 (bs, 1H), 8.57 (s, 1H), 8.19 (d, J=10.0 Hz, 1H), 8.05 (d, J=3.4 Hz, 2H), 7.53-7.29 (m, 5H), 7.18 (m, 3H), 7.02-6.88 (m, 2H), 6.53 (d, J=9.9 Hz, 1H), 5.46 (d, J=8.2 Hz, 1H), 4.33 (m, 1H), 4.12 (bs, 2H), 4.02 (d, J=11.6 Hz, 2H), 2.99 (m, 3H), 2.67 (bs, 2H), 2.01-1.64 (m, 6H), 1.48-1.15 (m, 4H).

Intermediate 276 trans-4-[(tert-butoxycarbonyl)amino]cyclohexyl[4-(4-{[trans-3-(hydroxymethyl)cyclobutyl]amino}-4-oxobutyl)biphenyl-2-yl]carbamate To a solution of 4-(2-{[({trans-4-[(tert-butoxycarbonyl)amino]cyclohexyl}oxy)carbonyl]amino}biphenyl-4-yl)butanoic acid (synthesized as Intermediate 189; 550 mg, 1.11 mmol) in DMF (5 mL) was added ((1r,3r)-3-aminocyclobutyl)methanol (123 mg, 1.22 mmol) and diisopropylethylenediamine (0.578 mL, 3.32 mmol) under nitrogen atmosphere. Then HATU (631 mg, 1.66 mmol) was added. The reaction mixture was stirred at room temperature overnight. The solvent was removed under reduced pressure and the crude was partitioned between ethyl acetate and water, the organic layer was washed with water several times, dried, filtered and the solvent was removed under reduced pressure. The crude obtained was purified by column chromatography with silica gel giving the title compound as a solid (120 mg, 18%).
LRMS (m/z): 581 (M+1)+

Intermediate 277 trans-4-[(tert-butoxycarbonyl)amino]cyclohexyl(4-{4-[(trans-3-formylcyclobutyl)amino]-4-oxobutyl}biphenyl-2-yl)carbamate A round-bottomed flask fitted with stir bar was charged with trans-4-[(tert-butoxycarbonyl)amino]cyclohexyl[4-(4-{[trans-3-(hydroxymethyl)cyclobutyl]amino}-4-oxobutyl)biphenyl-2-yl]carbamate (Intermediate 276; 120 mg, 0.21 mmol) in DCM (10 mL). Dess-Martin periodinane (115 mg, 0.27 mmol) was added portionwise and the mixture stirred at room temperature for 2 hours. The reaction was quenched by addition of saturated bicarbonate (little bubbling) and diluted with DCM. The organic layer was washed with more bicarbonate solution (twice), brine, dried over MgSO4, filtered and concentrated. The residue was used in the next step without further purification (119 mg, 99%).
LRMS (m/z): 578 (M+1)+

Intermediate 278 trans-4-[(tert-butoxycarbonyl)amino]cyclohexyl[4-(4-{[trans-3-({[(2R)-2-{[tert-butyl(dimethyl)silyl]oxy}-2-(8-hydroxy-2-oxo-1,2-dihydroquinolin-5-yl)ethyl]amino}methyl)cyclobutyl]amino}-4-oxobutyl)biphenyl-2-yl]carbamate A mixture of trans-4-[(tert-butoxycarbonyl)amino]cyclohexyl(4-{4-[(trans-3-formylcyclobutyl)amino]-4-oxobutyl}biphenyl-2-yl)carbamate (Intermediate 277; 119 mg, 0.21 mmol) and 5-((1R)-2-amino-1-{[tert-butyl(dimethyl)-silyl]oxy}ethyl)-8-hydroxyquinolin-2(1H)-one acetate (62 mg, 0.19 mmol) (prepared according to preparation 8 from US20060035931) in 20 mL of DCE/methanol (4:1) is stirred for 1 hour. Then sodium triacetoxyborohydride (474 mg, 2.22 mmol) was added. The mixture was stirred overnight at room temperature. The reaction mixture was diluted with DCM and washed with sodium bicarbonate solution and water, dried, filtered and the solvent was removed under reduced pressure. The crude obtained was purified by column chromatography with silica gel using basic media giving the title compound as a solid (49 mg, 29%).

LRMS (m/z): 897 (M+1)+

Example 51 trans-4-aminocyclohexyl[4-(4-{[trans-3-({[(2R)-2-hydroxy-2-(8-hydroxy-2-oxo-1,2-dihydroquinolin-5-yl)ethyl]amino}methyl)cyclobutyl]amino}-4-oxobutyl)biphenyl-2-yl]carbamate dihydrochloride A solution trans-4-[(tert-butoxycarbonyl)amino]cyclohexyl[4-(4-{[trans-3-({[(2R)-2-{[tert-butyl(dimethyl)silyl]oxy}-2-(8-hydroxy-2-oxo-1,2-dihydroquinolin-5-yl)ethyl]amino}methyl)cyclobutyl]amino}-4-oxobutyl)biphenyl-2-yl]carbamate (Intermediate 278; 49 mg, 0.05 mmol) in 2 mL of hydrogen chloride (4N in dioxane) was stirred for 3 hours at room temperature. The solvent was removed under reduced pressure and the crude obtained was treated with acetonitrile and diethyl ether giving a white solid as the title compound (15 mg, 40%)

LRMS (m/z): 683 (M+1)+

1H NMR (300 MHz, dmso) δ 10.74 (bs, 1H), 8.62 (s, 2H), 7.90 (d, J=2.8 Hz, 2H), 7.36 (dd, J=16.3, 6.0 Hz, 3H), 7.27-7.05 (m, 3H), 6.98 (d, J=8.5 Hz, 1H), 6.58 (d, J=7.3 Hz, 1H), 5.53-5.27 (m, 3H), 4.32 (d, J=3.4 Hz, 3H), 4.18-3.95 (m, 1H), 3.57 (s, 2H), 2.99 (d, J=9.0 Hz, 3H), 2.09 (d, J=7.6 Hz, 2H), 1.97-1.72 (m, 5H), 1.67 (d, J=6.2 Hz, 2H), 1.50-1.15 (m, 5H).

Intermediate 279

5-chloro-4-cyano-2-methoxybenzoic acid

To a suspension of 4-amino-5-chloro-2-methoxybenzoic acid (4.0 g, 19.8 mmol) in water (66 mL) was added concentrated hydrogen chloride (6.6 mL of a 35% solution in water, 79.2 mmol) and the resulting mixture was cooled to 0° C. with vigorous stirring. Then, a solution of sodium nitrite (1.95 g, 28.3 mmol) in water (6 mL) was added dropwise while maintaining the internal temperature below 4° C. After 5 min, the mixture containing the diazonium salt was slowly added, through an addition funnel and maintaining the temperature below 5° C., over a mechanically stirred solution of copper cyanide (2.4 g, 26.8 mmol) and sodium cyanide (3.7 g, 75.5 mmol) in water (20 mL, this solution was freshly prepared from a suspension of the copper cyanide in water and slow addition of sodium cyanide while keeping the temperature below 40° C. and allowed to cool to rt). Once the addition was finished, the reaction mixture was allowed to warm to rt and vigorous stirring was maintained for 4 hours. Then, water and hydrogen chloride (5N) were added to the mixture and the aqueous phase was extracted with ethyl acetate. The whole mixture was filtered to remove the solids and the phases were separated. The aqueous phase was further extracted twice with ethyl acetate and the combined organic extracts were washed with brine, dried, decolorized with active carbon, filtered and concentrated to dryness to afford the title compound as light yellow solid (3.0 g, 70%).

LRMS (m/z): 210 (M−1)−

Intermediate 280

2-chloro-4-(hydroxymethyl)-5-methoxybenzonitrile

To a solution of 5-chloro-4-cyano-2-methoxybenzoic acid (Intermediate 279, 3.0 g, 14.2 mmol) in tetrahydrofuran (50 mL) was added slowly, at 0° C. and under argon atmosphere, borane dimethylsufide complex (2.7 mL, 28.4 mmol). After the addition was finished, the reaction mixture was stirred at 0° C. for 5 min and then allowed to warm up to rt and stirred for 3 hours. Then, water was slowly added (6 mL) and the mixture was concentrated to dryness. The residue was suspended in ethyl acetate and filtered. The solid was washed with further ethyl acetate and the combined organic phases were decolorized with active carbon, filtered and concentrated under reduced pressure to afford the title compound as a yellowish solid (2.3 g, 80%).

LRMS (m/z): 215 (M+18[NH4+])+

Intermediate 281

2-chloro-4-(hydroxymethyl)-5-methoxybenzoic acid

To a suspension of 2-chloro-4-(hydroxymethyl)-5-methoxybenzonitrile (Intermediate 280, 1.8 g, 9.1 mmol) in ethanol (20 mL) in a sealed tube was added NaOH (8 mL of a 32% aqueous solution, 64 mmol) and the reaction mixture was heated at 110° C. overnight. Then, water was added and the aqueous phase was washed with ethyl acetate twice, acidified with hydrochloric acid (5N) up to pH=2, and extracted with ethyl acetate twice. The combined organic extracts were dried and concentrated to dryness to provide the title compound as a white solid (1.3 g, 66%)

LRMS (m/z): 215 (M−1)−

Intermediate 282 trans-4-[(tert-butoxycarbonyl)amino]cyclohexyl[4-(3-{[(benzyloxy)carbonyl]-amino}propyl)biphenyl-2-yl]carbamate 4-(2-{[({trans-4-[(tert-butoxycarbonyl)amino]cyclohexyl}oxy)carbonyl]amino}biphenyl-4-yl)butanoic acid (synthesized as Intermediate 189; 5 g, 10.1 mmol) was suspended in toluene (70 mL) and cooled to −10° C. under nitrogen atmosphere. To this suspension, diphenylphosphorylazide (2.16 mL, 10.1 mmol) and triethylamine (1.95 mL, 14.1 mmol) were added and the mixture was heated to 70° C. for 3 h. The reaction mixture was cooled to 50° C., phenylmethanol (2.9 mL, 28.2 mmol) was added, and then heated again to 110° C. overnight. The solvent is removed and water and dichloromethane were added. The phases were separated and the organic phase was washed with water and brine, dried, filtered and concentrated to dryness. The residue is purified twice by column chromatography with silica gel and eluting with a mixture of hexane:ether. The title compound was obtained (4.7 g of 87% purity, 66%) as a beige solid.

LRMS (m/z): 603 (M+1)+

Intermediate 283 trans-4-[(tert-butoxycarbonyl)amino]cyclohexyl[4-(3-aminopropyl)biphenyl-2-yl]carbamate To a solution of trans-4-[(tert-butoxycarbonyl)amino]cyclohexyl[4-(3-{[(benzyloxy)-carbonyl]amino}propyl)biphenyl-2-yl]carbamate (Intermediate 282, 3.7 g, 6.1 mmol) in a mixture of ethanol (20 mL) and methanol (5 mL) was added palladium on carbon (0.65 g of a 10% suspension, 0.61 mmol), and the reaction mixture was stirred under hydrogen atmosphere overnight. The suspension was filtered through a pad of Celite® and the solvent was removed under reduced pressure. The residue obtained was washed with hexane and dried to provide the title compound as a yellowish solid (2.5 g, 82%).

LRMS (m/z): 468 (M+1)+

Intermediate 284 trans-4-[(tert-butoxycarbonyl)amino]cyclohexyl[4-(3-{[2-chloro-4-(hydroxymethyl)-5-methoxybenzoyl]amino}propyl)biphenyl-2-yl]carbamate To a solution of 2-chloro-4-(hydroxymethyl)-5-methoxybenzoic acid (Intermediate 281, 240 mg, 1.11 mmol) and trans-4-[(tert-butoxycarbonyl)amino]cyclohexyl[4-(3-aminopropyl)biphenyl-2-yl]carbamate (Intermediate 284, 622 mg, 1.33 mmol) in DMF (10 mL) were added sequentially diisopropylethylenediamine (0.77 mL, 4.43 mmol) and HATU (843 mg, 2.22 mmol) under nitrogen atmosphere. After 3 hours the solvent was removed and the remaining residue was suspended in water and the aqueous phase was extracted with ethyl acetate (3 times). The combined organic extracts were washed with water and brine, dried, filtered and concentrated to dryness. The residue was purified by column chromatography over silica gel using a mixture hexane:ether:methanol as eluent, and the crude obtained was further purified over C18 modified silica gel using a mixture of water:methanol as eluent to afford the title compound as a white solid (70 mg, 10%).

LRMS (m/z): 667 (M+1)+

Intermediate 285 trans-4-[(tert-butoxycarbonyl)amino]cyclohexyl(4-{3-[(2-chloro-4-formyl-5-methoxybenzoyl)amino]propyl}biphenyl-2-yl)carbamate Obtained as a black oil (70 mg, 100%) from trans-4-[(tert-butoxycarbonyl)amino]cyclohexyl[4-(3-{[2-chloro-4-(hydroxymethyl)-5-methoxybenzoyl]amino}propyl)biphenyl-2-yl]carbamate (Intermediate 284, 70 mg, 0.11 mmol) and manganese dioxide (91 mg, 1.1 mmol) in chloroform (6 mL) following the experimental procedure as described for Intermediate 218 and the crude obtained was used in the next step without further purification.

LRMS (m/z): 665 (M+1)+

Intermediate 286 trans-4-[(tert-butoxycarbonyl)amino]cyclohexyl[4-(3-{[4-({[(2R)-2-{[tert-butyl-(dimethyl)silyl]oxy}-2-(8-hydroxy-2-oxo-1,2-dihydroquinolin-5-yl)ethyl]amino}-methyl)-2-chloro-5-methoxybenzoyl]amino}propyl)biphenyl-2-yl]carbamate Obtained as a beige solid (25 mg, 24%) from trans-4-[(tert-butoxycarbonyl)amino]cyclohexyl(4-{3-[(2-chloro-4-formyl-5-methoxybenzoyl)amino]-propyl}biphenyl-2-yl) carbamate (70 mg, 0.11 mmol), 5-((1R)-2-amino-1-{[tert-butyl(dimethyl)silyl]oxy}ethyl)-8-hydroxyquinolin-2(1H)-one acetate (35 mg, 0.10 mmol) (prepared according to preparation 8 from US20060035931), sodium cyanoborohydride (13 mg, 0.21 mmol) and DIEA (38 µL, 0.22 mmol) in MeOH (3 mL), following the experimental procedure as described for Intermediate 7. The crude obtained was purified by column chromatography with silica gel, eluting with a mixture of chloroform and chloroform:methanol:amomonium hydroxide (40:4:0.2).

LRMS (m/z): 464 (M/2+1-56 (tert-butyl))+, 927 (M+1-56 (tert-butyl))+

Example 52 trans-4-aminocyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl) biphenyl-2-yl]carbamate Obtained as white solid (15 mg of a 90% purity, 69%) from trans-4-[(tert-butoxycarbonyl)amino]cyclohexyl[4-(3-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}propyl) biphenyl-2-yl]carbamate (25 mg, 0.03 mmol) and hydrogen chloride (0.1 mL of a 4M solution in dioxane, 0.4 mmol) in dioxane (2 mL), following the experimental procedure as described for Intermediate 21.

LRMS (m/z): 768 (M+1)+

1H NMR (300 MHz, dmso) δ 10.55 (d, J=12.9 Hz, 2H), 9.40 (bs, 1H), 9.03 (bs, 1H), 8.67 (s, 1H), 8.61 (t, J=12.9 Hz, 1H), 8.23 (d, J=10.0 Hz, 1H), 8.07-7.89 (m, 3H), 7.70 (s, 1H), 7.51-7.35 (m, 4H), 7.31-7.25 (m, 2H), 7.20 (d, J=7.9 Hz, 1H), 7.17 (d, J=3.2 Hz, 1H), 7.03 (d, J=8.2 Hz, 1H), 6.62 (d, J=9.8 Hz, 1H), 6.25 (s, 1H), 5.50 (ddd, J=10.3, 7.7, 3.7 Hz, 1H), 4.45-4.32 (m, 1H), 4.32-4.21 (m, 2H), 3.90 (s, 3H), 3.38-3.25 (m, 2H), 3.23-3.12 (m, 1H), 3.12-2.94 (m, 2H), 2.85-2.64 (m, 2H), 2.10-1.71 (m, 6H), 1.55-1.21 (m, 4H).

Intermediate 287

4-allylphenol

To a solution of 1-allyl-4-methoxybenzene (2.0 g, 13.5 mmol) in dichloromethane (100 mL) was added, at 0° C. and under nitrogen atmosphere, boron tribromide (15 mL of a 1M solution in dichloromethane, 15.0 mmol) and the reaction was stirred for 3 hours at 0° C. and overnight at rt. The reaction mixture was poured over an ice-water mixture and the resulting phases were separated. The aqueous phase was extracted with dichloromethane (4 times) and the combined organic extracts were washed with water and brine, dried over sodium sulphate, filtered and concentrated. The oil obtained was purified by column chromatography with silica gel using a mixture of hexane:ethyl acetate as eluent. The title compound was obtained as a light yellow oil (0.73 g, 41%).

1H NMR (300 MHz, cdcl3) d 7.05 (d, J=8.6 Hz, 2H), 6.76 (d, J=8.6 Hz, 2H), 6.07-5.76 (m, 1H), 5.09-5.04 (m, 1H), 5.02 (t, J=1.4 Hz, 1H), 4.77 (s, 1H), 3.32 (d, J=6.7 Hz, 2H).

Intermediate 288

4-(4-allylphenoxyl)benzaldehyde 4-fluorobenzaldehyde (0.16 mL, 1.5 mmol) and 4-allylphenol (200 mg, 1.5 mmol) were dissolved in DMF (5 mL). To this solution, potassium carbonate was added (412 mg, 2.98 mmol) and the mixture was heated to 110° C. for 2 days. The reaction mixture was filtered and the filtrate was diluted with ethyl acetate. The organic phase was washed with aqueous NaOH (2N), water and brine, dried, filtered and concentrated to dryness. The residue was purified by column chromatography with silica gel using a mixture of hexane:ether as eluent to provide the title compound as a colorless oil (224 mg, 63%).

LRMS (m/z): 239 (M+1)+

Intermediate 289 trans-4-[(tert-butoxycarbonyl)amino]cyclohexyl (4-{(1E)-3-[4-(4-formylphenoxyl)phenyl]prop-1-en-1-yl}biphenyl-2-yl)carbamate Obtained as a brownish foam (263 mg, 100%) from trans-4-tert-butylaminocyclohexyl(4-bromobiphenyl-2-yl)carbamate (Intermediate 183, 200 mg, 0.41 mmol), 4-(4-allylphenoxyl)benzaldehyde (Intermediate 288, 97 mg, 0.41 mmol), tri-o-tolylphosphine (125 mg, 0.41 mmol), N,N-diisopropylethylamine (142 µL, 0.82 mmol) and palladium acetate (46 mg, 0.20 mmol) in acetonitrile (2 mL) following the experimental procedure as described for Intermediate 6. The crude obtained was used without further purification.

LRMS (m/z): 645 (M−1)−

Intermediate 290 trans-4-[(tert-butoxycarbonyl)amino]cyclohexyl[4-((1E)-3-{4-[4-({[(2R)-2-{[tert-butyl(dimethyl)silyl]oxy}-2-(8-hydroxy-2-oxo-1,2-dihydroquinolin-5-yl)ethyl]-amino}methyl)phenoxy]phenyl}prop-1-en-1-yl)biphenyl-2-yl]carbamate Obtained as a beige solid (171 mg of a 80% purity, 35%) from trans-4-[(tert-butoxycarbonyl)amino]cyclohexyl (4-{(1E)-3-[4-(4-formylphenoxyl)phenyl]prop-1-en-1-yl}biphenyl-2-yl)carbamate (263 mg, 0.41 mmol), 5-((1R)-2-amino-1-{[tert-butyl(dimethyl)-silyl]oxy}ethyl)-8-hydroxyquinolin-2(1H)-one acetate (136 mg, 0.41 mmol) (prepared according to preparation 8 from US20060035931), sodium cyanoborohydride (64 mg, 1.02 mmol) and DIEA (85 µL, 0.49 mmol) in MeOH (2 mL), following the experimental procedure as described for Intermediate 7. The crude obtained was purified by column chromatography with silica gel, eluting with a mixture of chloroform and chloroform:methanol:amomonium hydroxide (40:4:0.2) and the residue was purified again using a mixture of hexane:ether:ethanol as eluent.

Intermediate 291 trans-4-[(tert-butoxycarbonyl)amino]cyclohexyl[4-(3-{4-[4-({[(2R)-2-{[tert-butyl-(dimethyl) silyl]oxy}-2-(8-hydroxy-2-oxo-1,2-dihydroquinolin-5-yl) ethyl]amino}-methyl)phenoxy]phenyl}propyl) biphenyl-2-yl]carbamate Obtained as a beige foam (184 mg of a 80% purity, 86%) from trans-4-[(tert-butoxycarbonyl)amino]cyclohexyl[4-((1E)-3-{4-[4-({[(2R)-2-{[tert-butyl(dimethyl)silyl]-oxy}-2-(8-hydroxy-2-oxo-1,2-dihydroquinolin-5-yl)ethyl]amino}methyl)phenoxy]phenyl}-prop-1-en-1-yl)biphenyl-2-yl]carbamate (171 mg, 0.18 mmol) and palladium on carbon (10% palladium on carbon, 20 mg, 0.02 mmol) under hydrogen atmosphere in methanol (20 mL). The crude product was used without any further purification.

Example 53 trans-4-aminocyclohexyl[4-(3-{4-[4-({[(2R)-2-hydroxy-2-(8-hydroxy-2-oxo-1,2-dihydroquinolin-5-yl) ethyl]amino}methyl)phenoxy]phenyl}propyl)biphenyl-2-yl]carbamate Obtained as white solid (111 mg, 71%) from trans-4-[(tert-butoxycarbonyl)amino]cyclohexyl[4-(3-{4-[4-({[(2R)-2-{[tert-butyl(dimethyl)silyl]oxy}-2-(8-hydroxy-2-oxo-1,2-dihydroquinolin-5-yl)ethyl]amino}methyl)phenoxy]phenyl}propyl)-biphenyl-2-yl]carbamate (184 mg, 0.19 mmol) and hydrogen chloride (0.7 mL of a 4M solution in dioxane, 2.8 mmol) in dioxane (2 mL), following the experimental procedure as described for Intermediate 21.

LRMS (m/z): 753 (M+1)+

1H NMR (300 MHz, dmso) δ 10.55 (bs, 2H), 9.67 (bs, 1H), 9.12 (bs, 1H), 8.65 (s, 1H), 8.24 (dd, J=9.9, 3.3 Hz, 1H), 8.07 (bs, 2H), 7.60 (dd, J=8.6, 2.1 Hz, 2H), 7.49-7.35 (m, 4H), 7.31 (d, J=9.5 Hz, 1H), 7.27 (d, J=9.8 Hz, 1H), 7.25 (bs, 1H), 7.19 (d, J=7.5 Hz, 1H), 7.13 (d, J=7.8 Hz, 1H), 7.09-6.91 (m, 5H), 6.58 (d, J=9.9 Hz, 1H), 5.51 (dd, J=6.2, 1.8 Hz, 1H), 4.45-4.29 (m, 1H), 4.21 (bs, 2H), 3.15-2.90 (m, 3H), 2.68 (t, J=7.3 Hz, 2H), 2.05-1.79 (m, 6H), 1.50-1.18 (m, 4H).

Intermediate 292 methyl 4-({[4-(2-{[({trans-4-[(tert-butoxycarbonyl) amino]cyclohexyl}-oxy)carbonyl]-amino}biphenyl-4-yl)butanoyl]amino}methyl)benzoate To a solution of 4-(2-{[({trans-4-[(tert-butoxycarbonyl) amino]cyclohexyl}oxy)carbonyl]amino}biphenyl-4-yl)butanoic acid (synthesized as Intermediate 189; 200 mg, 0.40 mmol) in DMF (4 mL), were added diisopropylethylenediamine (0.28 mL, 1.61 mmol) and HATU (382 mg, 1.00 mmol) under nitrogen atmosphere. Then, methyl 4-(aminomethyl)benzoate hydrochloride (90 mg, 0.45 mmol) was added. The reaction mixture was stirred at room temperature overnight. The solvent was removed under reduced pressure and the crude was partitioned between dichloromethane and water, the organic layer was washed with water several times and brine, dried over sodium sulfate, filtered and the solvent was removed under reduced pressure. The crude obtained was purified by reverse phase column chromatography with C18 modified silica gel, eluting with a mixture of water:acetonitrile, giving the title compound as a colorless foam (189 mg, 71%).

LRMS (m/z): 645 (M+1)+

Intermediate 293 trans-4-[(tert-butoxycarbonyl)amino]cyclohexyl[4-(4-{[4-(hydroxymethyl)-benzyl]amino}-4-oxobutyl) biphenyl-2-yl]carbamate To a suspension of lithium aluminum hydride (16 mg, 0.42 mmol) in tetrahydrofuran (0.5 mL) was added, at 0° C. and under argon atmosphere, a solution of methyl 4-({[4-(2-{[({trans-4-[(tert-butoxycarbonyl)amino] cyclohexyl}oxy)carbonyl]amino}biphenyl-4-yl)butanoyl] amino}methyl)benzoate (Intermediate 292, 189 mg, 0.29 mmol) in tetrahydrofuran (1.5 mL). The reaction mixture was allowed to warm to rt and stirring was maintained overnight. The reaction was then quenched by sequential addition of H₂O (20 μL), NaOH (4N, 20 μL) and H₂O (60 μL), and was stirred for 30 min at rt. The solid formed was filtered, washed with dichloromethane, and the resulting solution was concentrated under reduced pressure. The residue obtained was purified by reverse phase column chromatography with C18 modified silica gel, eluting with a mixture of water:acetonitrile, to afford the title compound as colorless foam (95 mg, 50%).

LRMS (m/z): 617 (M+1)+

Intermediate 294 trans-4-[(tert-butoxycarbonyl)amino]cyclohexyl(4-{4-[(4-formylbenzyl)amino]-4-oxobutyl}biphenyl-2-yl)carbamate Obtained as a brownish foam (99 mg of a 90% purity, 94%) from trans-4-[(tert-butoxycarbonyl)amino]cyclohexyl[4-(4-{[4-(hydroxymethyl)benzyl]amino}-4-oxobutyl)-biphenyl-2-yl]carbamate (Intermediate 293, 95 mg, 0.15 mmol) and Dess-Martin periodinane (80 mg, 0.19 mmol) in DCM (2 mL) following the experimental procedure as described for Intermediate 64 and the crude obtained was used in the next step without further purification.

LRMS (m/z): 615 (M+1)+

Intermediate 295 trans-4-[(tert-butoxycarbonyl)amino]cyclohexyl[4-(4-{[4-({[(2R)-2-{[tert-butyl(dimethyl) silyl]oxy}-2-(8-hydroxy-2-oxo-1,2-dihydroquinolin-5-yl)ethyl]-amino}methyl)benzyl]amino}-4-oxobutyl)biphenyl-2-yl]carbamate Obtained as a beige solid (83 mg, 56%) from trans-4-[(tert-butoxycarbonyl)amino]-cyclohexyl(4-{4-[(4-formylbenzyl)amino]-4-oxobutyl}biphenyl-2-yl)carbamate (Intermediate 294, 98 mg, 0.16 mmol), 5-((1R)-2-amino-1-{[tert-butyl(dimethyl)-silyl]oxy}ethyl)-8-hydroxyquinolin-2(1H)-one acetate (63 mg, 0.16 mmol) (prepared according to preparation 8 from US20060035931), sodium cyanoborohydride (26 mg, 0.41 mmol) and DIEA (28 μL, 0.16 mmol), following the experimental procedure as described for Intermediate 7. The crude obtained was purified by column chromatography with silica gel, eluting with a mixture of chloroform:methanol.

LRMS (m/z): 933 (M+1)+

Example 54 trans-4-aminocyclohexyl[4-(4-{[4-({[(2R)-2-hydroxy-2-(8-hydroxy-2-oxo-1,2-dihydroquinolin-5-yl)ethyl]amino}methyl)benzyl]amino}-4-oxobutyl)biphenyl-2-yl]carbamate dihydrochloride Obtained as white solid (55 mg of a 92% purity, 72%) from trans-4-[(tert-butoxycarbonyl)amino]cyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)benzyl]amino}-4-oxobutyl)biphenyl-2-yl]carbamate (Intermediate 295; 83 mg, 0.09 mmol) and hydrogen chloride (0.45 mL of a 4M solution in dioxane, 1.8 mmol) in tetrahydrofuran (1 mL), following the experimental procedure as described for Intermediate 21.

LRMS (m/z): 719 (M+1)+

1H NMR (300 MHz, dmso) δ 10.54 (bs, 1H), 9.78 (bs, 1H), 9.16 (bs, 1H), 8.66 (s, 1H), 8.47 (t, J=5.9 Hz, 1H), 8.25 (d, J=9.0 Hz, 1H), 8.10 (bs, 3H), 7.55 (d, J=8.5 Hz, 2H), 7.49-7.28 (m, 7H), 7.25 (d, J=9.0 Hz, 2H), 7.23 (bs, 1H) 7.15 (d, J=8.5 Hz, 2H), 7.02 (d, J=9.0 Hz, 1H), 6.57 (d, J=9.5 Hz, 1H), 5.52 (d, J=8.5 Hz, 1H), 4.43-4.28 (m, J=9.5 Hz, 3H), 4.21 (bs, 2H), 3.10-2.87 (m, 3H), 2.61 (t, J=7.5 Hz, 2H), 2.25 (t, J=7.5 Hz, 2H), 2.02-1.79 (m, 6H), 1.52-1.21 (m, 4H).

Intermediate 296

(5-aminopyridin-2-yl)methanol

To a suspension of lithium aluminium hydride (302 mg, 7.96 mmol) in tetrahydrofuran (0.5 mL) was added, at 0° C. and under argon atmosphere, a solution of ethyl 6-aminonicotinate (602 mg, 3.62 mmol) in tetrahydrofuran (1.5 mL). The reaction mixture was allowed to warm to rt. After 5 hours the reaction was then quenched by sequential addition of H₂O (0.3 mL), NaOH (4N, 0.3 mL) and H₂O (0.6 mL), and stirring was continued for 30 min at rt. The solid formed was filtered, washed with dichloromethane, and the resulting solution was concentrated under reduced pressure. The residue obtained was washed with ether and dried to afford the title compound as a colorless foam (500 mg of a 90% purity, 100%). The compound was used without further purification.

LRMS (m/z): 125 (M+1)+

Intermediate 297 trans-4-[(tert-butoxycarbonyl)amino]cyclohexyl[4-(4-{[6-(hydroxymethyl)pyridin-3-yl]amino}-4-oxobutyl)biphenyl-2-yl]carbamate Obtained as a colorless foam (244 mg of a 58% purity, 58%) from 4-(2-{[({trans-4-[(tert-butoxycarbonyl)amino]cyclohexyl}oxy)carbonyl]amino}biphenyl-4-yl)butanoic acid (synthesized as Intermediate 189; 200 mg, 0.40 mmol), (5-aminopyridin-2-yl)methanol (Intermediate 296, 73 mg, 0.53 mmol) diisopropylethylenediamine (85 μL, 0.49 mmol) and HATU (170 mg, 0.45 mmol) in DMF (5 mL) following the experimental procedure as described for intermediate 292. The crude residue was purified by column chromatography using a mixture of chloroform:methanol as eluent.

LRMS (m/z): 603 (M+1)+

Intermediate 298 trans-4-[(tert-butoxycarbonyl)amino]cyclohexyl(4-{4-[(6-formylpyridin-3-yl)amino]-4-oxobutyl}biphenyl-2-yl)carbamate Obtained as a brownish foam (145 mg of a 63% purity, 27%) from trans-4-[(tert-butoxycarbonyl)amino]cyclohexyl[4-(4-{[6-(hydroxymethyl)pyridin-3-yl]amino}-4-oxobutyl)biphenyl-2-yl]carbamate (Intermediate 297, 243 mg, 0.24 mmol) and Dess-Martin periodinane (175 mg, 0.41 mmol) following the experimental procedure as described for Intermediate 64 and the crude obtained was used in the next step without further purification.

LRMS (m/z): 601 (M+1)+

Intermediate 299 trans-4-[(tert-butoxycarbonyl)amino]cyclohexyl[4-(4-{[6-({[(2R)-2-{[tert-butyl(dimethyl)silyl]oxy}-2-(8-hydroxy-2-oxo-1,2-dihydroquinolin-5-yl)ethyl]-amino}methyl)pyridin-3-yl]amino}-4-oxobutyl)biphenyl-2-yl]carbamate Obtained as a yellow foam (18 mg, 28%) from trans-4-[(tert-butoxycarbonyl)amino]cyclohexyl(4-{4-[(6-formylpyridin-3-yl)amino]-4-oxobutyl}-biphenyl-2-yl)carbamate (Intermediate 298, 61 mg of a 65% purity, 0.07 mmol), 5-((1R)-2-amino-1-{[tert-butyl(dimethyl)-silyl]oxy}ethyl)-8-hydroxyquinolin-2(1H)-one acetate (22 mg, 0.07 mmol) (prepared according to preparation 8 from US20060035931), sodium cyanoborohydride (11 mg, 0.18 mmol) and DIEA (12 µL, 0.07 mmol), following the experimental procedure as described for Intermediate 7. The crude obtained was purified by column chromatography with silica gel, eluting with a mixture of chloroform:methanol.

LRMS (m/z): 920 (M+1)+

Example 55 trans-4-aminocyclohexyl[4-(4-{[5-({[(2R)-2-hydroxy-2-(8-hydroxy-2-oxo-1,2-dihydroquinolin-5-yl)ethyl]amino}methyl)pyridin-2-yl]amino}-4-oxobutyl) biphenyl-2-yl]carbamate dihydrochloride Obtained as a white solid (8 mg, 53%) from trans-4-[(tert-butoxycarbonyl)amino]-cyclohexyl[4-(4-{[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]amino}-4-oxobutyl)biphenyl-2-yl]carbamate (Intermediate 299; 18 mg, 0.02 mmol) and hydrogen chloride (0.15 mL of a 4M solution in dioxane, 0.6 mmol) in tetrahydrofuran (0.5 mL), following the experimental procedure as described for Intermediate 21.

LRMS (m/z): 705 (M+1)+

1H NMR (300 MHz, dmso) δ 10.73 (s, 1H), 10.55 (bs, 2H), 9.84 (bs, 1H), 9.19 (bs, 1H), 8.66 (s, 1H), 8.49 (s, 1H), 8.29 (d, J=10.0 Hz, 1H), 8.16 (d, J=8.5 Hz, 1H), 8.11-7.97 (m, 3H), 7.50-7.31 (m, 5H), 7.30-7.22 (m, 2H), 7.17 (d, J=8.5 Hz, 2H), 7.03 (d, J=8.5 Hz, 1H), 6.59 (d, J=9.9 Hz, 1H), 5.53 (d, J=9.2 Hz, 1H), 4.37 (m, 2H), 4.23 (bs, 2H), 3.18-2.90 (m, 4H), 2.67 (t, J=7.5 Hz, 2H), 2.10-1.69 (m, 6H), 1.57-1.09 (m, 4H).

Intermediate 300 trans-4-{[tert-butyl(dimethyl)silyl]oxy}-N-methylcyclohexanamine

To a solution of trans-4-(methylamino)cyclohexanol (3.4 g, 26.32 mmol) in dichloromethane (130 mL) was added imidazole (2.70 g, 39.66 mmol). The mixture was cooled to 0° C. and tert-butyldimethylsilyl chloride (4.40 g, 29.19 mmol) was added dropwise. The mixture was stirred at room temperature overnight. The crude was partitioned between water and more dichloromethane, the organic layer was washed with saturated solution of potassium carbonate, dried, filtered and evaporated to dryness. Pentane was added to the crude obtained, the mixture was filtered and the filtrate was evaporated giving the title compound (6.7 g, 99%).

1H NMR (300 MHz, cdcl3) δ 3.60-3.43 (m, 1H), 2.36 (s, 3H), 2.31-2.18 (m, 1H), 1.83 (ddd, J=16.2, 8.9, 3.6 Hz, 4H), 1.41-1.17 (m, 2H), 1.13-0.92 (m, 2H), 0.83 (s, 9H), 0.00 (s, 6H).

Intermediate 301 trans-4-{[tert-butyl(dimethyl)silyl]oxy}-N-hexyl-N-methylcyclohexanamine

Obtained (1.53 g, 978%) from trans-4-{[tert-butyl(dimethyl)silyl]oxy}-N-methylcyclohexanamine (Intermediate 300; 1.00 g, 4.11 mmol), hexanal (0.55 mL, 4.58 mmol) and sodium triacetoxyborohydride (2.60 g, 12.27 mmol) in dichloroethane (25 mL) following the experimental procedure as described for Intermediate 146.

1H NMR (300 MHz, dmso) δ 3.53 (s, 2H), 3.29 (s, 3H), 2.84 (d, J=3.1 Hz, 2H), 1.94 (d, J=11.7 Hz, 2H), 1.85-1.72 (m, 3H), 1.60-1.34 (m, 4H), 1.23 (s, 9H), 0.02-0.02 (m, 6H).

Intermediate 302 ethyl 4-(2-{[({trans-4-[hexyl(methyl)amino]cyclohexyl}oxy)carbonyl]amino}biphenyl-4-yl)butanoate To a solution of triphosgene (0.29 g, 0.96 mmol) in toluene (8 mL) was added dropwise at 0° C. a solution of ethyl 4-(2-aminobiphenyl-4-yl)butanoate (Intermediate 122; 0.69 g, 2.42 mmol), once the addition is finished triethylamine (0.67 mL, 4.84 mmol) was added.

The mixture was stirred 4 hours at room temperature. The solvent was partially removed under reduced pressure without heating and hexane was added to precipitate the salts, the mixture was filtered and the filtrate was evaporated. The corresponding isocyanate with trans-4-{[tert-butyl(dimethyl)silyl]oxy}-N-hexyl-N-methylcyclohexanamine (570 mg, 2.67 mmol) were stirred overnight at 110° C. The crude was purified by column chromatography with silica gel, eluting with a mixture of chloroform:methanol:ammonium (40:4:0.2), giving the title compound (174 mg, 14%).

LRMS (m/z): 523 (M+1)+

Intermediate 303 lithium 4-(2-{[({4-[hexyl(methyl)amino]cyclohexyl}oxy)carbonyl]amino}biphenyl-4-yl)butanoate Obtained as a solid (160 mg, 95%) from ethyl 4-(2-{[({trans-4-[hexyl(methyl)amino]-cyclohexyl}oxy)carbonyl]amino}biphenyl-4-yl)butanoate (Intermediate 302; 174 mg, 0.34 mg) and lithium hydroxide monohydrate (50 mg, 1.19 mmol) following the experimental procedure as described for Intermediate 124. After stirring overnight, and chloroform was added to precipitate the salts, the mixture was filtered and the filtrate was evaporated and the crude obtained was used in the next step without further purification.

LRMS (m/z): 493 (M−1)−

Intermediate 304

4-[hexyl(methyl)amino]cyclohexyl[4-(4-{[4-({[tert-butyl(dimethyl)silyl]oxy}-methyl)-2-chloro-5-methoxyphenyl]amino}-4-oxobutyl)biphenyl-2-yl]carbamate To a solution of lithium 4-(2-{[({4-[hexyl(methyl)amino]cyclohexyl}oxy)carbonyl]-amino}biphenyl-4-yl)butanoate (Intermediate 303; 160 mg, 0.32 mmol) in DMF (3 mL) was added HATU (145 mg, 0.38 mmol) under nitrogen atmosphere. After 1 hour stirring at room temperature, 4-((tert-butyldimethylsilyloxy)methyl)-2-chloro-5-methoxyaniline (Intermediate 39 WO2011/141180A1; 104 mg, 0.34 mmol), was added. The reaction mixture was stirred at 50° C. overnight. The solvent was removed under reduced pressure and the crude was partitioned between chloroform and water, the organic layer was washed with water several times, dried, filtered and the solvent was removed under reduced pressure. The crude obtained (242 mg of an 50% purity, 45%) was used in the next step without further purification.

LRMS (m/z): 779 (M+1)+

Intermediate 305 trans-4-[hexyl(methyl)amino]cyclohexyl[4-(4-{[2-chloro-4-(hydroxymethyl)-5-methoxyphenyl]amino}-4-oxobutyl)biphenyl-2-yl]carbamate Tetrabutylammonium fluoride solution (1M in THF, 311 μM) was added dropwise to a solution of trans-4-[hexyl(methyl)amino]cyclohexyl[4-(4-{[2-chloro-4-(hydroxymethyl)-5-methoxyphenyl]amino}-4-oxobutyl)biphenyl-2-yl]carbamate (Intermediate 304; 242 mg of an 50% purity, 0.16 mmol) in tetrahydrofurane. The mixture was stirring 3 h at room temperature. The solvent was removed under reduced pressure and the residue was suspended in MeOH and acidified by hydrogen chloride 1N. The solution was passed through an acidic sulphonic SCX column. The compound was released from the column with 33% ammonium in methanol and the solvent was removed under reduced pressure. The crude obtained (182 mg of an 50% purity, 88%) was used in the next step without further purification.

LRMS (m/z): 664 (M+1)+

Intermediate 306 trans-4-[hexyl(methyl)amino]cyclohexyl(4-{4-[(2-chloro-4-formyl-5-methoxy-phenyl)amino]-4-oxobutyl}biphenyl-2-yl)carbamate Obtained as a yellow foam (158 mg of an 50% purity, 87%) from trans-4-[hexyl(methyl)amino]cyclohexyl[4-(4-{[2-chloro-4-(hydroxymethyl)-5-methoxyphenyl]amino}-4-oxobutyl)biphenyl-2-yl]carbamate (Intermediate 305; 182 mg of an 50% purity, 0.13 mmol) and manganese oxide (238 mg, 2.74 mmol) following the experimental procedure as described for Intermediate 218 and the crude obtained was used in the next step without further purification.

LRMS (m/z): 662 (M+1)+

Intermediate 307 trans-4-[hexyl(methyl)amino]cyclohexyl[4-(4-{[4-({[(2R)-2-{[tert-butyl(dimethyl)-silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate Obtained as a solid (10 mg, 9%) from trans-4-[hexyl(methyl)amino]cyclohexyl(4-{4-[(2-chloro-4-formyl-5-methoxyphenyl)amino]-4-oxobutyl}biphenyl-2-yl)carbamate (Intermediate 306; 158 mg of an 50% purity, 0.12 mmol), 5-((1R)-2-amino-1-{[tert-butyl(dimethyl)-silyl]oxy}ethyl)-8-hydroxyquinolin-2(1H)-one acetate (45 mg, 0.13 mmol) (prepared according to preparation 8 from US20060035931), sodium cianoborohydride (19 mg, 0.30 mmol) and diethylethylenamine (25 μL, 0.14 mmol) following the experimental procedure as described for Intermediate 7. The crude obtained was purified by column chromatography in reverse phase using as eluents water and methanol.

LRMS (m/z): 491 (M/2+1)+

Example 56 trans-4-[hexyl(methyl)amino]cyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate dihydrofluoride Obtained as a white solid (8 mg, 87%) from trans-4-[hexyl(methyl)amino]cyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate (Intermediate 307; 10 mg, 0.01 mmol) and triethylamine trihydrofluoride (101 μL, 0.06 mmol) following the experimental procedure as described for Example 1.

LRMS (m/z): 867 (M+1)+, 434 (M/2+1)+, 865 (M−1)−

Intermediate 308

(5-aminopyridin-2-yl)methanol

Obtained as a solid (1.3 g of an 85% purity, 30%) from ethyl 5-aminopicolinate (5.0 g, 30.1 mmol) and lithium aluminium hydride (2.28 g, 60.1 mmol) in tetrahydrofuran (21 mL), following the experimental procedure as described for Intermediate 296. The crude was purified by column chromatography on silica gel, eluting with a mixture of chloroform:methanol.

LRMS (m/z): 125 (M+1)+

Intermediate 309 trans-4-[(tert-butoxycarbonyl)amino]cyclohexyl[4-(4-{[6-(hydroxymethyl)pyridin-3-yl]amino}-4-oxobutyl)biphenyl-2-yl]carbamate Obtained as an oil (326 mg of an 82% purity, over 100%) from 4-(2-{[({trans-4-[(tert-butoxycarbonyl)amino]cyclohexyl}oxy)carbonyl]amino}biphenyl-4-yl)butanoic acid (synthesized as Intermediate 189; 200 mg, 0.40 mmol), (5-aminopyridin-2-yl)methanol (Intermediate 308, 55 mg, 0.44 mmol), diisopropylethylenediamine (85 μL, 0.49 mmol) and HATU (190 mg, 0.50 mmol) in DMF (5 mL), following the experimental procedure as described for intermediate 292. The crude product was used without further purification.

LRMS (m/z): 604 (M+1)+

Intermediate 310 trans-4-[(tert-butoxycarbonyl)amino]cyclohexyl(4-{4-[(6-formylpyridin-3-yl)amino]-4-oxobutyl}biphenyl-2-yl)carbamate Obtained as a light brown foam (134 mg of an 83% purity, 97%) from trans-4-[(tert-butoxycarbonyl)amino]cyclohexyl[4-(4-{[6-(hydroxymethyl)pyridin-3-yl]amino}-4-oxobutyl)biphenyl-2-yl]carbamate (Intermediate 309, 138 mg, 0.19 mmol) and Dess-Martin periodinane (93 mg, 0.22 mmol) in dichloromethane (3 mL), following the experimental procedure as described for Intermediate 64 and the crude obtained was used in the next step without further purification.

LRMS (m/z): 601 (M+1)+

Intermediate 311 trans-4-[(tert-butoxycarbonyl)amino]cyclohexyl[4-(4-{[6-({[(2R)-2-{[tertbutyl(dimethyl)silyl]oxy}-2-(8-hydroxy-2-oxo-1,2-dihydroquinolin-5-yl)ethyl]-amino}methyl)pyridin-3-yl]amino}-4-oxobutyl) biphenyl-2-yl]carbamate Obtained as a yellow foam (139 mg, 81%) from trans-4-[(tert-butoxycarbonyl)-amino]cyclohexyl(4-{4-[(6-formylpyridin-3-yl)amino]-4-oxobutyl}biphenyl-2-yl)carbamate (Intermediate 310, 134 mg of a 83% purity, 0.18 mmol), 5-((1R)-2-amino-1-{[tert-butyl(dimethyl)-silyl]oxy}ethyl)-8-hydroxyquinolin-2(1H)-one acetate (80 mg, 0.20 mmol) (prepared according to preparation 8 from US20060035931), sodium cyanoborohydride (28 mg, 0.45 mmol) and DIEA (35 µL, 0.20 mmol), following the experimental procedure as described for Intermediate 7. The crude obtained was purified by column chromatography with silica gel, eluting with a mixture of chloroform:ethanol.

LRMS (m/z): 920 (M+1)+

Example 57 trans-4-aminocyclohexyl[4-(4-{[6-({[(2R)-2-hydroxy-2-(8-hydroxy-2-oxo-1,2-dihydroquinolin-5-yl) ethyl]amino}methyl)pyridin-3-yl]amino}-4-oxobutyl)-biphenyl-2-yl]carbamate dihydrochloride Obtained as a beige solid (108 mg of a 94% purity, 86%) from trans-4-[(tert-butoxycarbonyl)amino]cyclohexyl[4-(4-{[6-({[(2R)-2-{[tertbutyl(dimethyl)silyl]oxy}-2-(8-hydroxy-2-oxo-1,2-dihydroquinolin-5-yl)ethyl] amino}methyl)pyridin-3-yl]amino}-4-oxobutyl)biphenyl-2-yl]carbamate (Intermediate 311; 139 mg, 0.14 mmol) and hydrogen chloride (1.0 mL of a 4M solution in dioxane, 4.0 mmol) in tetrahydrofuran (2.0 mL), following the experimental procedure as described for Intermediate 21.

LRMS (m/z): 705 (M+1)+

$^1$H NMR (300 MHz, dmso) δ 10.57 (bs, 2H), 10.46 (s, 1H), 9.38 (bs, 1H), 8.91 (s, 1H), 8.68 (s, 1H), 8.25 (d, J=10.1 Hz, 1H), 8.21-8.00 (m, 3H), 7.54 (d, J=8.0 Hz, 1H), 7.49-7.33 (m, 4H), 7.29-7.24 (m, 2H), 7.19 (d, J=8.2 Hz, 2H), 7.04 (d, J=8.2 Hz, 1H), 6.61 (d, J=9.6 Hz, 1H), 5.53 (d, J=8.3 Hz, 1H), 4.37 (bs, 3H), 3.31-2.83 (m, 4H), 2.70 (t, J=7.5 Hz, 2H), 2.47 (t, J=7.5 Hz, 2H), 2.08-1.64 (m, 6H), 1.55-1.12 (m, 4H).

Intermediate 312 trans-4-(hydroxymethyl)cyclohexanecarboxylic acid

To a solution of trans-methyl 4-(hydroxymethyl)cyclohexanecarboxylate (165 mg, 0.96 mmol) in tetrahydrofuran (4 mL) and water (2 mL) was added LiOH monohydrate (120 mg, 2.86 mmol) and the final solution was allowed to stir for 2 hours. The solvents were removed under vacuum providing the title compound as a white solid (150 mg, 99%). The crude product was used without further purification.

Intermediate 313 trans-4-[(tert-butoxycarbonyl)amino]cyclohexyl{4-[3-({[trans-4-(hydroxymethyl)cyclohexyl] carbonyl}amino)propyl]biphenyl-2-yl}carbamate To a solution of trans-4-(hydroxymethyl)cyclohexanecarboxylic acid (Intermediate 312, 100 mg, 0.63 mmol) and trans-4-[(tert-butoxycarbonyl)amino]cyclohexyl[4-(3-aminopropyl)biphenyl-2-yl]carbamate (Intermediate 283, 295 mg, 0.63 mmol) in DMF (4 mL) were added sequentially HATU (264 mg, 0.70 mmol) and DIEA (143 µL, 0.82 mmol) and the reaction mixture was stirred overnight. Then, the solvent was removed under reduced pressure and ethyl acetate and water were added to the residue. The phases were separated and the organic phase was washed with saturated sodium bicarbonate solution and brine, dried over anhydrous sodium sulphate, filtered and concentrated to dryness. The title compound was obtained as a yellow oil (380 mg of a 90% purity, 89%) and was used without any further purification.

LRMS (m/z): 609 (M+1)+

Intermediate 314 trans-4-[(tert-butoxycarbonyl)amino]cyclohexyl[4-(3-{[(trans-4-formylcyclohexyl) carbonyl] amino}propyl)biphenyl-2-yl]carbamate Obtained as a brownish foam (374 mg of a 80% purity, 80%) from trans-4-[(tert-butoxycarbonyl)amino]cyclohexyl{4-[3-({[trans-4-(hydroxymethyl)cyclohexyl]carbonyl}-amino)propyl]biphenyl-2-yl}carbamate (Intermediate 313, 243 mg, 0.24 mmol) and Dess-Martin periodinane (175 mg, 0.41 mmol) in chloroform (5 mL) following the experimental procedure as described for Intermediate 64 and the crude obtained was used in the next step without further purification.

LRMS (m/z): 607 (M+1)+

Intermediate 315 trans-4-[(tert-butoxycarbonyl)amino]cyclohexyl{4-[3-({[trans-4-({[(2R)-2-{[tert-butyl(dimethyl)silyl] oxy}-2-(8-hydroxy-2-oxo-1,2-dihydroquinolin-5-yl) ethyl]-amino}methyl)cyclohexyl]carbonyl}amino) propyl]biphenyl-2-yl}carbamate Obtained as a yellow foam (110 mg of a 90% purity, 24%) from trans-4-[(tert-butoxycarbonyl)amino]cyclohexyl[4-(3-{[(trans-4-formylcyclohexyl)carbonyl]amino}-propyl)biphenyl-2-yl]carbamate (Intermediate 314, 374 mg of a 80% purity, 0.62 mmol), 5-((1R)-2-amino-1-{[tert-butyl(dimethyl)-silyl]oxy}ethyl)-8-hydroxyquinolin-2(1H)-one acetate (150 mg, 0.45 mmol) (prepared according to preparation 8 from US20060035931) and sodium cyanoborohydride (125 mg, 1.98 mmol), following the experimental procedure as described for Intermediate 7. The crude obtained was purified by column chromatography with silica gel, eluting with a mixture of chloroform and chloroform: methanol:ammonium hydroxide (40:4:0.2).

LRMS (m/z): 924 (M+1)+

Example 58 trans-4-aminocyclohexyl[4-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)biphenyl-2-yl]carbamate Obtained as a beige solid (35 mg, 41%) from trans-4-[(tert-butoxycarbonyl)-amino]cyclohexyl{4-[3-({[trans-4-({[(2R)-2-{[tert-butyl(dimethyl)silyl]oxy}-2-(8-hydroxy-2-oxo-1,2-dihydroquinolin-5-yl)ethyl]amino}methyl)cyclohexyl]carbonyl}amino)propyl]-biphenyl-2-yl}carbamate (Intermediate 315, 110 mg, 0.12 mmol) and hydrogen chloride (2.0 mL of a 4M solution in dioxane, 8.0 mmol) in dioxane (3.0 mL), following the experimental procedure as described for Intermediate 21. The crude residue was purified by reverse phase column chromatography with C18 modified silica gel using a mixture of water (with 0.1% of ammonium hydroxide):methanol.

LRMS (m/z): 711 (M+1)+

$^1$H NMR (300 MHz, dmso) δ 8.56 (s, 1H), 8.21 (d, J=10.0 Hz, 1H), 7.80 (bt, J=6.0 Hz, 1H), 7.49-7.30 (m, 4H), 7.26-7.21 (m, 2H), 7.15 (dd, J=8.0, 1.4 Hz, 1H), 7.09 (d, J=8.2 Hz, 1H), 6.93 (d, J=8.1 Hz, 1H), 6.53 (d, J=9.8 Hz, 1H), 5.04 (dd, J=7.6, 4.4 Hz, 1H), 4.37 (m, 2H), 3.09 (dd, J=11.9, 6.5 Hz, 2H), 2.77 (m, 1H), 2.73-2.50 (m, 6H), 2.47-2.34 (m, 2H), 2.31 (m, 1H), 2.07 (bt, J=12:0 Hz, 2H), 1.89-1.65 (m, 5H), 1.52-1.05 (m, 7H), 0.99-0.80 (m, 3H).

Intermediate 316 trans-4-[(tert-butoxycarbonyl)amino]cyclohexyl(4-{3-[({[4-({[tert-butyl(dimethyl)-silyl]oxy}methyl)-2-chloro-5-methoxyphenyl]amino}carbonyl)amino]propyl}-biphenyl-2-yl)carbamate To a solution of tert-butyl[(5-chloro-4-isocyanato-2-methoxybenzyl)oxy]dimethylsilane (Intermediate 267, 145 mg, 0.44 mmol) in toluene (10 mL) was added a solution of trans-4-[(tert-butoxycarbonyl)amino]cyclohexyl[4-(3-aminopropyl)biphenyl-2-yl]carbamate (Intermediate 283, 228 mg, 0.49 mmol) and triethylamine (74 μL, 0.53 mmol) in toluene (5 mL) at 0° C. and under argon atmosphere. After 2 hours, the suspension was filtered and the filtrate was concentrated under vacuum to afford the title compound (350 mg, 89%) as a colorless oil.

LRMS (m/z): 664 (M-131, tropilium cation (100%))+, 796 (M+1)+

Intermediate 317 trans-4-[(tert-butoxycarbonyl)amino]cyclohexyl(4-{3-[({[2-chloro-4-(hydroxymethyl)-5-methoxyphenyl]amino}carbonyl)amino]propyl}biphenyl-2-yl) carbamate To a solution of trans-4-[(tert-butoxycarbonyl)amino]cyclohexyl(4-{3-[({[4-({[tert-butyl(dimethyl)silyl]oxy}methyl)-2-chloro-5-methoxyphenyl]amino}carbonyl)amino]-propyl}biphenyl-2-yl) carbamate (Intermediate 316, 350 mg, 0.44 mmol) in tetrahydrofuran (10 mL) was added TBAF (0.44 mL of a 1M solution in tetrahydrofuran, 0.44 mmol) and the final solution was allowed to stir for 1 hour. The solvent is removed under reduced pressure and dichloromethane and water were added. The two phases were separated and the organic phase was dried, filtered and concentrated to dryness to provide the title compound (210 mg of a 95% purity, 67%) as a colorless foam.

LRMS (m/z): 664 (M-131, tropilium cation (100%))+, 682 (M+1)+

Intermediate 318 trans-4-[(tert-butoxycarbonyl)amino]cyclohexyl{4-[3-({[(2-chloro-4-formyl-5-methoxyphenyl)amino]carbonyl}amino)propyl]biphenyl-2-yl}carbamate Obtained as a brownish foam (209 mg, 100%) from trans-4-[(tert-butoxycarbonyl)amino]cyclohexyl(4-{3-[({[2-chloro-4-(hydroxymethyl)-5-methoxyphenyl]amino}carbonyl)-amino]propyl}biphenyl-2-yl)carbamate (Intermediate 317, 210 mg, 0.31 mmol) and manganese dioxide (268 mg, 3.10 mmol) following the experimental procedure as described for Intermediate 218 and the crude obtained was used in the next step without further purification.

LRMS (m/z): 679 (M+1)+

Intermediate 319 trans-4-[(tert-butoxycarbonyl)amino]cyclohexyl(4-{3-[({[4-({[(2R)-2-{[tert-butyl(dimethyl) silyl]oxy}-2-(8-hydroxy-2-oxo-1,2-dihydroquinolin-5-yl)ethyl]-amino}methyl)-2-chloro-5-methoxyphenyl]amino}carbonyl)amino]propyl}-biphenyl-2-yl) carbamate Obtained as a yellow foam (90 mg of a 90% purity, 26%) from trans-4-[(tert-butoxycarbonyl)amino]cyclohexyl{4-[3-({[(2-chloro-4-formyl-5-methoxyphenyl)amino]-carbonyl}amino)propyl]biphenyl-2-yl}carbamate (Intermediate 318, 210 mg, 0.31 mmol), 5-((1R)-2-amino-1-{[tert-butyl(dimethyl)-silyl]oxy}ethyl)-8-hydroxyquinolin-2(1H)-one acetate (104 mg, 0.31 mmol) (prepared according to preparation 8 from US20060035931) and sodium cyanoborohydride (97 mg, 1.55 mmol), following the experimental procedure as described for Intermediate 7. The crude obtained was purified by column chromatography with silica gel, eluting with a mixture of chloroform and chloroform:methanol:ammonium hydroxide (40:4:0.2).

Example 59 trans-4-aminocyclohexyl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}-carbonyl)amino]propyl}biphenyl-2-yl) carbamate Obtained as a beige solid (20 mg, 26%) from trans-4-[(tert-butoxycarbonyl)-amino]cyclohexyl(4-{3-[({[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-carbonyl)amino]propyl}biphenyl-2-yl)carbamate (Intermediate 319; 90 mg, 0.12 mmol) and hydrogen chloride (1.1 mL of a 4M solution in dioxane, 4.4 mmol) in dioxane (2.0 mL), following the experimental procedure as described for Intermediate 21. The crude residue was purified by reverse phase column chromatography with C18 modified silica gel using a mixture of water (with 0.1% of ammonium hydroxide):methanol.

LRMS (m/z): 783 (M+1)+

Intermediate 320 trans-4-[(tert-butoxycarbonyl)amino]cyclohexyl[4-(4-hydroxybutyl)biphenyl-2-yl]-carbamate To a solution of trans-4-[(tert-butoxycarbonyl)amino]cyclohexyl[4-(4-ethoxypent-4-en-1-yl)biphenyl-2-yl]carbamate (synthesized as Intermediate 188; 3.0 g, 5.72 mmol) in THF (30 mL) was added cautiously at −5° C. lithium borohydride (1.25 g, 57.39 mmol) and EtOH (9.5 mL). The reaction mixture was stirred overnight at room temperature. Ammonium chloride saturated was added into the mixture cautiously and was extracted with ethyl acetate. The organic layer was washed with water and brine, dried, filtered and the solvent was removed under reduced pressure to give the title compound (2.76 g, 95%), which was used in the next step without further purification.

LRMS (m/z): 483 (M+1)+, 481 (M−1)−

Intermediate 321

4-(2-{[({trans-4-[(tert-butoxycarbonyl)amino]cyclohexyl}oxy)carbonyl]amino}-biphenyl-4-yl)butyl methanesulfonate Obtained as a solid (1.41 g of an 80% purity, 97%) from trans-4-[(tert-butoxy-carbonyl)amino]cyclohexyl[4-(4-hydroxybutyl)biphenyl-2-yl]carbamate (Intermediate 320; 1 g, 2.07 mmol), triethylamine (0.32 mL, 2.31 mmol) and methanesulfonyl chloride (0.16 mL, 2.07 mmol) in dichloromethane (10 ml) following the experimental procedure as described for intermediate 262, the crude was used in the next step without further purification.

LRMS (m/z): 561 (M+1)+, 559 (M−1)−

Intermediate 322 trans-4-[(tert-butoxycarbonyl)amino]cyclohexyl[4-(4-azidobutyl)biphenyl-2-yl]-carbamate Sodium azide (0.35 g, 5.38 mmol) was added cautiously to a solution of 4-(2-{[({trans-4-[(tert-butoxycarbonyl)amino]cyclohexyl}oxy)carbonyl]amino}biphenyl-4-yl)butyl methanesulfonate (Intermediate 321; 1.41 g of an 80% purity, 2.51 mmol) in DMF (15 mL). The reaction mixture was stirred 4 h at 80° C. The reaction was poured onto ice, after stirring 30 min, dichloromethane was added. The organic layer was dried and the solvent was removed under reduced pressure to give 1.26 g of an 80% purity (79%) of an off white solid, which was used in the next step without further purification.

LRMS (m/z): 508 (M+1)+

Intermediate 323 trans-4-[(tert-butoxycarbonyl)amino]cyclohexyl[4-(4-aminobutyl)biphenyl-2-yl]-carbamate Triphenylphosphine (1.43 g, 5.45 mmol) was added to a solution of trans-4-[(tert-butoxy-carbonyl)amino]cyclohexyl[4-(4-azidobutyl)biphenyl-2-yl]carbamate (Intermediate 322; 1.26 g of an 80% purity, 2.48 mmol) in THF (25 mL) and water (1.25 mL). The reaction mixture was stirred overnight at room temperature. The solvent was removed under reduced pressure and the residue was suspended in MeOH. The solution was passed through an acidic sulphonic SCX column. The compound was released from the column with 33% ammonium in methanol and the solvent was removed under reduced pressure. The crude obtained (0.89 g, 93%) was used in the next step without further purification.

LRMS (m/z): 482 (M+1)+

Intermediate 324 trans-4-[(tert-butoxycarbonyl)amino]cyclohexyl[4-(4-{[2-chloro-4-(hydroxyl-methyl)-5-methoxybenzoyl]amino}butyl)biphenyl-2-yl]carbamate Obtained as a solid (0.48 g, 71%) from 2-chloro-4-(hydroxymethyl)-5-methoxybenzoic acid (Intermediate 281; 0.15 g, 0.69 mmol), trans-4-[(tert-butoxycarbonyl)-amino]cyclohexyl[4-(4-aminobutyl)biphenyl-2-yl]carbamate (Intermediate 323; 0.33 g, 0.69 mmol), diisopropylethylenediamine (0.48 mL, 2.77 mmol) and HATU (0.53 g, 1.39 mmol) in DMF (5 mL) following the experimental procedure as described for Intermediate 125. The crude was purified by column chromatography with silica gel, eluting with a mixture of chloroform:methanol:ammonium (40:4:0.2).

LRMS (m/z): 681 (M+1)+

Intermediate 325 trans-4-[(tert-butoxycarbonyl)amino]cyclohexyl(4-{4-[(2-chloro-4-formyl-5-methoxybenzoyl)amino]butyl}biphenyl-2-yl)carbamate Obtained as a yellow foam (255 mg, 53%) from trans-4-[(tert-butoxy-carbonyl)amino]cyclohexyl[4-(4-{[2-chloro-4-(hydroxymethyl)-5-methoxybenzoyl]-amino}butyl)biphenyl-2-yl]carbamate (Intermediate 324; 480 mg, 0.71 mmol) and manganese oxide (615 mg, 7.07 mmol) following the experimental procedure as described for Intermediate 218 and the crude obtained was used in the next step without further purification.

LRMS (m/z): 678 (M+1)+

Intermediate 326 trans-4-[(tert-butoxycarbonyl)amino]cyclohexyl[4-(4-{[4-({[(2R)-2-{[tert-butyl-(dimethyl)silyl]oxy}-2-(8-hydroxy-2-oxo-1,2-dihydroquinolin-5-yl)ethyl]amino}-methyl)-2-chloro-5-methoxybenzoyl]amino}butyl)biphenyl-2-yl]carbamate Obtained as a solid (92 mg, 25%) from trans-4-[(tert-butoxycarbonyl)amino]cyclohexyl(4-{4-[(2-chloro-4-formyl-5-methoxybenzoyl)amino]butyl}biphenyl-2-yl)carbamate (Intermediate 325; 255 mg, 0.38 mmol), 5-((1R)-2-amino-1-{[tert-butyl(dimethyl)-silyl]oxy}ethyl)-8-hydroxyquinolin-2(1H)-one acetate (126 mg, 0.38 mmol) (prepared according to preparation 8 from US20060035931), sodium cianoborohydride (60 mg, 0.95 mmol) and diethylethylenamine (80 μL, 0.46 mmol) following the experimental procedure as described for Intermediate 7. The crude obtained was purified by column chromatography with silica gel, eluting with a mixture of chloroform:methanol:ammonium (40:4:0.2).

LRMS (m/z): 942 [M-56 (tert-buthyl)+1]+

Example 60 trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)-biphenyl-2-yl]carbamate dihydrochloride Obtained as a white solid (33 mg, 46%) from trans-4-[(tert-butoxycarbonyl)-amino]cyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}butyl)-biphenyl-2-yl]carbamate (Intermediate 326; 92 mg, 0.09 mmol) and hydrogen chloride (4M in dioxane, 0.25 mL) in dioxane (2 mL) following the experimental procedure as described for Intermediate 21.

LRMS (m/z): 783 (M+1)+

1H NMR (300 MHz, dmso) δ 10.50 (d, J=8.4 Hz, 2H), 9.35 (s, 1H), 8.98 (s, 1H), 8.60 (s, 1H), 8.49 (t, J=5.5 Hz, 1H), 8.20 (d, J=10.0 Hz, 1H), 7.95 (s, 2H), 7.68-7.55 (m, 1H), 7.46-7.27 (m, 4H), 7.22 (d, J=7.8 Hz, 1H), 7.11 (dd, J=13.3, 6.4 Hz, 2H), 6.99 (d, J=8.2 Hz, 1H), 6.58 (d, J=10.0 Hz, 1H), 5.44 (s, 1H), 5.35 (s, 1H), 4.33 (s, 1H), 4.22 (s, 2H), 3.84 (s, 3H), 3.35-3.24 (m, J=5.5 Hz, 2H), 3.17-2.91 (m, 2H), 2.73-2.53 (m, 2H), 1.87 (d, J=13.1 Hz, 3H), 1.74-1.52 (m, 3H), 1.45-1.28 (m, 4H).

Intermediate 327

Ethyl 4-(2-{[(1-azabicyclo[2.2.2]oct-4-yloxy)carbonyl]amino}biphenyl-4-yl)-butanoate To a solution of triphosgene (0.42 g, 1.42 mmol) in toluene (5 mL) was added dropwise at 0° C. a solution of ethyl 4-(2-aminobiphenyl-4-yl)butanoate (Intermediate 122; 1.00 g, 3.53 mmol), once the addition is finished triethylamine (1.00 mL, 7.21 mmol) was added. The mixture was stirred 4 hours at room temperature. The solvent was partially removed under reduced pressure without heating and hexane was added to precipitate the salts, the mixture was filtered and the filtrate was evaporated. The corresponding isocyanate with quinuclidin-4-ol were stirred for 24 hours at 80° C. The crude was purified by column chromatography with silica gel, eluting with a mixture of chloroform:methanol:ammonium (40:4:0.2), giving the title compound as a solid (0.65 mg, 42%).

LRMS (m/z): 437 (M+1)+

Intermediate 328

4-(2-{[(1-azabicyclo[2.2.2]oct-4-yloxy)carbonyl]amino}biphenyl-4-yl)butanoic acid hydrochloride To a solution of ethyl 4-(2-{[(1-azabicyclo[2.2.2]oct-4-yloxy)carbonyl]amino}biphenyl-4-yl)butanoate (Intermediate 327; 500 mg, 1.1 mmol) in tetrahydrofurane (20 mL) was added lithium hydroxide monohydrate (150 mg, 3.6 mmol) in water (10 mL). The reaction mixture was stirred overnight at room temperature. The solvent was removed under reduced pressure and the crude obtained was diluted with water and acidified by acid chloride 2N until pH 2-3. Then the crude was extracted with diethyl ether using a continuous extractor at 40° C. overnight. The organic layer was dried, filtered and the solvent was removed under reduced pressure giving the title compound as a white solid (340 mg, 67%).

LRMS (m/z): 409 (M+1)+

Intermediate 329

1-azabicyclo[2.2.2]oct-4-yl[4-(4-{[4-(hydroxymethyl)phenyl]amino}-4-oxobutyl)biphenyl-2-yl]carbamate To a solution of 4-(2-{[(1-azabicyclo[2.2.2]oct-4-yloxy)carbonyl]amino}biphenyl-4-yl)-butanoic acid hydrochloride (Intermediate 328; 50 mg, 0.12 mmol) in DMF (2 mL) was added HATU (92 mg, 0.24 mmol) under nitrogen atmosphere. After 1 hour stirring at room temperature, (4-aminophenyl)methanol (16 mg, 0.13 mmol) was added. The reaction mixture was stirred at room temperature overnight. The solvent was removed under reduced pressure and the crude was partitioned between chloroform and water, the organic layer was washed with water several times, dried, filtered and the solvent was removed under reduced pressure. The crude obtained was used in the next step without further purification.

LRMS (m/z): 514 (M+1)+

Intermediate 330

1-azabicyclo[2.2.2]oct-4-yl(4-{4-[(4-formylphenyl)amino]-4-oxobutyl}biphenyl-2-yl)carbamate To a solution of 1-azabicyclo[2.2.2]oct-4-yl[4-(4-{[4-(hydroxymethyl)phenyl]amino}-4-oxobutyl)biphenyl-2-yl]carbamate (Intermediate 329; 62 mg, 0.12 mmol) in chloroform (5 mL) was added activated manganese oxide (105 mg, 1.21 mmol). The reaction mixture was stirred overnight at 45° C. The mixture was filtered and the solvent was removed under reduced pressure giving the title compound as an yellow foam (60 mg, 97%), which was used in the next step without further purification.

LRMS (m/z): 512 (M+1)+

Intermediate 331

1-azabicyclo[2.2.2]oct-4-yl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)phenyl]amino}-4-oxobutyl)biphenyl-2-yl]carbamate To a mixture of 1-azabicyclo[2.2.2]oct-4-yl(4-{4-[(4-formylphenyl)amino]-4-oxobutyl}-biphenyl-2-yl)carbamate (Intermediate 330; 60 mg, 0.12 mmol) and 5-((1R)-2-amino-1-{[tert-butyl(dimethyl)-silyl]oxy}ethyl)-8-hydroxyquinolin-2(1H)-one acetate (40 mg, 0.12 mmol) (prepared according to preparation 8 from US20060035931) in 3 mL of methanol was added sodium triacetoxyborohydride (75 mg, 0.35 mmol). The mixture was stirred overnight at room temperature. The solvent was removed under reduced pressure and the crude obtained was suspended in chloroform, the solid was filtrated and the solvent was evaporated. The crude obtained was purified by column chromatography with silica gel, eluting with a mixture of chloroform:methanol:ammonium (40:4:0.2) to give the title compound as a solid (37 mg, 38%).

LRMS (m/z): 831 (M+1)+

Example 61

1-Azabicyclo[2.2.2]oct-4-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl) biphenyl-2-yl]carbamate dihydrofluoride Obtained as a white solid (31 mg, 92%) from 1-azabicyclo [2.2.2]oct-4-yl[4-(4-{[4-({[(2R)-2-{[tert-butyl(dimethyl)silyl]oxy}-2-(8-hydroxy-2-oxo-1,2-dihydroquinolin-5-yl)-ethyl]amino}methyl)phenyl]amino}-4-oxobutyl)biphenyl-2-yl]carbamate (Intermediate 331; 37 mg, 0.04 mmol) and triethylamine trihydrofluoride (50 µL, 0.31 mmol) following the experimental procedure as described for Example 1.

LRMS (m/z): 716 (M+1)+

1H NMR (300 MHz, dmso) δ 10.30 (bs, 1H), 9.86 (s, 1H), 8.39 (s, 1H), 8.09 (d, J=10.0 Hz, 1H), 7.52 (d, J=8.5 Hz, 2H), 7.46-7.28 (m, 5H), 7.26-7.17 (m, 3H), 7.12 (d, J=6.3 Hz, 1H), 7.05 (d, J=8.2 Hz, 1H), 6.90 (d, J=8.1 Hz, 1H), 6.46 (d, J=9.9 Hz, 1H), 5.05 (dd, J=7.7, 4.5 Hz, 2H), 3.69 (s, 2H), 2.89-2.73 (m, 6H), 2.65 (dd, J=12.2, 7.9 Hz, 2H), 2.35 (t, J=7.4 Hz, 2H), 1.96-1.86 (m, 2H), 1.80-1.66 (m, 6H).

Intermediate 332 trans-4-(hydroxymethyl)cyclohexanol

To a solution of trans-4-cyclohexanecarboxylic acid (1.0 g, 6.9 mmol) in THF (70 mL) was added dropwise, at 0° C. and under argon atmosphere, borane dimethylsulphide complex (2.8 mL, 29.5 mmol). The resulting suspension is allowed to warm to rt and stirring is maintained overnight. The reaction mixture is concentrated under reduced pressure and the solid obtained is dissolved in MeOH (20 mL). The resulting solution is concentrated to dryness to afford the title compound as a white crystalline solid (0.95 g, 100%).

1H NMR (300 MHz, dmso) δ 4.50 (d, J=4.4 Hz, 1H), 4.40 (t, J=5.3 Hz, 1H), 3.37-3.26 (m, 1H), 3.21 (t, J=5.8 Hz, 1H), 1.84 (dd, J=12.6, 2.9 Hz, 1H), 1.72 (bd, J=13.5 Hz, 1H), 1.35-1.20 (m, 1H), 1.12 (ddd, J=19.2, 13.4, 3.1 Hz, 2H), 0.89 (ddd, J=19.0, 13.2, 2.9 Hz, 2H).

Intermediate 333 trans-4-({[tert-butyl(diphenyl)silyl]oxy}methyl)cyclohexanol

To a solution of trans-4-(hydroxymethyl)cyclohexanol (Intermediate 332, 420 mg, 3.23 mmol) in DMF (15 mL) were added sequentially imidazole (250 mg, 3.67 mmol) and tert-butyldiphenylsilyl chloride (0.85 mL, 3.28 mmol). After 4 hours the solvent was removed under reduced pressure and the residue was partitioned between water and ethyl acetate. The phases were separated and the aqueous phase was further extracted with ethyl acetate. The resulting organic phase was washed with water twice and brine, dried over anhydrous sodium sulphate, filtered and concentrated under reduced pressure. Purification by column chromatography over silica gel using a mixture of hexane:ether provided the title compound (814 mg, 69%) as a colorless oil.

LRMS (m/z): 391 (M+23[Na])+

Intermediate 334

{[trans-4-({[tert-butyl(diphenyl)silyl]oxy}methyl) cyclohexyl]oxy}acetic acid

To a suspension of NaH (280 mg of a 60% dispersion in oil, 7.0 mmol) was added dropwise, at 0° C. and under argon atmosphere, a solution of trans-4-({[tert-butyl(diphenyl)silyl]oxy}methyl)cyclohexanol (Intermediate 333, 790 mg, 2.14 mmol) and the reaction mixture was allowed to stir for 45 min. Then, 2-bromoacetic acid (300 mg, 2.16 mmol) was added and the resulting mixtures was heated at 90° C. for 4 hours. Upon cooling the reaction mixture, water was added and the organic solvent was removed under reduced pressure. Water and ether were added to the residue and the aqueous phase was further extracted with ether. The combined organic extracts were dried, filtered and concentrated to dryness. The crude was purified by column chromatography over silica gel using a mixture of hexane:ether providing the title compound (470 mg, 51%) as a colorless oil.

LRMS (m/z): 444 (M+18[NH$_4^+$])+

Intermediate 335 trans-4-[(tert-butoxycarbonyl)amino]cyclohexyl(4-{3-[({[trans-4-({[tert-butyl-(diphenyl)silyl] oxy}methyl)cyclohexyl]oxy}acetyl)(methyl)amino] propyl}biphenyl-2-yl)carbamate Obtained as an oil (113 mg of a 70% purity, 29%) from tert-butyl-trans-4-aminocyclohexyl{4-[3-(methylamino) propyl]biphenyl-2-yl}carbamate (Intermediate 252; 150 mg, 0.31 mmol), {[trans-4-({[tert-butyl(diphenyl)silyl] oxy}methyl)cyclohexyl]oxy}-acetic acid (Intermediate 334; 150 mg, 0.35 mmol), HATU (181 mg, 0.48 mmol) and DIEA (70 µL, 0.40 mmol) following the experimental procedure as described for Intermediate 125 and the crude obtained was purified by column chromatography with silica gel, eluting with a mixture of hexane:ether:ethanol.

LRMS (m/z): 891 (M+1)+

Intermediate 336 trans-4-[(tert-butoxycarbonyl)amino]cyclohexyl(4-{3-[({[trans-4-(hydroxymethyl)cyclohexyl] oxy}acetyl)(methyl)amino]propyl}biphenyl-2-yl) carbamate To a solution of trans-4-[(tert-butoxycarbonyl)amino]cyclohexyl(4-{3-[({[trans-4-({[tert-butyl(diphenyl)silyl] oxy}methyl)cyclohexyl]oxy}acetyl)(methyl)amino] propyl}biphenyl-2-yl)carbamate (Intermediate 335, 113 mg, 0.09 mmol) in tetrahydrofuran (2.5 mL) was added dropwise tetrabutylammonium fluoride (0.34 mL of a 1M solution in tetrahydrofuran, 0.34 mmol). After stirring for 1.5 hours a rt, saturated ammonium chloride and ethyl acetate were added. The aqueous phase was further extracted with ethyl acetate and the combined organic extracts were washed with water and brine, dried over anhydrous sodium sulphate, filtered and concentrated to dryness. The residue was purified by column chromatography with silica gel, eluting with a mixture of hexane:ether:ethanol. The title compound was obtained as a yellow solid (44 mg, 61%)

LRMS (m/z): 653 (M+1)+

Intermediate 337 trans-4-[(tert-butoxycarbonyl)amino]cyclohexyl(4-{3-[{[(trans-4-formyl-cyclohexyl)oxy]acetyl} (methyl)amino]propyl}biphenyl-2-yl)carbamate Obtained as a colorless foam (41 mg of an 81% purity, 95%) from trans-4-[(tert-butoxycarbonyl)amino]cyclohexyl (4-{3-[({[trans-4-(hydroxymethyl)cyclohexyl]oxy}acetyl)

(methyl)amino]propyl}biphenyl-2-yl)carbamate (Intermediate 336, 44 mg, 0.05 mmol), Dess-Martin periodinane (50 mg, 0.12 mmol) and sodium bicarbonate (18 mg, 0.21 mmol) in dichloromethane (1 mL), following the experimental procedure as described for Intermediate 64 and the crude obtained was used in the next step without further purification.

LRMS (m/z): 651 (M+1)+

Intermediate 338 trans-4-[(tert-butoxycarbonyl)amino]cyclohexyl(4-{3-[({[trans-4-({[(2R)-2-{[tert-butyl(dimethyl)silyl]oxy}-2-(8-hydroxy-2-oxo-1,2-dihydroquinolin-5-yl)ethyl]-amino}methyl)cyclohexyl]oxy}acetyl)(methyl)amino]propyl}biphenyl-2-yl)-carbamate Obtained as a yellow foam (49 mg, 100%) from trans-4-[(tert-butoxycarbonyl)amino]-cyclohexyl(4-{3-[{[(trans-4-formylcyclohexyl)oxy]acetyl}(methyl)amino]propyl}biphenyl-2-yl)carbamate (Intermediate 337, 41 mg, 0.06 mmol), 5-((1R)-2-amino-1-{[tert-butyl(dimethyl)-silyl]oxy}ethyl)-8-hydroxyquinolin-2(1H)-one acetate (32 mg, 0.08 mmol) (prepared according to preparation 8 from US20060035931), sodium cyanoborohydride (12 mg, 0.19 mmol) and DIEA (13 μL, 0.07 mmol), following the experimental procedure as described for Intermediate 7. The crude obtained was purified by column chromatography with silica gel, eluting with a mixture of chloroform:methanol.

LRMS (m/z): 969 (M+1)+

Example 62 trans-4-aminocyclohexyl(4-{3-[({[trans-4-({[(2R)-2-hydroxy-2-(8-hydroxy-2-oxo-1,2-dihydroquinolin-5-yl)ethyl]amino}methyl)cyclohexyl]oxy}acetyl)(methyl)-amino]propyl}biphenyl-2-yl)carbamate dihydrochloride Obtained as a white solid (38 mg of a 93% purity, 85%) from trans-4-[(tert-butoxycarbonyl)amino]cyclohexyl(4-{3-[({[trans-4-({[(2R)-2-{[tert-butyl(dimethyl)silyl]-oxy}-2-(8-hydroxy-2-oxo-1,2-dihydroquinolin-5-yl)ethyl]amino}methyl)cyclohexyl]oxy}-acetyl)(methyl)amino]propyl}biphenyl-2-yl)carbamate (Intermediate 338; 49 mg, 0.05 mmol) and hydrogen chloride (0.255 mL of a 4M solution in dioxane, 1.02 mmol) in tetrahydrofuran (1.0 mL), following the experimental procedure as described for Intermediate 21.

LRMS (m/z): 755 (M+1)+

1H NMR (300 MHz, dmso) δ 10.53 (bs, 2H), 9.25 (bs, 1H), 8.72 (bs, 1H), 8.65 (s, 1H), 8.37 (d, J=9.7 Hz, 1H), 8.15 (bs, 3H), 7.49-7.31 (m, 5H), 7.28-7.22 (m, 2H), 7.19 (d, J=8.2 Hz, 1H), 7.05 (d, J=8.0 Hz, 1H), 6.58 (d, J=9.7 Hz, 1H), 5.56 (d, J=8.6 Hz, 1H), 4.37 (t, J=11.5 Hz, 2H), 4.14 (d, J=13.6 Hz, 2H), 3.60 (s, 2H), 2.99 (m, 5H), 2.85 (bs, 2H), 2.67-2.57 (m, 2H), 2.15-1.66 (m, 10H), 1.52-0.90 (m, 9H).

Intermediate 339

Ethyl 4-{[4-(2-{[(1-azabicyclo[2.2.2]oct-4-yloxy)carbonyl]amino}biphenyl-4-yl)butanoyl]amino}-5-chloro-2-methoxybenzoate To a solution of 4-(2-{[(1-azabicyclo[2.2.2]oct-4-yloxy)carbonyl]amino}biphenyl-4-yl)butanoic acid hydrochloride (Intermediate 328; 2.0 g, 4.9 mmol) in thionyl chloride (20 mL) was stirred at room temperature under nitrogen atmosphere. After 1 hour, the solvent was removed under reduced pressure, the crude was dissolved in chloroform (20 mL) and ethyl 4-amino-5-chloro-2-methoxybenzoate (Intermediate 37 WO2011/141180A1; 1.24 g, 5.4 mmol) and triethylamine (1.0 mL, 7.2 mmol) were added. The reaction mixture was stirred at room temperature overnight. The solvent was removed under reduced pressure and the crude was partitioned between chloroform and sodium bicarbonate 4%, the organic layer was washed with brine, dried, filtered and the solvent was removed under reduced pressure. The crude obtained was purified by column chromatography with silica gel, eluting with a mixture of chloroform:methanol:ammonium (40:8:1) to give the title compound as a pale yellow foam (540 mg, 18%).

LRMS (m/z): 621 (M+1)+

Intermediate 340

1-azabicyclo[2.2.2]oct-4-yl[4-(4-{[2-chloro-4-(hydroxymethyl)-5-methoxyphenyl]-amino}-4-oxobutyl)biphenyl-2-yl]carbamate A round-bottomed flask fitted with stir bar was charged with ethyl 4-{[4-(2-{[(1-azabicyclo[2.2.2]oct-4-yloxy)carbonyl]amino}biphenyl-4-yl)butanoyl]amino}-5-chloro-2-methoxybenzoate (Intermediate 339; 540 mg, 0.9 mmol) in 20 mL anhydrous tetrahydrofurane and under Argon atmosphere. The mixture was cooled with an ice/water bath and lithium aluminium hydride 1M in tetrahydrofurane (1.37 mL, 0.14 mmol) was added cautiously. After stirring for 2 h at 0° C., the reaction was quenched by sequentially addition of n:n:3n (where n is the LiAlH4 mass), that was 50 μL H2O:50 μL NaOH 4N:150 μL H2O, and then was stirred 30 min at rt. The solid formed is filtered and the resulting solution is concentrated under reduced pressure to give 470 mg (90%) of an off white foam, which was used in the next step without further purification.

LRMS (m/z): 579 (M+1)+

Intermediate 341

1-azabicyclo[2.2.2]oct-4-yl(4-{4-[(2-chloro-4-formyl-5-methoxyphenyl)amino]-4-oxobutyl}biphenyl-2-yl)carbamate Obtained as a yellow foam (334 mg, 80%) from 1-azabicyclo[2.2.2]oct-4-yl[4-(4-{[2-chloro-4-(hydroxymethyl)-5-methoxyphenyl]amino}-4-oxobutyl)biphenyl-2-yl]carbamate (Intermediate 340; 421 mg, 0.73 mmol) and manganese oxide (633 mg, 7.28 mmol) following the experimental procedure as described for Intermediate 330 and the crude obtained was used in the next step without further purification.

LRMS (m/z): 576 (M+1)+

Intermediate 342

1-azabicyclo[2.2.2]oct-4-yl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate Obtained as a solid (285 mg, 55%) from 1-azabicyclo[2.2.2]oct-4-yl(4-{4-[(2-chloro-4-formyl-5-methoxyphenyl)amino]-4-oxobutyl}biphenyl-2-yl)carbamate (Intermediate 341; 334 mg, 0.58 mmol), 5-((1R)-2-amino-1-{[tert-butyl (dimethyl)-silyl]oxy}ethyl)-8-hydroxyquinolin-2(1H)-one acetate (194 mg, 0.58 mmol) (prepared according to preparation 8 from US20060035931), sodium triacetoxyborohydride (431 mg, 2.03 mmol) in MeOH (6 mL) and tetrahydrofurane (1 mL) following the experimental procedure as described for Intermediate 331. The crude obtained was purified by column chromatography with silica gel, eluting with a mixture of chloroform:methanol:ammonium (40:4: 0.2).

LRMS (m/z): 895 (M+1)+

Example 63

1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate Obtained as a white solid (160 mg, 64%) from 1-azabicyclo[2.2.2]oct-4-yl[4-(4-{[4-({[(2R)-2-{[tert-butyl(dimethyl)silyl]oxy}-2-(8-hydroxy-2-oxo-1,2-dihydroquinolin-5-yl)-ethyl]amino}methyl)-2-chloro-5-methoxyphenyl] amino}-4-oxobutyl)biphenyl-2-yl]-carbamate (Intermediate 342; 285 mg, 0.32 mmol) and triethylamine trihydrofluoride (364 µL, 2.23 mmol) following the experimental procedure as described for Example 1. The crude residue was purified by reverse phase column chromatography with C18 modified silica gel using a mixture of water (with 0.1% of ammonium hydroxide):methanol.

LRMS (m/z): 781 (M+1)+

1H NMR (600 MHz, dmso) δ 9.41 (s, 1H), 8.37 (s, 1H), 8.10 (d, J=9.9 Hz, 1H), 7.38 (t, J=7.6 Hz, 2H), 7.30 (ddd, J=11.2, 9.9, 4.2 Hz, 5H), 7.18 (d, J=7.7 Hz, 2H), 7.10 (d, J=7.8 Hz, 1H), 6.97 (d, J=8.2 Hz, 1H), 6.81 (d, J=8.1 Hz, 1H), 6.43 (d, J=9.8 Hz, 1H), 4.97 (dd, J=7.9, 4.5 Hz, 1H), 3.69 (s, 3H), 3.62 (s, 2H), 2.80-2.70 (m, 6H), 2.65-2.59 (m, 2H), 2.40 (t, J=7.1 Hz, 2H), 1.94-1.82 (m, 2H), 1.69 (d, J=12.8 Hz, 6H).

Intermediate 343

Methyl 4-(but-3-en-1-ylamino)-3-nitrobenzoate

To a solution of methyl 4-fluoro-3-nitrobenzoate (1 g; 5.02 mmol) in THF (10 mL) is added but-3-en-1-amine (1.01 g, 14.2 mmol) and the reaction mixture is stirred overnight at room temperature. The solvent was removed under reduced pressure and the crude was partitioned between ethyl acetate and water, the organic layer was washed with water several times, dried, filtered and the solvent was removed under reduced pressure. The crude obtained was purified by column chromatography with silica gel giving the title compound as a solid (1.1 g, 87%).

LRMS (m/z): 251 (M+1)+

Intermediate 344

Methyl 3-amino-4-(but-3-en-1-ylamino)benzoate

To a solution of methyl 4-(but-3-en-1-ylamino)-3-nitrobenzoate (Intermediate 343; 830 mg, 3.32 mol) in ethanol (5 mL) was added 4 mL of Hydrochloric Acid (37%). Tin(II)chloride (2.62 g, 11.6 mol) was added and the reaction mixture was stirred at 50° C. overnight. The solvent was partially removed and sodium hydroxide was added to precipitate salts, which were filtrated. The solvent was removed under reduced pressure and the residue was portioned between ethyl acetate and water. The organic layer was washed with brine, dried, filtered and the solvent was removed under reduced pressure. The crude obtained was used in the next step without further purification (684 mg, 87%).

LRMS (m/z): 221 (M+1)+

Intermediate 345

Methyl 1-but-3-en-1-yl-1H-benzimidazole-5-carboxylate methyl 3-amino-4-(but-3-en-1-ylamino)benzoate (Intermediate 344; 145 mg, 0.66 mmol) is solved in triethylorthoformiate (1.64 mL, 9.85 mmol) and two drops of formic acid are added. The reaction mixture is stirred for 1 h at 80° C. The solvent was removed under reduced pressure and the crude obtained was used in the next step without further purification (142 mg, 89%)

LRMS (m/z): 231 (M+1)+

Intermediate 346

(1-but-3-en-1-yl-1H-benzimidazol-5-yl)methanol

To a solution of methyl 1-but-3-en-1-yl-1H-benzimidazole-5-carboxylate (Intermediate 345; 140 mg, 0.61 mmol) in THF (3.6 mL) was added dropwise at 0° C. lithium aluminium hydride (1M in THF, 0.9 mL). The reaction mixture was stirred 30 minutes at 0° C. and 1 hour at room temperature. The stirred mixture was cooled in an ice bath and very carefully water (0.34 mL), NaOH 4N (0.34 mL) and water (0.1 mL) were added slowly. After stirring 15 minutes at room temperature the mixture was filtered through a thin layer (1 cm) of Celite and the filter cake was washed with dichloromethane. The combined filtrate and washings were evaporated to give a light pink solid as the title compound (118 mg, 91%).

LRMS (m/z): 204 (M+1)+

Intermediate 347

1-but-3-en-1-yl-1H-benzimidazole-5-carbaldehyde

To a solution of (1-but-3-en-1-yl-1H-benzimidazol-5-yl) methanol (Intermediate 346; 581 mg, 2.24 mmol) in chloroform (19 mL) was added activated manganese oxide (1.98 g, 22.7 mmol). The reaction mixture was stirred overnight at 45° C. The mixture was filtered and the solvent was removed under reduced pressure. The crude obtained was purified by column chromatography with silica gel eluting with a mixture of diethyl ether/methanol giving the title compound as an oil (390 mg, 96%).

LRMS (m/z): 201 (M+1)+

Intermediate 348 trans-4-[(tert-butoxycarbonyl)amino]cyclohexyl{4-[(1Z)-4-(5-formyl-1H-benzimidazol-1-yl)but-1-en-1-yl]biphenyl-2-yl}carbamate To a mixture of trans-4-tert-butylaminocyclohexyl(4-bromobiphenyl-2-yl)carbamate (Intermediate 183; 150 mg, 0.31 mmol) and 1-but-3-en-1-yl-1H-benzimidazole-5-carbaldehyde (Intermediate 347; 67 mg, 0.34 mmol) in acetonitrile (2 mL) in a sealed tube were added tri-o-tolylphosphine (93 mg, 0.31 mmol) and N,N-Diisopropylethylamine (0.106 mL, 0.61 mmol). The mixture was degassed under Argon during 5 minutes. Then palladium acetate (34 mg, 0.15 mmol) was added and the reaction mixture was stirred at 70° C. for 4 hours. The crude was filtrated and the filtrate was evaporated to dryness. The crude obtained was purified by column chromatography with silica gel, eluting with a mixture of chloroform:methanol:ammonium (40:4:0.2) to give the title compound as an oil (174 mg, 83%).

LRMS (m/z): 610 (M+1)+

Intermediate 349 trans-4-[(tert-butoxycarbonyl)amino]cyclohexyl{4-[4-(5-formyl-1H-benzimidazol-1-yl)butyl]biphenyl-2-yl}carbamate A round-bottomed flask fitted with stir bar was charged with trans-4-[(tert-butoxycarbonyl)amino]cyclohexyl{4-[(1Z)-4-(5-formyl-1H-benzimidazol-1-yl)but-1-en-1-yl]biphenyl-2-yl}carbamate (Intermediate 348; 168 mg, 0.28 mmol) in Acetic acid (3 mL) The flask was filled with Argon, and then Pd/C (29 mg, 0.28 mmol) was added under Argon atmosphere. The flask was coupled with a quick-fit T-adaptor with one outlet to the hydrogen balloon and the other to the vacuum line. The flask was emptied by connecting it to the vacuum and then filled with hydrogen. This operation was repeated twice. The mixture was stirred vigorously at room temperature for 4 h. The Pd/C was filtered off and the solution concentrated under reduced pressure. The residue was used without further purification (165 mg, 48%).

LRMS (m/z): 612 (M+1)+

Intermediate 350 trans-4-[(tert-butoxycarbonyl)amino]cyclohexyl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-benzimidazol-1-yl]butyl}biphenyl-2-yl)carbamate A mixture of trans-4-[(tert-butoxycarbonyl)amino]cyclohexyl{4-[4-(5-formyl-1H-benzimidazol-1-yl)butyl]biphenyl-2-yl}carbamate (Intermediate 349; 115 mg, 0.19 mmol) and 5-((1R)-2-amino-1-{[tert-butyl(dimethyl)silyl]oxy}ethyl)-8-hydroxyquinolin-2(1H)-one acetate (63 mg, 0.19 mmol) (prepared according to preparation 8 from US20060035931) in 4 mL of methanol was stirred at room temperature for 2 hours. Then the crude was cooled to 0° C. and sodium triacetoxyborohydride (118 mg, 1.88 mmol) was added. The mixture was stirred overnight at room temperature. The solvent was removed under reduced pressure and the crude was portioned between ethyl acetate and water. The organic layer was washed with sodium bicarbonate, water and brine, dried, filtered and the solvent was removed under reduced pressure. The crude obtained was purified by column chromatography with silica gel, using as eluents a mixture of hexane:ethyl acetate:methanol to give the title compound as an oil (98 mg, 53%).

LRMS (m/z): 930 (M+1)+

Example 64 trans-4-aminocyclohexyl(4-{4-[5-({[(2R)-2-hydroxy-2-(8-hydroxy-2-oxo-1,2-dihydroquinolin-5-yl)ethyl]amino}methyl)-1H-benzimidazol-1-yl]butyl}biphenyl-2-yl)carbamate dihydrochloride A solution trans-4-[(tert-butoxycarbonyl)amino]cyclohexyl(4-{4-[5-({[(2R)-2-{[tert-butyl(dimethyl)silyl]oxy}-2-(8-hydroxy-2-oxo-1,2-dihydroquinolin-5-yl)ethyl]amino}methyl)-1H-benzimidazol-1-yl]butyl}biphenyl-2-yl)carbamate (Intermediate 350; 98 mg, 0.11 mmol) in 2.64 mL of hydrogen chloride (4N in dioxane) was stirred overnight at room temperature. The solvent was removed under reduced pressure and the crude obtained was treated with acetonitrile giving a white solid as the title compound (55 mg, 73%)

LRMS (m/z): 716 (M+1)+

1H NMR (300 MHz, dmso) δ 10.49 (d, J=16.5 Hz, 2H), 9.85 (bs, 1H), 9.45 (bs, 1H), 9.21 (bs, 1H), 8.62 (s, 1H), 8.20 (d, J=9.9 Hz, 1H), 8.09 (s, 1H), 7.99 (dd, J=15.2, 5.9 Hz, 2H), 7.73 (d, J=10.4 Hz, 1H), 7.38 (d, J=6.7 Hz, 1H), 7.31 (d, J=7.7 Hz, 1H), 7.23-7.14 (m, 1H), 7.09 (d, J=6.6 Hz, 1H), 6.95 (d, J=8.2 Hz, 1H), 6.57-6.44 (m, 1H), 4.47 (dd, J=7.3, 4.1 Hz, 1H), 4.39 (s, 2H), 4.31 (d, J=1.7 Hz, 2H), 3.55 (s, 2H), 2.94 (d, J=11.4 Hz, 2H), 2.71 (s, 1H), 2.67-2.56 (m, 2H), 2.25 (s, 1H), 1.99-1.85 (m, 4H), 1.81 (dd, J=11.0, 4.9 Hz, 2H), 1.68-1.52 (m, 2H), 1.42-1.10 (m, 4H).

Intermediate 351 ethyl 4-(2-isocyanatobiphenyl-4-yl)butanoate

To a solution of triphosgene (840 mg; 2.82 mmol) in 15 mL of dichloromethane was added dropwise at 0° C. a solution of ethyl 4-(2-aminobiphenyl-4-yl)butanoate (Intermediate 122; 2 g, 7.06 mmol) in 5 mL of dichloromethane. Once the addition is finished triethylamine (2.45 mL, 17.65 mmol) was added dropwise. The reaction mixture was stirred for 3 hours at room temperature. Cold pentane was added into the reaction mixture. The mixture was filtrated and the pentane of the filtrate was reduced under reduced pressure. The crude was solved in toluene, which was used in the next step without further manipulation.

Intermediate 352 trans-4-(dibenzylamino)-1-methylcyclohexanol

To a solution of 4-(Dibenzylamino)-cyclohexanone (5 g, 17 mmol) in 100 mL of tetrahydrofuran was added during one hour at −78° C. methyl lithium 1.6M in diethyl ether (16 mL, 25.5 mmol). Once the addition finished, the reaction mixture was stirred for one hour and a half more. Saturated ammonium chloride was added to the reaction mixture as well as ethyl acetate. The aqueous layer was extracted twice with ethyl acetate and the combined organic layer was dried, filtered and the solvent was removed under reduced pressure. The crude obtained was purified by column chromatography with silica gel to give the title compound as an oil (570 mg, 11%).

LRMS (m/z): 310 (M+1)+

Intermediate 353 ethyl4-{2-[({[trans-4-(dibenzylamino)-1-methylcyclohexyl]oxy}carbonyl)amino]biphenyl-4-yl}butanoate A mixture of ethyl 4-(2-isocyanatobiphenyl-4-yl)butanoate (Intermediate 351; 1 g, 3.23 mmol) and trans-4-(dibenzylamino)-1-methylcyclohexanol (Intermediate 352; 1 g, 3.23 mmol) in toluene (1 mL) is heated overnight at 70° C. The solvent was removed under reduced pressure and the crude was portioned between dichloromethane and water.

The organic layer was washed with water, sodium bicarbonate and brine, dried, filtered and the solvent was removed under reduced pressure. The crude obtained was purified by column chromatography with silica gel to give the title compound as an oil (1 g, 50%)

LRMS (m/z): 619 (M+1)+

Intermediate 354

Ethyl 4-[2-({[(trans-4-amino-1-methylcyclohexyl)oxy]carbonyl}amino)biphenyl-4-yl]butanoate To a solution of ethyl 4-{2-[({[trans-4-(dibenzylamino)-1-methylcyclohexyl]oxy}carbonyl)amino]biphenyl-4-yl}butanoate (Intermediate 353; 345 mg, 0.56 mmol) in ethanol (10 mL) was added palladium on charcoal (10%, 154 mg). The crude mixture was submitted under an H2 balloon 4 hours at room temperature. The catalyst was filtered through Celite and the solvent was removed under reduced pressure. The crude obtained was used without any further purification (242 mg, 99%).

LRMS (m/z): 439 (M+1)+

Intermediate 355 ethyl4-{2-[({[trans-1-methyl-4-({[(4-nitrobenzyl)oxy]carbonyl}amino)cyclohexyl]oxy}carbonyl)amino]biphenyl-4-yl}butanoate To a solution of ethyl 4-[2-({[(trans-4-amino-1-methylcyclohexyl)oxy]carbonyl}amino)biphenyl-4-yl]butanoate (Intermediate 354; 250 mg, 0.57 mmol) in tetrahydrofuran (5 mL) was added triethylamine (119 uL, 0.86 mmol). The reaction mixture is cooled to 0° C. and a solution of 4-nitrobenzyl carbonchloridate (122 mg, 0.57 mmol) in 2 mL of tetrahydrofuran is added dropwise. The reaction mixture is stirred overnight at room temperature. The solvent was removed under reduced pressure and the crude was portioned between ethyl acetate and water. The organic layer was washed with water, brine, dried, filtered and the solvent was removed under reduced pressure. The crude obtained was purified by column chromatography with silica gel to give the title compound (274 mg, 70%)

LRMS (m/z): 618 (M+1)+

Intermediate 356

4-{2-[({[trans-1-methyl-4-({[(4-nitrobenzyl)oxy]carbonyl}amino)cyclohexyl]oxy}carbonyl)amino]biphenyl-4-yl}butanoic acid To a solution of ethyl4-{2-[({[trans-1-methyl-4-({[(4-nitrobenzyl)oxy]carbonyl}amino)cyclohexyl]oxy}carbonyl)amino]biphenyl-4-yl}butanoate (Intermediate 355; 275 mg, 0.45 mmol) in THF (6 mL) was added water (3 mL) and lithium hydroxide (300 mg, 6.69 mmol). The reaction mixture was stirred for overnight at room temperature. The solvent was removed under reduced pressure and the aqueous phase was acidified until acid pH and then extracted with ethyl acetate. The organic layer was washed with brine, dried, filtered and the solvent was removed under reduced pressure to give the title compound (208 mg, 79%), which was used in the next step without further purification.

LRMS (m/z): 588 (M−1)−

Intermediate 357 trans-4-({[(4-nitrobenzyl)oxy]carbonyl}amino)-1-methylcyclohexyl[4-(4-{[4-({[tert-butyl(dimethyl)silyl]oxy}methyl)-2-chloro-5-methoxyphenyl]amino}-4-oxobutyl) biphenyl-2-yl]carbamate Obtained as an oil (308 mg, 100%) from 4-{2-[({[trans-1-methyl-4-({[(4-nitrobenzyl)oxy]carbonyl}amino)cyclohexyl]oxy}carbonyl)amino]biphenyl-4-yl}butanoic acid (Intermediate 356; 208 mg, 0.35 mmol), 4-((tert-butyldimethylsilyloxy)methyl)-2-chloro-5-methoxyaniline (Intermediate 39 WO2011/141180A1; 106 mg, 0.35 mmol), DIEA (0.092 mL, 0.53 mmol) and HATU (147 mg, 0.39 mmol) following the experimental procedure as described for Intermediate 125 and the crude obtained was used without further purification LRMS (m/z): 874 (M+1)+

Intermediate 358 trans-4-({[(4-nitrobenzyl)oxy]carbonyl}amino)-1-methylcyclohexyl[4-(4-{[2-chloro-4-(hydroxymethyl)-5-methoxyphenyl]amino}-4-oxobutyl)biphenyl-2-yl]carbamate To a solution of trans-4-({[(4-nitrobenzyl)oxy]carbonyl}amino)-1-methylcyclohexyl[4-(4-{[4-({[tert-butyl(dimethyl)silyl]oxy}methyl)-2-chloro-5-methoxyphenyl]amino}-4-oxobutyl) biphenyl-2-yl]carbamate (Intermediate 357; 308 mg, 0.42 mmol) in tetrahydrofuran (30 mL) was added dropwise TBAF 1M in THF (423 uL, 0.42 mmol). The reaction mixture was stirred at room temperature for 3 hours. The solvent was removed under reduced pressure and the crude obtained was used in the next step without further purification (267 mg, 89%).

Intermediate 359 trans-4-({[(4-nitrobenzyl)oxy]carbonyl}amino)-1-methylcyclohexyl(4-{4-[(2-chloro-4-formyl-5-methoxyphenyl)amino]-4-oxobutyl}biphenyl-2-yl)carbamate To a solution of trans-4-({[(4-nitrobenzyl)oxy]carbonyl}amino)-1-methylcyclohexyl[4-(4-{[2-chloro-4-(hydroxymethyl)-5-methoxyphenyl]amino}-4-oxobutyl)biphenyl-2-yl]carbamate (Intermediate 358; 265 mg, 0.35 mmol) in chloroform (10 mL) was added activated manganese oxide (424 mg, 4.88 mmol). The reaction mixture was stirred overnight at 45° C. The mixture was filtered and the solvent was removed under reduced pressure. The crude obtained was used without further purification (264 mg, 99%)

LRMS (m/z): 758 (M+1)+

Intermediate 360 trans-4-({[(4-nitrobenzyl)oxy]carbonyl}amino)-1-methylcyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate A mixture of trans-4-({[(4-nitrobenzyl)oxy]carbonyl}amino)-1-methylcyclohexyl(4-{4-[(2-chloro-4- formyl-5-methoxyphenyl)amino]-4-oxobutyl}biphenyl-2-yl)carbamate (Intermediate 359; 265 mg, 0.35 mmol) and 5-((1R)-2-amino-1-{[tert-butyl(dimethyl)-silyl]oxy}ethyl)-8-hydroxyquinolin-2(1H)-one acetate (117 mg, 0.35 mmol) (prepared according to preparation 8 from US20060035931) in 4 mL of methanol was stirred at room temperature for 3 hours. Then the crude was cooled to 0° C. and sodium cyanoborohydride (219 mg, 3.5 mmol) was added. The mixture was stirred overnight at room temperature overweekend. The solvent was removed under reduced pressure and the crude was portioned between ethyl acetate and water. The organic layer was washed with water, sodium bicarbonate and brine, dried, filtered and the solvent was removed under reduced pressure. The crude obtained was purified by column chromatography with silica gel to give the title compound (115 mg, 29%)

Intermediate 361 trans-4-amino-1-methylcyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate To a solution of trans-4-({[(4-nitrobenzyl)oxy]carbonyl}amino)-1-methylcyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate (Intermediate 360; 115 mg, 0.11 mmol) in tetrahydrofuran was added palladium on charcoal (10%, 11 mg). The mixture was submitted to a H2 balloon pressure during 3 hours. The catalyst was filtered trough celite and the filtrate was evaporated. The crude was partioned between ethyl acetate and water and the organic layer was washed with sodium bicartonate and brine, dried, filtered and the solvent was removed under reduced pressure. The crude obtained was used without any further purification (95 mg, 99%)
LRMS (m/z): 897 (M+1)+

Example 65 trans-4-amino-1-methylcyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)biphenyl-2-yl]carbamate dihydrofluoride Obtained as a solid dihydrofluoride salt (20 mg, 19%) from trans-4-amino-1-methylcyclohexyl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxyphenyl]amino}-4-oxobutyl)biphenyl-2-yl]carbamate (Intermediate 361; 95 mg, 0.11 mmol) and triethylamine trihydrofluoride (69 μL, 0.42 mmol) following the experimental procedure as described for Example 1.
LRMS (m/z): 783 (M+1)+
1H NMR (300 MHz, dmso) δ 9.42 (d, J=5.7 Hz, 1H), 8.35 (s, 1H), 8.09 (d, J=11.9 Hz, 1H), 7.48-7.24 (m, 5H), 7.20 (d, J=8.5 Hz, 1H), 7.12 (d, J=8.3 Hz, 1H), 7.02 (d, J=8.2 Hz, 1H), 6.92-6.79 (m, 1H), 6.54-6.37 (m, 2H), 5.08-4.92 (m, 1H), 4.76 (s, 1H), 3.69 (s, 3H), 3.63 (s, 2H), 2.63 (d, J=7.7 Hz, 3H), 2.55 (s, 2H), 2.42 (s, 3H), 2.12 (d, J=10.0 Hz, 2H), 1.91 (d, J=4.7 Hz, 3H), 1.61 (d, J=19.1 Hz, 3H), 1.27 (d, J=8.8 Hz, 6H).

Intermediate 362

1-azabicyclo[2.2.2]oct-4-yl(4-bromobiphenyl-2-yl)carbamate

A mixture of 4-bromo-2-isocyanatobiphenyl (Intermediate 4; 1.65 g, 6.05 mmol) and (R)-quinuclidin-4-ol (0.77 g, 6.05 mmol) in toluene (1 mL) is heated overnight at 80° C. The solvent was removed under reduced pressure and the crude was purified by column chromatography with silica gel, eluting with a mixture of chloroform:methanol:ammonium (40:4:0.2) to give the title compound as an oil (1.99 g, 80%).
LRMS (m/z): 401; 403 (M+1/M+3)+

Intermediate 363 tert-butyl allyl(methyl)carbamate

To a solution of N-methylprop-2-en-1-amine (1 g, 14.06 mmol) in dichloromethane (10 mL) was added triethylamine (2.35 mL, 16.87 mmol) and at 0° C. was added di-tert-butyl dicarbonate (3.06 g, 14.06 mmol) in portions. The reaction mixture was stirred 10 minutes at 0° C. and overnight at room temperature. The crude was partitioned between ethyl acetate and water, and the organic layer was washed with saturated ammonium chloride solution and brine. The organics were dried, filtered and the solvent was removed under reduced pressure giving the title compound as an oil. (1.92 g, 79%)

Intermediate 364

1-azabicyclo[2.2.2]oct-4-yl(4-{(1E)-3-[(tert-butoxycarbonyl)(methyl)amino]prop-1-en-1-yl}biphenyl-2-yl)carbamate To a mixture 1-azabicyclo[2.2.2]oct-4-yl(4-bromobiphenyl-2-yl)carbamate (Intermediate 362; 320 mg, 0.80 mmol) and tert-butyl allyl(methyl)carbamate (Intermediate 363; 216 mg, 1.26 mmol) in acetonitrile (4 mL) in a sealed tube were added tri-o-tolylphosphine (243 mg, 0.80 mmol) and N,N-Diisopropylethylamine (0.25 mL, 1.43 mmol). The mixture was degassed under Argon during 5 minutes. Then palladium acetate (106 mg, 0.47 mmol) was added and the reaction mixture was stirred at 90° C. for 2 hours. The crude was filtrated and the filtrate was evaporated to dryness. The crude obtained was purified by column chromatography with silica gel, eluting with a mixture of chloroform:methanol:ammonium (40:4:0.2) to give the title compound as an oil (511 mg, 99%).
LRMS (m/z): 492 (M+1)+

Intermediate 365

1-azabicyclo[2.2.2]oct-4-yl(4-{3-[(tert-butoxycarbonyl)(methyl)amino]propyl}biphenyl-2-yl)carbamate A round-bottomed flask fitted with stir bar was charged with 1-azabicyclo[2.2.2]oct-4-yl(4-{(1E)-3-[(tert-butoxycarbonyl)(methyl)amino]prop-1-en-1-yl}biphenyl-2-yl)carbamate (Intermediate 364; 511 mg, 1.04 mmol) in Acetic acid (7 mL) The flask was filled with Argon, and then Pd/C (132 mg, 1.24 mmol) was added under Argon atmosphere. The flask was coupled with a quick-fit T-adaptor with one outlet to the hydrogen balloon and the other to the vacuum line. The flask was emptied by connecting it to the vacuum and then filled with hydrogen. This operation was repeated twice. The mixture was stirred vigorously at room temperature for 3 h. The Pd/C was filtered off and the solution concentrated under reduced pressure. The residue was partitioned between chloroform and sodium bicarbonate (solution 4%) and the organic layer was washed with water and brine. The organics were dried, filtered and the solvent was removed under reduced. The residue was purified by column chromatography using as eluents CHCl3-MeOH—NH4OH 40:2:0.2 to give the title compound as an oil (357 mg, 64%).
LRMS (m/z): 495 (M+1)+

Intermediate 366

1-azabicyclo[2.2.2]oct-4-yl{4-[3-(methylamino) propyl]biphenyl-2-yl}carbamate

Obtained as an oil (323 mg, 99%) from 1-azabicyclo [2.2.2]oct-4-yl(4-{3-[(tert-butoxycarbonyl)(methyl)amino] propyl}biphenyl-2-yl)carbamate (Intermediate 365; 357 mg, 0.72 mmol) and acid chloride (4M in dioxane, 1.1 mL) following the experimental procedure as described for Intermediate 58. The crude was diluted with more chloroform and washed with sodium bicartonate (solution 4%). The organics were dried, filtered and the solvent was removed under reduced pressure.
LRMS (m/z): 394 (M+1)+

Intermediate 367 tert-butyl[2-chloro-4-(hydroxymethyl)-5-methoxyphenoxy]acetate

To a solution of 2-chloro-4-(hydroxymethyl)-5-methoxyphenol (Intermediate 247; 1.5 g, 7.95 mmol) in acetonitrile (5 mL) was added tert-butyl 2-bromoacetate (1.18 mL, 7.95 mmol) and potassium carbonate (1.37 g, 9.94 mmol) in a sealed tub. The mixture was stirred 3 hours at 90° C. The solid was filtrated, washed with acetonitrile and the solvent of the filtrate was removed under reduced pressure giving the title compound as a brown oil (1.6 g, 59%), which was used in the next step without further purification.

Intermediate 368 tert-butyl(2-chloro-4-formyl-5-methoxyphenoxy) acetate

Obtained as a solid (700 mg, 55%) from tert-butyl[2-chloro-4-(hydroxymethyl)-5-methoxyphenoxy]acetate (Intermediate 367; 1.60 g, 4.23 mmol) and manganese oxide (2.57 g, 29.6 mmol) following the experimental procedure as described for Intermediate 218 and the crude obtained was used in the next step without further purification.
LRMS (m/z): 301 (M+1)+

Intermediate 369

(2-chloro-4-formyl-5-methoxyphenoxy)acetic acid

To a solution of tert-butyl(2-chloro-4-formyl-5-methoxyphenoxy)acetate (Intermediate 368; 1.15 g, 3.82 mmol) in chloroform (8 mL) was added trifluoroacetic acid (2.95 mL, 38.24 mmol). The reaction mixture was stirred for 4 hours at 45° C. The solvent was removed under reduced pressure and the residue was treated with diethyl ether, filtered and dried to give the title compound as a solid (870 mg, 93%), which was used in the next step without further purification.
LRMS (m/z): 245 (M+1)+

Intermediate 370

1-azabicyclo[2.2.2]oct-4-yl(4-{3-[[(2-chloro-4-formyl-5-(ethoxyphenoxy)acetyl](methyl)amino] propyl}biphenyl-2-yl)carbamate To a solution of 1-azabicyclo[2.2.2]oct-4-yl{4-[3-(methylamino)propyl]biphenyl-2-yl}carbamate (Intermediate 366; 322 mg, 0.82 mmol) in chloroform (8.4 mL) was added (2-chloro-4-formyl-5-methoxyphenoxy)acetic acid (Intermediate 369; 183 mg, 0.75 mmol) and diisopropylethylendiamine (0.58 mL, 3.36 mmol) under nitrogen atmosphere. Then HATU (367 mg, 0.97 mmol) was added. The reaction mixture was stirred at room temperature for 5 hours. The solvent was removed under reduced pressure and the crude was partitioned between chloroform and water, the organic layer was washed with water several times, dried, filtered and the solvent was removed under reduced pressure. The crude obtained was purified by column chromatography with silica gel, eluting with a mixture of chloroform:methanol, giving the title compound as an oil (370 mg, 69%).
LRMS (m/z): 620 (M+1)+

Intermediate 371

1-azabicyclo[2.2.2]oct-4-yl(4-{3-[{[4-({[2-{[tert-butyl(dimethyl)silyl]oxy}-2-(8-hydroxy-2-oxo-1,2-dihydroquinolin-5-yl)ethyl]amino}methyl)-2-chloro-5-methoxyphenoxy]acetyl}(methyl)amino] propyl}biphenyl-2-yl)carbamate A mixture of 1-azabicyclo[2.2.2]oct-4-yl(4-{3-[[(2-chloro-4-formyl-5-methoxyphenoxy) acetyl](methyl) amino]propyl}biphenyl-2-yl)carbamate (Intermediate 370; 370 mg, 0.60 mmol) and 5-((1R)-2-amino-1-{[tert-butyl (dimethyl)-silyl]oxy}ethyl)-8-hydroxyquinolin-2(1H)-one acetate (200 mg, 0.60 mmol) (prepared according to preparation 8 from US20060035931) in 4 mL of methanol and 2 mL of THF was stirred at room temperature for 4 hours. Then the crude was cooled to 0° C. and sodium triacetoxyborohydride (476 mg, 2.25 mmol) was added. The mixture was stirred overnight at room temperature. Sodium bicarbonate (solution 4%) was added dropwise to the previously cooled reaction mixture and chloroform was added. The organic layer was washed with water and brine, dried, filtered and the solvent was removed under reduced pressure. The crude obtained was purified by column chromatography with silica gel, using as eluents CHCl3-MeOH—NH4OH 40:2:0.2 to give the title compound as an oil (64 mg, 11%).
LRMS (m/z): 939 (M+1)+

Example 66

1-azabicyclo[2.2.2]oct-4-yl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]propyl}biphenyl-2-yl) carbamate dihydrofluoride Obtained as a pale yellow solid dihydrofluoride salt (49 mg, 80%) from 1-azabicyclo[2.2.2]oct-4-yl(4-{3-[{[4-({[2-{[tert-butyl(dimethyl)silyl]oxy}-2-(8-hydroxy-2-oxo-1,2- dihydroquinolin-5-yl)ethyl]amino}methyl)-2-chloro-5-methoxyphenoxy]acetyl}(methyl)amino]propyl}biphenyl-2-yl)carbamate (Intermediate 371; 64 mg, 0.07 mmol) and triethylamine trihydrofluoride (56 μL, 0.34 mmol) following the experimental procedure as described for Example 1.

LRMS (m/z): 825 (M+1)+

1H NMR (300 MHz, dmso) δ 10.34 (bs, 1H), 8.44 (d, J=3.3 Hz, 1H), 8.09 (d, J=10.0 Hz, 1H), 7.48-7.23 (m, 5H), 7.11 (ddd, J=30.2, 16.3, 7.3 Hz, 4H), 6.88 (d, J=8.1 Hz, 1H), 6.61 (d, J=6.5 Hz, 1H), 6.46 (d, J=9.9 Hz, 1H), 5.08-4.99 (m, 2H), 4.94 (d, J=9.4 Hz, 3H), 3.69 (s, 3H), 3.63 (s, 2H), 3.01 (s, 2H), 2.84 (s, 6H), 2.69-2.62 (m, 2H), 2.54 (s, 2H), 2.41 (d, J=3.6 Hz, 2H), 1.73 (s, 6H).

Intermediate 372 benzyl but-3-en-1-ylcarbamate

Benzyl chloridocarbonate (0.31 mL, 2.19 mmol) was added dropwise at 0° C. a solution of but-3-en-1-amine (0.20 mL, 2.19 mmol) and triethylamine (0.50 mL, 3.61 mmol) in tetrahydrofurane (8 mL). When the addition was finished, the mixture was stirred at room temperature. After overnight, water and ethyl acetate were added to the mixture, the organic layer washed with sodium bicarbonate 4%, dried ($Na_2SO_4$) and the solvent was removed under reduced pressure giving the title compound (315 mg, 71%), which was used in the next step without further purification.

LRMS (m/z): 206 (M+1)+

Intermediate 373

1-azabicyclo[2.2.2]oct-4-yl[4-((1E)-4-{[(benzyloxy)carbonyl]amino}but-1-en-1-yl)biphenyl-2-yl]carbamate Obtained (158 mg, 48%) from 1-azabicyclo[2.2.2]oct-4-yl(4-bromobiphenyl-2-yl)carbamate (Intermediate 362; 250 mg, 0.62 mmol), benzyl but-3-en-1-ylcarbamate (Intermediate 372; 128 mg, 0.62 mmol), tri-o-tolylphosphine (76 mg, 0.25 mmol), N,N-diisopropylethylamine (196 μL, 1.12 mmol) and palladium acetate (28 mg, 0.12 mmol) following the experimental procedure as described for Intermediate 6. The crude obtained was purified by column chromatography with silica gel, eluting with a mixture of chloroform:methanol:ammonium (40:4:0.2).

LRMS (m/z): 526 (M+1)+

Intermediate 374

1-azabicyclo[2.2.2]oct-4-yl[4-(4-aminobutyl)biphenyl-2-yl]carbamate 1-azabicyclo[2.2.2]oct-4-yl[4-((1E)-4-{[(benzyloxy)carbonyl]amino}but-1-en-1-yl)biphenyl-2-yl]carbamate (Intermediate 373; 158 mg, 0.30 mmol) in EtOH (5 mL) and hydrogen chloride 1.25 M in EtOH (5 mL) was added palladium on charcoal (10%, 0.16 g). The reaction mixture was submitted to a hydrogenation with a hydrogen balloon 6 h at room temperature. The catalyst was removed by filtration through Celite and the solvent was removed under reduced pressure giving the title compound an oil (140 mg, 99%), which was used in the next step without further purification.

LRMS (m/z): 394 (M+1)+

Intermediate 375

1-azabicyclo[2.2.2]oct-4-yl[4-(4-{[2-chloro-4-(hydroxymethyl)-5-methoxybenzoyl]amino}butyl)biphenyl-2-yl]carbamate Obtained as a colorless foam (59 mg, 33%) from 2-chloro-4-(hydroxymethyl)-5-methoxybenzoic acid (Intermediate 281; 70 mg, 0.32 mmol), 1-azabicyclo[2.2.2]oct-4-yl[4-(4-aminobutyl)biphenyl-2-yl]carbamate (Int 67 C, 140 mg, 0.30 mmol), diisopropylethylenediamine (250 μL, 1.44 mmol) and HATU (275 mg, 0.72 mmol) in chloroform (5 mL) following the experimental procedure as described for Intermediate 329. The crude residue was purified by column chromatography using a mixture of chloroform:methanol:ammonium (40:4:0.2).

LRMS (m/z): 592 (M+1)+

Intermediate 376

1-azabicyclo[2.2.2]oct-4-yl(4-{4-[(2-chloro-4-formyl-5-methoxybenzoyl)amino]butyl}biphenyl-2-yl)carbamate Obtained as a yellow foam (58 mg, 99%) from 1-azabicyclo[2.2.2]oct-4-yl[4-(4-{[2-chloro-4-(hydroxymethyl)-5-methoxybenzoyl]amino}butyl)biphenyl-2-yl]carbamate (Intermediate 375; 59 mg, 0.10 mmol) and manganese oxide (90 mg, 10.4 mmol) following the experimental procedure as described for Intermediate 330 and the crude obtained was used in the next step without further purification.

LRMS (m/z): 590 (M+1)+

Intermediate 377

1-azabicyclo[2.2.2]oct-4-yl(4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}butyl)biphenyl-2-yl]carbamate Obtained as a solid (78 mg, 86%) from 1-azabicyclo[2.2.2]oct-4-yl(4-{4-[(2-chloro-4-formyl-5-methoxybenzoyl)amino]butyl}biphenyl-2-yl)carbamate (Intermediate 376; 59 mg, 0.10 mmol), 5-((1R)-2-amino-1-{[tert-butyl(dimethyl)silyl]oxy}ethyl)-8-hydroxyquinolin-2(1H)-one acetate (34 mg, 0.10 mmol) (prepared according to preparation 8 from US20060035931), sodium triacetoxyborohydride (74 mg, 0.35 mmol) in MeOH (2 mL) following the experimental procedure as described for Intermediate 331 and the crude obtained was used in the next step without further purification.

LRMS (m/z): 907 (M+1)+

Example 67

1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate dihydrofluoride Obtained as a white solid (48 mg, 63%) from 1-azabicyclo[2.2.2]oct-4-yl[4-(4-{[4-({[(2R)-2-{[tert-butyl(dimethyl)silyl]oxy}-2-(8-hydroxy-2-oxo-1,2-dihydroquinolin-5-yl)ethyl]amino}methyl)-2-chloro-5-methoxybenzoyl]amino}butyl)biphenyl-2-yl]carbamate (Intermediate 377;

78 mg, 0.09 mmol) and triethylamine trihydrofluoride (70 μL, 0.43 mmol) following the experimental procedure as described for Example 1.

LRMS (m/z): 795 (M+1)+

1H NMR (300 MHz, dmso) δ 10.31 (bs, 1H), 8.36 (bs, 1H), 8.13 (d, J=10.0 Hz, 1H), 7.47-7.25 (m, 5H), 7.22-7.13 (m, J=7.9 Hz, 2H), 7.06 (dd, J=17.4, 8.0 Hz, 2H), 6.95-6.84 (m, 3H), 6.46 (d, J=9.9 Hz, 1H), 5.03 (bs, 1H), 3.75 (d, J=4.5 Hz, 3H), 3.66 (s, 2H), 2.78 (bs, 6H), 2.72-2.58 (m, 4H), 2.55 (dd, J=3.6, 1.8 Hz, 2H), 2.41 (dd, J=3.6, 1.8 Hz, 2H), 1.70 (bs, 6H).

Intermediate 378

Ethyl 5-{[4-(2-{[(1-azabicyclo[2.2.2]oct-4-yloxy)carbonyl]amino}biphenyl-4-yl) butanoyl]amino}pyridine-2-carboxylate To a solution of 4-(2-{[(1-azabicyclo[2.2.2]oct-4-yloxy)carbonyl]amino}biphenyl-4-yl)butanoic acid (Intermediate 328; 293 mg, 0.72 mmol) in chloroform (7.5 mL) was added ethyl 5-aminopicolinate (119 mg, 0.72 mmol) and diisopropylethylendiamine (0.51 mL, 2.94 mmol) under nitrogen atmosphere. Then HATU (644 mg, 1.7 mmol) was added. The reaction mixture was stirred at room temperature for 48 hours. The reaction mixture was diluted with more chloroform and the organic layer was washed with sodium bicarbonate (solution 4%), water and brine, dried, filtered and the solvent was removed under reduced pressure. The crude obtained was purified by column chromatography with silica gel, eluting using as eluents CHCl3-MeOH—NH4OH 40:4:0.2, giving the title compound as an oil (264 mg, 64%).

LRMS (m/z): 557 (M+1)+

Intermediate 379

1-azabicyclo[2.2.2]oct-4-yl[4-(4-{[6-(hydroxymethyl)pyridin-3-yl]amino}-4-oxobutyl)biphenyl-2-yl]carbamate A round-bottomed flask fitted with stir bar was charged with methyl ethyl 5-{[4-(2-{[(1-azabicyclo[2.2.2]oct-4-yloxy)carbonyl]amino}biphenyl-4-yl)butanoyl]amino}pyridine-2-carboxylate (Intermediate 378; 260 mg, 0.47 mmol) in 2.7 mL anhydrous tetrahydrofurane and under Argon atmosphere. The mixture was cooled with an acetone/CO2 bath at −10° C. and lithium aluminium hydride 1M in THF (700 uL, 0.7 mmol) was added cautiously. The solution is stirred at −10° C. for 2 hours. The reaction is quenched by adding sodium hydroxide 1N (1.3 mL) maintaining the temperature below 0° C. Ethyl acetate is added to the reaction mixture and the organic layer is washed with water, brine, dried, filtered and the solvent was removed under reduced pressure. The crude obtained was purified by column chromatography with silica gel, eluting using as eluents CHCl3—MeOH—NH4OH 40:8:1, giving the title compound as an oil (71 mg, 25%).

LRMS (m/z): 516 (M+1)+

Intermediate 380

1-azabicyclo[2.2.2]oct-4-yl(4-{4-[(6-formylpyridin-3-yl)amino]-4-oxobutyl}biphenyl-2-yl)carbamate A round-bottomed flask fitted with stir bar was charged with 1-azabicyclo[2.2.2]oct-4-yl[4-(4-{[6-(hydroxymethyl)pyridin-3-yl]amino}-4-oxobutyl)biphenyl-2-yl]carbamate (Intermediate 379; 71 mg, 0.12 mmol) in chloroform (1.5 mL). Dess-Martin periodinane (64 mg, 0.15 mmol) was added portionwise and the mixture stirred at room temperature for 1 hour. The reaction was quenched by addition of saturated bicarbonate and sodium thiosulfate solution. The organic layer was dried over MgSO4, filtered and concentrated to give the title compound as a solid (80 mg, 100%), which was used in the next step without further purification.

LRMS (m/z): 514 (M+1)+

Intermediate 381

1-azabicyclo[2.2.2]oct-4-yl[4-(4-{[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]amino}-4-oxobutyl)biphenyl-2-yl]carbamate A mixture of 1-azabicyclo[2.2.2]oct-4-yl(4-{4-[(6-formylpyridin-3-yl)amino]-4-oxobutyl}biphenyl-2-yl)carbamate (Intermediate 380; 80 mg, 0.12 mmol) and 5-((1R)-2-amino-1-{[tert-butyl(dimethyl)-silyl]oxy}ethyl)-8-hydroxyquinolin-2(1H)-one acetate (48 mg, 0.12 mmol) (prepared according to preparation 8 from US20060035931) in 2 mL of methanol and was stirred at room temperature for 4 hours. Then the crude was cooled to 0° C. and sodium triacetoxyborohydride (20 mg, 0.31 mmol) was added. The mixture was stirred overnight at room temperature. The solvent was removed under reduced pressure and the residue was purified by column chromatography with silica gel, eluting using as eluents CHCl3-MeOH—NH4OH 40:4:0.2, giving the title compound as an oil (36 mg, 32%).

LRMS (m/z): 832 (M+1)+

Example 68

1-azabicyclo[2.2.2]oct-4-yl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl) biphenyl-2-yl]carbamate dihydrofluoride Obtained as a pale yellow solid dihydrofluoride salt (29 mg, 92%) from 1-azabicyclo[2.2.2]oct-4-yl[4-(4-{[6-({[(2R)-2-{[tert-butyl(dimethyl)silyl]oxy}-2-(8-hydroxy-2-oxo-1,2-dihydroquinolin-5-yl)ethyl]amino}methyl)pyridin-3-yl]amino}-4-oxobutyl) biphenyl-2-yl]carbamate (Intermediate 381; 36 mg, 0.04 mmol) and triethylamine trihydrofluoride (35 μL, 0.21 mmol) following the experimental procedure as described for Example 1.

LRMS (m/z): 718 (M+1)+

1H NMR (300 MHz, dmso) δ 10.38 (bs, 1H), 10.14 (s, 1H), 8.71 (d, J=2.2 Hz, 1H), 8.56 (s, 1H), 8.15 (d, J=9.9 Hz, 1H), 8.00 (d, J=10.7 Hz, 1H), 7.48-7.26 (m, 5H), 7.24-7.01 (m, 4H), 6.98-6.84 (m, 1H), 6.49 (d, J=9.9 Hz, 1H), 5.21 (bs, 2H), 4.00 (s, 2H), 3.13-2.89 (m, 6H), 2.84 (d, J=4.2 Hz, 2H), 2.71-2.57 (m, 2H), 2.43-2.27 (m, 2H), 1.88 (d, J=5.7 Hz, 6H).

Biological Tests

Test 1: Human Adrenergic $\beta_1$ and $\beta_2$ Receptor Binding Assays

The study of binding to human adrenergic beta1 and beta2 receptors was performed using commercial membranes prepared from Sf9 cells where they are overexpressed (Perkin Elmer). The membrane suspensions (16 μg/well for beta1 and 5 μg/well for beta2) in assay buffer (75 mM Tris/HCl with 12.5 mM MgCl2 and 2 mM EDTA pH=7.4) were incubated with 0.14 or 0.6 nM of 3H-CGP12177 (Amersham) for beta 1 and beta 2 receptors respectively in a final volume of 250 µl, in GFC Multiscreen 96 well plates (Millipore) previously treated with assay buffer containing 0.3% PEI (Sigma). Non specific binding was measured in the presence of 1 µM propanolol. Incubation was maintained for 60 minutes at room temperature and with gentle shaking. The binding reactions were terminated by filtration and washing with 2.5 volumes of Tris/HCl 50 mM pH=7.4. The affinity of each test compound to the receptor was determined by using ten different concentrations ran in duplicate. $IC_{50}$s were calculated using Activity Base software from IDBS and the four parameters-log equation.

Compounds of the present invention were found to have $IC_{50}$ values less than 10 nM for $\beta_2$ receptor and more than 60 nM for $\beta_1$ receptor, with $\beta 1/\beta 2$ ratios from 3 to 25.

Test 2: Human Muscarinic $M_1$, $M_2$, $M_3$, $M_4$ and $M_5$ Receptors Binding Assays The study of binding to human muscarinic M1, M2, M3, M4 and M5 receptors was performed using commercial membranes (Perkin Elmer) prepared from CHO-K1 cells. Radioligand binding experiments were conducted in 96 polypropylene well plates in a total volume of 200 µl. All reagents were dissolved in assay binding buffer (PBS with calcium and magnesium, SIGMA), except compounds that were dissolved in DMSO 100%. Non-specific binding (NSB) was measured in the presence of 1 µM atropine. [3H]-NMS was used as the radioligand at a concentration of 1 nM for M2, M3 and M5 and 0.3 nM for M1 and M4. [3H]-NMS and antagonists were incubated with membranes that express human muscarinic receptors M1, M2, M3, M4 and M5 at concentrations of 8.1, 10, 4.9, 4.5 and 4.9 µg/well, respectively.

After an incubation period of two hours with gentle shaking, 150 µl of the reaction mix were transferred to 96 GF/C filter plates (Millipore), previously treated with wash buffer (Tris 50 mM; NaCl 100 mM; pH:7.4), containing 0.05% PEI (Sigma) during one hour. Bound and free [3H]-NMS were separated by rapid vacuum filtration in a manifold from Millipore and washed four times with ice cold wash buffer. After drying 30 min, 30 µl of OPTIPHASE Supermix were added to each well and radioactivity quantified using a Microbeta microplate scintillation counter.

The affinity of each test compound to the receptors was determined by using ten different concentrations ran in duplicate. $IC_{50}$s were calculated using Activity Base software from IDBS and the four parameters-log equation.

In the table 1 are shown some $IC_{50}$ values for $\beta_2$ and $M_3$ bindings.

TABLE 1

| Compound | Binding, $IC_{50}$, nM | |
|---|---|---|
| Example nr | $\beta_2$ | $M_3$ |
| 2 | 18 | 0.24 |
| 7 | 30 | 0.5 |
| 9 | 47 | 0.68 |
| 10 | 69 | 0.57 |
| 13 | 9.5 | 3.2 |
| 14 | 10 | 0.13 |
| 15 | 15 | 0.32 |
| 16 | 12 | 0.65 |
| 17 | 19 | 0.5 |
| 19 | 6.6 | 0.19 |
| 21 | 1.3 | 1.2 |
| 22 | 8.5 | 1 |
| 23 | 31 | 0.78 |
| 25 | 1.5 | 0.14 |
| 29 | 19 | 1.1 |

TABLE 1-continued

| Compound | Binding, $IC_{50}$, nM | |
|---|---|---|
| Example nr | $\beta_2$ | $M_3$ |
| 31 | 19 | 0.3 |
| 34 | 14 | 0.84 |
| 35 | 16 | 0.33 |
| 37 | 18 | 1.2 |
| 39 | 10 | 0.56 |
| 40 | 2 | 0.78 |
| 44 | 6.3 | 1.2 |
| 45 | 4.7 | 1.3 |
| 47 | 8.5 | 0.65 |
| 49 | 7.2 | 0.59 |
| 52 | 8.2 | 1.5 |
| 57 | 7.4 | 0.86 |
| 58 | 8.4 | 1.4 |
| 60 | 4.9 | 0.37 |
| 66 | 9.6 | 0.99 |
| 67 | 8.2 | 0.41 |
| 68 | 23 | 1.7 |

As it can be seen from Table 1, compounds of the present invention exhibit potency at either beta2 adrenoceptor and M3 muscarinic receptors. For example, for the human M3 muscarininc receptor, compounds of the present invention were found to have an $IC_{50}$ values of less than 50 nM, preferably less than 10 nM, more preferably less than 5 nM, even less than 1 nM.

In case of beta2 of adrenoceptor, compounds of the present invention were found to have an $IC_{50}$ values of less than 100 nM, preferably less than 50 nM, more preferably less than 10 nM, even less than 5 nM. This particular ratio balanced towards M3 activity makes the compounds safer in terms of cardiovascular adrenergic side-effects like tachycardia compared to pure LABA compounds. The combination of both activities, in addition to provide additive effect in terms of bronchodilation also combines the faster onset of action of the beta2 component and the duration of action of the M3 component. This long duration of action of the muscarinic activity is related to the long residence time at the human M3 receptor that show many compounds of this invention.

Pharmaceutical Compositions

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Each capsule or cartridge may generally contain between 2 μg and 150 μg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler.

Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e. g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described in the following patent applications Nos.: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e. g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. WO 91/14468 and International Patent Application No. WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e. g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants, for example, oleic acid or lecithin and cosolvens, for example, ethanol. Pressurised formulations will generally be retained in a canister (for example, an aluminium canister) closed with a valve (for example, a metering valve) and fitted into an actuator provided with a mouthpiece.

Medicaments for administration by inhalation desirably have a controlled particle size. The optimum particle size for inhalation into the bronchial system is usually 1-10µ, preferably 2-5µ. Particles having a size above 20µ are generally too large when inhaled to reach the small airways. To achieve these particle sizes the particles of the active ingredient as produced may be size reduced by conventional means, for example, by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit contains suitably from 0.5 µg to 500 µg, and preferably from 5 µg to 100 µg of a compound according to the invention.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

Examples of suitable PDE4 inhibitors that can be combined with compounds of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), CDC-801, UK-500001, BLX-914, 2-carbomethoxy-4-cyano-4-(3-cyclopropylmethoxy-4-difluromethoxyphenyl)cyclohexan1-one, cis[4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the salts claimed in the PCT patent applications number WO03/097613, WO2004/058729, WO 2005/049581, WO 2005/123693 and WO 2005/123692

Examples of suitable corticosteroids and glucocorticoids that can be combined with compounds of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone farnesylate, ciclesonide, butixocort propionate, RPR- 106541, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, Desisobutyrylciclesonide, hydrocortisone acetate, hydrocortisone sodium succinate, NS-126, prednisolone sodium phosphate and hydrocortisone probutate, Prednisolone sodium metasulfobenzoate and clobetasol propionate.

Particularly preferred pharmaceutical composition according to the invention comprises a compound of formula (I) and a therapeutically effective amount of one or more additional therapeutic agents selected from the group consisting of mometasone, mometasone furoate, ciclesonide, budesonide, fluticasone, fluticasone propionate, fluticasone furoate, rolipram, roflumilast, cilomilast and the compounds claimed in the PCT patent applications number WO03/097613, WO2004/058729, WO 2005/049581, WO 2005/123693 and WO 2005/123692

Still particularly preferred pharmaceutical composition according to the invention comprise a compound of formula (I) and a therapeutically effective amount of one or more additional therapeutic agents selected from the group consisting of mometasone furoate, ciclesonide, budesonide, fluticasone propionate, fluticasone furoate, rolipram, roflumilast and cilomilast The combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combination and the PDE4 inhibitors, corticosteroids or glucocorticoids may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

Additional suitable carriers for formulations of the active compounds of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

FORMULATION EXAMPLE

Formulation Example 1

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

Gelatin Cartridge for Inhalation

| Ingredient | Amount |
| --- | --- |
| Active Compound (micronized) | 0.2 mg |
| Lactose | 25 mg |

Formulation Example 4

Formulation for Inhalation with a DPI

| Ingredient | Amount |
| --- | --- |
| Active Compound (micronized) | 15 mg |
| Lactose | 3000 mg |

Formulation Example 5

Formulation for a MDI

| Ingredient | Amount |
| --- | --- |
| Active Compound (micronized) | 10 g |
| 1,1,1,2,3,3,3-heptafluoro-n-propane | q.s. to 200 ml |

The invention claimed is:
1. A compound of Formula (A), or a pharmaceutically acceptable salt or deuterated derivative thereof:

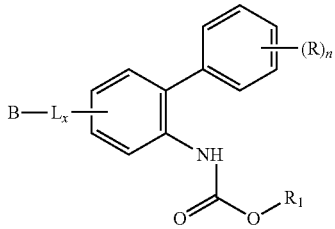

Formula (A)

wherein:
R is chosen from the group consisting of a hydrogen atom, a halogen atom, a hydroxyl group, a linear or branched $C_{1-4}$ alkyl group, a linear or branched $C_{1-4}$ hydroxyalkyl group, and a linear or branched $C_{1-4}$ alkoxy group,
n is 1 or 2,
$R_1$ is:

i)

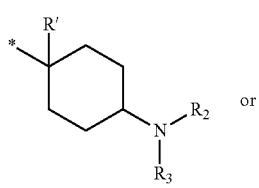

or ii)

wherein:
$R_2$ and $R_3$ are independently chosen from a hydrogen atom, a linear or branched $C_{1-4}$ alkyl group, a ($C_{5-6}$ aryl)-($C_{1-4}$)alkyl group, and a linear or branched $C_{1-4}$ alkoxy group,
R' is chosen from a hydrogen atom or a linear or branched $C_{1-4}$ alkyl group,
* is a point of attachment of $R_1$ to the remainder of the molecule of Formula (A),
$L_x$ is a suitable covalent linker, and
B represents a group of Formula (IB):

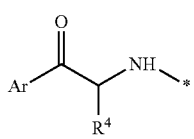

Formula (IB)

wherein:
$R^4$ is chosen from the group consisting of a hydrogen atom, a linear or branched $C_{1-4}$ alkyl group, and a linear or branched $C_{1-4}$ alkoxy group,
Ar is chosen from the group consisting of a $C_{3-10}$ saturated or unsaturated, mono- or bicyclic cycloalkyl group; a $C_5$-$C_{14}$ mono- or bicyclic aryl group; a 3 to 14-membered saturated or unsaturated mono- or bicyclic heterocyclyl group having one or more heteroatoms chosen from N, S, and O; and a 5- to 14-membered mono- or bicyclic heteroaryl group having one or more heteroatoms chosen from N, S, and O; and wherein the cyclic groups independently are optionally substituted with one or more substituents chosen from a halogen atom, a cyano group, a nitro group, an oxo group, a carboxy group, a $C_{1-4}$ alkyl group, a $C_{1-4}$ alkoxy group, —$CF_3$, —$OCF_3$, —$NR^eR^f$, —$(CH_2)_p$—OH, —$NR^e(CO)R^f$, —$NR^e$—$SO_2$—$R^g$, —$SO_2NR^eR^f$, —$OC(O)R^h$, and —$NR^e(CH_2)_{(0-2)}$—$R^i$, wherein p is 0, 1 or 2 and wherein:
$R^e$ and $R^f$ are independently chosen from a hydrogen atom and a linear or branched $C_{1-4}$ alkyl group,
$R^g$ is chosen from the group consisting of a linear or branched $C_{1-4}$ alkyl group, a $C_{5-6}$ aryl group, and a saturated or unsaturated $C_{3-8}$ cycloalkyl, wherein the cyclic groups independently are optionally substituted with one or more substituents chosen from a halogen atom, a $C_{1-4}$ alkyl group, and a $C_{1-4}$ alkoxy group, $R^h$ is chosen from a hydrogen atom, —$NR^eR^f$, and a $C_{5-6}$ aryl group, which is optionally substituted with one or more substituents chosen from a $C_{1-4}$ alkyl group and a $C_{1-4}$ alkoxy group,
$R^i$ is chosen from the group consisting of a $C_{5-6}$ aryl group, a $C_{3-8}$ cycloalkyl group, and a 3 to 8 membered saturated or unsaturated heterocyclyl group, which groups independently are optionally substituted with one or more substituents chosen from a halogen atom, a $C_{1-4}$ alkyl group, and a $C_{1-4}$ alkoxy group.

2. The compound according to claim 1, wherein $L_x$ is Formula (La) or Formula (Lb):

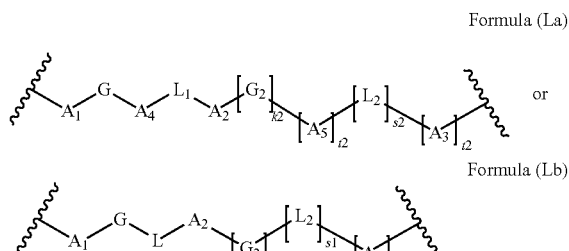

Formula (La)

or

Formula (Lb)

wherein k1, k2, s1, s2, l2, t1, and t2 are independently 0 or 1;
$A_1$, $A_2$, $A_3$, $A_4$ and $A_5$ are independently chosen from the group consisting of a direct bond, a $C_{1-10}$ alkylene group, a $C_{2-10}$ alkenylene group, and a $C_{2-10}$ alkynylene group, wherein said groups are optionally substituted with one or more substituents chosen from a halogen atom, a hydroxy group, a linear or branched $C_{1-4}$ alkyl group, a linear or branched $C_{1-4}$ alkoxy group, a $C_{5-6}$ aryl group, and a $C_{3-7}$ cycloalkyl group,
L, $L_1$ and $L_2$ are independently chosen from a direct bond, —O—, —$NR^c$—, —S—, —S(O)—, —$SO_2$—, —$NR^c(CO)$—, —(CO)$NR^c$—, —$NR^c(CO)(CH_2)_qO$—, —$O(CH_2)_q(CO)NR^c$—, —$NR^c(CO)(CH_2)_qNR^c(CO)$—, —$O(CH_2)_qNR^c$—, —$NR^c(CH_2)_qO$—, —$NR^c(CO)NR^d$—, —C(O)—, —C(O)O—, —OC(O)—, —$S(O)_2NR^c$—, —$NR^cS(O)_2$—, —NR$^c$S(O)$_2$NR$^d$—, —C(O)NR$^c$S(O)$_2$—, and —S(O)$_2$NR$^c$C(O)—, wherein R$^c$ and R$^d$ are independently chosen from a hydrogen atom and a linear or branched C$_{1-4}$ alkyl group and q is 0, 1, 2, 3 or 4, G and G$_2$ are independently chosen from the group consisting of a direct bond; a C$_{3-10}$ mono- or bicyclic cycloalkyl group; a C$_5$-C$_{14}$ mono- or bicyclic aryl group; a 3 to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; and a bicyclic ring system comprising two monocyclic ring systems which are linked between each other by a covalent bond or by a —O— or —NH— group; wherein said monocyclic ring systems are independently chosen from a C cydcloalkyl group; a C$_{5-6}$ aryl group; a 3 to 8-membered saturated or unsaturated heterocyclyl group having one or more heteroatoms chosen from N, S, and O; and a 5- to 6-membered heteroaryl group having one or more heteroatoms chosen from N, S, and O; wherein the cyclic groups independently are optionally substituted with one or more substituents chosen from a halogen atom, a C$_{1-4}$ alkyl group, a C$_{1-4}$ alkoxy group, a carboxy group, a cyano group, a nitro group, a hydroxy group, an oxo group, a trifluoromethyl group, and a trifluoromethoxy group.

3. The compound according to claim 2, wherein k1, k2, s1, s2, l2, t1 and t2 are 0.

4. The compound according to claim 3, wherein Lx is Formula (Lb1):

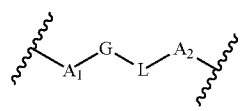

Formula (Lb1)

5. The compound according to claim 1, wherein Lx is -A$_1$-G-L-A$_2$-.

6. The compound according to claim 1, wherein Ar is formula (a), (b), (c), or (d):

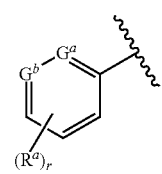

(a)

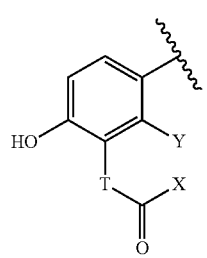

(b)

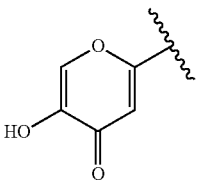

(c)

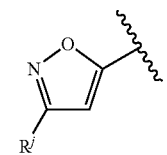

(d)

wherein

G$^a$ and G$^b$ are independently chosen from a nitrogen atom and a carbon atom, r is 0, 1, 2 or 3 and R$^a$ is chosen from the group consisting of a halogen atom, an amino group, a cyano group, a nitro group, an oxo group, a carboxy group, a C$_{1-4}$ alkyl group, a C$_{1-4}$ alkoxy group, —CF$_3$, —OCF$_3$, —(CH$_2$)$_p$—OH, —NH(CO)H, —NH—SO$_2$—R$^g$, —SO$_2$NH$_2$, —OC(O)H, —O(CO)-(4-methyl)phenyl, —O(CO)—N(CH$_3$)$_2$, —OC(O)NH$_2$, or —NH(CH$_2$)$_{(1-2)}$—R$^i$, wherein p is as defined above and R$^g$ and R$^i$ are independently chosen from a phenyl group optionally substituted with a one substituent chosen from a methyl group and a methoxy group, R$^j$ is a halogen atom, T is chosen from the group consisting of —CH$_2$— and —NH—, Both X and Y are a hydrogen atom or X together with Y forms —CH$_2$—CH$_2$—, —CH=CH—, —CH$_2$—O—, or —S—, wherein in the case of —CH$_2$—O— the methylene group is bound to the carbonyl group holding X and the oxygen atom is bound to the carbon atom in the phenyl ring holding Y.

7. The compound according to claim 6, wherein Ar is formula (a) or (b) wherein:

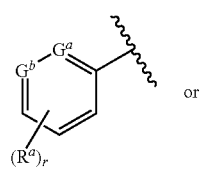

(a)

or

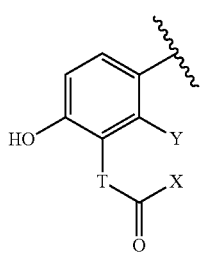

(b)

Both G$^a$ and G$^b$ are a carbon atom,

R$^a$ is chosen from the group consisting of halogen atom, amino group, cyano group, nitro group, —(CH$_2$)$_p$—

OH, —NH(CO)H, —NH—SO$_2$—CH$_3$, —SO$_2$NH$_2$, —OC(O)H, —O(CO)-(4-methyl)phenyl, —O(CO)—N(CH$_3$)$_2$, —OC(O)NH$_2$, or —CF$_3$, wherein p is 0, 1 or 2, T is —NH—, Both X and Y are a hydrogen atom or X together with Y forms —CH═CH—, —CH$_2$—CH$_2$—, —CH$_2$—O—, or —S—, wherein in the case of —CH$_2$—O— the methylene group is bound to the carbon atom in the amido substituent holding X and the oxygen atom is bound to the carbon atom in the phenyl ring holding Y.

8. The compound according to claim 6 or 7, wherein Ar is chosen from the group consisting of 3-bromoisoxazol-5-yl, 3,4-dihydroxyphenyl, 4-hydroxy-3-(methylsulfonamido)phenyl, 3,4-bis(4-methylbenzoyloxy)phenyl, 3,5-bis(dimethylcarbamoyloxy)phenyl, (5-hydroxy-6-hydroxymethyl)pyrid-2-yl, (4-amino-3,5-dichloro)phenyl, 4-hydroxyphenyl, 4-hydroxy-3-(2-hydroxyethyl)phenyl, 4-hydroxy-3-(hydroxymethyl)phenyl, [4-amino-3-chloro-5-(trifluoromethyl)]phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, 5-hydroxy-3-oxo-3,4-dihydro-2H-benzo[b][1,4]oxazin-8-yl, or 4-hydroxy-2-oxo-2,3-dihydrobenzo[d]thiazol-7-yl.

9. The compound according to claim 7, wherein Ar is the compound of formula (b) wherein T is —NH.

10. The compound according to claim 1, wherein Formula (I) is:

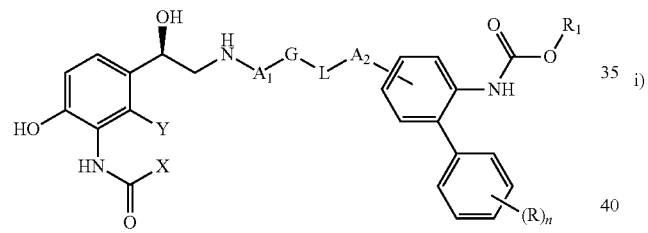

Formula (I)

wherein:
R is chosen from the group consisting of a hydrogen atom, a halogen atom, a hydroxyl group, a linear or branched C$_{1-4}$ alkyl group, a linear or branched C$_{1-4}$ hydroxyalkyl group, and a linear or branched C$_{1-4}$ alkoxy group, n is 1 or 2, X and Y are both a hydrogen atom or X together with Y forms —CH═CH—, —CH$_2$—O—, or —S—, wherein in the case of —CH$_2$—O— the methylene group is bound to the carbon atom in the amido substituent holding X and the oxygen atom is bound to the carbon atom in the phenyl ring holding Y, A$_1$ and A$_2$ are independently chosen from the group consisting of a direct bond, a C$_{1-10}$ alkylene group, a C$_{2-10}$ alkenylene group, and a C$_{2-10}$ alkynylene group, wherein said groups are optionally substituted with one or more substituents chosen from a halogen atom, a hydroxy group, a linear or branched C$_{1-4}$ alkyl group, a linear or branched a C$_{1-4}$ alkoxy group, a C$_{5-6}$ aryl group, and a C$_{3-7}$ cycloalkyl group, G is chosen from the group consisting of a direct bond; a C$_{3-10}$ mono- or bicyclic cycloalkyl group; a C$_{5-14}$ mono- or bicyclic aryl group; a 3- to 14-membered saturated or unsaturated mono- or bicyclic heterocyclyl group having one or more heteroatoms chosen from N, S, and O; a 5- to 14-membered mono- or bicyclic heteroaryl group having one or more heteroatoms chosen from N, S, and O; and a bicyclic ring system consisting of two monocyclic ring systems which are linked between each other by a covalent bond or by a —O— group, wherein said monocyclic ring systems are independently chosen from a C$_{3-8}$ cycloalkyl group; a C$_{5-6}$ aryl group; a 3- to 8-membered saturated or unsaturated heterocyclyl group having one or more heteroatoms chosen from N, S, and O; and a 5- to 6-membered heteroaryl group having one or more heteroatoms chosen from N, S, and O; wherein the cyclic groups independently are optionally substituted with one or more substituents chosen from a halogen atom, a C$_{1-4}$ alkyl group, a C$_{1-4}$ alkoxy group, a carboxy, group, a cyano group, a nitro group, a hydroxy group, an oxo group, a trifluoromethyl group, and a trifluoromethoxy group, L is chosen from a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$—, or —S(O)$_2$NR$^c$C(O)—, wherein R$^c$ and R$^d$ are independently chosen from a hydrogen atom and a linear or branched C$_{1-4}$ alkyl group and q is 0, 1, 2, 3 or 4, R$_1$ is:

i) 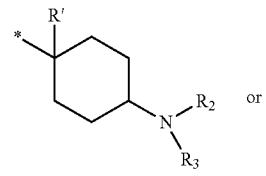

or ii) 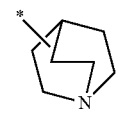

wherein:
R$_2$ and R$_3$ are independently chosen from a hydrogen atom, a linear or branched C$_{1-4}$ alkyl group, and a (C$_{5-6}$ aryl)-(C$_{1-4}$) alkyl group and R' is chosen from a hydrogen atom and a linear or branched C$_{1-4}$ alkyl group.

11. The compound according to claim 1, wherein A$_1$ and A$_2$ are independently chosen from the group consisting of C$_{1-6}$ alkylene group, C$_{1-6}$ alkenylene group, and C$_{1-6}$ alkynylene group, wherein said groups are optionally substituted with one or more substituents chosen from a halogen atom, a hydroxy group, a C$_{1-2}$ alkyl group, a C$_{1-2}$ alkoxy group, a C$_{5-6}$ aryl group, and a C$_{3-6}$ cycloalkyl group.

12. The compound according to claim 1, wherein X together with Y forms —CH═CH— or —CH$_2$—O—.

13. The compound according to claim 1, wherein L is chosen from the group consisting of a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)

NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$—, or —S(O)$_2$NR$^c$C(O)—, wherein R$^c$ and R$^d$ are independently chosen from a hydrogen atom and a linear or branched C$_{1-4}$ alkyl group and q has a value of 0, 1, 2, 3 or 4.

14. The compound according to claim 13, wherein L is chosen from a direct bond, —NR$^c$(CO)—, —(CO)NR$^c$—, —O(CH$_2$)$_q$(CO)NR$^c$— or —C(O)—.

15. The compound according to claim 1, wherein G is chosen from the group consisting of a direct bond; a C$_{3-7}$ cycloalkyl group; a C$_{5-14}$ mono- or bicyclic aryl group; a 3- to 14-membered saturated or unsaturated mono- or bicyclic heterocyclyl group having one or more heteroatoms selected from N, S, and O; a 5- to 14-membered mono- or bicyclic heteroaryl group having one or more heteroatoms chosen from N, S, and O; or a bicyclic ring system comprising two monocyclic ring systems which are linked between each other by a covalent bond or by a —O— group, wherein said monocyclic ring system are independently chosen from the group consisting of a C$_{3-8}$ cycloalkyl group and a C$_{5-6}$ aryl group, wherein the cyclic groups independently are optionally substituted with one or more substituents chosen from a halogen atom, a C$_{1-4}$ alkyl group, a C$_{1-4}$ alkoxy group, a carboxy group, a cyano group, a nitro group, a hydroxy group, an oxo group, a trifluoromethyl group, and a trifluoromethoxy group.

16. The compound according to claim 15, wherein, G is chosen from the group consisting of a C$_{3-7}$ cycloalkyl group, a C$_5$-C$_6$ aryl group, or a group of Formula (Iwa):

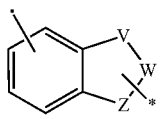

Formula (Iwa)

wherein
V, W and Z are independently chosen from —N—, —NH—, —C—, —CH—, —S—, —O—, and —C(O)—,
wherein the cyclic groups independently are optionally substituted with one or more substituents chosen from a halogen atom, a C$_{1-4}$ alkyl group and a C$_{1-4}$ alkoxy group.

17. The compound according to claim 16, wherein W is chosen from —N—, —NH—, or a —C(O)— group.

18. The compound according to claim 16, wherein V is chosen from —N—, —NH—, —S—, or —O—.

19. The compound according to claim 16, wherein G is chosen from a phenylene group, a cyclohexyl group, or a group of Formula (Iwb):

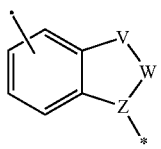

Formula (Iwb)

wherein V is chosen from —N—, —NH—, or —O— and W is a —C(O)— group, and wherein the cyclic groups are independently optionally substituted with one or two substituents chosen from a chlorine atom, methyl group, and methoxy group.

20. The compound according to claim 1, wherein R$_1$ is formula:

i)

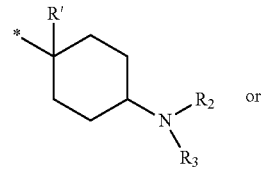

ii)

wherein R', R$_2$ and R$_3$ are independently chosen from a hydrogen atom and a C$_{1-2}$ alkyl group.

21. A compound according to claim 20, wherein R$_1$ is formula:

i)

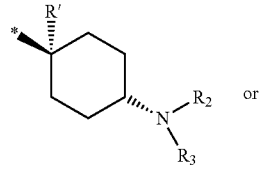

ii)

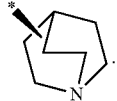

22. The compound according to claim 1, wherein R is chosen from the group consisting of a hydrogen atom, a halogen atom, or a hydroxy group.

23. The compound according to claim 1, wherein n is 1 or 2.

24. The compound according to claim 1, wherein A$_1$ and A$_2$ independently are a C$_{1-4}$ alkylene group optionally substituted with one or two methyl groups, X together with Y forms —CH═CH—, L is chosen from the group consisting of a direct bond, —NR$^c$(CO)—, or —(CO)NR$^c$—, wherein R$^c$ is chosen from a hydrogen atom and a methyl group, G is chosen from a phenylene group, a cyclohexyl group, or a group of Formula (Iwb):

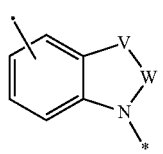

Formula (Iwb)

wherein V is chosen from —N—, —NH—, or —O— and W is a —C(O) group, and wherein the cyclic groups are independently optionally substituted with one or two substituents chosen from a chlorine atom, a methyl group, and a methoxy group, and $R_1$ has formula:

i)

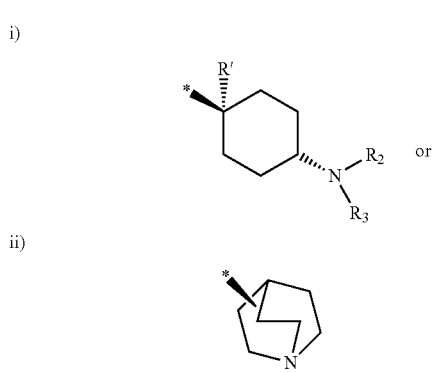

ii)

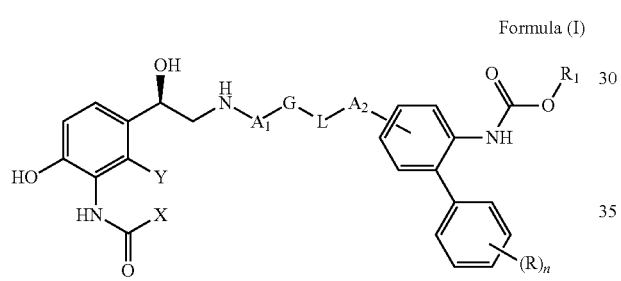

wherein both $R_2$ and $R_3$ are a hydrogen atom and R' is chosen from a hydrogen atom or a methyl group, R is a hydrogen atom and n is 1.

25. The compound according to claim 1, having Formula (I):

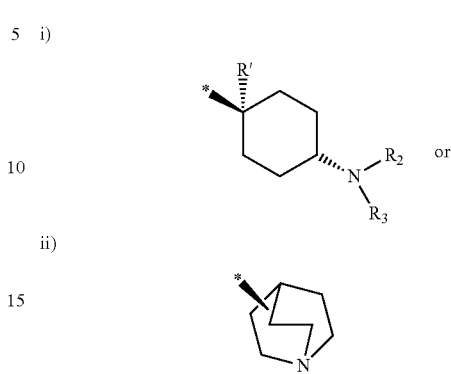

Formula (I)

wherein, R is a hydrogen atom and n is 1, $A_1$ and $A_2$ are independently chosen from a direct bond and a $C_{1-6}$ alkylene group optionally substituted with a methyl group, X together with Y forms —CH=CH—, —CH$_2$—CH$_2$— or —CH$_2$—O—, L is chosen from the group consisting of a direct bond, —O—, —NR$^c$(CO)O—, —O(CH$_2$)(CO)NR$^c$—, —NR$^c$(CO)— —(CH$_2$)$_4$NR$^c$(CO)—, —(CH$_2$)$_{(0-1)}$NR$^c$(CO)—, —(CO)NR$^c$—, or —NH(CO)NH—, wherein R$^c$ is chosen from a hydrogen atom or a methyl group, G is chosen from a direct bond, a phenylene group, a pyridyl group, a cyclobutyl group, a cyclohexyl group, or a group of Formula (Iwa):

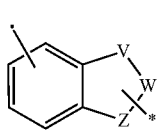

Formula (Iwa)

wherein V and Z independently are chosen from the group consisting of —N—, —NH—, —C—, —O—, and —S—, and W is chosen from —N—, —NH—, —C—, and a —C(O)— group, and wherein the phenylene group, pyridyl group, cyclobutyl group, cyclohexyl group, and the group of Formula (Iwa) are independently optionally substituted with one or two substituents chosen from a chlorine atom, methyl group, and methoxy group, $R^1$ has formula:

i)

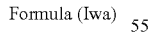

ii)

wherein both $R_2$ and $R_3$ are independently chosen from a hydrogen atom, a methyl group, a hexyl group, and a propyl group substituted with a phenyl group and R' is a hydrogen atom or a methyl group.

26. The compound according to claim 1, wherein the compound is chosen from:
 (3R)-1-azabicyclo[2.2.2]oct-3-yl(4-{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate,
 (3R)-1-azabicyclo[2.2.2]oct-3-yl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate
 trans-4-(methylamino)cyclohexyl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate,
 (3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}biphenyl-2-yl)carbamate,
 (3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}biphenyl-2-yl)carbamate,
 (3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-1H-indol-1-yl]propyl}biphenyl-2-yl)carbamate,
 (3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate,
 trans-4-aminocyclohexyl(4-{3-[5-({[(2R)-2-hydroxy-2-(8-hydroxy-2-oxo-1,2-dihydro-quinolin-5-yl)ethyl]amino}methyl)-1H-1,2,3-benzotriazol-1-yl]propyl}biphenyl-2-yl)carbamate,
 (3R)-1-azabicyclo[2.2.2]oct-3-yl(4-{4-[3-({[(2R)-2-hydroxy-2-(8-hydroxy-2-oxo-1,2-dihydroquinolin-5-yl)ethyl]amino}methyl)phenoxy]butyl}biphenyl-2-yl)carbamate,
 (3R)-1-azabicyclo[2.2.2]oct-3-yl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate, trans-4-aminocyclohexyl(4-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2,3,4-tetrahydroquinolin-5-yl)ethyl]amino}methyl)-1,3-benzoxazol-2-yl]butyl}biphenyl-2-yl)carbamate, (3R)-1-azabicyclo[2.2.2]oct-3-yl(4-{3-[3-(2-{[(2R)-2-hydroxy-2-(8-hydroxy-2-oxo-1,2-dihydroquinolin-5-yl]amino}ethyl)phenoxy]propyl}biphenyl-2-yl)carbamate, (3R)-1-azabicyclo[2.2.2]oct-3-yl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]-propyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl-1H-indol-1-yl]butyl}biphenyl-2-yl)carbamate, (3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-2-oxo-1,3-benzothiazol-3(2H)-yl]butyl}biphenyl-2-yl)carbamate, (3R)-1-azabicyclo[2.2.2]oct-3-yl(4-{3-[4-(2-{[(2R)-2-hydroxy-2-(8-hydroxy-2-oxo-1,2-dihydroquinolin-5-yl)ethyl]amino}ethyl)phenoxy]propyl}biphenyl-2-yl)carbamate, (3R)-1-azabicyclo[2.2.2]oct-3-yl(4-{4-[6-({[(2R)-2-hydroxy-2-(8-hydroxy-2-oxo-1,2-dihydroquinolin-5-yl)ethyl]amino}methyl)-1,3-benzoxazol-2-y]butyl}biphenyl-2-yl)carbamate, (3R)-1-azabicyclo[2.2.2]oct-3-yl(4-{4-[5-({[(2R)-2-hydroxy-2-(8-hydroxy-2-oxo-1,2-dihydroquinolin-5-yl)ethyl]amino}methyl)-2H-1,2,3-benzotriazol-2-yl]butyl}biphenyl-2-yl)carbamate, trans-4-aminocyclohexyl(4-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, (3R)-1-azabicyclo[2.2.2]oct-3-yl(5-{4-[4-(2-{[(2R)-2-hydroxy-2-(8-hydroxy-2-oxo-1,2-dihydroquinolin-5-yl)ethyl]amino}ethyl)phenoxy]butyl}biphenyl-2-yl)carbamate, (3R)-1-azabicyclo[2.2.2]oct-3-yl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, trans-4-aminocyclohexyl[4-(4-{[4-({[(2R)-2-hydroxy-2-(8-hyroxy-2-oxo-1,2-dihydroquinolin-5-yl)ethyl]amino}methyl)phenyl]amino}-4-oxobutyl)biphenyl-2-yl]carbamate, (3R)-1-azabicyclo[2.2.2]oct-3-yl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-y)carbamate, (3R)-1-azabicyclo[2.2.2]oct-3-yl(4-{4-[6-({[(2R)-2-hydroxy-2-(5-hydroxy-3-oxo-3,4-dihydro-2H-1,4-benzoxazin-8-yl)ethyl]amino}methyl)-2-oxo-1,3-benzoxazol-3(2H)-yl]butyl}biphenyl-2-yl)carbamate, trans-4-aminocyclohexyl(4-{3-[5-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}biphenyl-2-yl)carbamate, trans-4-aminocyclohexyl(4-{4-[5-({[(2R)-2-hydroxy-2-(8-hydroxy-2-oxo-1,2-dihydroquinolin-5-yl)ethyl]amino}methyl)-1H-indol-1-yl]butyl}biphenyl-2-yl)carbamate, (3R)-1-azabicyclo[2.2.2]oct-3-yl(4-{4-[6-(2-{[(2R)-2-hydroxy-2-(8-hydroxy-2-oxo-1,2-dihydroquinolin-5-yl)ethyl]amino}ethyl)-2-oxo-1,3-benzoxazol-3(2H)-yl]butyl}biphenyl-2-yl)carbamate, trans-4-aminocyclohexyl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate, (3R)-1-azabicyclo[2.2.2]oct-3-yl(4-{3-[6-(2-{[(2R)-2-hydroxy-2-(8-hydroxy-2-oxo-1,2-dihydroquinolin-5-yl)ethyl]amino}ethyl)-2-oxo-1,3-benzoxazol-3(2H)-yl]propyl}biphenyl-2-yl)carbamate, (3R)-1-azabicyclo[2.2.2]oct-3-yl(4-{5-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]pentyl}biphenyl-2-yl)carbamate, trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate, trans-4-aminocyclohexyl {4-[(6-{[(2R)-2-hydroxy-2-(8-hydroxy-2-oxo-1,2-dihydroquinolin-5-yl)ethyl]amino}hexyl)oxy]biphenyl-2-yl}carbamate, trans-4-aminocyclohexyl(5-{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}biphenyl-2-yl)carbamate, trans-4-aminocyclohexyl(4-{4-[5-({[(2R)-2-hydroxy-2-(8-hydroxy-2-oxo-1,2-dihydroquinolin-5-yl)ethyl]amino}methyl)-1H-1,2,3-benzotriazol-1-yl]butyl}biphenyl-2-yl)carbamate, trans-4-aminocyclohexyl[5-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate, trans-4-aminocyclohexyl[4-(5-{[4-({[(2R)-2-hydroxy-2-(8-hydroxy-2-oxo-1,2-dihydroquinolin-5-yl)ethyl]amino}methyl)phenyl]amino}5-oxopentyl)biphenyl-2-yl]carbamate, trans-4-aminocyclohexyl[4-(4-({[4-(2-{[(2R)-2-hydroxy-2-(8-hydroxy-2-oxo-1,2-dihydroquinolin-5-yl)ethyl]amino}ethyl)phenyl]amino}-4-oxobutyl)biphenyl-2-yl]carbamate, trans-4-aminocyclohexyl(4-{4-[6-({[(2R)-2-hydroxy-2-(8-hydroxy-2-oxo-1,2-dihydroquinolin-5-yl)ethyl]amino}methyl)-5-methoxy-2-oxo-1,3-benzoxazol-3(2H)-yl]butyl}biphenyl-2-yl)carbamate, trans-4-[methyl(3-phenylpropyl)amino]cyclohexyl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate, trans-4-aminocyclohexyl[4-(3-{[4-({[(2R)-2-hydroxy-2-(8-hydroxy-2-oxo-1,2-dihydroquinolin-5-yl)ethyl]amino}methyl)phenyl]amino}-3-oxopropyl)biphenyl-2-yl]carbamate, (3R)-1-azabicyclo[2.2.2]oct-3-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate, trans-4-aminocyclohexyl(4-{4-[[4-({[(2R)-2-hydroxy-2-(8-hydroxy-2-oxo-1,2-dihydroquinolin-5-yl)ethyl]amino}methyl)phenyl](methyl)amino]-4-oxobutyl}biphenyl-2-yl)carbamate, trans-4-aminocyclohexyl[4-(4-(4-{[trans-4-({[(2R)-2-hydroxy-2-(8-hydroxy-2-oxo-1,2-dihydroquinolin-5-yl)ethyl]amino}methyl)cyclohexyl]amino}-4-oxobutyl)biphenyl-2-yl]carbamate,
trans-4-aminocyclohexyl[4-(4-{[4-(2-{[(2R)-2-hydroxy-2-(8-hydroxy-2-oxo-1,2-dihydroquinolin-5-yl)ethyl]amino}propyl)phenyl]amino}-4-oxobutyl)biphenyl-2-yl]carbamate,
trans-4-aminocyclohexyl(4-{4-[(5-{[4-({[(2R)-2-hydroxy-2-(8-hydroxy-2-oxo-1,2-dihydroquinolin-5-yl)ethyl]amino}methyl)phenyl]amino}-5-oxopentyl)(methyl)amino]-4-oxobutyl}biphenyl-2-yl)carbamate,
trans-4-aminocyclohexyl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]-propyl}biphenyl-2-yl)carbamate,
trans-4-amino-1-methylcyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)biphenyl-2-yl]carbamate,
trans-4-amino-1-methylcyclohexyl[4-(3-{[trans-4-({[(2R)-2-hydroxy-2-(8-hydroxy-2-oxo-1,2-dihydroquinolin-5-yl)ethyl]amino}methyl)cyclohexyl]amino}-3-oxopropyl)biphenyl-2-yl]carbamate,
1-azabicyclo[2.2.2]oct-4-yl[4-(3-{[2-chloro-4-({[(2R)-2-hydroxy-2-(8-hydroxy-2-oxo-1,2-dihydroquinolin-5-yl)ethyl]amino}methyl)-5-methoxyphenyl]amino}-3-oxopropyl)biphenyl-2-yl]carbamate,
trans-4-aminocyclohexyl(4-{2-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]ethyl}biphenyl-2-yl)carbamate,
trans-4-aminocyclohexyl(4-{2-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)oxy]ethyl}biphenyl-2-yl)carbamate,
trans-4-aminocyclohexyl(4-{4-[4-({[(2R)-2-hydroxy-2-(8-hydroxy-2-oxo-1,2-dihydroquinolin-5-yl)ethyl]amino}methyl)phenoxy]butyl}biphenyl-2-yl)carbamate,
trans-4-aminocyclohexyl[4-(4-{[trans-3-({[(2R)-2-hydroxy-2-(8-hydroxy-2-oxo-1,2-dihydroquinolin-5-yl)ethyl]amino}methyl)cyclobutyl]amino}-4-oxobutyl)biphenyl-2-yl]carbamate,
trans-4-aminocyclohexyl[4-(3-{[2-chloro-4-({[(2R)-2-hydroxy-2-(8-hydroxy-2-oxo-1,2-dihydroquinolin-5-yl)ethyl]amino}methyl)-5-methoxybenzoyl]amino}propyl)biphenyl-2-yl]carbamate,
trans-4-aminocyclohexyl[4-(3-{4-[4-({[(2R)-2-hydroxy-2-(8-hydroxy-2-oxo-1,2-dihydroquinolin-5-yl)ethyl]amino}methyl)phenoxy]phenyl}propyl)biphenyl-2-yl]carbamate,
trans-4-aminocyclohexyl[4-(4-{[4-({[(2R)-2-hydroxy-2-(8-hydroxy-2-oxo-1,2-dihydroquinolin-5-yl)ethyl]amino}methyl)benzyl]amino}-4-oxobutyl)biphenyl-2-yl]carbamate,
trans-4-aminocyclohexyl[4-(4-{[5-({[(2R)-2-hydroxy-2-(8-hydroxy-2-oxo-1,2-dihydroquinolin-5-yl)ethyl]amino}methyl)pyridin-2-yl]amino}-4-oxobutyl)biphenyl-2-yl]carbamate,
trans-4-[hexyl(methyl)amino]cyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate,
trans-4-aminocyclohexyl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)biphenyl-2-yl]carbamate,
Trans-4-aminocyclohexyl(4-(3-(Trans-4-(((((2R)-2-hydroxy-2-(8-hydroxy-2-oxo-1,2-dihydroquinolin-5-yl)ethyl)amino)methyl)cyclohexanecarboxamido)propyl)-biphenyl-2-yl)carbamate,
trans-4-aminocyclohexyl(4-{3-[({[2-chloro-4-({[(2R)-2-hydroxy-2-(8-hydroxy-2-oxo-1,2-dihydroquinolin-5-yl)ethyl]amino}methyl)-5-methoxyphenyl]amino}carbonyl)amino]propyl}biphenyl-2-yl)carbamate,
trans-4-aminocyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate,
1-azabicyclo[2.2.2]oct-4-yl[4-(4-{[4-({[(2R)-2-hydroxy-2-(8-hydroxy-2-oxo-1,2-dihydroquinolin-5-yl)ethyl]amino}methyl)phenyl]amino}-4-oxobutyl)biphenyl-2-yl]carbamate,
trans-4-aminocyclohexyl(4-{3-[({[trans-4-({[(2R)-2-hydroxy-2-(8-hydroxy-2-oxo-1,2-dihydroquinolin-5-yl)ethyl]amino}methyl)cyclohexyl]oxy}acetyl)methyl)amino]propyl}biphenyl-2-yl)carbamate,
1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate
trans-4-aminocyclohexyl(4-{4-[5-({[(2R)-2-hydroxy-2-(8-hydroxy-2-oxo-1,2-dihydroquinolin-5-yl)ethyl]amino}methyl)-1H-benzimidazol-1-yl]butyl}biphenyl-2-yl)carbamate,
trans-4-amino-1-methylcyclohexyl[4-(4-{[2-chloro-4-({[(2R)-2-hydroxy-2-(8-hydroxy-2-oxo-1,2-dihydroquinolin-5-yl)ethyl]amino}methyl)-5-methoxyphenyl]amino}-4-oxobutyl)biphenyl-2-yl]carbamate,
1-azabicyclo[2.2.2]oct-4-yl(4-{3-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino propyl}biphenyl-2-yl)carbamate,
1-azabicyclo[2.2.2]oct-4-yl[4-(4-{[2-chloro-4-({[(2R)-2-hydroxy-2-(8-hydroxy-2-oxo-1,2-dihydroquinolin-5-yl)ethyl]amino}methyl)-5-methoxybenzoyl]amino}butyl)biphenyl-2-yl]carbamate and
1-azabicyclo[2.2.2]oct-4-yl[4-(4-{[6-({[(2R)-2-hydroxy-2-(8-hydroxy-2-oxo-1,2-dihydroquinolin-5-yl)ethyl]amino}methyl)pyridin-3-yl]amino}-4-oxobutyl)biphenyl-2-yl]carbamate,
or pharmaceutically acceptable salts or deuterated derivates thereof.

27. A pharmaceutical composition comprising the compound according to claim 1 and a pharmaceutically acceptable diluent or carrier.

28. A combination product comprising (i) the compound according to claim 1; and (ii) at least one additional compound chosen from a corticosteroid and a PDE4 inhibitor, for simultaneous, separate or sequential use in the treatment of the human or animal body.

29. The compound according to claim 8, wherein Ar is chosen from the group consisting of 4-hydroxy-3-(hydroxymethyl)phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, or 5-hydroxy-3-oxo-3,4-dihydro-2H-benzo[b][1,4]oxazin-8-yl.

30. The compound according to claim 11, wherein $A_1$ and $A_2$ independently are a $C_{1-6}$ alkylene group optionally substituted with one or more substituents selected from a $C_{1-2}$ alkyl group, a $C_{1-2}$ alkoxy group, and a phenyl group.

31. The compound according to claim 30, wherein $A_1$ and $A_2$ independently are a $C_{1-4}$ alkylene group optionally substituted with one or two substituents selected from a methyl group and a methoxy group.

32. The compound according to claim 31, wherein $A_1$ and $A_2$ independently are a $C_{1-4}$ alkylene group optionally substituted with one or two methyl groups.

33. The compound according to claim 12, wherein X together with Y forms —CH=CH—.

34. The compound according to claim 13, wherein L is chosen from the group consisting of direct bond, —O—, —NR$^c$—, —NR$^c$(CO)—, —(CO)NR$^c$—, —NR$^c$(CO)(CH$_2$)$_q$—O—, —O(CH$_2$)$_q$(CO)NR$^c$—, —NR$^c$(CO)(CH$_2$)$_q$NR$^c$(CO)—, —O(CH$_2$)$_q$NR$^c$—, —NR$^c$(CH$_2$)$_q$O—, —NR$^c$(CO)NR$^d$—, —C(O)—, —C(O)O—, or —OC(O)— wherein R$^c$ and R$^d$ are independently selected from a hydrogen atom and a methyl group and q has a value of 0, 1, 2, 3 or 4.

35. The compound according to claim 34, wherein, L is selected from a direct bond, —O—, —NR$^c$(CO)—, —(CO)NR$^c$—, —NR$^c$(CO)(CH$_2$)$_q$O—, —O(CH$_2$)$_q$(CO)NR$^c$— or —C(O)—, wherein R$^c$ and R$^d$ independently are selected from a hydrogen atom and a methyl group and q has a value of 0, 1, 2, 3 or 4.

36. The compound according to claim 14, wherein L is chosen from a direct bond, —NR$^c$(CO)— or —(CO)NR$^c$—, wherein R$^c$ is chosen from a hydrogen atom or a methyl group.

37. The compound according to claim 15, wherein G is chosen from the group consisting of a direct bond; a $C_{3-7}$ cycloalkyl group; a $C_5$-$C_6$ aryl group; a 8- to 10-membered saturated or unsaturated bicyclic heterocyclyl group having one or more heteroatoms selected from N, S, and O; and a 8- to 10-membered bicyclic heteroaryl group having one or more heteroatoms chosen from N, S, and O, wherein the cyclic groups independently are optionally substituted with one or more substituents chosen from a halogen atom, a $C_{1-4}$ alkyl group, a $C_{1-4}$ alkoxy group, a cyano group, a nitro group, a hydroxy group and an oxo group.

38. The compound according to claim 17, wherein W is a —C(O)— group.

39. The compound according to claim 18, wherein V is chosen from —N—, —NH—, or —O.

40. The compound according to claim 16, wherein W is a —C(O)— group and Z is a —N— or —NH— group.

41. A compound accordingly to claim 21, wherein R', $R_2$ and $R_3$ are independently chosen from a hydrogen atom and a methyl group.

42. A compound accordingly to claim 41, wherein $R_2$ and $R_3$ are a hydrogen atom and R' is a hydrogen atom or a methyl group.

43. The compound according to claim 22, wherein R is chosen from a hydrogen atom or a hydroxy group.

44. The compound according to claim 43, wherein R is a hydrogen atom.

45. The compound according to claim 23, wherein n is 1.

46. A method for treating a subject afflicted with a pathological condition or disease, wherein the pathological condition or disease is chosen from asthma and/or chronic obstructive pulmonary disease, the method comprising administering to said subject an effective amount of a compound according to claim 1.

\* \* \* \* \*

UNITED STATES PATENT AND TRADEMARK OFFICE
CERTIFICATE OF CORRECTION

| | |
|---|---|
| PATENT NO. | : 9,518,050 B2 |
| APPLICATION NO. | : 14/653048 |
| DATED | : December 13, 2016 |
| INVENTOR(S) | : Laia Sole Feu et al. |

It is certified that error appears in the above-identified patent and that said Letters Patent is hereby corrected as shown below:

In the Claims

Claim 1, Column 177, Line 23, "lor" should read as -- 1 or --;

Claim 2, Column 179, Line 18, "cydcloalkyl" should read as -- cycloalkyl --; and Claim 34, Column 191, Lines 14-15, "$NR^c(CO)(CH_2)_q$ O—," should read as -- $NR^c(CO)(CH_2)_qO$—, --.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*